US00RE48060E

(19) United States
(12) Reissued Patent
Bhanot et al.

(10) Patent Number: US RE48,060 E
(45) Date of Reissued Patent: Jun. 23, 2020

(54) ANTISENSE MODULATION OF PTP1B EXPRESSION

(71) Applicant: Ionis Pharmaceuticals, Inc., Carlsbad, CA (US)

(72) Inventors: Sanjay Bhanot, Carlsbad, CA (US); Susan M. Freier, San Diego, CA (US)

(73) Assignee: Ionis Pharmaceuticals, Inc., Carlsbad, CA (US)

(21) Appl. No.: 15/183,700

(22) Filed: Jun. 15, 2016

Related U.S. Patent Documents

Reissue of:
(64) Patent No.: 9,034,842
Issued: May 19, 2015
Appl. No.: 14/152,896
Filed: Jan. 10, 2014

U.S. Applications:
(62) Division of application No. 13/446,763, filed on Apr. 13, 2012, now Pat. No. 8,658,783.

(60) Provisional application No. 61/474,981, filed on Apr. 13, 2011.

(51) Int. Cl.

| | |
|---|---|
| ***A61K 48/00*** | (2006.01) |
| ***C07H 21/02*** | (2006.01) |
| ***C07H 21/04*** | (2006.01) |
| ***C12N 15/113*** | (2010.01) |
| ***A61K 31/7088*** | (2006.01) |

(52) U.S. Cl.
CPC ..... *C12N 15/1137* (2013.01); *A61K 31/7088* (2013.01); *C12Y 301/03048* (2013.01); *C12N 2310/11* (2013.01); *C12N 2310/315* (2013.01); *C12N 2310/321* (2013.01); *C12N 2310/322* (2013.01); *C12N 2310/3231* (2013.01); *C12N 2310/3341* (2013.01); *C12N 2310/34* (2013.01); *C12N 2310/341* (2013.01); *C12N 2310/346* (2013.01); *C12N 2320/30* (2013.01)

(58) Field of Classification Search
CPC ..... A61K 48/00; C07H 21/02; C07H 21/04; C12N 15/113
See application file for complete search history.

(56) References Cited

U.S. PATENT DOCUMENTS

| | | | |
|---|---|---|---|
| 5,726,027 | A | 3/1998 | Olefsky |
| 5,801,154 | A | 9/1998 | Baracchini et al. |
| 6,261,840 | B1 | 7/2001 | Cowsert et al. |
| 6,261,849 | B1 | 7/2001 | Lee |
| 6,506,559 | B1 | 1/2003 | Fire et al. |
| 6,582,908 | B2 | 6/2003 | Fodor et al. |
| 6,602,857 | B1 | 8/2003 | Cowsert et al. |
| 7,179,796 | B2 | 2/2007 | Cowsert et al. |
| 7,427,672 | B2 | 9/2008 | Imanishi et al. |
| 7,563,884 | B2 | 7/2009 | Cowsert et al. |
| 7,687,616 | B1 | 3/2010 | Bentwich et al. |
| 7,834,170 | B2 | 11/2010 | Khvorova et al. |
| 8,017,760 | B2 | 9/2011 | Bhanot et al. |
| 8,039,608 | B1 | 10/2011 | Bentwich |
| 2001/0053519 | A1 | 12/2001 | Fodor et al. |
| 2002/0055479 | A1 | 5/2002 | Cowsert et al. ..... A61K 48/00 514/44 A |
| 2002/0198203 | A1 | 12/2002 | Robert Vitou et al. |
| 2003/0108883 | A1 | 6/2003 | Rondinone et al. |
| 2003/0220282 | A1 | 11/2003 | Cowsert et al. |
| 2003/0228597 | A1 | 12/2003 | Cowsert et al. |
| 2004/0005618 | A1 | 1/2004 | Yu et al. |
| 2004/0009946 | A1 | 1/2004 | Lewis et al. |
| 2004/0019001 | A1 | 1/2004 | McSwiggen |
| 2005/0070497 | A1 | 3/2005 | McSwiggen et al. |
| 2005/0095710 | A1 | 5/2005 | Cowsert et al. |
| 2006/0025372 | A1 | 2/2006 | Bhanot et al. |
| 2006/0089325 | A1 | 4/2006 | Bhanot et al. |
| 2007/0031844 | A1 | 2/2007 | Khvorova et al. |
| 2008/0015162 | A1 | 1/2008 | Bhanot et al. |
| 2008/0097092 | A1 | 4/2008 | Khvorova et al. |
| 2009/0036355 | A1 | 2/2009 | Bhanot et al. |
| 2009/0124009 | A1 | 5/2009 | Bhanot et al. |
| 2009/0318532 | A1 | 12/2009 | Bhanot et al. |
| 2009/0318536 | A1 | 12/2009 | Freier et al. |
| 2010/0105134 | A1 | 4/2010 | Quay et al. |
| 2010/0197773 | A1 | 8/2010 | Bramlage et al. ..... C12N 15/1137 514/44 R |
| 2012/0077862 | A1 | 3/2012 | Bhanot et al. |

FOREIGN PATENT DOCUMENTS

| | | |
|---|---|---|
| WO | WO 97/32595 | 9/1997 |
| WO | WO 98/20024 | 5/1998 |
| WO | WO 01/05954 | 1/2001 |
| WO | WO 01/07655 | 1/2001 |
| WO | WO 01/16312 | 3/2001 |
| WO | WO 01/30801 | 5/2001 |
| WO | WO 01/53528 | 7/2001 |

(Continued)

OTHER PUBLICATIONS

Abrahamson, "Clinical use of thiazolidinediones: Recommendations" The American Journal of Medicine (2003) 115:116S-120S.

Adjei et al., "A Phase I trial of ISIS 2503, an antisense inhibitor of H-ras, in combination with gemcitabine in patients with advanced cancer" Clinical Cancer Research (2003) 9:115-123.

Agrawal et al., "Antisense Therapeutics: Is It as Simple as Complementary Base Recognition?" Molecular Medicine Today (2000) 6(2):72-81.

Ahmad et al., "Improved Sensitivity to Insulin in Obese Subjects Following Weight Loss is Accompanied by Reduced Protein-Tyrosine Phosphatases in Adipose Tissue" *Metabolism* (1997) 46:1140-1145.

(Continued)

*Primary Examiner* — Sharon Turner
(74) *Attorney, Agent, or Firm* — Knobbe, Martens, Olson & Bear, LLP

(57) ABSTRACT

Provided herein are methods, compounds, and compositions for reducing expression of PTP1B mRNA and protein in an animal. Such methods, compounds, and compositions are useful to treat, prevent, delay, or ameliorate metabolic disease, for example, diabetes, or a symptom thereof.

37 Claims, 3 Drawing Sheets

Specification includes a Sequence Listing.

(56) References Cited

FOREIGN PATENT DOCUMENTS

| | | |
|---|---|---|
| WO | WO 02/59137 | 1/2002 |
| WO | WO 02/10378 | 2/2002 |
| WO | WO 02/44321 | 6/2002 |
| WO | WO 02/064840 | 8/2002 |
| WO | WO 02/092772 | 11/2002 |
| WO | WO 03/007951 | 1/2003 |
| WO | WO 03/070881 | 8/2003 |
| WO | WO 03/099227 | 12/2003 |
| WO | WO 2004/016735 | 2/2004 |
| WO | WO 2004/046161 | 6/2004 |
| WO | WO 2004/071407 | 8/2004 |
| WO | WO 2005/021572 | 3/2005 |
| WO | WO 2006/044531 | 4/2006 |
| WO | WO 2007/131237 | 11/2007 |
| WO | WO 2007/146511 | 12/2007 |
| WO | WO 2008/109470 | 9/2008 |
| WO | WO 2009/046141 | 4/2009 |
| WO | WO 2010/089221 | 8/2010 |

OTHER PUBLICATIONS

Arregui et al., "Impaired integrin-mediated adhesion and signaling in fibroblasts expressing a dominant-negative mutant PTP1B" *J. Cell. Biol.* (1998) 143:861-873.

Asante-Appiah et al., "Protein tyrosine phosphatase: the quest for negative regulators of insulin action" *Am. J. Physiol. Endocrinol. Metab.* (2003) 284:E663-E670.

Balsamo et al., "The nonreceptor protein tyrosine phosphatase PTP1B binds to the cytoplasmic domain of N-cadherin and regulates the cadherin-actin linkage" *J. Cell. Biol.* (1998) 143:523-532.

Bhanot et al., "A Novel PTP-1B Antisense Inhibitor (ISIS 113715) Improves Insulin Sensitivity in Obese Hyperinsulinemic Rhesus Monkeys" *ADA Annual Meeting* (2003) Abstract 477-P.

Branch et al., "A good antisense molecule is hard to fin" *TIBS* (1998) 23:45-50.

Brand et al., "Dual PPAR alpha/gamma activation provides enhanced improvement of insulin sensitivity and glycemic control in ZDF rats" American Journal of Physiology—Endocrinology and Metabolism (2003) 284:E841-854.

Brown-Shimer et al., "Effect of protein tyrosine phosphatase 1B expression on transformation by the human neu oncogene" *Cancer Res.* (1992) 52:478-482.

Cheetham et al., "Novel targets for the treatment of obesity: a review of progress" *Drug Discovery Today: Therapeutic Strategies* (2004) 1:227-235.

Chen et al., "A phosphotyrosyl mimetic peptide reverses impairment of insulin-stimulated transolcation of GLUT4 caused by overexpression of PTP1B in rat adipose cells" *Biochemistry* (1999) 38:384-389.

Chen et al., "Protein-tyrosine phosphatases PTP1B and syp are modulators of insulin-stimulated translocation of GLUT4 in transfected rat adipose cells" *J. Biol. Chem.* (1997) 272:8026-8031.

Chernoff et al., "Cloning of a cDNA for a Major Human Protein-Tyrosine-Phosphatase" Proc. Natl. Acad. Sci. USA (1990) 87:2735-2739.

Chin, "On the preparation and Utilization of Isolated and Purified Oligonucleotides" Document purportedly located on a CD-ROM and contributed to the public collection of the Katherine R. Everett Law Library of the University of North Carolina on Mar. 14, 2002.

Clampit et al., "Reduction of protein-tyrosine phosphatase-1B increases insulin signaling in FAO hepatoma cells" *Biochem. Biophys. Res. Commun.* (2003) 300:261-267.

Cox et al., "Absorption, disposition, and metabolism of rosigitazone, a potent thiazolidinedione insulin sensitizer, in humans" Drug Metabolism and Disposition (2000) 28:772-780.

Crooke et al., "Basic Principles of Antisense Therapeutics" Antisense Research and Application (1998) Chapter 1:1-50.

Crooke, "Antisense therapeutics" Biotechnology & Genetic Engineering Reviews (1998) 15:121-157.

Crystal et al., "Transfer of genes to humans: early lessons and obstacles to success" Science (1995) 270:404-410.

Day, "Thiazolidinediones: a new class of antidiabetic drugs" Diabetic Medicine (1999) 16:179-192.

Desmarais et al., "Inhibition of protein tyrosine phosphatases PTP1B and CD45 by sulfotyrosyl peptides" *Arch. Biochem. Biophys.* (1998) 354:225-231.

Elchebly et al., "Increased insulin sensitivity and obesity resistance in mice lacking the protein tyrosine phosphatase-1B gene" *Science* (1999) 283:1544-1548.

Ferber, "New Clues Found to Diabetes and Obesity" Science (1999) 283:1423-1424.

Friedmann et al., "Overcoming the Obstacles to gene therapy" Scientific American (1997) 276:96-101.

Geary et al., "Pharmacokinetics of a tumor necrosis factor-alpha phosphorothiaote 2'-O-(2'-methoxyethyl) modified antisense oligonucleotide: comparison across species" Drug Metabolism and Disposition (2003) 31:1419-1428.

Goldstein et al., "Regulation of the insulin signalling pathway by ceullular protein-tyrosine phosphatases" *Mol. Cell. Biochem.* (1998) 182:91-99.

Goldstein et al., "Protein-Tyrosine Phosphatase 1B (PTP1B): A Novel Therapeutic Target for Type 2 Diabetes Mellitus, Obesity and Related States of Insulin Resistance" *Curr. Drug Targets—Immun. Endocrin. Metab. Disorders* (2001) 1:265-275.

Goldstein, "Protein-tyrosine phosphatases: Emerging targets for therapeutic intervention in type 2 diabetes and related states of insulin resistance" The Journal of Clinical Endocrinology & Metabolism (2002) 87:2474-2480.

Goldstein et al., "Tests of Glycemia in Diabetes" *Diabetes Care* (2004) 27:1761-1773.

Graham et al., "In Vivo Distribution and Metabolism of a Phosphorothioate Oligonucleotides Within Rat Liver after Intravenous Administration" J. Pharm. Exp. Ther. (1998) 286:447-458.

Guan et al., "Cloning and Expression of Protein-Tyrosine-Phosphatase" Proc. Natl. Acad. Sci. USA (1990) 87:1501-1505.

Gum et al., "Antisense Protein Tyrosine Phosphatase 1B Reverses Activation of p38 Mitogen-Activated Protein Kinase in Liver of ob/ob Mice" *Molecular Endocrin.* (2003) 17:1131-1143.

Gum et al., "Reduction of Protein Tyrosine Phosphatase 1B Increases Insulin-Dependent Signaling in ob/ob Mice" *Diabetes* (2003) 52:21-28.

Ham et al., "Selective inactivation of protein tyrosine phosphatase PTP1B by sulfone analogue of naphthoquinone" *Bioorg. Med. Chem. Lett.* (1999) 9:185-186.

Hassid et al., "Antisense oligonucleotides against protein tyrosine phosphatase 1B increase focal adhesion protein phosphorylation and migration in rat aortic smooth muscle cells" in Supplement to Circulation, Journal of the American Heart Association, Abstracts from 71st Scientific Sessions (1998) Abstract No. 1733.

Hassid et al., "NO Alters Cell Shape and Motility in Aortic Smooth Muscle Cells via Protein Tyrosine Phosphatase 1B Activation" Am. J. Phys. (1999) 277:H1014-1026.

Hassid et al., "Role of PTP1B in Aortic Smooth Muscle Cell Motility and Tyrosine Phosphorylation of Focal Adhesion Proteins" Am. J. Phys. (1999) 277:H192-198.

Henry et al., "Toxicology and Pharmacokinetic Properties of Chemically Modified Antisense Oligonucleotide Inhibitors of PKC-Alpha and C-Raf Kinase" Anti-Cancer Drug Design (1997) 12:409-420.

Ho et al., "Mapping or RNA Accessible Sites for Antisense Experiments with Oligonucleotide Libraries" Nature Biotech. (1998) 16:59-63.

Hormes et al., "The subcellular localization and length of hammerhead ribozymes determine efficacy in human cells" Nucleic Acids Res. (1997) 25:769-775.

Huang et al., "Antisense to protein tyrosine phosphatase 1B increases Tyrosine Phosphorylation of Focal Adhesion Protein in Aortic Smooth Muscle Cells of Rats" FASEB (1998) 12:A188, Abstract No. 1099.

James et al., "Towards Gene-Inhibition Therapy: A Review of Progress and Prospects in the Field of Antiviral Antisense Nucleic Acids and Ribozymes" Antiviral Chem. and Chemotherapy (1991) 2:191-214.

(56) References Cited

OTHER PUBLICATIONS

Koizumi et al., "In vivo antisense activity of ENA oligonucleotides targeting PTP1B mRNA in comparison of that of 2'-MOE-modified oligonucleotides." Nucleic Acids Symp. Ser. (2007) 51:111-112.
Kjems et al., "Increased Insulin Sensitivity in Humans by Protein Tyrosine Phosphatase 1B (PTP-1B) Inhibition-Evaluation of ISIS 113715, an Antisense Inhibitor of PTP-1B" *San Diego ADA Annual Meeting* (2005) Abstract 2201-PO.
Ko et al., "The effect of rosiglitazone on serum lipoprotein(a) levels in Korean patients with type 2 diabetes mellitus" Metabolism (2003) 52:731-734.
Lamontagne et al., "Protein tyrosine phosphatase PTP1B suppresses p210 bcr-abl-induced transformation of rat-1 fibroblasts and promotes differentiation of K562 cells" *Proc. Natl. Acad. Sci. USA* (1998) 95:14094-14099.
Lee et al., "Reversible inactivation of protein-tyrosine phosphatase 1B in A431 cells stimulated with epidermal growth factor" *J. Biol. Chem.* (1998) 273:15366-15372.
Liu et al., "Protein tyrosine phosphatase 1B interacts with and is tyrosine phosphorylated by the epidermal growth factor receptor" Biochem. J. (1997) 327:139-145.
Liu et al., "Protein tyrosine phosphatase 1B negatively regulates integrin signaling" *Curr. Biol.* (1998) 8:173-176.
Liu et al., "Transformation suppression by protein tyrosine phosphatase 1B requires a functional SH3 ligand" *Mol. Cell. Biol.* (1998) 18:250-259.
Liu et al., "Protein tyrosine phosphatase 1B as a target for the treatment of impaired glucose tolerance and Type II diabetes" *Curr. Opin. Invest. Drugs* (2002) 3:1608-1616.
Liu, "Technology evaluation: ISIS-113715, Isis," *Curr. Opin. Mol. Therap.* (2004) 6:331-336.
Madsbad et al., "Improved glycemic control with no weight increase in patients with type 2 diabetes after once-daily treatment with the long-acting glucagan-like peptide 1 analog liraglutide (NN2211): a week, double-blind, randomized, controlled trial" Diabetes Care (2004) 27:1335-1342.
Mani et al., "Phase I clinical and pharmacokinetic study of protein kinase C-a antisense oligonucleotide ISIS 3521 administered in combination with 5-fluorouracil and leucovorin in patients with advanced cancer" Clinical Cancer Research (2002) 8:1042-1048.
Mauvais-Jarvis et al., "Therapeutic perspectives for type 2 diabetes mellitus: Molecular and clinical insights" Diabetes & Metabolism (2001) 27:415-423.
McKay et al., "Effects of a Novel PTP-1B Antisense Oligonucleotide Inhibitor (ISIS 113715) on PTP-1B Expression in Different Liver Cell Types" *ADA Annual Meeting* (2003) Abstract 611-P.
Meriden, "Progress with thiazolidinediones in the management of type 2 diabetes mellitus" Clinical Therapeutics (2004) 26:177-190.
Milner et al., "Selecting effective antisense reagents on combinatorial oligonucleotide arrays" *Nature* (1997) 15:537-541.
Moller et al., "Protein tyrosine phosphatases (PTPs) as drug targets: Inhibitors of PTP1B for the treatment of diabetes" *Curr. Opin. Drug Discov. Dev.* (2000) 3:527-540.
Monia, "Protein Phosphatases" *FASEB Summer Conference presentation on Protein Phosphatases in Colorado*, Jul. 23-28, 2000, poster presentation, 14 pages.
Monia, "Protein Phosphatases" *FASEB Summer Conference presentation on Protein Phosphatases in Colorado*, Jul. 23-28, 2000, oral presentation, 20 pages.
Murray et al., "Additive Glucose Lowering Effects of a Novel PTP-1B Antisense Oligonucleotide (ISIS 113715) with Rosiglitazone and Metformin in ZDF Rats" *San Diego ADA Annual Meeting* (2005) Abstract 1545-P.
New England Biolabs 1998/1999 Catalog, cover page, pp. 121 and 284.
Nuss et al., "Effects of Protein Tyrosine Phosphatase 1B (PTP1B) Antisense Oligonucleotide (ASO) Treatment on Fat Volume Using MRI in Zucker Fatty Rats" *Diabetes* (2001) 50:A377.
Palu et al., "In Pursuit of new developments for gene therapy of human disease" J. Biotech. (1999) 68:1-13.
Parker, "Preclinical studies and clinical trials for diabetes—second annual forum: Identify emerging therapies and improve trial efficacy" Idrugs (2004) 7:37-39.
Peracchi et al., "Prospects for antiviral ribozymes and deoxyribozymes" Rev. in Med. (2004) 14:47-64.
Pihl-Carey, "Isis to Restructure as Crohn's Disease Drug Fails in Phase III" BioWorld Today (The Daily Biotechnology Newspaper) (1999) 10:1-2.
Reynolds et al., "Rational siRNA design for RNA interference" Nature Biotechnology (2004) 22(3):326-330.
Roller et al., "Potent inhibition of protein-tyrosine phosphatase-1B using the phosphotyrosyl mimetic fluoro-O-malonyl tyrosine (FOMT)" *Bioorg. Med. Chem. Lett.* (1998) 8:2149-2150.
Rondinone et al., "Inhibition of PTP1B Induces Differential Expression of PI3-Kinase Regulatory Subunit (p85alpha) Isoforms" *Diabetes* (2001) 50:A400.
Rondinone et al., "Protein Tyrosine Phosphatase 1B Reduction Regulates Adiposity and Expression of Genes Involved in Lipogenesis" *Diabetes* (2002) 51:2405-2411.
Sanghvi et al., "Heterocyclic Base Modifications in Nucleic Acids and Their Applications in Antisense Oligonucleotides" Antisense Research and Applications (1993) pp. 273-288.
Schievella et al., "Protein tyrosine phosphatase 1B undergoes mitosis-specific phosphorylation on serine" *Cell. Growth Differ.* (1993) 4:239-246.
Schofield et al., "Non-viral approaches to gene therapy" Brit. Med. Bull. (1995) 51:56-71.
Seely et al., "Protein tyrosine phosphatase 1B interacts with the activated insuliun receptor" *Diabetes* (1996) 45:1379-1385.
Sell et al., "Insulin-inducible changes in the relative ratio of PTP1B splice variants" *Mol. Genet. Metab.* (1999) 66:189-192.
Shifrin et al., "Growth factor-inducible alternative splicing of nontransmembrane phosphotyrosine phosphatase PTP1B pre-mRNA" *J. Biol. Chem.* (1993) 268:25376-25384.
Skorey et al., "How does alendronate inhibit protein-tyrosine phosphatases?" *J. Biol. Chem.* (1997) 272:22472-22480.
Skrumsager et al., "Ragaglitazar: the parmacokinetics, pharmacodynamics, and tolerability of a novel dual PPARalpha and gamma agonist in healthy subjects and patients with type 2 diabetes" Journal of Clinical Pharmacology (2003) 43:1244-1256.
Standl et al., "Effect of acarbose on additional insulin therapy in type 2 diabetic patients with late failure of sulphonylurea therapy" *Diabetes, Obesity and Metabolism* (1999) 1:215-220.
Stein et al., "Antisense oligonucleotides as therapeutic agents—is the bullet really magical?" Science (1993) 261:1004-1012.
Stull et al., "An In Vitro Messenger RNA Binding Assay as a Tool for Identifying Hybridization-Competent Antisense Oligonucleotides" Antisense & Nucleic Acid Drug Development (1996) 6:221-228.
Strickland et al., "Antisense RNA Directed Against the 3' Noncoding Region Prevents Dormant mRNA Activation in Mouse Oocytes" Science (1988) 241:680-684.
Taing et al., "Potent and highly selective inhibitors of the protein tyrosine phosphatase 1B" *Biochemistry* (1999) 38:3793-3803.
Taylor et al., "Potent non-peptidyl inhibitors of protein tyrosine phosphatase 1B [published erratum appears in Bioorg Med Chem Nov. 1998;6(11):2235]" *Bioorg. Med. Chem.* (1998) 6:1457-1468.
Tonks et al., "Characterization of the major protein-tyrosine-phosphatases of human placenta" *J. Biol. Chem.* (1998) 263:6731-6737.
Tonks et al., "Purification of the major protein-tyrosine-phosphatases of human placenta" *J. Biol. Chem.* (1998) 263: 6722-6730.
Van Huijsduijnen et al., "Selecting protein tyrosine phosphatases as drug targets" DDT (2002) 7(19): 1013-1019.
Verma et al., "Gene Therapy: promises, problems and prospects" Nature (1997) 389:239-242.
Vickers et al., "Efficient reduction of target RNAs by small interfering RNA and Rnase H-dependent antisense agents" *The Journal of Biological Chemistry* (2003) 278:7108-7118.

(56) References Cited

OTHER PUBLICATIONS

Wagner, "Early clinical development of pharmaceuticals for type 2 diabetes mellitus: From preclinical models to human investigation" The Journal of Clinical Endocrinology & Metabolism (2002) 87:5362-5366.
Walczak, "Diabetes Technology News" Diabetes Technology & Therapeutics (2001) 3:307-331.
Wang et al., "Naphthalenebis [alpha, alpha-difluoromethylenephosphonates] as potent inhibitors of protein tyrosine phosphatases" *Bioorg. Med. Chem. Lett.* (1998) 8:345-350.
Wang et al., "Mechanism of inhibition of protein-tyrosine phosphatases by disodium aurothiomalate" *Biochem. Pharmacol.* (1997) 54:703-711.
Waring et al., "PTP1B antisense-treated mice show regulation of genes involved in lipogenesis in liver and fat" Mol. Cell. Endocrin. (2003) 203:155-168.
Wiener et al., "Overexpression of the Protein Tyrosine Phosphatase PTP1B in Human Breast Cancer: Association with p185 Protein Expression" *J. Nat. Cancer Inst.* (1994) 86:372-378.
Wiener et al., "Overexpression of the tyrosine phosphatase PTP1B is associated with human ovarian carcinomas" *Am. J. Obstet. Gynecol.* (1994) 170:1177-1183.
Wu et al., "Rosiglitazone ameliorates abnormal expression and activity of protein tyrosine phosphatase 1B in the skeletal muscle of fat-fed, streptozotocin-treated diabetic rats" Br. J. Pharm. (2005) 146:234-243.
Yao et al., "Structure-based design and synthesis of small molecule protein-tyrosine phsphatase 1B inhibitors" *Bioorg. Med. Chem.* (1998) 6:1799-1810.
Yu et al., "Abstract of International Patent Publication No. WO-02/59137" published Aug. 1, 2002.
Zhang et al., "Protein-tyrosine phosphatases: biological function, structural characteristics, and mechanism of catalysis" *Crit. Rev. Biochem. Mol. Biol.* (1998) 33:1-52.
Zinker et al., "PTP1B antisense oligonucleotide lowers PTP1B protein, normalizes blood glucose, and improves insulin sensitivity in diabetic mice" PNAS (2002) 99:11357-11362.
International Search Report for PCT/US12/33588 dated Aug. 31, 2012.

Comparison of Key Tolerability Parameters for 409826, 404173 and 142082

| 40 mpk/week | | | Fold over Saline | | |
|---|---|---|---|---|---|
| ISIS # | Chemistry | Walk Position | Spleen Wt | Kidney Wt | Liver Wt |
| 409826 | 5-10-5 | 4518 | 2.5 | 1.4 | 1.7 |
| 142082 | 5-10-5 | 4522 | 3.0 | 2.1 | 1.7 |
| 404173 | 5-10-5 | 4521 | 1.6 | 1.5 | 1.5 |

| 40 mpk/week | Fold Change vs Baseline | | | |
|---|---|---|---|---|
| ISIS # | C3 | CRP | MCP1 | IL-1 |
| Saline | -0.05 | 0.23 | -0.29 | -0.44 |
| 409826 | -0.30 | 3.90 | 2.31 | 2.37 |
| 142082 | -0.16 | 14.52 | 5.36 | 1.64 |
| 404173 | -0.18 | -0.48 | 0.82 | 0.09 |

* 1 animal very high at day 93; otherwise fold-increase was ~3-4 fold

Figure 2

ANTISENSE MODULATION OF PTP1B EXPRESSION

Matter enclosed in heavy brackets [ ] appears in the original patent but forms no part of this reissue specification; matter printed in italics indicates the additions made by reissue; a claim printed with strikethrough indicates that the claim was canceled, disclaimed, or held invalid by a prior post-patent action or proceeding.

CROSS-REFERENCE TO RELATED APPLICATIONS

This application is a divisional of U.S. application Ser. No. 13/446,763, filed Apr. 13, 2012, which claims priority under 35 U.S.C. §119(e) to U.S. Provisional Application No. 61/474,981, filed Apr. 13, 2011, each of which are herein incorporated by reference in their entirety.

SEQUENCE LISTING

The present application is being filed along with a Sequence Listing in electronic format. The Sequence Listing is provided as a file entitled BIOL0149USD1SEQ.txt created Jan. 10, 2014, which is 112 Kb in size. The information in the electronic format of the sequence listing is incorporated herein by reference in its entirety.

FIELD

Provided herein are methods, compounds, and compositions for reducing expression of PTP1B mRNA and protein in an animal. Such methods, compounds, and compositions are useful, for example, to treat, prevent, delay or ameliorate diseases associated with metabolic disorders, particularly disorders associated with diabetes.

BACKGROUND

Protein tyrosine phosphatase 1B (PTP1B) is a member of a family of PTPs (Barford, et al., Science 1994. 263: 1397-1404) and is a cytosolic enzyme (Neel and Tonks, Curr. Opin. Cell Biol. 1997. 9: 193-204). PTP1B is expressed ubiquitously including tissues that are key regulators of insulin metabolism such as liver, muscle and fat (Goldstein, Receptor 1993. 3: 1-15), where it is the main PTP enzyme.

PTP1B is considered to be a negative regulator of insulin signaling. PTP1B interacts with and dephosphorylates the insulin receptor, thus attenuating and potentially terminating the insulin signaling transduction (Goldstein et al., J. Biol. Chem. 2000. 275: 4383-4389). The physiological role of PTP1B in insulin signaling has been demonstrated in knockout mice models. Mice lacking the PTP1B gene were protected against insulin resistance and obesity (Elchebly et al., Science 1999. 283: 1544-1548). PTP1B-deficient mice had low adiposity, increased basal metabolic rate as well as total energy expenditure and were protected from diet-induced obesity. Insulin-stimulated glucose uptake was elevated in skeletal muscle, whereas adipose tissue was unaffected providing evidence that increased insulin sensitivity in PTP1B-deficient mice was tissue-specific (Klaman et al., Mol. Cell. Biol. 2000. 20: 5479-5489). These mice were phenotypically normal and were also resistant to diet-induced obesity, insulin resistance and had significantly lower triglyceride levels on a high-fat diet. Therefore, inhibition of PTP1B in patients suffering from Type II diabetes, metabolic syndrome, diabetic dyslipidemia, or related metabolic diseases would be beneficial.

Antisense inhibition of PTP1B provides a unique advantage over traditional small molecule inhibitors in that antisense inhibitors do not rely on competitive binding of the compound to the protein and inhibit activity directly by reducing the expression of PTP1B. Antisense technology is emerging as an effective means for reducing the expression of certain gene products and may therefore prove to be uniquely useful in a number of therapeutic, diagnostic, and research applications for the modulation of PTP1B.

There is a currently a lack of acceptable options for treating metabolic disorders. It is therefore an object herein to provide compounds and methods for the treatment of such diseases and disorder.

All documents, or portions of documents, cited in this application, including, but not limited to, patents, patent applications, articles, books, and treatises, are hereby expressly incorporated-by-reference for the portions of the document discussed herein, as well as in their entirety.

SUMMARY

Provided herein are methods, compounds, and compositions for modulating expression of PTP1B and treating, preventing, delaying or ameliorating diseases associated with metabolic disorders, particularly disorders associated with diabetes and/or a symptom thereof.

BRIEF DESCRIPTION OF THE FIGURES

The numerous objects and advantages of the present invention can be better understood by those skilled in the art by reference to the accompanying figures, in which:

FIG. 2 is a summary table of key tolerability studies in cynomolgus monkeys (see Example 17).

DETAILED DESCRIPTION

Figure 1:
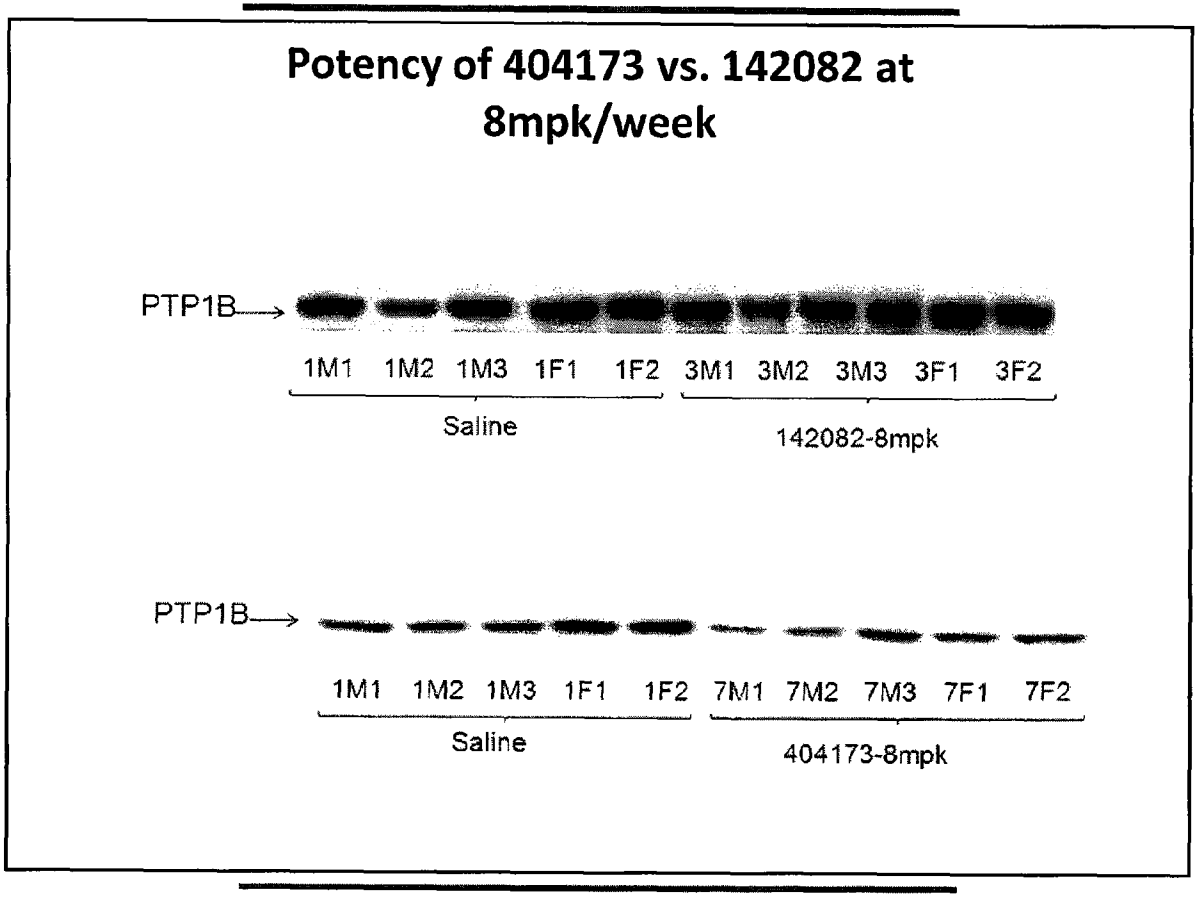
FIG. 1 shows a western blot of PTP1B antisense oligonucleotides, ISIS 404173 and ISIS 142082, decreasing PTP1B protein expression at 8 mgk/week demonstrating potency of the compounds. See Table 47.
Figure 3:
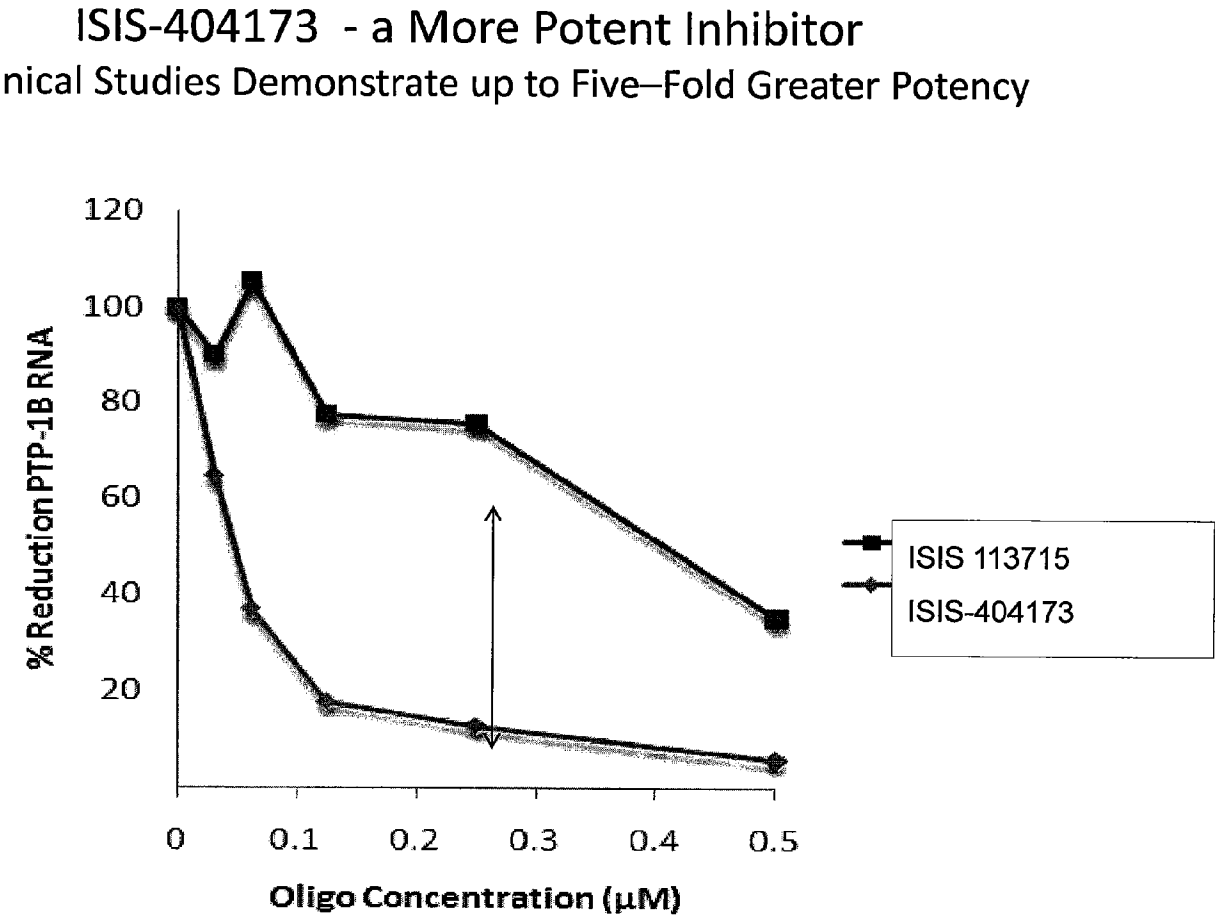
FIG. 3 is a graphical representation reduction of human PTP1B mRNA in a dose response preclinical study. Treatment with ISIS 404173 was compared with that of ISIS 113715, the previous clinical candidate. As shown here, dosing with ISIS 404173 was more potent and caused significant reduction in PTP1B mRNA levels compared to dosing with ISIS 113715. Particularly, at 0.3 μM dose, there was a five-fold decrease in PTP1B mRNA levels with ISIS 404173 compared to ISIS 113715.

It is to be understood that both the foregoing general description and the following detailed description are exemplary and explanatory only and are not restrictive of the invention, as claimed. Herein, the use of the singular includes the plural unless specifically stated otherwise. As used herein, the use of "or" means "and/or" unless stated otherwise. Furthermore, the use of the term "including" as well as other forms, such as "includes" and "included", is not limiting. Also, terms such as "element" or "component" encompass both elements and components comprising one unit and elements and components that comprise more than one subunit, unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated-by-reference for the portions of the document discussed herein, as well as in their entirety.

Definitions

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques can be used for chemical synthesis, and chemical analysis. Where permitted, all documents, or portions of documents, cited in this application, including, but not limited to, all patents, applications, published applications and other journal publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless specific definitions are provided, the nomenclature utilized in connection with, and the procedures and techniques of, analytical chemistry, synthetic organic chemistry, and medicinal and pharmaceutical chemistry described herein are those well known and commonly used in the art. Standard techniques can be used for chemical synthesis, and chemical analysis. Where permitted, all patents, applications, published applications and other publications, GENBANK Accession Numbers and associated sequence information obtainable through databases such as National Center for Biotechnology Information (NCBI) and other data referred to throughout in the disclosure herein are incorporated by reference for the portions of the document discussed herein, as well as in their entirety.

Unless otherwise indicated, the following terms have the following meanings:

"2'-O-methoxyethyl" (also 2'-MOE and 2'-O$(CH_2)_2$—$OCH_3$) refers to an O-methoxy-ethyl modification of the 2' position of a furosyl ring. A 2'-O-methoxyethyl modified sugar is a modified sugar.

"2'-O-methoxyethyl nucleotide" means a nucleotide comprising a 2'-O-methoxyethyl modified sugar moiety.

"3' target site" refers to the nucleotide of a target nucleic acid which is complementary to the 3'-most nucleotide of a particular antisense compound.

"5' target site" refers to the nucleotide of a target nucleic acid which is complementary to the 5'-most nucleotide of a particular antisense compound.

"5-methylcytosine" means a cytosine modified with a methyl group attached to the 5' position. A 5-methylcytosine is a modified nucleobase.

"About" means within ±10% of a value. For example, if it is stated, "a marker may be increased by about 50%", it is implied that the marker may be increased between 45%-55%.

"Active pharmaceutical agent" means the substance or substances in a pharmaceutical composition that provide a therapeutic benefit when administered to an individual. For example, in certain embodiments an antisense oligonucleotide targeted to PTP1B is an active pharmaceutical agent.

"Active target region" or "target region" means a region to which one or more active antisense compounds is targeted. "Active antisense compounds" means antisense compounds that reduce target nucleic acid levels or protein levels.

"Adipogenesis" means the development of fat cells from preadipocytes. "Lipogenesis" means the production or formation of fat, either fatty degeneration or fatty infiltration.

"Adiposity" or "Obesity" refers to the state of being obese or an excessively high amount of body fat or adipose tissue in relation to lean body mass. The amount of body fat includes concern for both the distribution of fat throughout the body and the size and mass of the adipose tissue deposits. Body fat distribution can be estimated by skin-fold measures, waist-to-hip circumference ratios, or techniques such as ultrasound, computed tomography, or magnetic resonance imaging. According to the Center for Disease Control and Prevention, individuals with a body mass index (BMI) of 30 or more are considered obese. The term "Obesity" as used herein includes conditions where there is an increase in body fat beyond the physical requirement as a result of excess accumulation of adipose tissue in the body. The term "obesity" includes, but is not limited to, the following conditions: adult-onset obesity; alimentary obesity; endogenous or inflammatory obesity; endocrine obesity; familial obesity; hyperinsulinar obesity; hyperplastic-hypertrophic obesity; hypogonadal obesity; hypothyroid obesity; lifelong obesity; morbid obesity and exogenous obesity.

"Administered concomitantly" refers to the co-administration of two agents in any manner in which the pharmacological effects of both are manifest in the patient at the same time. Concomitant administration does not require that both agents be administered in a single pharmaceutical composition, in the same dosage form, or by the same route of administration. The effects of both agents need not manifest themselves at the same time. The effects need only be overlapping for a period of time and need not be coextensive.

"Administering" means providing an agent to an animal, and includes, but is not limited to, administering by a medical professional and self-administering.

"Agent" means an active substance that can provide a therapeutic benefit when administered to an animal. "First Agent" means a therapeutic compound provided herein. For example, a first agent can be an antisense oligonucleotide targeting PTP1B. "Second agent" means a second therapeutic compound of the invention (e.g. a second antisense oligonucleotide targeting PTP1B) and/or a non-PTP1B therapeutic compound.

"Amelioration" refers to a lessening of at least one indicator, sign, or symptom of an associated disease, disorder, or condition. The severity of indicators can be determined by subjective or objective measures, which are known to those skilled in the art.

"Animal" refers to a human or non-human animal, including, but not limited to, mice, rats, rabbits, dogs, cats, pigs, and non-human primates, including, but not limited to, monkeys and chimpanzees.

"Antisense activity" means any detectable or measurable activity attributable to the hybridization of an antisense compound to its target nucleic acid. In certain embodiments, antisense activity is a decrease in the amount or expression of a target nucleic acid or protein encoded by such target nucleic acid.

"Antisense compound" means an oligomeric compound that is capable of undergoing hybridization to a target nucleic acid through hydrogen bonding.

"Antisense inhibition" means reduction of target nucleic acid levels or target protein levels in the presence of an antisense compound complementary to a target nucleic acid compared to target nucleic acid levels or target protein levels in the absence of the antisense compound.

"Antisense oligonucleotide" means a single-stranded oligonucleotide having a nucleobase sequence that permits hybridization to a corresponding region or segment of a target nucleic acid.

"Bicyclic sugar" means a furosyl ring modified by the bridging of two non-geminal ring atoms. A bicyclic sugar is a modified sugar.

"Bicyclic nucleic acid" or "BNA" refers to a nucleoside or nucleotide wherein the furanose portion of the nucleoside or nucleotide includes a bridge connecting two carbon atoms on the furanose ring, thereby forming a bicyclic ring system.

"Cap structure" or "terminal cap moiety" means chemical modifications, which have been incorporated at either terminus of an antisense compound.

"Chemically distinct region" refers to a region of an antisense compound that is in some way chemically different than another region of the same antisense compound. For example, a region having 2'-O-methoxyethyl nucleotides is chemically distinct from a region having nucleotides without 2'-O-methoxyethyl modifications.

"Chimeric antisense compound" means an antisense compound that has at least two chemically distinct regions.

"Co-administration" means administration of two or more agents to an individual. The two or more agents can be in a single pharmaceutical composition, or can be in separate pharmaceutical compositions. Each of the two or more agents can be administered through the same or different routes of administration. Co-administration encompasses parallel or sequential administration.

"Cholesterol" is a sterol molecule found in the cell membranes of all animal tissues. Cholesterol must be transported in an animal's blood plasma by lipoproteins including very low density lipoprotein (VLDL), intermediate density lipoprotein (IDL), low density lipoprotein (LDL), and high density lipoprotein (HDL). "Plasma cholesterol" refers to the sum of all lipoproteins (VDL, IDL, LDL, HDL) esterified and/or non-esterified cholesterol present in the plasma or serum.

"Cholesterol absorption inhibitor" means an agent that inhibits the absorption of exogenous cholesterol obtained from diet.

"Complementarity" means the capacity for pairing between nucleobases of a first nucleic acid and a second nucleic acid.

"Contiguous nucleobases" means nucleobases immediately adjacent to each other.

"Deoxyribonucleotide" means a nucleotide having a hydrogen at the 2' position of the sugar portion of the nucleotide. Deoxyribonucleotides may be modified with any of a variety of substituents.

"Diabetes mellitus" or "diabetes" is a syndrome characterized by disordered metabolism and abnormally high blood sugar (hyperglycemia) resulting from insufficient levels of insulin or reduced insulin sensitivity. The characteristic symptoms are excessive urine production (polyuria) due to high blood glucose levels, excessive thirst and increased fluid intake (polydipsia) attempting to compensate for increased urination, blurred vision due to high blood glucose effects on the eye's optics, unexplained weight loss, and lethargy.

"Diabetic dyslipidemia" or "type 2 diabetes with dyslipidemia" means a condition characterized by Type 2 diabetes, reduced HDL-C, elevated triglycerides, and elevated small, dense LDL particles.

"Diluent" means an ingredient in a composition that lacks pharmacological activity, but is pharmaceutically necessary or desirable. For example, the diluent in an injected composition can be a liquid, e.g. saline solution.

"Dyslipidemia" refers to a disorder of lipid and/or lipoprotein metabolism, including lipid and/or lipoprotein overproduction or deficiency. Dyslipidemias may be manifested by elevation of lipids such as cholesterol and triglycerides as well as lipoproteins such as low-density lipoprotein (LDL) cholesterol.

"Dosage unit" means a form in which a pharmaceutical agent is provided, e.g. pill, tablet, or other dosage unit known in the art. In certain embodiments, a dosage unit is a vial containing lyophilized antisense oligonucleotide. In certain embodiments, a dosage unit is a vial containing reconstituted antisense oligonucleotide.

"Dose" means a specified quantity of a pharmaceutical agent provided in a single administration, or in a specified time period. In certain embodiments, a dose can be administered in one, two, or more boluses, tablets, or injections. For example, in certain embodiments where subcutaneous administration is desired, the desired dose requires a volume not easily accommodated by a single injection, therefore, two or more injections can be used to achieve the desired dose. In certain embodiments, the pharmaceutical agent is administered by infusion over an extended period of time or continuously. Doses can be stated as the amount of pharmaceutical agent per hour, day, week, or month.

"Effective amount" or "therapeutically effective amount" means the amount of active pharmaceutical agent sufficient to effectuate a desired physiological outcome in an individual in need of the agent. The effective amount can vary among individuals depending on the health and physical condition of the individual to be treated, the taxonomic group of the individuals to be treated, the formulation of the composition, assessment of the individual's medical condition, and other relevant factors.

"Fully complementary" or "100% complementary" means each nucleobase of a nucleobase sequence of a first nucleic acid has a complementary nucleobase in a second nucleobase sequence of a second nucleic acid. In certain embodiments, a first nucleic acid is an antisense compound and a target nucleic acid is a second nucleic acid.

"Gapmer" means a chimeric antisense compound in which an internal region having a plurality of nucleosides that support RNase H cleavage is positioned between external regions having one or more nucleosides, wherein the nucleosides comprising the internal region are chemically distinct from the nucleoside or nucleosides comprising the external regions. The internal region can be referred to as a "gap segment" and the external regions can be referred to as "wing segments."

"Gap-widened" means a chimeric antisense compound having a gap segment of 12 or more contiguous 2'-deoxyribonucleosides positioned between and immediately adjacent to 5' and 3' wing segments having from one to six nucleosides.

"Glucose" is a monosaccharide used by cells as a source of energy and inflammatory intermediate. "Plasma glucose" refers to glucose present in the plasma.

"HMG-CoA reductase inhibitor" means an agent that acts through the inhibition of the enzyme HMG-CoA reductase, such as atorvastatin, rosuvastatin, fluvastatin, lovastatin, pravastatin, and simvastatin.

"Hybridization" means the annealing of complementary nucleic acid molecules. In certain embodiments, complementary nucleic acid molecules include an antisense compound and a target nucleic acid.

"Hyperlipidemia" or "hyperlipemia" is a condition characterized by elevated serum lipids or circulating (plasma) lipids. This condition manifests an abnormally high concentration of fats. The lipid fractions in the circulating blood are cholesterol, low density lipoproteins, very low density lipoproteins and triglycerides.

"Hypertriglyceridemia" means a condition characterized by elevated triglyceride levels.

"Identifying" or "selecting an animal with metabolic" means identifying or selecting a subject having been diagnosed with a metabolic disease, or a metabolic disorder; or, identifying or selecting a subject having any symptom of a metabolic disease, including, but not limited to, metabolic syndrome, hyperglycemia, hypertriglyceridemia, hypertension increased insulin resistance, decreased insulin sensitivity, above normal body weight, and/or above normal body fat or any combination thereof. Such identification may be accomplished by any method, including but not limited to, standard clinical tests or assessments, such as measuring serum or circulating (plasma) blood-glucose, measuring serum or circulating (plasma) triglycerides, measuring blood-pressure, measuring body fat, measuring body weight, and the like.

"Immediately adjacent" means there are no intervening elements between the immediately adjacent elements.

"Individual" or "subject" or "animal" means a human or non-human animal selected for treatment or therapy.

"Inhibiting the expression or activity" refers to a reduction or blockade of the expression or activity of a RNA or protein and does not necessarily indicate a total elimination of expression or activity.

"Insulin resistance" is defined as the condition in which normal amounts of insulin are inadequate to produce a normal insulin response from fat, muscle and liver cells. Insulin resistance in fat cells results in hydrolysis of stored triglycerides, which elevates free fatty acids in the blood plasma. Insulin resistance in muscle reduces glucose uptake whereas insulin resistance in liver reduces glucose storage, with both effects serving to elevate blood glucose. High plasma levels of insulin and glucose due to insulin resistance often leads to metabolic syndrome and type 2 diabetes.

"Insulin sensitivity" is a measure of how effectively an individual processes glucose. An individual having high insulin sensitivity effectively processes glucose whereas an individual with low insulin sensitivity does not effectively process glucose.

"Internucleoside linkage" refers to the chemical bond between nucleosides.

"Intravenous administration" means administration into a vein.

"Linked nucleosides" means adjacent nucleosides which are bonded together.

"Lipid-lowering therapy" or "lipid lowering agent" means a therapeutic regimen provided to a subject to reduce one or more lipids in a subject. In certain embodiments, a lipid-lowering therapy is provided to reduce one or more of ApoB, total cholesterol, LDL-C, VLDL-C, IDL-C, non-HDL-C, triglycerides, small dense LDL particles, and Lp(a) in a subject. Examples of lipid-lowering therapy include statins, fibrates, and MTP inhibitors.

"Major risk factors" refers to factors that contribute to a high risk for a particular disease or condition. In certain embodiments, major risk factors for coronary heart disease include, without limitation, cigarette smoking, hypertension, low HDL-C, family history of coronary heart disease, age, and other factors disclosed herein.

"Metabolic disease" or "metabolic disorder" refers to a condition characterized by an alteration or disturbance in metabolic function. "Metabolic" and "metabolism" are terms well known in the art and generally include the whole range of biochemical processes that occur within a living organism. Metabolic diseases or disorders include, but are not limited to, obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

"Metabolic syndrome" means a condition characterized by a clustering of lipid and non-lipid cardiovascular risk factors of metabolic origin. In certain embodiments, metabolic syndrome is identified by the presence of any 3 of the following factors: waist circumference of greater than 102 cm in men or greater than 88 cm in women; serum triglyceride of at least 150 mg/dL; HDL-C less than 40 mg/dL in men or less than 50 mg/dL in women; blood pressure of at least 130/85 mmHg; and fasting glucose of at least 110 mg/dL. These determinants can be readily measured in clinical practice (JAMA, 2001, 285: 2486-2497).

"Mismatch" or "non-complementary nucleobase" refers to the case when a nucleobase of a first nucleic acid is not capable of pairing with the corresponding nucleobase of a second or target nucleic acid.

"Mixed dyslipidemia" means a condition characterized by elevated cholesterol and elevated triglycerides.

"Modified internucleoside linkage" refers to a substitution or any change from a naturally occurring internucleoside bond (i.e. a phosphodiester internucleoside bond).

"Modified nucleobase" refers to any nucleobase other than adenine, cytosine, guanine, thymidine, or uracil. An "unmodified nucleobase" means the purine bases adenine (A) and guanine (G), and the pyrimidine bases thymine (T), cytosine (C), and uracil (U).

"Modified nucleoside" means a nucleoside having, independently, a modified sugar moiety or modified nucleobase.

"Modified nucleotide" means a nucleotide having, independently, a modified sugar moiety, modified internucleoside linkage, or modified nucleobase. A "modified nucleoside" means a nucleoside having, independently, a modified sugar moiety or modified nucleobase.

"Modified oligonucleotide" means an oligonucleotide comprising at least one modified nucleotide.

"Modified sugar" refers to a substitution or change from a natural sugar.

"Motif" means the pattern of chemically distinct regions in an antisense compound.

"MTP inhibitor" means an agent inhibits the enzyme, microsomal triglyceride transfer protein.

"Naturally occurring internucleoside linkage" means a 3' to 5' phosphodiester linkage.

"Natural sugar moiety" means a sugar found in DNA (2'-H) or RNA (2'-OH).

"Non-alcoholic fatty liver disease" or "NAFLD" means a condition characterized by fatty inflammation of the liver that is not due to excessive alcohol use (for example, alcohol consumption of over 20 g/day). In certain embodiments, NAFLD is related to insulin resistance and the metabolic syndrome. NAFLD encompasses a disease spectrum ranging from simple triglyceride accumulation in hepatocytes (hepatic steatosis) to hepatic steatosis with inflammation (steatohepatitis), fibrosis, and cirrhosis.

"Nonalcoholic steatohepatitis" (NASH) occurs from progression of NAFLD beyond deposition of triglycerides. A "second hit" capable of inducing necrosis, inflammation, and fibrosis is required for development of NASH. Candidates for the second-hit can be grouped into broad categories: factors causing an increase in oxidative stress and factors promoting expression of proinflammatory cytokines "Nucleic acid" refers to molecules composed of monomeric nucleotides. A nucleic acid includes ribonucleic acids (RNA), deoxyribonucleic acids (DNA), single-stranded nucleic acids, double-stranded nucleic acids, small interfering ribonucleic acids (siRNA), and microRNAs (miRNA). A nucleic acid can also comprise a combination of these elements in a single molecule.

"Nucleobase" means a heterocyclic moiety capable of pairing with a base of another nucleic acid.

"Nucleobase sequence" means the order of contiguous nucleobases independent of any sugar, linkage, or nucleobase modification.

"Nucleoside" means a nucleobase linked to a sugar.

"Nucleoside mimetic" includes those structures used to replace the sugar or the sugar and the base and not necessarily the linkage at one or more positions of an oligomeric compound such as for example nucleoside mimetics having morpholino, cyclohexenyl, cyclohexyl, tetrahydropyranyl, bicyclo or tricyclo sugar mimetics e.g. non furanose sugar units.

"Nucleotide" means a nucleoside having a phosphate group covalently linked to the sugar portion of the nucleoside.

"Nucleotide mimetic" includes those structures used to replace the nucleoside and the linkage at one or more positions of an oligomeric compound such as for example peptide nucleic acids or morpholinos (morpholinos linked by —N(H)—C(═O)—O— or other non-phosphodiester linkage).

"Oligomeric compound" or "oligomer" refers to a polymeric structure comprising two or more sub-structures and capable of hybridizing to a region of a nucleic acid molecule. In certain embodiments, oligomeric compounds are oligonucleosides. In certain embodiments, oligomeric compounds are oligonucleotides. In certain embodiments, oligomeric compounds are antisense compounds. In certain embodiments, oligomeric compounds are antisense oligonucleotides. In certain embodiments, oligomeric compounds are chimeric oligonucleotides.

"Oligonucleotide" means a polymer of linked nucleosides each of which can be modified or unmodified, independent one from another.

"Parenteral administration" means administration through injection or infusion. Parenteral administration includes subcutaneous administration, intravenous administration, intramuscular administration, intraarterial administration, intraperitoneal administration, or intracranial administration, e.g. intrathecal or intracerebroventricular administration. Administration can be continuous, or chronic, or short or intermittent.

"Peptide" means a molecule formed by linking at least two amino acids by amide bonds. Peptide refers to polypeptides and proteins.

"Pharmaceutical agent" means a substance that provides a therapeutic benefit when administered to an individual. For example, in certain embodiments, an antisense oligonucleotide targeted to PTP1B is pharmaceutical agent.

"Pharmaceutical composition" means a mixture of substances suitable for administering to an individual. For example, a pharmaceutical composition can comprise one or more active agents and a sterile aqueous solution.

"Pharmaceutically acceptable carrier" means a medium or diluent that does not interfere with the structure of the oligonucleotide. Certain, of such carries enable pharmaceutical compositions to be formulated as, for example, tablets, pills, dragees, capsules, liquids, gels, syrups, slurries, suspension and lozenges for the oral ingestion by a subject. For example, a pharmaceutically acceptable carrier can be a sterile aqueous solution.

"Pharmaceutically acceptable derivative" encompasses pharmaceutically acceptable salts, conjugates, prodrugs or isomers of the compounds described herein.

"Pharmaceutically acceptable salts" means physiologically and pharmaceutically acceptable salts of antisense compounds, i.e., salts that retain the desired biological activity of the parent oligonucleotide and do not impart undesired toxicological effects thereto.

"Phosphorothioate linkage" means a linkage between nucleosides where the phosphodiester bond is modified by replacing one of the non-bridging oxygen atoms with a sulfur atom. A phosphorothioate linkage is a modified internucleoside linkage.

"Portion" means a defined number of contiguous (i.e. linked) nucleobases of a nucleic acid. In certain embodiments, a portion is a defined number of contiguous nucleobases of a target nucleic acid. In certain embodiments, a portion is a defined number of contiguous nucleobases of an antisense compound.

"Prevent" refers to delaying or forestalling the onset or development of a disease, disorder, or condition for a period of time from minutes to indefinitely. Prevent also means reducing risk of developing a disease, disorder, or condition.

"Prodrug" means a therapeutic agent that is prepared in an inactive form that is converted to an active form within the body or cells thereof by the action of endogenous enzymes or other chemicals or conditions.

"Protein tyrosine phosphatase 1B" or "PTP1B" (also known as PTPN1; protein tyrosine phosphatase, non-receptor type 1; PTP-1B; RKPTP) means any nucleic acid or protein of PTP1B.

"PTP1B expression" means the level of mRNA transcribed from the gene encoding PTP1B or the level of protein translated from the mRNA. PTP1B expression can be determined by art known methods such as a Northern or Western blot.

"PTP1B nucleic acid" means any nucleic acid encoding PTP1B. For example, in certain embodiments, a PTP1B nucleic acid includes a DNA sequence encoding PTP1B, a RNA sequence transcribed from DNA encoding PTP1B (including genomic DNA comprising introns and exons), and a mRNA sequence encoding PTP1B. "PTP1B mRNA" means a mRNA encoding a PTP1B protein.

"Side effects" means physiological responses attributable to a treatment other than the desired effects. In certain embodiments, side effects include injection site reactions, liver function test abnormalities, renal function abnormalities, liver toxicity, renal toxicity, central nervous system abnormalities, myopathies, and malaise. For example, increased aminotransferase levels in serum can indicate liver toxicity or liver function abnormality. For example, increased bilirubin can indicate liver toxicity or liver function abnormality.

"Single-stranded oligonucleotide" means an oligonucleotide which is not hybridized to a complementary strand.

"Specifically hybridizable" refers to an antisense compound having a sufficient degree of complementarity between an antisense oligonucleotide and a target nucleic acid to induce a desired effect, while exhibiting minimal or no effects on non-target nucleic acids under conditions in which specific binding is desired, i.e. under physiological conditions in the case of in vivo assays and therapeutic treatments.

"Statin" means an agent that inhibits the activity of HMG-CoA reductase.

"Subcutaneous administration" means administration just below the skin.

"Targeting" or "targeted" means the process of design and selection of an antisense compound that will specifically hybridize to a target nucleic acid and induce a desired effect.

"Target nucleic acid," "target RNA," and "target RNA transcript" all refer to a nucleic acid capable of being targeted by antisense compounds.

"Target segment" means the sequence of nucleotides of a target nucleic acid to which an antisense compound is targeted. "5' target site" refers to the 5'-most nucleotide of a target segment. "3' target site" refers to the 3'-most nucleotide of a target segment.

"Therapeutically effective amount" means an amount of an agent that provides a therapeutic benefit to an individual.

"Therapeutic lifestyle change" means dietary and lifestyle changes intended to lower fat/adipose tissue mass and/or cholesterol. Such change can reduce the risk of developing heart disease, and may includes recommendations for dietary intake of total daily calories, total fat, saturated fat, polyunsaturated fat, monounsaturated fat, carbohydrate, protein, cholesterol, insoluble fiber, as well as recommendations for physical activity.

"Triglyceride" or "TG" means a lipid or neutral fat consisting of glycerol combined with three fatty acid molecules.

"Type 2 diabetes," (also known as "type 2 diabetes mellitus" or "diabetes mellitus, type 2", and formerly called "diabetes mellitus type 2", "non-insulin-dependent diabetes (NIDDM)", "obesity related diabetes", or "adult-onset diabetes") is a metabolic disorder that is primarily characterized by insulin resistance, relative insulin deficiency, and hyperglycemia.

"Treat" refers to administering a pharmaceutical composition to an animal to effect an alteration or improvement of a disease, disorder, or condition.

"Unmodified nucleotide" means a nucleotide composed of naturally occurring nucleobases, sugar moieties, and internucleoside linkages. In certain embodiments, an unmodified nucleotide is an RNA nucleotide (i.e. β-D-ribonucleosides) or a DNA nucleotide (i.e. β-D-deoxyribonucleoside).

Certain Embodiments

Certain embodiments provide methods, compounds, and compositions for inhibiting PTP1B expression.

Certain embodiments provide antisense compounds targeted to a PTP1B nucleic acid. In certain embodiments, the PTP1B nucleic acid is any of the sequences set forth in GENBANK Accession No. NM_002827.2 (incorporated herein as SEQ ID NO: 1), GENBANK Accession No. NT_011362.9 truncated from nucleotides 14178000 to 14256000 (incorporated herein as SEQ ID NO: 2); and a concatenation of sequences from exons 1-9, intron 9 and exon 10 of the rhesus monkey PTP1B scaffold (incorporated herein as SEQ ID NO: 3).

In certain embodiments, the compounds or compositions provided herein comprise a modified oligonucleotide consisting of 10 to 30 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 10 to 30 linked nucleosides and having a nucleobase sequence comprising at least 8, 9, 10, 11, 12, 13, 14, 15, 16, 17, 18, 19, 20, 21, 22, 23, 24, 25, 26, 27, 28, 29 or 30 contiguous nucleobases complementary to an equal length portion of any of SEQ ID NOs: 1-3.

In certain embodiments, the compounds or compositions provided herein can consist of 10 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 4-32 or 100-111.

In certain embodiments, the compounds or compositions provided herein can consist of 10 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 26 or 44.

In certain embodiments, the compounds or compositions provided herein can consist of 10 to 30 linked nucleosides and have a nucleobase sequence comprising at least 8, 9, 10, 11, 12, 13, 14, 15, 16, 17, 18, 19, or 20 contiguous nucleobases of any of ISIS NOs: 404173, 410002, 438373, 438383, 438445, 438454, 438463, or 438472.

In certain embodiments, the compounds or compositions provided herein can consist of 10 to 30 linked nucleosides and have a nucleobase sequence comprising at least 8, 9, 10, 11, 12, 13, 14, 15, 16, 17, 18, 19, or 20 contiguous nucleobases of ISIS NO: 404173

In certain embodiments, the compounds or compositions provided herein comprise a modified oligonucleotide consisting of 15 to 30 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 15 to 30 linked nucleosides and having a nucleobase sequence comprising at least 8, 9, 10, 11, 12, 13, 14, 15, 16, 17, 18, 19, 20, 21, 22, 23, 24, 25, 26, 27, 28, 29 or 30 contiguous nucleobases complementary to an equal length portion of any of SEQ ID NOs: 1-3.

In certain embodiments, the compounds or compositions provided herein can consist of 15 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 4-32 or 100-111.

In certain embodiments, the compounds or compositions provided herein can consist of 15 to 30 linked nucleosides and have a nucleobase sequence comprising at least 8, 9, 10, 11, 12, 13, 14, 15, 16, 17, 18, 19, or 20 contiguous nucleobases of any of SEQ ID NOs: 26 or 44.

In certain embodiments, the compounds or compositions provided herein can consist of 15 to 30 linked nucleosides and have a nucleobase sequence comprising at least 8, 9, 10, 11, 12, 13, 14, 15, 16, 17, 18, 19, or 20 contiguous nucleobases of any of ISIS NOs: 404173, 410002, 438373, 438383, 438445, 438454, 438463, or 438472.

In certain embodiments, the compounds or compositions provided herein can consist of 15 to 30 linked nucleosides and have a nucleobase sequence comprising at least 8, 9, 10, 11, 12, 13, 14, 15, 16, 17, 18, 19, or 20 contiguous nucleobases of ISIS NO: 404173

In certain embodiments, the compounds or compositions provided herein comprise a modified oligonucleotide consisting of 18 to 21 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 18 to 21 linked nucleosides and having a nucleobase sequence comprising at least 8, 9, 10, 11, 12, 13, 14, 15, 16, 17, 18, 19, 20, or 21 contiguous nucleobases complementary to an equal length portion of any of SEQ ID NOs: 1-3.

In certain embodiments, the compounds or compositions provided herein consist of 18 to 21 linked nucleosides and have a nucleobase sequence comprising at least 8, 9, 10, 11, 12, 13, 14, 15, 16, 17, 18, 19, or contiguous nucleobases of any of SEQ ID NOs: 4-32 or 39-49.

In certain embodiments, the compounds or compositions provided herein consist of 18 to 21 linked nucleosides and have a nucleobase sequence comprising at least 8, 9, 10, 11, 12, 13, 14, 15, 16, 17, 18, 19, or contiguous nucleobases of any of SEQ ID NOs: 26 or 44.

In certain embodiments, the compounds or compositions provided herein consist of 18 to 21 linked nucleosides and have a nucleobase sequence comprising at least 8, 9, 10, 11, 12, 13, 14, 15, 16, 17, 18, 19, or contiguous nucleobases of any of ISIS NOs: 404173, 410002, 438373, 438383, 438445, 438454, 438463, or 438472.

In certain embodiments, the compounds or compositions provided herein consist of 18 to 21 linked nucleosides and have a nucleobase sequence comprising at least 8, 9, 10, 11, 12, 13, 14, 15, 16, 17, 18, 19, or contiguous nucleobases of ISIS NO: 404173.

In certain embodiments, the compounds or compositions provided herein comprise a modified oligonucleotide consisting of 20 to 35 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 to 35 linked nucleosides and having a nucleobase sequence comprising at least 8, 9, 10, 11, 12, 13, 14, 15, 16, 17, 18, 19, 20, 21, 22, 23, 24, 25, 26, 27, 28, 29, 30, 31, 32, 33, 34 or 35 contiguous nucleobases complementary to an equal length portion of any of SEQ ID NOs: 1-3.

In certain embodiments, the compounds or compositions provided herein consist of 20 to 35 linked nucleosides and have a nucleobase sequence comprising at least 8, 9, 10, 11, 12, 13, 14, 15, 16, 17, 18, 19, or 20 contiguous nucleobases of SEQ ID NOs: 4-32 or 50.

In certain embodiments, the compounds or compositions provided herein consist of 20 to 35 linked nucleosides and have a nucleobase sequence comprising at least 8, 9, 10, 11, 12, 13, 14, 15, 16, 17, 18, 19, or contiguous nucleobases of SEQ ID NO: 26.

In certain embodiments, the compounds or compositions provided herein consist of 20 to 35 linked nucleosides and have a nucleobase sequence comprising at least 8, 9, 10, 11, 12, 13, 14, 15, 16, 17, 18, 19, or contiguous nucleobases of any of ISIS NOs: 404173, 410002, 438373, 438383, 438445, 438454, 438463, or 438472.

In certain embodiments, the compounds or compositions provided herein consist of 20 to 35 linked nucleosides and have a nucleobase sequence comprising at least 8, 9, 10, 11, 12, 13, 14, 15, 16, 17, 18, 19, or contiguous nucleobases of ISIS NO: 404173.

In certain embodiments, the compounds or compositions provided herein comprise a modified oligonucleotide consisting of 20 to 30 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 to 30 linked nucleosides and having a nucleobase sequence comprising at least 8, 9, 10, 11, 12, 13, 14, 15, 16, 17, 18, 19, 20, 21, 22, 23, 24, 25, 26, 27, 28, 29 or 30 contiguous nucleobases complementary to an equal length portion of any of SEQ ID NOs: 1-3.

In certain embodiments, the compounds or compositions provided herein consist of 20 to 30 linked nucleosides and have a nucleobase sequence comprising at least 8, 9, 10, 11, 12, 13, 14, 15, 16, 17, 18, 19, or 20 contiguous nucleobases of SEQ ID NO: 4-32 or 50.

In certain embodiments, the compounds or compositions provided herein consist of 20 to 30 linked nucleosides and have a nucleobase sequence comprising at least 8, 9, 10, 11, 12, 13, 14, 15, 16, 17, 18, 19, or contiguous nucleobases of SEQ ID NO: 26.

In certain embodiments, the compounds or compositions provided herein consist of 20 to 30 linked nucleosides and have a nucleobase sequence comprising at least 8, 9, 10, 11, 12, 13, 14, 15, 16, 17, 18, 19, or contiguous nucleobases of any of ISIS NOs: 404173, 410002, 438383, 438445, 438454, 438463, or 438472, In certain embodiments, the compounds or compositions provided herein consist of 20 to 30 linked nucleosides and have a nucleobase sequence comprising at least 8, 9, 10, 11, 12, 13, 14, 15, 16, 17, 18, 19, or contiguous nucleobases of ISIS NO: 404173.

In certain embodiments, the compounds or compositions provided herein comprise a modified oligonucleotide consisting of 20 to 25 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 to 25 linked nucleosides and having a nucleobase sequence comprising at least 8, 9, 10, 11, 12, 13, 14, 15, 16, 17, 18, 19, 20, 21, 22, 23, 24, or 25 contiguous nucleobases complementary to an equal length portion of any of SEQ ID NOs: 1-3.

In certain embodiments, the compounds or compositions provided herein consist of 20 to 25 linked nucleosides and have a nucleobase sequence comprising at least 8, 9, 10, 11, 12, 13, 14, 15, 16, 17, 18, 19, or contiguous nucleobases of SEQ ID NOs: 4-32.

In certain embodiments, the compounds or compositions provided herein consist of 20 to 25 linked nucleosides and have a nucleobase sequence comprising at least 8, 9, 10, 11, 12, 13, 14, 15, 16, 17, 18, 19, or contiguous nucleobases of SEQ ID NO: 26.

In certain embodiments, the compounds or compositions provided herein consist of 20 to 25 linked nucleosides and have a nucleobase sequence comprising at least 8, 9, 10, 11, 12, 13, 14, 15, 16, 17, 18, 19, or contiguous nucleobases of any of ISIS NOs: 404173, 410002, 438383, 438445, 438454, 438463, or 438472, In certain embodiments, the compounds or compositions provided herein consist of 20 to 25 linked nucleosides and have a nucleobase sequence comprising at least 8, 9, 10, 11, 12, 13, 14, 15, 16, 17, 18, 19, or contiguous nucleobases of ISIS NO: 404173.

In certain embodiments, the compounds or compositions of the invention comprise a modified oligonucleotide consisting of 20 to 24 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 to 24 linked nucleosides and having a nucleobase sequence comprising at least 8, 9, 10, 11, 12, 13, 14, 15, 16, 17, 18, 19, 20, 21, 22, 23, or 24 contiguous nucleobases complementary to an equal length portion of any of SEQ ID NOs: 1-3.

In certain embodiments, the compounds or compositions provided herein consist of 20 to 24 linked nucleosides and have a nucleobase sequence comprising at least 8, 9, 10, 11, 12, 13, 14, 15, 16, 17, 18, 19, or contiguous nucleobases of SEQ ID NOs: 4-32.

In certain embodiments, the compounds or compositions provided herein consist of 20 to 24 linked nucleosides and have a nucleobase sequence comprising at least 8, 9, 10, 11, 12, 13, 14, 15, 16, 17, 18, 19, or contiguous nucleobases of SEQ ID NO: 26.

In certain embodiments, the compounds or compositions provided herein consist of 20 to 24 linked nucleosides and have a nucleobase sequence comprising at least 8, 9, 10, 11, 12, 13, 14, 15, 16, 17, 18, 19, or contiguous nucleobases of any of ISIS NOs: 404173, 410002, 438373, 438383, 438445, 438454, 438463, or 438472.

In certain embodiments, the compounds or compositions provided herein consist of 20 to 24 linked nucleosides and have a nucleobase sequence comprising at least 8, 9, 10, 11, 12, 13, 14, 15, 16, 17, 18, 19, or contiguous nucleobases of ISIS NO: 404173

In certain embodiments, the compounds or compositions provided herein comprise a modified oligonucleotide consisting of 20 to 23 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 to 23 linked nucleosides and having a nucleobase sequence comprising at least 8, 9, 10, 11, 12, 13, 14, 15, 16, 17, 18, 19, 20, 21, 22, or 23 contiguous nucleobases complementary to an equal length portion of any of SEQ ID NOs: 1-3.

In certain embodiments, the compounds or compositions provided herein consist of 20 to 23 linked nucleosides and have a nucleobase sequence comprising at least 8, 9, 10, 11, 12, 13, 14, 15, 16, 17, 18, 19, or contiguous nucleobases of SEQ ID NOs: 4-32.

In certain embodiments, the compounds or compositions provided herein consist of 20 to 23 linked nucleosides and have a nucleobase sequence comprising at least 8, 9, 10, 11, 12, 13, 14, 15, 16, 17, 18, 19, or contiguous nucleobases of SEQ ID NO: 26.

In certain embodiments, the compounds or compositions provided herein consist of 20 to 23 linked nucleosides and have a nucleobase sequence comprising at least 8, 9, 10, 11, 12, 13, 14, 15, 16, 17, 18, 19, or contiguous nucleobases of any of ISIS NOs: 404173, 410002, 438373, 438383, 438445, 438454, 438463, or 438472.

In certain embodiments, the compounds or compositions provided herein consist of 20 to 23 linked nucleosides and have a nucleobase sequence comprising at least 8, 9, 10, 11, 12, 13, 14, 15, 16, 17, 18, 19, or contiguous nucleobases of ISIS NO: 404173.

In certain embodiments, the compounds or compositions provided herein comprise a modified oligonucleotide consisting of 20 to 22 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 to 22 linked nucleosides and having a nucleobase sequence comprising at least 8, 9, 10, 11, 12, 13, 14, 15, 16, 17, 18, 19, 20, 21, or 22 contiguous nucleobases complementary to an equal length portion of any of SEQ ID NOs: 1-3.

In certain embodiments, the compounds or compositions provided herein consist of 20 to 22 linked nucleosides and have a nucleobase sequence comprising at least 8, 9, 10, 11, 12, 13, 14, 15, 16, 17, 18, 19, or contiguous nucleobases of SEQ ID NOs: 4-32.

In certain embodiments, the compounds or compositions provided herein consist of 20 to 22 linked nucleosides and have a nucleobase sequence comprising at least 8, 9, 10, 11, 12, 13, 14, 15, 16, 17, 18, 19, or contiguous nucleobases of SEQ ID NO: 26.

In certain embodiments, the compounds or compositions provided herein consist of 20 to 22 linked nucleosides and have a nucleobase sequence comprising at least 8, 9, 10, 11, 12, 13, 14, 15, 16, 17, 18, 19, or contiguous nucleobases of any of ISIS NOs: 404173, 410002, 438373, 438383, 438445, 438454, 438463, or 438472.

In certain embodiments, the compounds or compositions provided herein consist of 20 to 22 linked nucleosides and have a nucleobase sequence comprising at least 8, 9, 10, 11, 12, 13, 14, 15, 16, 17, 18, 19, or contiguous nucleobases of ISIS NO: 404173.

In certain embodiments, the compounds or compositions provided herein comprise a modified oligonucleotide consisting of 20 to 21 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 to 21 linked nucleosides and having a nucleobase sequence comprising at least 8, 9, 10, 11, 12, 13, 14, 15, 16, 17, 18, 19, 20, or 21 contiguous nucleobases complementary to an equal length portion of any of SEQ ID NOs: 1-3.

In certain embodiments, the compounds or compositions provided herein consist of 20 to 21 linked nucleosides and have a nucleobase sequence comprising at least 8, 9, 10, 11, 12, 13, 14, 15, 16, 17, 18, 19, or contiguous nucleobases of SEQ ID NOs: 4-32.

In certain embodiments, the compounds or compositions provided herein consist of 20 to 21 linked nucleosides and have a nucleobase sequence comprising at least 8, 9, 10, 11, 12, 13, 14, 15, 16, 17, 18, 19, or contiguous nucleobases of SEQ ID NO: 26.

In certain embodiments, the compounds or compositions provided herein consist of 20 to 21 linked nucleosides and have a nucleobase sequence comprising at least 8, 9, 10, 11, 12, 13, 14, 15, 16, 17, 18, 19, or contiguous nucleobases of any of ISIS NOs: 404173, 410002, 438373, 438383, 438445, 438454, 438463, or 438472.

In certain embodiments, the compounds or compositions provided herein consist of 20 to 21 linked nucleosides and have a nucleobase sequence comprising at least 8, 9, 10, 11, 12, 13, 14, 15, 16, 17, 18, 19, or contiguous nucleobases of ISIS NO: 404173.

In certain embodiments, the compounds or compositions provided herein comprise a modified oligonucleotide consisting of 20 nucleosides having a nucleobase sequence comprising at least 8 contiguous nucleobases complementary to an equal length portion of any of SEQ ID NOs: 1-3.

In certain embodiments, the compounds or compositions provided herein comprise a modified oligonucleotide consisting of 20 linked nucleosides and having a nucleobase sequence comprising at least 8, 9, 10, 11, 12, 13, 14, 15, 16, 17, 18, 19, or 20 contiguous nucleobases complementary to an equal length portion of any of SEQ ID NOs: 1-3.

In certain embodiments, the compounds or compositions provided herein consist of 20 linked nucleosides and have a nucleobase sequence comprising at least 8, 9, 10, 11, 12, 13, 14, 15, 16, 17, 18, 19, or contiguous nucleobases of SEQ ID NOs: 4-32.

In certain embodiments, the compounds or compositions provided herein consist of 20 linked nucleosides and have a nucleobase sequence comprising at least 8, 9, 10, 11, 12, 13, 14, 15, 16, 17, 18, 19, or contiguous nucleobases of SEQ ID NO: 26.

In certain embodiments, the compounds or compositions provided herein consist of any of ISIS NOs: 404173, 410002, 438373, 438383, 438445, 438454, 438463, or 438472.

In certain embodiments, the compounds or compositions provided herein consist of ISIS NO: 404173.

In certain embodiments, the compounds or compositions provided herein consist of SEQ ID NO: 26.

In certain embodiments, the compounds or compositions provided herein comprise a salt of the modified oligonucleotide.

In certain embodiments, the compounds or compositions provided herein further comprise a pharmaceutically acceptable carrier or diluent.

In certain embodiments, the nucleobase sequence of the modified oligonucleotide is at least 70%, 75%, 80%, 85%, 90%, 95%, 96%, 97%, 98%, 99% or 100% complementary to any one of SEQ ID NOs: 1-3 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to any one of SEQ ID NO: 4-32 or 39-50. as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to any one of SEQ ID NO: 26 or 44. as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to any one ISIS NOs: 404173, 410002, 438373, 438383, 438445, 438454, 438463, or 438472 as measured over the entirety of the modified oligonucleotide.

In certain embodiments, the nucleobase sequence of the modified oligonucleotide has at least 70%, 75%, 80%, 85%, 90%, 95%, 96%, 97%, 98%, 99% or 100% identity to ISIS NO: 404173 as measured over the entirety of the modified oligonucleotide.

In certain embodiments, the compound provided herein consists of a single-stranded modified oligonucleotide.

In certain embodiments, the modified oligonucleotide consists of 8, 9, 10, 11, 12, 13, 14, 15, 16, 17, 18, 19, 20, 21, 22, 23, 24, 25, 26, 27, 28, 29, 30, 31, 32, 33, 34 or 35 linked nucleosides. In certain embodiments, the modified oligonucleotide consists of 20 linked nucleosides. In certain embodiments, the modified oligonucleotide consists of 18 linked nucleosides.

In certain embodiments, at least one internucleoside linkage of the modified oligonucleotide is a modified internucleoside linkage. In certain embodiments, each internucleoside linkage is a phosphorothioate internucleoside linkage.

In certain embodiments, at least one nucleoside of said modified oligonucleotide comprises a modified nucleobase. In certain embodiments, the modified nucleobase is a 5-methylcytosine.

In certain embodiments, the modified oligonucleotide comprises: a) a gap segment consisting of linked deoxynucleosides; b) a 5' wing segment consisting of linked nucleosides; and c) a 3' wing segment consisting of linked nucleosides. The gap segment is positioned between the 5' wing segment and the 3' wing segment and each nucleoside of each wing segment comprises a modified sugar.

In certain embodiments, the modified oligonucleotide consists of 20 linked nucleosides, the gap segment consisting of ten linked deoxynucleosides, the 5' wing segment consisting of five linked nucleosides, the 3' wing segment consisting of five linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the modified oligonucleotide consists of 20 linked nucleosides, the gap segment consisting of eight linked deoxynucleosides, the 5' wing segment consisting of six linked nucleosides, the 3' wing segment consisting of six linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the modified oligonucleotide consists of 20 linked nucleosides, the gap segment consisting of thirteen linked deoxynucleosides, the 5' wing segment consisting of two linked nucleosides, the 3' wing segment consisting of five linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the modified oligonucleotide consists of 18 linked nucleosides, the gap segment consisting of eight linked deoxynucleosides, the 5' wing segment consisting of five linked nucleosides, the 3' wing segment consisting of five linked nucleosides, each nucleoside of each wing segment comprises a 2'-O-methoxyethyl modified sugar, each internucleoside linkage is a phosphorothioate linkage and each cytosine is a 5-methylcytosine.

In certain embodiments, the compounds or compositions provided herein comprise a modified oligonucleotide consisting of 20 linked nucleosides having a nucleobase sequence comprising at least 8 contiguous nucleobases complementary to an equal length portion of any of SEQ ID NOs: 1-3, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 18 linked nucleosides having a nucleobase sequence comprising at least 8 contiguous nucleobases complementary to an equal length portion of any of SEQ ID NOs: 1-3, wherein the modified oligonucleotide comprises: a) a gap segment consisting of eight linked deoxynucleosides; b) a 5' wing segment consisting of six linked nucleosides; and c) a 3' wing segment consisting of six linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NOs: 4-32, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NO: 26, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having the nucleobase sequence of SEQ ID NO: 26, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 19 contiguous nucleobases of SEQ ID NO: 26 or 44, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine. In certain embodiments, the compound or composition comprises the compound of any of ISIS NOs: 404173, 410002, 438383, 438445, 438454, 438463, or 438472.

In certain embodiments, the compounds or compositions provided herein comprise a modified oligonucleotide consisting of 20 linked nucleosides having a nucleobase sequence comprising at least 20 contiguous nucleobases of SEQ ID NOs: 4-32, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 20 contiguous nucleobases of SEQ ID NO: 26, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine.

In certain embodiments, the compounds or compositions provided herein comprise a modified oligonucleotide consisting of 20 linked nucleosides having a nucleobase sequence comprising at least 20 contiguous nucleobases of SEQ ID NO: 26, wherein the modified oligonucleotide comprises: a) a gap segment consisting of ten linked deoxynucleosides; b) a 5' wing segment consisting of five linked nucleosides; and c) a 3' wing segment consisting of five linked nucleosides. The gap segment is positioned between the 5' wing segment and the 3' wing segment, each nucleoside of each wing segment comprises a 2'-O-methoxyethyl modified sugar, each internucleoside linkage is a phosphorothioate linkage and each cytosine residue is a 5-methylcytosine. In certain embodiments, the compound or composition comprises the compound ISIS NOs: 404173.

Certain embodiments provide methods, compounds, and compositions for inhibiting PTP1B expression.

Certain embodiments provide a method of reducing PTP1B expression in an animal comprising administering to the animal a compound as described herein. In certain embodiments, the compound comprises a modified oligonucleotide 10 to 30 linked nucleosides in length targeted to PTP1B. In certain embodiments, the compound comprises a modified oligonucleotide 20 to 35 linked nucleosides in length targeted to PTP1B. In certain embodiments, the compound comprises a modified oligonucleotide 20 to 25 linked nucleosides in length targeted to PTP1B. In certain embodiments, the compound comprises a modified oligonucleotide 20 to 24 linked nucleosides in length targeted to PTP1B. In certain embodiments, the compound comprises a modified oligonucleotide 20 to 23 linked nucleosides in length targeted to PTP1B. In certain embodiments, the compound comprises a modified oligonucleotide 20 to 22 linked nucleosides in length targeted to PTP1B. In certain embodiments, the compound comprises a modified oligonucleotide 20 to 21 linked nucleosides in length targeted to PTP1B. In certain embodiments, the compound comprises a modified oligonucleotide 20 linked nucleosides in length targeted to PTP1B.

Certain embodiments provide a method of preventing, ameliorating or treating an metabolic disease in an animal comprising administering to the animal a compound as described herein. In certain embodiments, the compound comprises a modified oligonucleotide 10 to 30 linked nucleosides in length targeted to PTP1B. In certain embodiments, the compound comprises a modified oligonucleotide 20 linked nucleosides in length targeted to PTP1B. Examples of metabolic diseases or disorders include, but are not limited to obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

Certain embodiments provide a method of reducing glucose levels in an animal comprising administering to the animal a compound as described herein. In certain embodiments, the compound comprises a modified oligonucleotide 10 to 30 linked nucleosides in length targeted to PTP1B. In certain embodiments, the compound comprises a modified oligonucleotide 20 linked nucleosides in length targeted to PTP1B. In certain embodiments, reduction of glucose levels in an animal prevents, ameliorates or treats a metabolic disease. In certain embodiments, reduction of glucose levels in an animal prevents, ameliorates or treats diabetes. In certain embodiments, reduction of glucose levels in an animal prevents, ameliorates or treats obesity. In certain embodiments, reduction of glucose levels in an animal prevents, ameliorates or treats metabolic syndrome. In certain embodiments, reduction of glucose levels in an animal prevents, ameliorates or treats insulin resistance. In certain embodiments, reduction of glucose levels in an animal prevents, ameliorates or treats hyperglycemia. In certain embodiments, reduction of glucose levels in an animal prevents, ameliorates or treats NAFLD. In certain embodiments, reduction of glucose levels in an animal prevents, ameliorates or treats diabetic dyslipidemia. In certain embodiments, the glucose level is reduced by at least 5%, 10%, 20%, 30%, 35%, 40%, 45%, 50%, 55%, 60%, 65%, 70%, 75%, 80%, 85%, 90%, 95% or 100%.

In certain embodiments, PTP1B has the sequence as set forth in any of the GenBank Accession Numbers GENBANK Accession No. NM_002827.2 (incorporated herein as SEQ ID NO: 1), GENBANK Accession No. NT_011362.9 truncated from nucleotides 14178000 to 14256000 (incorporated herein as SEQ ID NO: 2); and a concatenation of sequences from exons 1-9, intron 9 and exon 10 of the rhesus monkey PTP1B scaffold (incorporated herein as SEQ ID NO: 3). In certain embodiments, PTP1B has the human sequence as set forth in SEQ ID NOs: 1-2. In certain embodiments, PTP1B has the rhesus monkey sequence as set forth in SEQ ID NOs: 3).

In certain embodiments, the compounds or compositions provided herein comprise a salt thereof, and a pharmaceutically acceptable carrier or diluent. In certain embodiments, the composition comprises a modified oligonucleotide consisting of 20 to 35 linked nucleosides and having a nucleobase sequence comprising at least 20 contiguous nucleobases of a nucleobase sequence recited in SEQ ID NOs: 4-32, 50 or a salt thereof and a pharmaceutically acceptable carrier or diluent. In certain embodiments, the composition comprises a modified oligonucleotide consisting of 20 to 25 linked nucleosides and having a nucleobase sequence comprising at least 20 contiguous nucleobases of a nucleobase sequence recited in SEQ ID NOs: 4-32, 50 or a salt thereof and a pharmaceutically acceptable carrier or diluent. In certain embodiments, the composition comprises a modified oligonucleotide consisting of 20 linked nucleosides and having a nucleobase sequence comprising at least 20 contiguous nucleobases of a nucleobase sequence recited in SEQ ID NO: 4-32, 50 or a salt thereof and a pharmaceutically acceptable carrier or diluent.

In certain embodiments, the compounds or compositions provided herein comprise a salt thereof, and a pharmaceutically acceptable carrier or diluent. In certain embodiments, the composition comprises a modified oligonucleotide consisting of 20 to 35 linked nucleosides and having a nucleobase sequence comprising at least 20 contiguous nucleobases of a nucleobase sequence recited in SEQ ID NO: 26 or a salt thereof and a pharmaceutically acceptable carrier or diluent. In certain embodiments, the composition comprises a modified oligonucleotide consisting of 20 to 25 linked nucleosides and having a nucleobase sequence comprising at least 20 contiguous nucleobases of a nucleobase sequence recited in SEQ ID NO: 26 or a salt thereof and a pharmaceutically acceptable carrier or diluent. In certain embodiments, the composition comprises a modified oligonucleotide consisting of 20 linked nucleosides and having a nucleobase sequence comprising at least 20 contiguous nucleobases of a nucleobase sequence recited in SEQ ID NO: 26 or a salt thereof and a pharmaceutically acceptable carrier or diluent.

In certain embodiments, the compounds or compositions of the invention comprise a salt thereof, and a pharmaceutically acceptable carrier or diluent. In certain embodiments, the composition comprises a modified oligonucleotide consisting of 20 to 35 linked nucleosides and having a nucleobase sequence comprising at least 20 contiguous nucleobases of a nucleobase sequence selected from among the nucleobase sequences recited in ISIS NOs: 404173, 410002, 438383, 438445, 438454, 438463, or 438472 or a salt thereof and a pharmaceutically acceptable carrier or diluent. In certain embodiments, the composition comprises a modified oligonucleotide consisting of 20 to 25 linked nucleosides and having a nucleobase sequence comprising at least 20 contiguous nucleobases of a nucleobase sequence selected from among the nucleobase sequences recited in ISIS NOs: 404173, 410002, 438383, 438445, 438454, 438463, or 438472 or a salt thereof and a pharmaceutically acceptable carrier or diluent. In certain embodiments, the composition comprises a modified oligonucleotide consisting of 20 linked nucleosides and having a nucleobase sequence comprising at least 20 contiguous nucleobases of a nucleobase sequence selected from among the nucleobase sequences recited in ISIS NOs: 404173, 410002, 438383, 438445, 438454, 438463, or 438472 or a salt thereof and a pharmaceutically acceptable carrier or diluent.

In certain embodiments, the compounds or compositions of the invention comprise a salt thereof, and a pharmaceutically acceptable carrier or diluent. In certain embodiments, the composition comprises a modified oligonucleotide consisting of 20 to 35 linked nucleosides and having a nucleobase sequence comprising at least 20 contiguous nucleobases of a nucleobase sequence selected from among the nucleobase sequences recited in ISIS NO: 404173 or a salt thereof and a pharmaceutically acceptable carrier or diluent. In certain embodiments, the composition comprises a modified oligonucleotide consisting of 20 to 25 linked nucleosides and having a nucleobase sequence comprising at least 20 contiguous nucleobases of a nucleobase sequence selected from among the nucleobase sequences recited in ISIS NO: 404173 or a salt thereof and a pharmaceutically acceptable carrier or diluent. In certain embodiments, the composition comprises a modified oligonucleotide consisting of 20 linked nucleosides and having a nucleobase sequence comprising at least 20 contiguous nucleobases of a nucleobase sequence selected from among the nucleobase sequences recited in ISIS NO: 404173 or a salt thereof and a pharmaceutically acceptable carrier or diluent.

Certain embodiments provide a method for treating an animal with a PTP1B related disease or condition comprising: a) identifying said animal with the PTP1B related disease or condition, and b) administering to said animal a therapeutically effective amount of a compound comprising a modified oligonucleotide consisting of 10 to 30 linked nucleosides and having a nucleobase sequence at least 90% complementary to any of SEQ ID NOs: 1-3 as measured over the entirety of said modified oligonucleotide. In certain embodiments, the therapeutically effective amount of the compound administered to the animal treats or reduces the PTP1B related disease or condition, or a symptom thereof, in the animal. In certain embodiments, the PTP1B related disease or condition is diabetes.

Certain embodiments provide a method for treating an animal with a PTP1B related disease or condition comprising: a) identifying said animal with the PTP1B related disease or condition, and b) administering to said animal a therapeutically effective amount of a compound comprising a modified oligonucleotide consisting of 20 linked nucleosides and having a nucleobase sequence at least 100% complementary to any of SEQ ID NOs: 1-3 as measured over the entirety of said modified oligonucleotide. In certain embodiments, the therapeutically effective amount of the compound administered to the animal treats or reduces the PTP1B related disease or condition, or a symptom thereof, in the animal. In certain embodiments, the PTP1B related disease or condition is diabetes.

Certain embodiments provide methods of treating, preventing, or ameliorating a metabolic disease. In certain embodiments the metabolic disease is obesity, diabetes, hyperglycemia, prediabetes, non-alcoholic fatty liver disease (NAFLD), metabolic syndrome, insulin resistance, diabetic dyslipidemia, or hypertriglyceridemia or a combination thereof.

Certain embodiments provide methods of treating, preventing, or ameliorating a hyperproliferative disorder.

Certain embodiments provide methods comprising administering to an animal a compound as described herein to an animal. In certain embodiments, the method comprises administering to an animal a modified oligonucleotide consisting of 20 to 35 linked nucleosides and having a nucleobase sequence comprising at least 20 contiguous nucleobases of a nucleobase sequence recited in SEQ ID NOs: 4-32 or 50 Certain embodiments provide methods comprising administering to an animal a compound as described herein to an animal. In certain embodiments, the method comprises administering to an animal a modified oligonucleotide consisting of 20 to 35 linked nucleosides and having a nucleobase sequence comprising at least 20 contiguous nucleobases of a nucleobase sequence recited in SEQ ID NO: 26.

Certain embodiments provide methods comprising administering to an animal a compound as described herein to an animal. In certain embodiments, the method comprises administering to an animal a modified oligonucleotide consisting of 20 to 35 linked nucleosides and having a nucleobase sequence comprising at least 20 contiguous nucleobases of a nucleobase sequence selected from among the nucleobase sequences recited in ISIS NOs: 404173, 410002, 438383, 438445, 438454, 438463, or 438472.

Certain embodiments provide methods comprising administering to an animal a compound as described herein to an animal. In certain embodiments, the method comprises administering to an animal a modified oligonucleotide consisting of 20 to 35 linked nucleosides and having a nucleobase sequence comprising at least 20 contiguous nucleobases of a nucleobase sequence selected from among the nucleobase sequences recited in ISIS NO: 404173.

In certain embodiments, the animal is a human.

In certain embodiments, the administering prevents, treats, ameliorates, or slows progression of a metabolic disease as described herein.

In certain embodiments, the administering prevents, treats, ameliorates, or slows progression of diabetes as described herein.

In certain embodiments, the compound is co-administered with a second agent.

In certain embodiments, the compound and the second agent are administered concomitantly.

In certain embodiments, the administering is parenteral administration.

Certain embodiments further provide a method to reduce PTP1B mRNA or protein expression in an animal comprising administering to the animal a compound or composition as described herein to reduce PTP1B mRNA or protein expression in the animal. In certain embodiments, the animal is a human. In certain embodiments, reducing PTP1B mRNA or protein expression prevents, treats, ameliorates, or slows progression of metabolic disease. In certain embodiments, the metabolic disease or condition is diabetes.

Certain embodiments provide a method for treating a human with a metabolic disease comprising identifying the human with the disease and administering to the human a therapeutically effective amount of a compound or composition as described herein. In certain embodiments, the treatment reduces a symptom selected from the group consisting of metabolic syndrome, hyperglycemia, hypertriglyceridemia, hypertension, increased glucose levels, increased insulin resistance, decreased insulin sensitivity, above normal body weight, and/or above normal body fat or any combination thereof.

Certain embodiments provide a method for treating a human with diabetes comprising identifying the human with the disease and administering to the human a therapeutically effective amount of a compound or composition as described herein. In certain embodiments, the treatment reduces a symptom selected from the group consisting of metabolic syndrome, hyperglycemia, hypertriglyceridemia, hypertension, increased glucose levels, increased insulin resistance, decreased insulin sensitivity, above normal body weight, and/or above normal body fat or any combination thereof.

Further provided is a method for reducing or preventing metabolic disease comprising administering to a human a therapeutically effective amount compound or composition as described herein, thereby reducing or preventing metabolic disease.

Further provided is a method for reducing or preventing diabetes comprising administering to a human a therapeutically effective amount compound or composition as described herein, thereby reducing or preventing diabetes.

Further provided is a method for ameliorating a symptom of metabolic disease, comprising administering to a human in need thereof a compound comprising a modified oligonucleotide consisting of 20 to 35 linked nucleosides, wherein said modified oligonucleotide specifically hybridizes to SEQ ID NO: 1, 2, or 3, thereby ameliorating a symptom of metabolic disease in the human.

Further provided is a method for ameliorating a symptom of diabetes, comprising administering to a human in need thereof a compound comprising a modified oligonucleotide consisting of 10 to 30 linked nucleosides, wherein said modified oligonucleotide specifically hybridizes to SEQ ID NO: 1, 2, or 3, thereby ameliorating a symptom of diabetes in the human.

Further provided is a method for ameliorating a symptom of diabetes, comprising administering to a human in need thereof a compound comprising a modified oligonucleotide consisting of 20 linked nucleosides, wherein said modified oligonucleotide specifically hybridizes to SEQ ID NO: 1, 2, or 3, thereby ameliorating a symptom of diabetes in the human.

Further provided is a method for reducing the rate of progression of a symptom associated with metabolic disease, comprising administering to a human in need thereof a compound comprising a modified oligonucleotide consisting of 10 to 30 linked nucleosides, wherein said modified oligonucleotide specifically hybridizes to SEQ ID NO: 1, 2, or 3, thereby reducing the rate of progression a symptom of metabolic disease in the human.

Further provided is a method for reducing the rate of progression of a symptom associated with diabetes, comprising administering to a human in need thereof a compound comprising a modified oligonucleotide consisting of 20 to 35 linked nucleosides, wherein said modified oligonucleotide specifically hybridizes to SEQ ID NO: 1, 2, or 3, thereby reducing the rate of progression a symptom of diabetes in the human.

Further provided is a method for reducing the rate of progression of a symptom associated with diabetes, comprising administering to a human in need thereof a compound comprising a modified oligonucleotide consisting of 20 linked nucleosides, wherein said modified oligonucleotide specifically hybridizes to SEQ ID NO: 1, 2, or 3, thereby reducing the rate of progression a symptom of diabetes in the human.

Also provided are methods and compounds for the preparation of a medicament for the treatment, prevention, or amelioration of metabolic disease.

Also provided are methods and compounds for the preparation of a medicament for the treatment, prevention, or amelioration of diabetes.

Certain embodiments provide the use of a compound as described herein in the manufacture of a medicament for treating, ameliorating, or preventing metabolic disease.

Certain embodiments provide the use of a compound as described herein in the manufacture of a medicament for treating, ameliorating, or preventing diabetes.

Certain embodiments provide a compound as described herein for use in treating, preventing, or ameliorating metabolic disease as described herein by combination therapy with an additional agent or therapy as described herein. Agents or therapies can be co-administered or administered concomitantly.

Certain embodiments provide a compound as described herein for use in treating, preventing, or ameliorating diabetes as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating metabolic disease as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating diabetes as described herein by combination therapy with an additional agent or therapy as described herein. Agents or therapies can be co-administered or administered concomitantly.

Certain embodiments provide the use of a compound as described herein in the manufacture of a medicament for treating, preventing, or ameliorating metabolic disease as described herein in a patient who is subsequently administered an additional agent or therapy as described herein.

Certain embodiments provide the use of a compound as described herein in the manufacture of a medicament for treating, preventing, or ameliorating diabetes as described herein in a patient who is subsequently administered an additional agent or therapy as described herein.

Certain embodiments provide a kit for treating, preventing, or ameliorating metabolic disease as described herein wherein the kit comprises:

(i) a compound as described herein; and alternatively (ii) an additional agent or therapy as described herein.

Certain embodiments provide a kit for treating, preventing, or ameliorating diabetes as described herein wherein the kit comprises:

(i) a compound as described herein; and alternatively (ii) an additional agent or therapy as described herein.

A kit as described herein may further include instructions for using the kit to treat, prevent, or ameliorate metabolic disease as described herein by combination therapy as described herein. In certain embodiments, the metabolic disease is diabetes.

Antisense Compounds

Oligomeric compounds include, but are not limited to, oligonucleotides, oligonucleosides, oligonucleotide analogs, oligonucleotide mimetics, antisense compounds, antisense oligonucleotides, and siRNAs. An oligomeric compound may be "antisense" to a target nucleic acid, meaning that is capable of undergoing hybridization to a target nucleic acid through hydrogen bonding.

In certain embodiments, an antisense compound has a nucleobase sequence that, when written in the 5' to 3' direction, comprises the reverse complement of the target segment of a target nucleic acid to which it is targeted. In certain such embodiments, an antisense oligonucleotide has a nucleobase sequence that, when written in the 5' to 3' direction, comprises the reverse complement of the target segment of a target nucleic acid to which it is targeted.

In certain embodiments, an antisense compound targeted to a PTP1B nucleic acid is 10 to 30 nucleotides in length. In other words, antisense compounds are from 10 to 30 linked nucleobases. In other embodiments, the antisense compound comprises a modified oligonucleotide consisting of 8 to 80, 10 to 50, 15 to 30, 18 to 21, 20 to 80, 20 to 35, 20 to 30, 20 to 29, 20 to 28, 20 to 27, 20 to 26, 20 to 25, 20 to 24, 20 to 23, 20 to 22, 20 to 21 or 20 linked nucleobases. In certain such embodiments, the antisense compound comprises a modified oligonucleotide consisting of 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50, 51, 52, 53, 54, 55, 56, 57, 58, 59, 60, 61, 62, 63, 64, 65, 66, 67, 68, 69, 70, 71, 72, 73, 74, 75, 76, 77, 78, 79, or 80 linked nucleobases in length, or a range defined by any two of the above values.

In certain embodiments, the antisense compound comprises a shortened or truncated modified oligonucleotide. The shortened or truncated modified oligonucleotide can have a single nucleoside deleted from the 5' end (5' truncation), or alternatively from the 3' end (3' truncation). A shortened or truncated oligonucleotide may have two nucleosides deleted from the 5' end, or alternatively may have two subunits deleted from the 3' end. Alternatively, the deleted nucleosides may be dispersed throughout the modified oligonucleotide, for example, in an antisense compound having one nucleoside deleted from the 5' end and one nucleoside deleted from the 3' end.

When a single additional nucleoside is present in a lengthened oligonucleotide, the additional nucleoside may be located at the 5' or 3' end of the oligonucleotide. When two or more additional nucleosides are present, the added nucleosides may be adjacent to each other, for example, in an oligonucleotide having two nucleosides added to the 5' end (5' addition), or alternatively to the 3' end (3' addition), of the oligonucleotide. Alternatively, the added nucleoside may be dispersed throughout the antisense compound, for example, in an oligonucleotide having one nucleoside added to the 5' end and one subunit added to the 3' end.

It is possible to increase or decrease the length of an antisense compound, such as an antisense oligonucleotide, and/or introduce mismatch bases without eliminating activity. For example, in Woolf et al. (Proc. Natl. Acad. Sci. USA 89:7305-7309, 1992), a series of antisense oligonucleotides 13-25 nucleobases in length were tested for their ability to induce cleavage of a target RNA in an oocyte injection model. Antisense oligonucleotides 25 nucleobases in length with 8 or 11 mismatch bases near the ends of the antisense oligonucleotides were able to direct specific cleavage of the target mRNA, albeit to a lesser extent than the antisense oligonucleotides that contained no mismatches. Similarly, target specific cleavage was achieved using 13 nucleobase antisense oligonucleotides, including those with 1 or 3 mismatches.

Gautschi et al (J. Natl. Cancer Inst. 93:463-471, March 2001) demonstrated the ability of an oligonucleotide having 100% complementarity to the bcl-2 mRNA and having 3 mismatches to the bcl-xL mRNA to reduce the expression of both bcl-2 and bcl-xL in vitro and in vivo. Furthermore, this oligonucleotide demonstrated potent anti-tumor activity in vivo.

Maher and Dolnick (Nuc. Acid. Res. 16:3341-3358, 1988) tested a series of tandem 14 nucleobase antisense oligonucleotides, and a 28 and 42 nucleobase antisense oligonucleotides comprised of the sequence of two or three of the tandem antisense oligonucleotides, respectively, for their ability to arrest translation of human DHFR in a rabbit reticulocyte assay. Each of the three 14 nucleobase antisense oligonucleotides alone was able to inhibit translation, albeit at a more modest level than the 28 or 42 nucleobase antisense oligonucleotides.

Antisense Compound Motifs

In certain embodiments, antisense compounds targeted to a PTP1B nucleic acid have chemically modified subunits arranged in patterns, or motifs, to confer to the antisense compounds properties such as enhanced inhibitory activity, increased binding affinity for a target nucleic acid, or resistance to degradation by in vivo nucleases.

Chimeric antisense compounds typically contain at least one region modified so as to confer increased resistance to nuclease degradation, increased cellular uptake, increased binding affinity for the target nucleic acid, and/or increased inhibitory activity. A second region of a chimeric antisense compound may optionally serve as a substrate for the cellular endonuclease RNase H, which cleaves the RNA strand of an RNA:DNA duplex.

Antisense compounds having a gapmer motif are considered chimeric antisense compounds. In a gapmer an internal region having a plurality of nucleotides that supports RNaseH cleavage is positioned between external regions having a plurality of nucleotides that are chemically distinct from the nucleosides of the internal region. In the case of an antisense oligonucleotide having a gapmer motif, the gap segment generally serves as the substrate for endonuclease cleavage, while the wing segments comprise modified nucleosides. In certain embodiments, the regions of a gapmer are differentiated by the types of sugar moieties comprising each distinct region. The types of sugar moieties that are used to differentiate the regions of a gapmer may in some embodiments include β-D-ribonucleosides, β-D-deoxyribonucleosides, 2'-modified nucleosides (such 2'-modified nucleosides may include 2'-MOE and 2'-O—$CH_3$, among others), and bicyclic sugar modified nucleosides (such bicyclic sugar modified nucleosides may include those having a constrained ethyl). In certain embodiments, wings may include several modified sugar moieties, including, for example 2'-MOE and constrained ethyl. In certain embodiments, wings may include several modified and unmodified sugar moieties. In certain embodiments, wings may include various combinations of 2'-MOE nucleosides, constrained ethyl nucleosides, and 2'-deoxynucleosides.

Each distinct region may comprise uniform sugar moieties, variant, or alternating sugar moieties. The wing-gap-wing motif is frequently described as "X-Y-Z", where "X" represents the length of the 5'-wing, "Y" represents the length of the gap, and "Z" represents the length of the 3'-wing. "X" and "Z" may comprise uniform, variant, or alternating sugar moieties. In certain embodiments, "X" and "Y" may include one or more 2'-deoxynucleosides. "Y" may comprise 2'-deoxynucleosides. As used herein, a gapmer described as "X-Y-Z" has a configuration such that the gap is positioned immediately adjacent to each of the 5'-wing and the 3' wing. Thus, no intervening nucleotides exist between the 5'-wing and gap, or the gap and the 3'-wing. Any of the antisense compounds described herein can have a gapmer motif. In certain embodiments, "X" and "Z" are the same, in other embodiments they are different. In certain embodiments, "Y" is between 8 and 15 nucleosides. X, Y, or Z can be any of 1, 2, 3, 4, 5, 6, 7, 8, 9, 10, 11, 12, 13, 14, 15, 16, 17, 18, 19, 20, 25, 30 or more nucleosides.

In certain embodiments, antisense compounds targeted to a PTP1B nucleic acid possess a 5-10-5 gapmer motif.

In certain embodiments, antisense compounds targeted to a PTP1B nucleic acid possess a 6-8-6 gapmer motif.

In certain embodiments, antisense compounds targeted to a PTP1B nucleic acid possess a 5-8-5 gapmer motif.

In certain embodiments, an antisense compound targeted to a PTP1B nucleic acid has a gap-widened motif.

In certain embodiments, antisense compounds targeted to a PTP1B nucleic acid possess a 2-13-5 gap-widened motif Target Nucleic Acids, Target Regions and Nucleotide Sequences In certain embodiments, the PTP1B nucleic acid is any of the sequences set forth in GENBANK Accession No. NM_002827.2 (incorporated herein as SEQ ID NO: 1), GENBANK Accession No. NT_011362.9 truncated from nucleotides 14178000 to 14256000 (incorporated herein as SEQ ID NO: 2); and a concatenation of sequences from exons 1-9, intron 9 and exon 10 of the rhesus monkey PTP1B scaffold (incorporated herein as SEQ ID NO: 3).

It is understood that the sequence set forth in each SEQ ID NO in the Examples contained herein is independent of any modification to a sugar moiety, an internucleoside linkage, or a nucleobase. As such, antisense compounds defined by a SEQ ID NO may comprise, independently, one or more modifications to a sugar moiety, an internucleoside linkage, or a nucleobase. Antisense compounds described by Isis Number (Isis No) indicate a combination of nucleobase sequence and motif.

In certain embodiments, a target region is a structurally defined region of the target nucleic acid. For example, a target region may encompass a 3' UTR, a 5' UTR, an exon, an intron, an exon/intron junction, a coding region, a translation initiation region, translation termination region, or other defined nucleic acid region. The structurally defined regions for PTP1B can be obtained by accession number from sequence databases such as NCBI and such information is incorporated herein by reference. In certain embodiments, a target region may encompass the sequence from a 5' target site of one target segment within the target region to a 3' target site of another target segment within the same target region.

Targeting includes determination of at least one target segment to which an antisense compound hybridizes, such that a desired effect occurs. In certain embodiments, the desired effect is a reduction in mRNA target nucleic acid levels. In certain embodiments, the desired effect is reduction of levels of protein encoded by the target nucleic acid or a phenotypic change associated with the target nucleic acid.

A target region may contain one or more target segments. Multiple target segments within a target region may be overlapping. Alternatively, they may be non-overlapping. In certain embodiments, target segments within a target region are separated by no more than about 300 nucleotides. In certain emodiments, target segments within a target region are separated by a number of nucleotides that is, is about, is no more than, is no more than about, 250, 200, 150, 100, 90, 80, 70, 60, 50, 40, 30, 20, or 10 nucleotides on the target nucleic acid, or is a range defined by any two of the preceeding values. In certain embodiments, target segments within a target region are separated by no more than, or no more than about, 5 nucleotides on the target nucleic acid. In certain embodiments, target segments are contiguous. Contemplated are target regions defined by a range having a starting nucleic acid that is any of the 5' target sites or 3' target sites listed herein.

Suitable target segments may be found within a 5' UTR, a coding region, a 3' UTR, an intron, an exon, or an exon/intron junction. Target segments containing a start codon or a stop codon are also suitable target segments. A suitable target segment may specifcally exclude a certain structurally defined region such as the start codon or stop codon.

The determination of suitable target segments may include a comparison of the sequence of a target nucleic acid to other sequences throughout the genome. For example, the BLAST algorithm may be used to identify regions of similarity amongst different nucleic acids. This comparison can prevent the selection of antisense compound sequences that may hybridize in a non-specific manner to sequences other than a selected target nucleic acid (i.e., non-target or off-target sequences).

There may be variation in activity (e.g., as defined by percent reduction of target nucleic acid levels) of the antisense compounds within an active target region. In certain embodiments, reductions in PTP1B mRNA levels are indicative of inhibition of PTP1B expression. Reductions in levels of a PTP1B protein are also indicative of inhibition of target mRNA expression. Further, phenotypic changes are indicative of inhibition of PTP1B expression. In certain embodiments, reduced glucose levels, reduced lipid levels, and reduced body weight can be indicative of inhibition of PTP1B expression. In certain embodiments, amelioration of symptoms associated with metabolic disease can be indicative of inhibition of PTP1B expression. In certain embodiments, amelioration of symptoms associated with diabetes can be indicative of inhibition of PTP1B expression. In certain embodiments, reduction of insulin resistance is indicative of inhibition of PTP1B expression. In certain embodiments, reduction of diabetes biomarkers can be indicative of inhibition of PTP1B expression.

Hybridization

In some embodiments, hybridization occurs between an antisense compound disclosed herein and a PTP1B nucleic acid. The most common mechanism of hybridization involves hydrogen bonding (e.g., Watson-Crick, Hoogsteen or reversed Hoogsteen hydrogen bonding) between complementary nucleobases of the nucleic acid molecules.

Hybridization can occur under varying conditions. Stringent conditions are sequence-dependent and are determined by the nature and composition of the nucleic acid molecules to be hybridized.

Methods of determining whether a sequence is specifically hybridizable to a target nucleic acid are well known in the art. In certain embodiments, the antisense compounds provided herein are specifically hybridizable with a PTP1B nucleic acid.

Complementarity

An antisense compound and a target nucleic acid are complementary to each other when a sufficient number of nucleobases of the antisense compound can hydrogen bond with the corresponding nucleobases of the target nucleic acid, such that a desired effect will occur (e.g., antisense inhibition of a target nucleic acid, such as a PTP1B nucleic acid).

An antisense compound may hybridize over one or more segments of a PTP1B nucleic acid such that intervening or adjacent segments are not involved in the hybridization event (e.g., a loop structure, mismatch or hairpin structure).

In certain embodiments, the antisense compounds provided herein, or a specified portion thereof, are, or are at least, 70%, 80%, 85%, 86%, 87%, 88%, 89%, 90%, 91%, 92%, 93%, 94%, 95%, 96%, 97%, 98%, 99%, or 100% complementary to a PTP1B nucleic acid, a target region, target segment, or specified portion thereof. Percent complementarity of an antisense compound with a target nucleic acid can be determined using routine methods.

For example, an antisense compound in which 18 of 20 nucleobases of the antisense compound are complementary to a target region, and would therefore specifically hybridize, would represent 90 percent complementarity. In this example, the remaining noncomplementary nucleobases may be clustered or interspersed with complementary nucleobases and need not be contiguous to each other or to complementary nucleobases. As such, an antisense compound which is 18 nucleobases in length having 4 (four) noncomplementary nucleobases which are flanked by two regions of complete complementarity with the target nucleic acid would have 77.8% overall complementarity with the target nucleic acid and would thus fall within the scope of the present invention. Percent complementarity of an antisense compound with a region of a target nucleic acid can be determined routinely using BLAST programs (basic local alignment search tools) and PowerBLAST programs known in the art (Altschul et al., J. Mol. Biol., 1990, 215, 403 410; Zhang and Madden, Genome Res., 1997, 7, 649 656). Percent homology, sequence identity or complementarity, can be determined by, for example, the Gap program (Wisconsin Sequence Analysis Package, Version 8 for Unix, Genetics Computer Group, University Research Park, Madison Wis.), using default settings, which uses the algorithm of Smith and Waterman (Adv. Appl. Math., 1981, 2, 482 489).

In certain embodiments, the antisense compounds provided herein, or specified portions thereof, are fully complementary (i.e. 100% complementary) to a target nucleic acid, or specified portion thereof. For example, antisense compound may be fully complementary to a PTP1B nucleic acid, or a target region, or a target segment or target sequence thereof. As used herein, "fully complementary" means each nucleobase of an antisense compound is capable of precise base pairing with the corresponding nucleobases of a target nucleic acid. For example, a 20 nucleobase antisense compound is fully complementary to a target sequence that is 400 nucleobases long, so long as there is a corresponding 20 nucleobase portion of the target nucleic acid that is fully complementary to the antisense compound. Fully complementary can also be used in reference to a specified portion of the first and/or the second nucleic acid. For example, a 20 nucleobase portion of a 30 nucleobase antisense compound can be "fully complementary" to a target sequence that is 400 nucleobases long. The 20 nucleobase portion of the 30 nucleobase oligonucleotide is fully complementary to the target sequence if the target sequence has a corresponding 20 nucleobase portion wherein each nucleobase is complementary to the 20 nucleobase portion of the antisense compound. At the same time, the entire 30 nucleobase antisense compound may or may not be fully complementary to the target sequence, depending on whether the remaining 10 nucleobases of the antisense compound are also complementary to the target sequence.

The location of a non-complementary nucleobase may be at the 5' end or 3' end of the antisense compound. Alternatively, the non-complementary nucleobase or nucleobases may be at an internal position of the antisense compound. When two or more non-complementary nucleobases are present, they may be contiguous (i.e. linked) or non-contiguous. In one embodiment, a non-complementary nucleobase is located in the wing segment of a gapmer antisense oligonucleotide.

In certain embodiments, antisense compounds that are, or are up to 12, 13, 14, 15, 16, 17, 18, 19, or nucleobases in length comprise no more than 4, no more than 3, no more than 2, or no more than 1 non-complementary nucleobase(s) relative to a target nucleic acid, such as a PTP1B nucleic acid, or specified portion thereof.

In certain embodiments, antisense compounds that are, or are up to 12, 13, 14, 15, 16, 17, 18, 19, 20, 21, 22, 23, 24, 25, 26, 27, 28, 29, or 30 nucleobases in length comprise no more than 6, no more than 5, no more than 4, no more than 3, no more than 2, or no more than 1 non-complementary nucleobase(s) relative to a target nucleic acid, such as a PTP1B nucleic acid, or specified portion thereof.

The antisense compounds provided herein also include those which are complementary to a portion of a target nucleic acid. As used herein, "portion" refers to a defined number of contiguous (i.e. linked) nucleobases within a region or segment of a target nucleic acid. A "portion" can also refer to a defined number of contiguous nucleobases of an antisense compound. In certain embodiments, the antisense compounds, are complementary to at least an 8 nucleobase portion of a target segment. In certain embodiments, the antisense compounds are complementary to at least a 12 nucleobase portion of a target segment. In certain embodiments, the antisense compounds are complementary to at least a 13 nucleobase portion of a target segment. In certain embodiments, the antisense compounds are complementary to at least a 14 nucleobase portion of a target segment. In certain embodiments, the antisense compounds are complementary to at least a 15 nucleobase portion of a target segment. In certain embodiments, the antisense compounds are complementary to at least a 16 nucleobase portion of a target segment. In certain embodiments, the antisense compounds are complementary to at least a 17 nucleobase portion of a target segment. In certain embodiments, the antisense compounds are complementary to at least a 18 nucleobase portion of a target segment. In certain embodiments, the antisense compounds are complementary to at least a 19 nucleobase portion of a target segment. In certain embodiments, the antisense compounds are complementary to at least a 20 nucleobase portion of a target segment. Also contemplated are antisense compounds that are complementary to at least a 9, 10, 11, 12, 13, 14, 15, 16, 17, 18, 19, 20, or more nucleobase portion of a target segment, or a range defined by any two of these values.

Identity

The antisense compounds provided herein may also have a defined percent identity to a particular nucleotide sequence, SEQ ID NO, or compound represented by a specific Isis number, or portion thereof. As used herein, an antisense compound is identical to the sequence disclosed herein if it has the same nucleobase pairing ability. For example, a RNA which contains uracil in place of thymidine in a disclosed DNA sequence would be considered identical to the DNA sequence since both uracil and thymidine pair with adenine. Shortened and lengthened versions of the antisense compounds described herein as well as compounds having non-identical bases relative to the antisense compounds provided herein also are contemplated. The non-identical bases may be adjacent to each other or dispersed throughout the antisense compound. Percent identity of an antisense compound is calculated according to the number of bases that have identical base pairing relative to the sequence to which it is being compared.

In certain embodiments, the antisense compounds, or portions thereof, are at least 70%, 75%, 80%, 85%, 90%, 91%, 92%, 93%, 94%, 95%, 96%, 97%, 98%, 99% or 100% identical to one or more of the antisense compounds or SEQ ID NOs, or a portion thereof, disclosed herein.

Modifications

A nucleoside is a base-sugar combination. The nucleobase (also known as base) portion of the nucleoside is normally a heterocyclic base moiety. Nucleotides are nucleosides that further include a phosphate group covalently linked to the sugar portion of the nucleoside. For those nucleosides that include a pentofuranosyl sugar, the phosphate group can be linked to the 2', 3' or 5' hydroxyl moiety of the sugar. Oligonucleotides are formed through the covalent linkage of adjacent nucleosides to one another, to form a linear polymeric oligonucleotide. Within the oligonucleotide structure, the phosphate groups are commonly referred to as forming the internucleoside linkages of the oligonucleotide.

Modifications to antisense compounds encompass substitutions or changes to internucleoside linkages, sugar moieties, or nucleobases. Modified antisense compounds are often preferred over native forms because of desirable properties such as, for example, enhanced cellular uptake, enhanced affinity for nucleic acid target, increased stability in the presence of nucleases, or increased inhibitory activity.

Chemically modified nucleosides may also be employed to increase the binding affinity of a shortened or truncated antisense oligonucleotide for its target nucleic acid. Consequently, comparable results can often be obtained with shorter antisense compounds that have such chemically modified nucleosides.

Modified Internucleoside Linkages

The naturally occurring internucleoside linkage of RNA and DNA is a 3' to 5' phosphodiester linkage. Antisense compounds having one or more modified, i.e. non-naturally occurring, internucleoside linkages are often selected over antisense compounds having naturally occurring internucleoside linkages because of desirable properties such as, for example, enhanced cellular uptake, enhanced affinity for target nucleic acids, and increased stability in the presence of nucleases.

Oligonucleotides having modified internucleoside linkages include internucleoside linkages that retain a phosphorus atom as well as internucleoside linkages that do not have a phosphorus atom. Representative phosphorus containing internucleoside linkages include, but are not limited to, phosphodiesters, phosphotriesters, methylphosphonates, phosphoramidate, and phosphorothioates. Methods of preparation of phosphorous-containing and non-phosphorous-containing linkages are well known.

In certain embodiments, antisense compounds targeted to a PTP1B nucleic acid comprise one or more modified internucleoside linkages. In certain embodiments, the modified internucleoside linkages are phosphorothioate linkages. In certain embodiments, each internucleoside linkage of an antisense compound is a phosphorothioate internucleoside linkage.

Modified Sugar Moieties

Antisense compounds provided herein can optionally contain one or more nucleosides wherein the sugar group has been modified. Such sugar modified nucleosides may impart enhanced nuclease stability, increased binding affinity, or some other beneficial biological property to the antisense compounds. In certain embodiments, nucleosides comprise a chemically modified ribofuranose ring moiety. Examples of chemically modified ribofuranose rings include, without limitation, addition of substitutent groups (including 5' and 2' substituent groups); bridging of non-geminal ring atoms to form bicyclic nucleic acids (BNA); replacement of the ribosyl ring oxygen atom with S, N(R), or C(R1)(R)2 (R═H, $C_1$-$C_{12}$ alkyl or a protecting group); and combinations thereof. Examples of chemically modified sugars include, 2'-F-5'-methyl substituted nucleoside (see, PCT International Application WO 2008/101157, published on Aug. 21, 2008 for other disclosed 5',2'-bis substituted nucleosides), replacement of the ribosyl ring oxygen atom with S with further substitution at the 2'-position (see, published U.S. Patent Application US2005/0130923, published on Jun. 16, 2005), or, alternatively, 5'-substitution of a BNA (see, PCT International Application WO 2007/134181, published on Nov. 22, 2007, wherein LNA is substituted with, for example, a 5'-methyl or a 5'-vinyl group).

Examples of nucleosides having modified sugar moieties include, without limitation, nucleosides comprising 5'-vinyl, 5'-methyl (R or S), 4'-S, 2'-F, 2'-$OCH_3$, and 2'—$O(CH_2)2OCH_3$ substituent groups. The substituent at the 2' position can also be selected from allyl, amino, azido, thio, O-allyl, O—$C_1$-$C_{10}$ alkyl, $OCF_3$, $O(CH_2)2SCH_3$, $O(CH_2)2$—O—N(Rm)(Rn) and O—$CH_2$—C(═O)—N(Rm)(Rn), where each Rm and Rn is, independently, H or substituted or unsubstituted $C_1$-$C_{10}$ alkyl.

As used herein, "bicyclic nucleosides" refer to modified nucleosides comprising a bicyclic sugar moiety. Examples of bicyclic nucleosides include, without limitation, nucleosides comprising a bridge between the 4' and the 2' ribosyl ring atoms. In certain embodiments, antisense compounds provided herein include one or more bicyclic nucleosides wherein the bridge comprises a 4' to 2' bicyclic nucleoside. Examples of such 4' to 2' bicyclic nucleosides, include, but are not limited to, one of the formulae: 4'-$(CH_2)$—O-2' (LNA); 4'-$(CH_2)$—S-2; 4'-$(CH_2)_2$—O-2' (ENA); 4'-CH$(CH_3)$—O-2' and 4'-CH$(CH_2OCH_3)$—O-2', and analogs thereof (see, U.S. Pat. No. 7,399,845, issued on Jul. 15, 2008); 4'-C$(CH_3)(CH_3)$—O-2', and analogs thereof (see, published PCT International Application WO2009/006478, published Jan. 8, 2009); 4'-$CH_2$—N$(OCH_3)$-2', and analogs thereof (see, published PCT International Application WO2008/150729, published Dec. 11, 2008); 4'-$CH_2$—O—N$(CH_3)$-2' (see, published U.S. Patent Application US2004/0171570, published Sep. 2, 2004); 4'-$CH_2$—N(R)—O-2', wherein R is H, $C_1$-$C_{12}$ alkyl, or a protecting group (see, U.S. Pat. No. 7,427,672, issued on Sep. 23, 2008); 4'-$CH_2$—C(H)$(CH_3)$-2' (see, Chattopadhyaya, et al., J. Org. Chem., 2009, 74, 118-134); and 4'-$CH_2$—C(═$CH_2$)-2', and analogs thereof (see, published PCT International Application WO 2008/154401, published on Dec. 8, 2008). Also see, for example: Singh et al., Chem. Commun., 1998, 4, 455-456; Koshkin et al., Tetrahedron, 1998, 54, 3607-3630; Wahlestedt et al., Proc. Natl. Acad. Sci. U.S. A., 2000, 97, 5633-5638; Kumar et al., Bioorg. Med. Chem. Lett., 1998, 8, 2219-2222; Singh et al., J. Org. Chem., 1998, 63, 10035-10039; Srivastava et al., J. Am. Chem. Soc., 129(26) 8362-8379 (Jul. 4, 2007); Elayadi et al., Curr. Opinion Invens. Drugs, 2001, 2, 558-561; Braasch et al., Chem. Biol., 2001, 8, 1-7; Orum et al., Curr. Opinion Mol. Ther., 2001, 3, 239-243; U.S. Pat. Nos. 6,670,461, 7,053,207, 6,268,490, 6,770,748, 6,794,499, 7,034,133, 6,525,191, 7,399,845; published PCT International applications WO 2004/106356, WO 94/14226, WO 2005/021570, and WO 2007/134181; U.S. Patent Publication Nos. US2004/0171570, US2007/0287831, and US2008/0039618; and U.S. patent Ser. Nos. 12/129,154, 60/989,574, 61/026,995, 61/026,998, 61/056,564, 61/086,231, 61/097,787, and 61/099,844; and PCT International Application Nos. PCT/US2008/064591, PCT/US2008/066154, and PCT/US2008/068922. Each of the foregoing bicyclic nucleosides can be prepared having one or more stereochemical sugar configurations including for example α-L-ribofuranose and β-D-ribofuranose (see PCT international application PCT/DK98/00393, published on Mar. 25, 1999 as WO 99/14226).

In certain embodiments, bicyclic sugar moieties of BNA nucleosides include, but are not limited to, compounds having at least one bridge between the 4' and the 2' position of the pentofuranosyl sugar moiety wherein such bridges independently comprises 1 or from 2 to 4 linked groups independently selected from —$[C(R_a)(R_b)]_n$—, —$C(R_a)$═$C(R_b)$—, —$C(R_a)$═N—, —C(═$NR_a$)—, —C(═O)—, —C(═S)—, —O—, —$Si(R_a)_2$—, —$S(═O)_x$—, and —$N(R_a)$—;

wherein:

x is 0, 1, or 2;

n is 1, 2, 3, or 4;

each $R_a$ and $R_b$ is, independently, H, a protecting group, hydroxyl, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, heterocycle radical, substituted heterocycle radical, heteroaryl, substituted heteroaryl, $C_5$-$C_7$ alicyclic radical, substituted $C_5$-$C_7$ alicyclic radical, halogen, $OJ_1$, $NJ_1J_2$, $SJ_1$, $N_3$, $COOJ_1$, acyl (C(═O)—H), substituted acyl, CN, sulfonyl $(S(═O)_2—J_1)$, or sulfoxyl (S(═O)—$J_1$); and each $J_1$ and $J_2$ is, independently, H, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_5$-$C_{20}$ aryl, substituted $C_5$-$C_{20}$ aryl, acyl (C(═O)—H), substituted acyl, a heterocycle radical, a substituted heterocycle radical, $C_1$-$C_{12}$ aminoalkyl, substituted $C_1$-$C_{12}$ aminoalkyl, or a protecting group.

In certain embodiments, the bridge of a bicyclic sugar moiety is, —$[C(R_a)(R_b)]_n$—, —$[C(R_a)(R_b)]_n$—O—, —$C(R_aR_b)$—N(R)—O— or, —$C(R_aR_b)$—O—N(R)—. In certain embodiments, the bridge is 4'-$CH_2$-2', 4'-$(CH_2)_2$-2', 4'-$(CH_2)_3$-2', 4'-$CH_2$—O-2', 4'-$(CH_2)_2$—O-2', 4'-$CH_2$—O—N(R)-2', and 4'-$CH_2$—N(R)—O-2'-, wherein each R is, independently, H, a protecting group, or $C_1$-$C_{12}$ alkyl.

In certain embodiments, bicyclic nucleosides are further defined by isomeric configuration. For example, a nucleoside comprising a 4'-2' methylene-oxy bridge, may be in the α-L configuration or in the β-D configuration. Previously, α-L-methyleneoxy (4'-$CH_2$—O-2') BNA's have been incorporated into antisense oligonucleotides that showed antisense activity (Frieden et al., Nucleic Acids Research, 2003, 21, 6365-6372).

In certain embodiments, bicyclic nucleosides include, but are not limited to, (A) α-L-Methyleneoxy (4'-$CH_2$—O-2') BNA, (B) β-D-Methyleneoxy (4'-$CH_2$—O-2') BNA, (C) Ethyleneoxy (4'-$(CH_2)_2$—O-2') BNA, (D) Aminooxy (4'-$CH_2$—O—N(R)-2') BNA, (E) Oxyamino (4'-$CH_2$—N(R)—O-2') BNA, (F) Methyl(methyleneoxy) (4'-CH($CH_3$)—O-2') BNA, (G) methylene-thio (4'-$CH_2$—S-2') BNA, (H) methylene-amino (4'-CH2—N(R)-2') BNA, (I) methyl carbocyclic (4'-$CH_2$—CH($CH_3$)-2') BNA, and (J) propylene carbocyclic (4'-$(CH_2)_3$-2') BNA as depicted below.

(A)

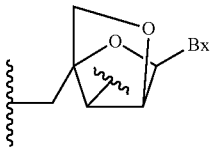

(B)

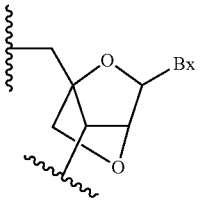

(C)

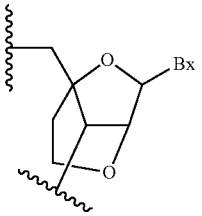

(D)

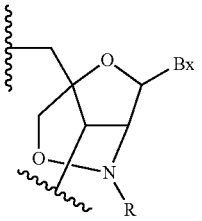

-continued (E)

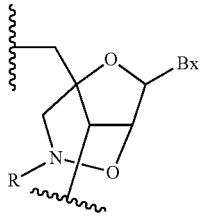

(F)

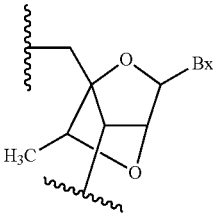

(G)

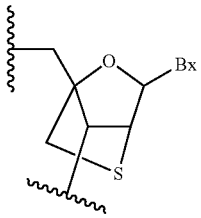

(H)

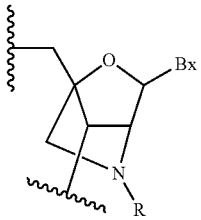

(I)

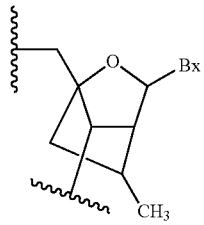

(J)

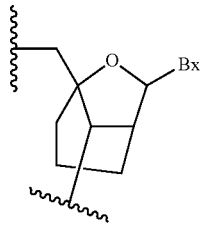

wherein Bx is the base moiety and R is, independently, H, a protecting group or $C_1$-$C_{12}$ alkyl.

In certain embodiments, bicyclic nucleoside having Formula I:

I

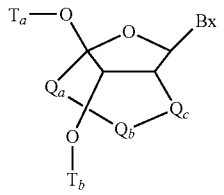

wherein:

Bx is a heterocyclic base moiety;

$-Q_a-Q_b-Q_c-$ is $—CH_2—N(R_c)—CH_2—$, $—C(=O)—N(R_c)—CH_2—$, $—CH_2—O—N(R_c)—$, $—CH_2—N(R_c)—O—$, or $—N(R_c)—O—CH_2$;

$R_c$ is $C_1$-$C_{12}$ alkyl or an amino protecting group; and $T_a$ and $T_b$ are each, independently, H, a hydroxyl protecting group, a conjugate group, a reactive phosphorus group, a phosphorus moiety, or a covalent attachment to a support medium.

In certain embodiments, bicyclic nucleoside having Formula II:

II

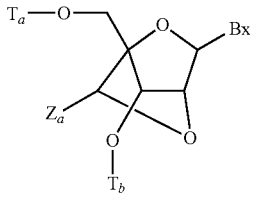

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$Z_a$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, acyl, substituted acyl, substituted amide, thiol, or substituted thio.

In one embodiment, each of the substituted groups is, independently, mono or poly substituted with substituent groups independently selected from halogen, oxo, hydroxyl, $OJ_c$, $NJ_cJ_d$, $SJ_c$, $N_3$, $OC(=X)J_c$, and $NJ_eC(=X)NJ_cJ_d$, wherein each $J_c$, $J_d$, and $J_e$ is, independently, H, $C_1$-$C_6$ alkyl, or substituted $C_1$-$C_6$ alkyl and X is O or $NJ_c$.

In certain embodiments, bicyclic nucleoside having Formula III:

III

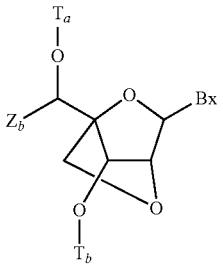

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$Z_b$ is $C_1$-$C_6$ alkyl, $C_2$-$C_6$ alkenyl, $C_2$-$C_6$ alkynyl, substituted $C_1$-$C_6$ alkyl, substituted $C_2$-$C_6$ alkenyl, substituted $C_2$-$C_6$ alkynyl, or substituted acyl (C(=O)—).

In certain embodiments, bicyclic nucleoside having Formula IV:

IV

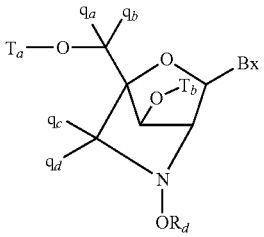

wherein:

Bx is a heterocyclic base moiety;

$T_a$ and $T_b$ are each, independently H, a hydroxyl protecting group, a conjugate group, a reactive phosphorus group, a phosphorus moiety, or a covalent attachment to a support medium;

$R_d$ is $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl;

each $q_a$, $q_b$, $q_c$ and $q_d$ is, independently, H, halogen, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl, $C_1$-$C_6$ alkoxyl, substituted $C_1$-$C_6$ alkoxyl, acyl, substituted acyl, $C_1$-$C_6$ aminoalkyl, or substituted $C_1$-$C_6$ aminoalkyl;

In certain embodiments, bicyclic nucleoside having Formula V:

V

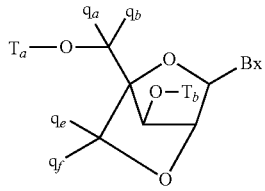

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

$q_a$, $q_b$, $q_e$ and $q_f$ are each, independently, hydrogen, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxy, substituted $C_1$-$C_{12}$ alkoxy, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O—C(=O)NJ_jJ_k$, $N(H)C(=NH)NJ_jJ_k$, $N(H)C(=O)NJ_jJ_k$ or $N(H)C(=S)NJ_jJ_k$;

or $q_e$ and $q_f$ together are $=C(q_g)(q_h)$;

$q_g$ and $q_h$ are each, independently, H, halogen, $C_1$-$C_{12}$ alkyl, or substituted $C_1$-$C_{12}$ alkyl.

The synthesis and preparation of the methyleneoxy (4'-$CH_2$—O-2') BNA monomers adenine, cytosine, guanine, 5-methyl-cytosine, thymine, and uracil, along with their oligomerization, and nucleic acid recognition properties have been described (see, e.g., Koshkin et al., Tetrahedron, 1998, 54, 3607-3630). BNAs and preparation thereof are also described in WO 98/39352 and WO 99/14226.

Analogs of methyleneoxy (4'-$CH_2$—O-2') BNA, methyleneoxy (4'-$CH_2$—O-2') BNA, and 2'-thio-BNAs, have also been prepared (see, e.g., Kumar et al., Bioorg. Med. Chem. Lett., 1998, 8, 2219-2222). Preparation of locked nucleoside analogs comprising oligodeoxyribonucleotide duplexes as substrates for nucleic acid polymerases has also been described (see, e.g., Wengel et al., WO 99/14226). Furthermore, synthesis of 2'-amino-BNA, a novel comformationally restricted high-affinity oligonucleotide analog, has been described in the art (see, e.g., Singh et al., J. Org. Chem., 1998, 63, 10035-10039). In addition, 2'-amino- and 2'-methylamino-BNA's have been prepared and the thermal stability of their duplexes with complementary RNA and DNA strands has been previously reported. In certain embodiments, bicyclic nucleoside having Formula VI:

VI

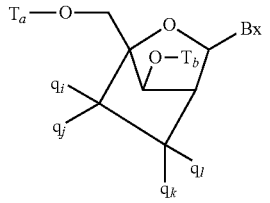

wherein:

Bx is a heterocyclic base moiety;

$T_a$ and $T_b$ are each, independently, H, a hydroxyl protecting group, a conjugate group, a reactive phosphorus group, a phosphorus moiety, or a covalent attachment to a support medium;

each $q_i$, $q_j$, $q_k$ and $q_l$ is, independently, H, halogen, $C_1$-$C_{12}$ alkyl, substituted $C_1$-$C_{12}$ alkyl, $C_2$-$C_{12}$ alkenyl, substituted $C_2$-$C_{12}$ alkenyl, $C_2$-$C_{12}$ alkynyl, substituted $C_2$-$C_{12}$ alkynyl, $C_1$-$C_{12}$ alkoxyl, substituted $C_1$-$C_{12}$ alkoxyl, $OJ_j$, $SJ_j$, $SOJ_j$, $SO_2J_j$, $NJ_jJ_k$, $N_3$, CN, $C(=O)OJ_j$, $C(=O)NJ_jJ_k$, $C(=O)J_j$, $O—C(=O)NJ_jJ_k$, $N(H)C(=NH)NJ_jJ_k$, $N(H)C(=O)NJ_jJ_k$, or $N(H)C(=S)NJ_jJ_k$; and $q_i$ and $q_j$ or $q_l$ and $q_k$ together are $=C(q_g)(q_h)$, wherein $q_g$ and $q_h$ are each, independently, H, halogen, $C_1$-$C_{12}$ alkyl, or substituted $C_1$-$C_{12}$ alkyl.

One carbocyclic bicyclic nucleoside having a 4'-$(CH_2)_3$-2' bridge and the alkenyl analog, bridge 4'-CH=CH—$CH_2$-2', have been described (see, e.g., Freier et al., Nucleic Acids Research, 1997, 25(22), 4429-4443 and Albaek et al., J. Org. Chem., 2006, 71, 7731-7740). The synthesis and preparation of carbocyclic bicyclic nucleosides along with their oligomerization and biochemical studies have also been described (see, e.g., Srivastava et al., J. Am. Chem. Soc. 2007, 129(26), 8362-8379).

As used herein, "4'-2' bicyclic nucleoside" or "4' to 2' bicyclic nucleoside" refers to a bicyclic nucleoside comprising a furanose ring comprising a bridge connecting the 2' carbon atom and the 4' carbon atom.

As used herein, "monocylic nucleosides" refer to nucleosides comprising modified sugar moieties that are not bicyclic sugar moieties. In certain embodiments, the sugar moiety, or sugar moiety analogue, of a nucleoside may be modified or substituted at any position.

As used herein, "2'-modified sugar" means a furanosyl sugar modified at the 2' position. In certain embodiments, such modifications include substituents selected from: a halide, including, but not limited to substituted and unsubstituted alkoxy, substituted and unsubstituted thioalkyl, substituted and unsubstituted amino alkyl, substituted and unsubstituted alkyl, substituted and unsubstituted allyl, and substituted and unsubstituted alkynyl. In certain embodiments, 2' modifications are selected from substituents including, but not limited to: $O[(CH_2)_nO]_mCH_3$, $O(CH_2)_nNH_2$, $O(CH_2)_nCH_3$, $O(CH_2)_nONH_2$, $OCH_2C(=O)N(H)CH_3$, and $O(CH_2)_nON[(CH_2)_nCH_3]_2$, where n and m are from 1 to about 10. Other 2'-substituent groups can also be selected from: $C_1$-$C_{12}$ alkyl; substituted alkyl; alkenyl; alkynyl; alkaryl; aralkyl; O-alkaryl or O-aralkyl; SH; $SCH_3$; OCN; Cl; Br; CN; $CF_3$; $OCF_3$; $SOCH_3$; $SO_2CH_3$; $ONO_2$; $NO_2$; $N_3$; $NH_2$; heterocycloalkyl; heterocycloalkaryl; aminoalkylamino; polyalkylamino; substituted silyl; an RNA cleaving group; a reporter group; an intercalator; a group for improving pharmacokinetic properties; and a group for improving the pharmacodynamic properties of an antisense compound, and other substituents having similar properties. In certain embodiments, modified nucleosides comprise a 2'-MOE side chain (see, e.g., Baker et al., J. Biol. Chem., 1997, 272, 11944-12000). Such 2'-MOE substitution have been described as having improved binding affinity compared to unmodified nucleosides and to other modified nucleosides, such as 2'-O-methyl, O-propyl, and O-aminopropyl. Oligonucleotides having the 2'-MOE substituent also have been shown to be antisense inhibitors of gene expression with promising features for in vivo use (see, e.g., Martin, P., Helv. Chim. Acta, 1995, 78, 486-504; Altmann et al., Chimia, 1996, 50, 168-176; Altmann et al., Biochem. Soc. Trans., 1996, 24, 630-637; and Altmann et al., Nucleosides Nucleotides, 1997, 16, 917-926).

As used herein, a "modified tetrahydropyran nucleoside" or "modified THP nucleoside" means a nucleoside having a six-membered tetrahydropyran "sugar" substituted in for the pentofuranosyl residue in normal nucleosides (a sugar surrogate). Modified THP nucleosides include, but are not limited to, what is referred to in the art as hexitol nucleic acid (HNA), anitol nucleic acid (ANA), manitol nucleic acid (MNA) (see Leumann, C J. Bioorg. & Med. Chem. (2002) 10:841-854), fluoro HNA (F—HNA), or those compounds having Formula X:

Formula X:

X

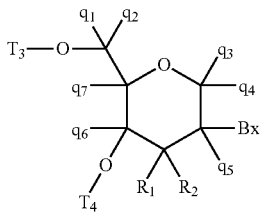

wherein independently for each of said at least one tetrahydropyran nucleoside analog of Formula X:

Bx is a heterocyclic base moiety;

$T_3$ and $T_4$ are each, independently, an internucleoside linking group linking the tetrahydropyran nucleoside analog to the antisense compound or one of $T_3$ and $T_4$ is an internucleoside linking group linking the tetrahydropyran nucleoside analog to the antisense compound and the other of $T_3$ and $T_4$ is H, a hydroxyl protecting group, a linked conjugate group, or a 5' or 3'-terminal group;

$q_1$, $q_2$, $q_3$, $q_4$, $q_5$, $q_6$ and $q_7$ are each, independently, H, $C_1$-$C_6$ alkyl, substituted $C_1$-$C_6$ alkyl, $C_2$-$C_6$ alkenyl, substituted $C_2$-$C_6$ alkenyl, $C_2$-$C_6$ alkynyl, or substituted $C_2$-$C_6$ alkynyl; and one of $R_1$ and $R_2$ is hydrogen and the other is selected from halogen, substituted or unsubstituted alkoxy, $NJ_1J_2$, $SJ_1$, $N_3$, $OC(=X)NJ_1$, $OC(=X)NJ_1J_2$, $NJ_3C(=X)NJ_1J_2$, and CN, wherein X is O, S, or $NJ_1$, and each $J_1$, $J_2$, and $J_3$ is, independently, H or $C_1$-$C_6$ alkyl.

In certain embodiments, the modified THP nucleosides of Formula X are provided wherein $q_m$, $q_n$, $q_p$, $q_r$, $q_s$, $q_t$, and $q_u$ are each H. In certain embodiments, at least one of $q_m$, $q_n$, $q_p$, $q_r$, $q_s$, $q_t$, and $q_u$ is other than H. In certain embodiments, at least one of $q_m$, $q_n$, $q_p$, $q_r$, $q_s$, $q_t$ and $q_u$ is methyl. In certain embodiments, THP nucleosides of Formula X are provided wherein one of $R_1$ and $R_2$ is F. In certain embodiments, $R_1$ is fluoro and $R_2$ is H, $R_1$ is methoxy and $R_2$ is H, and $R_1$ is methoxyethoxy and $R_2$ is H.

As used herein, "2'-modified" or "2'-substituted" refers to a nucleoside comprising a sugar comprising a substituent at the 2' position other than H or OH. 2'-modified nucleosides, include, but are not limited to, bicyclic nucleosides wherein the bridge connecting two carbon atoms of the sugar ring connects the 2' carbon and another carbon of the sugar ring and nucleosides with non-bridging 2' substituents, such as allyl, amino, azido, thio, O-allyl, O—$C_1$-$C_{10}$ alkyl, —$OCF_3$, O—$(CH_2)_2$—O—$CH_3$, 2'-O$(CH_2)_2SCH_3$, O—$(CH_2)_2$—O—$N(R_m)(R_n)$, or O—$CH_2$—C(=O)—$N(R_m)(R_n)$, where each $R_m$ and $R_n$ is, independently, H or substituted or unsubstituted $C_1$-$C_{10}$ alkyl. 2'-modified nucleosides may further comprise other modifications, for example, at other positions of the sugar and/or at the nucleobase.

As used herein, "2'-F" refers to a sugar comprising a fluoro group at the 2' position.

As used herein, "2'-OMe" or "2'-$OCH_3$" or "2'-O-methyl" each refers to a sugar comprising an —$OCH_3$ group at the 2' position of the sugar ring.

As used herein, "oligonucleotide" refers to a compound comprising a plurality of linked nucleosides. In certain embodiments, one or more of the plurality of nucleosides is modified. In certain embodiments, an oligonucleotide comprises one or more ribonucleosides (RNA) and/or deoxyribonucleosides (DNA).

Many other bicyclo and tricyclo sugar surrogate ring systems are also known in the art that can be used to modify nucleosides for incorporation into antisense compounds (see, e.g., review article: Leumann, J. C, Bioorganic & Medicinal Chemistry, 2002, 10, 841-854). Such ring systems can undergo various additional substitutions to enhance activity.

Methods for the preparations of modified sugars are well known to those skilled in the art.

In nucleotides having modified sugar moieties, the nucleobase moieties (natural, modified, or a combination thereof) are maintained for hybridization with an appropriate nucleic acid target.

In certain embodiments, antisense compounds comprise one or more nucleotides having modified sugar moieties. In certain embodiments, the modified sugar moiety is 2'-MOE. In certain embodiments, the 2'-MOE modified nucleotides are arranged in a gapmer motif. In certain embodiments, the modified sugar moiety is a cEt. In certain embodiments, the cEt modified nucleotides are arranged throughout the wings of a gapmer motif.

Modified Nucleobases

Nucleobase (or base) modifications or substitutions are structurally distinguishable from, yet functionally interchangeable with, naturally occurring or synthetic unmodified nucleobases. Both natural and modified nucleobases are capable of participating in hydrogen bonding. Such nucleobase modifications may impart nuclease stability, binding affinity or some other beneficial biological property to antisense compounds. Modified nucleobases include synthetic and natural nucleobases such as, for example, 5-methylcytosine (5-me-C). Certain nucleobase substitutions, including 5-methylcytosine substitutions, are particularly useful for increasing the binding affinity of an antisense compound for a target nucleic acid. For example, 5-methylcytosine substitutions have been shown to increase nucleic acid duplex stability by 0.6-1.2° C. (Sanghvi, Y. S., Crooke, S. T. and Lebleu, B., eds., Antisense Research and Applications, CRC Press, Boca Raton, 1993, pp. 276-278).

Additional unmodified nucleobases include 5-hydroxymethyl cytosine, xanthine, hypoxanthine, 2-aminoadenine, 6-methyl and other alkyl derivatives of adenine and guanine, 2-propyl and other alkyl derivatives of adenine and guanine, 2-thiouracil, 2-thiothymine and 2-thiocytosine, 5-halouracil and cytosine, 5-propynyl (—C≡C—$CH_3$) uracil and cytosine and other alkynyl derivatives of pyrimidine bases, 6-azo uracil, cytosine and thymine, 5-uracil (pseudouracil), 4-thiouracil, 8-halo, 8-amino, 8-thiol, 8-thioalkyl, 8-hydroxyl and other 8-substituted adenines and guanines, 5-halo particularly 5-bromo, 5-trifluoromethyl and other 5-substituted uracils and cytosines, 7-methylguanine and 7-methyladenine, 2-F-adenine, 2-amino-adenine, 8-azaguanine and 8-azaadenine, 7-deazaguanine and 7-deazaadenine and 3-deazaguanine and 3-deazaadenine.

Heterocyclic base moieties may also include those in which the purine or pyrimidine base is replaced with other heterocycles, for example 7-deaza-adenine, 7-deazaguanosine, 2-aminopyridine and 2-pyridone. Nucleobases that are particularly useful for increasing the binding affinity of antisense compounds include 5-substituted pyrimidines, 6-azapyrimidines and N2, N-6 and O-6 substituted purines, including 2 aminopropyladenine, 5-propynyluracil and 5-propynylcytosine.

In certain embodiments, antisense compounds targeted to a PTP1B nucleic acid comprise one or more modified nucleobases. In certain embodiments, gap-widened antisense oligonucleotides targeted to a PTP1B nucleic acid comprise one or more modified nucleobases. In certain embodiments, the modified nucleobase is 5-methylcytosine. In certain embodiments, each cytosine is a 5-methylcytosine.

Compositions and Methods for Formulating Pharmaceutical Compositions

Antisense oligonucleotides may be admixed with pharmaceutically acceptable active or inert substance for the preparation of pharmaceutical compositions or formulations. Compositions and methods for the formulation of pharmaceutical compositions are dependent upon a number of criteria, including, but not limited to, route of administration, extent of disease, or dose to be administered.

Antisense compound targeted to a PTP1B nucleic acid can be utilized in pharmaceutical compositions by combining the antisense compound with a suitable pharmaceutically acceptable diluent or carrier. A pharmaceutically acceptable diluent includes phosphate-buffered saline (PBS). PBS is a diluent suitable for use in compositions to be delivered parenterally. Accordingly, in one embodiment, employed in the methods described herein is a pharmaceutical composition comprising an antisense compound targeted to a PTP1B nucleic acid and a pharmaceutically acceptable diluent. In certain embodiments, the pharmaceutically acceptable diluent is PBS. In certain embodiments, the antisense compound is an antisense oligonucleotide.

Pharmaceutical compositions comprising antisense compounds encompass any pharmaceutically acceptable salts, esters, or salts of such esters, or any other oligonucleotide which, upon administration to an animal, including a human, is capable of providing (directly or indirectly) the biologically active metabolite or residue thereof. Accordingly, for example, the disclosure is also drawn to pharmaceutically acceptable salts of antisense compounds, prodrugs, pharmaceutically acceptable salts of such prodrugs, and other bioequivalents. Suitable pharmaceutically acceptable salts include, but are not limited to, sodium and potassium salts.

Pharmaceutically acceptable salts of the compounds described herein may be prepared by methods well-known in the art. For a review of pharmaceutically acceptable salts, see Stahl and Wermuth, Handbook of Pharmaceutical Salts: Properties, Selection and Use (Wiley-VCH, Weinheim, Germany, 2002). Sodium salts of antisense oligonucleotides are useful and are well accepted for therapeutic administration to humans. Accordingly, in one embodiment the compounds described herein are in the form of a sodium salt.

A prodrug can include the incorporation of additional nucleosides at one or both ends of an antisense compound which are cleaved by endogenous nucleases within the body, to form the active antisense compound.

Conjugated Antisense Compounds

Antisense compounds may be covalently linked to one or more moieties or conjugates which enhance the activity, cellular distribution or cellular uptake of the resulting antisense oligonucleotides. Typical conjugate groups include cholesterol moieties and lipid moieties. Additional conjugate groups include carbohydrates, phospholipids, biotin, phenazine, folate, phenanthridine, anthraquinone, acridine, fluoresceins, rhodamines, coumarins, and dyes.

Antisense compounds can also be modified to have one or more stabilizing groups that are generally attached to one or both termini of antisense compounds to enhance properties such as, for example, nuclease stability. Included in stabilizing groups are cap structures. These terminal modifications protect the antisense compound having terminal nucleic acid from exonuclease degradation, and can help in delivery and/or localization within a cell. The cap can be present at the 5'-terminus (5'-cap), or at the 3'-terminus (3'-cap), or can be present on both termini. Cap structures are well known in the art and include, for example, inverted deoxy abasic caps. Further 3' and 5'-stabilizing groups that can be used to cap one or both ends of an antisense compound to impart nuclease stability include those disclosed in WO 03/004602 published on Jan. 16, 2003.

Cell Culture and Antisense Compounds Treatment

The effects of antisense compounds on the level, activity or expression of PTP1B nucleic acids can be tested in vitro in a variety of cell types. Cell types used for such analyses are available from commercial vendors (e.g. American Type Culture Collection, Manassus, Va.; Zen-Bio, Inc., Research Triangle Park, N.C.; Clonetics Corporation, Walkersville, Md.) and cells are cultured according to the vendor's instructions using commercially available reagents (e.g. Invitrogen Life Technologies, Carlsbad, Calif.). Illustrative cell types include, but are not limited to, HepG2 cells, Hep3B cells, primary hepatocytes, A549 cells, GM04281 fibroblasts and LLC-MK2 cells.

In Vitro Testing of Antisense Oligonucleotides

Described herein are methods for treatment of cells with antisense oligonucleotides, which can be modified appropriately for treatment with other antisense compounds.

In general, cells are treated with antisense oligonucleotides when the cells reach approximately 60-80% confluence in culture.

One reagent commonly used to introduce antisense oligonucleotides into cultured cells includes the cationic lipid transfection reagent LIPOFECTIN® (Invitrogen, Carlsbad, Calif.). Antisense oligonucleotides are mixed with LIPOFECTIN® in OPTI-MEM® 1 (Invitrogen, Carlsbad, Calif.) to achieve the desired final concentration of antisense oligonucleotide and a LIPOFECTIN® concentration that typically ranges 2 to 12 ug/mL per 100 nM antisense oligonucleotide.

Another reagent used to introduce antisense oligonucleotides into cultured cells includes LIPOFECTAMINE 2000® (Invitrogen, Carlsbad, Calif.). Antisense oligonucleotide is mixed with LIPOFECTAMINE 2000® in OPTI-MEM® 1 reduced serum medium (Invitrogen, Carlsbad, Calif.) to achieve the desired concentration of antisense oligonucleotide and a LIPOFECTAMINE® concentration that typically ranges 2 to 12 ug/mL per 100 nM antisense oligonucleotide.

Another reagent used to introduce antisense oligonucleotides into cultured cells includes Cytofectin® (Invitrogen, Carlsbad, Calif.). Antisense oligonucleotide is mixed with Cytofectin® in OPTI-MEM® 1 reduced serum medium (Invitrogen, Carlsbad, Calif.) to achieve the desired concentration of antisense oligonucleotide and a Cytofectin® concentration that typically ranges 2 to 12 ug/mL per 100 nM antisense oligonucleotide.

Another technique used to introduce antisense oligonucleotides into cultured cells includes electroporation.

Cells are treated with antisense oligonucleotides by routine methods. Cells are typically harvested 16-24 hours after antisense oligonucleotide treatment, at which time RNA or protein levels of target nucleic acids are measured by methods known in the art and described herein. In general, when treatments are performed in multiple replicates, the data are presented as the average of the replicate treatments.

The concentration of antisense oligonucleotide used varies from cell line to cell line. Methods to determine the optimal antisense oligonucleotide concentration for a particular cell line are well known in the art. Antisense oligonucleotides are typically used at concentrations ranging from 1 nM to 300 nM when transfected with LIPOFECTAMINE2000®, Lipofectin or Cytofectin. Antisense oligonucleotides are used at higher concentrations ranging from 625 to 20,000 nM when transfected using electroporation.

RNA Isolation

RNA analysis can be performed on total cellular RNA or poly(A)+ mRNA. Methods of RNA isolation are well known in the art. RNA is prepared using methods well known in the art, for example, using the TRIZOL® Reagent (Invitrogen, Carlsbad, Calif.) according to the manufacturer's recommended protocols.

Analysis of Inhibition of Target Levels or Expression

Inhibition of levels or expression of a PTP1B nucleic acid can be assayed in a variety of ways known in the art. For example, target nucleic acid levels can be quantitated by, e.g., Northern blot analysis, competitive polymerase chain reaction (PCR), or quantitative real-time PCR. RNA analysis can be performed on total cellular RNA or poly(A)+ mRNA. Methods of RNA isolation are well known in the art. Northern blot analysis is also routine in the art. Quantitative real-time PCR can be conveniently accomplished using the commercially available ABI PRISM® 7600, 7700, or 7900 Sequence Detection System, available from PE-Applied Biosystems, Foster City, Calif. and used according to manufacturer's instructions.

Quantitative Real-Time PCR Analysis of Target RNA Levels

Quantitation of target RNA levels may be accomplished by quantitative real-time PCR using the ABI PRISM® 7600, 7700, or 7900 Sequence Detection System (PE-Applied Biosystems, Foster City, Calif.) according to manufacturer's instructions. Methods of quantitative real-time PCR are well known in the art.

Prior to real-time PCR, the isolated RNA is subjected to a reverse transcriptase (RT) reaction, which produces complementary DNA (cDNA) that is then used as the substrate for the real-time PCR amplification. The RT and real-time PCR reactions are performed sequentially in the same sample well. RT and real-time PCR reagents are obtained from Invitrogen (Carlsbad, Calif.). RT, real-time-PCR reactions are carried out by methods well known to those skilled in the art.

Gene (or RNA) target quantities obtained by real time PCR are normalized using either the expression level of a gene whose expression is constant, such as cyclophilin A, or by quantifying total RNA using RIBOGREEN® (Invitrogen, Inc. Carlsbad, Calif.). Cyclophilin A expression is quantified by real time PCR, by being run simultaneously with the target, multiplexing, or separately. Total RNA is quantified using RIBOGREEN® RNA quantification reagent (Invitrogen, Inc. Eugene, Oreg.). Methods of RNA quantification by RIBOGREEN® are taught in Jones, L. J., et al, (Analytical Biochemistry, 1998, 265, 368-374). A CYTOFLUOR® 4000 instrument (PE Applied Biosystems) is used to measure RIBOGREEN® fluorescence.

Probes and primers are designed to hybridize to a PTP1B nucleic acid. Methods for designing real-time PCR probes and primers are well known in the art, and may include the use of software such as PRIMER EXPRESS® Software (Applied Biosystems, Foster City, Calif.).

Analysis of Protein Levels

Antisense inhibition of PTP1B nucleic acids can be assessed by measuring PTP1B protein levels. Protein levels of PTP1B can be evaluated or quantitated in a variety of ways well known in the art, such as immunoprecipitation, Western blot analysis (immunoblotting), enzyme-linked immunosorbent assay (ELISA), quantitative protein assays, protein activity assays (for example, caspase activity assays), immunohistochemistry, immunocytochemistry or fluorescence-activated cell sorting (FACS). Antibodies directed to a target can be identified and obtained from a variety of sources, such as the MSRS catalog of antibodies (Aerie Corporation, Birmingham, Mich.), or can be prepared via conventional monoclonal or polyclonal antibody generation methods well known in the art. Antibodies useful for the detection of human and rat PTP1B are commercially available.

In Vivo Testing of Antisense Compounds

Antisense compounds, for example, antisense oligonucleotides, are tested in animals to assess their ability to inhibit expression of PTP1B and produce phenotypic changes. Testing may be performed in normal animals, or in experimental disease models. For administration to animals, antisense oligonucleotides are formulated in a pharmaceutically acceptable diluent, such as phosphate-buffered saline. Administration includes parenteral routes of administration. Following a period of treatment with antisense oligonucleotides, RNA is isolated from tissue and changes in PTP1B nucleic acid expression are measured. Changes in PTP1B protein levels are also measured.

Certain Indications

In certain embodiments, provided herein are methods of treating an individual comprising administering one or more pharmaceutical compositions as described herein. In certain embodiments, the individual has metabolic related disease.

As shown in the examples below, compounds targeted to PTP1B, as described herein, have been shown to reduce the severity of physiological symptoms of metabolic related diseases, including metabolic syndrome, diabetes mellitus, insulin resistance, diabetic dyslipidemia, hypertriglyceridemia, obesity and weight gain. In certain of the experiments, the compounds reduced blood glucose levels, e.g., the animals continued to experience symptoms, but the symptoms were less severe compared to untreated animals. In other of the experiments, however, the compounds appear to reduce the symptoms of diabetes; e.g., animals treated for a longer period of time experienced less severe symptoms than those administered the compounds for a shorter period of time. In other of the experiments, however, the compounds appear to inhibit weight gain; e.g., animals treated for a longer period of time experienced less severe symptoms than those administered the compounds for a shorter period of time. In other of the experiments, however, the compounds appear to inhibit hypertriglyceridemia; e.g., animals treated for a longer period of time experienced less severe symptoms than those administered the compounds for a shorter period of time. The ability of the compounds exemplified below to restore function therefore demonstrates that symptoms of the disease may be reversed by treatment with a compound as described herein.

Diabetes mellitus is characterized by numerous physical and physiological symptoms. Any symptom known to one of skill in the art to be associated with Type 2 diabetes can be ameliorated or otherwise modulated as set forth above in the methods described above. In certain embodiments, the symptom is a physical symptom selected from the group consisting of increased glucose levels, increased weight gain, frequent urination, unusual thirst, extreme hunger, extreme fatigue, blurred vision, frequent infections, tingling or numbness at the extremities, dry and itchy skin, weight loss, slow-healing sores, and swollen gums.

In certain embodiments, the symptom is a physiological symptom selected from the group consisting of increased insulin resistance, increased glucose levels, increased fat mass, decreased metabolic rate, decreased glucose clearance, decreased glucose tolerance, decreased insulin sensitivity, decreased hepatic insulin sensitivity, increased adipose tissue size and weight, increased body fat, and increased body weight.

In certain embodiments, the physical symptom is increased weight gain. In certain embodiments, the symptom is frequent urination. In certain embodiments, the symptom is unusual thirst. In certain embodiments, the symptom is extreme hunger. In certain embodiments, the symptom is extreme fatigue. In certain embodiments, the symptom is blurred vision. In certain embodiments, the symptom is frequent infections. In certain embodiments, the symptom is tingling or numbness at the extremities. In certain embodiments, the symptom is dry and itchy skin. In certain embodiments, the symptom is weight loss. In certain embodiments, the symptom is slow-healing sores. In certain embodiments, the symptom is swollen gums. In certain embodiments, the symptom is increased insulin resistance. In certain embodiments, the symptom is increased fat mass. In certain embodiments, the symptom is decreased metabolic rate. In certain embodiments, the symptom is decreased glucose clearance. In certain embodiments, the symptom is decreased glucose tolerance. In certain embodiments, the symptom is decreased insulin sensitivity. In certain embodiments, the symptom is decreased hepatic insulin sensitivity. In certain embodiments, the symptom is increased adipose tissue size and weight. In certain embodiments, the symptom is increased body fat. In certain embodiments, the symptom is increased body weight.

Liu and Chemoff have shown that PTP1B binds to and serves as a substrate for the epidermal growth factor receptor (EGFR) (Liu and Chemoff, Biochem. J., 1997, 327, 139-145). Furthermore, in A431 human epidermoid carcinoma cells, PT1B was found to be inactivated by the presence of $H_2O_2$ generated by the addition of EGF. These studies indicate that PTP1B can be negatively regulated by the oxidation state of the cell, which is often deregulated during tumorigenesis (Lee et al., J. Biol. Chem., 1998, 273, 15366-15372).

Overexpression of PTP1B has been demonstrated in malignant ovarian cancers and this correlation was accompanied by a concomitant increase in the expression of the associated growth factor receptor (Wiener et al., Am. J. Obstet. Gynecol., 1994, 170, 1177-1183).

PTP1B has been shown to suppress transformation in NIH3T3 cells induced by the neu oncogene (Brown-Shimer et al., Cancer Res., 1992, 52, 478-482), as well as in rat 3Y1 fibroblasts induced by v-srk, v-src, and v-ras (Liu et al., Mol. Cell. Biol., 1998, 18, 250-259) and rat-1 fibroblasts induced by bcr-abl (LaMontagne et al., Proc. Natl. Acad. Sci. U.S.A., 1998, 95, 14094-14099). It has also been shown that PTP1B promotes differentiation of K562 cells, a chronic myelogenous leukemia cell line, in a similar manner as does an inhibitor of the bcr-abl oncoprotein. These studies describe the possible role of PTP1B in controlling the pathogenesis of chronic myeloid leukemia (LaMontagne et al., Proc. Natl. Acad. Sci. U.S.A., 1998, 95, 14094-14099).

Accordingly, provided herein are methods for ameliorating a symptom associated with hyperproliferative disorders in a subject in need thereof. In certain embodiments, the hyperproliferative disorder is cancer. In certain embodiments, provided herein are methods for ameliorating a symptom associated with cancer. In certain embodiments, provided is a method for reducing the rate of onset of a symptom associated with hyperproliferative disorders. In certain embodiments, provided is a method for reducing the rate of onset of a symptom associated with cancer. In certain embodiments, provided is a method for reducing the severity of a symptom associated with hyperproliferative disorders. In certain embodiments, provided is a method for reducing the severity of a symptom associated with cancer. In such embodiments, the methods comprise administering to an individual in need thereof a therapeutically effective amount of a compound targeted to a PTP1B nucleic acid.

In certain embodiments, provided are methods of treating an individual comprising administering one or more pharmaceutical compositions as described herein. In certain embodiments, the individual has metabolic related disease.

In certain embodiments, administration of an antisense compound targeted to a PTP1B nucleic acid results in reduction of PTP1B expression by at least about 15, 20, 25, 30, 35, 40, 45, 50, 55, 60, 65, 70, 75, 80, 85, 90, 95 or 99%, or a range defined by any two of these values.

In certain embodiments, pharmaceutical compositions comprising an antisense compound targeted to transthyretin are used for the preparation of a medicament for treating a patient suffering or susceptible to metabolic related disease.

In certain embodiments, the methods described herein include administering a compound comprising a modified oligonucleotide having a contiguous nucleobases portion as described herein of a sequence recited in SEQ ID NO: 26 (ISIS 404173).

Administration

In certain embodiments, the compounds and compositions as described herein may be administered in a number of ways depending upon whether local or systemic treatment is desired and upon the area to be treated. Administration may be topical, pulmonary, e.g., by inhalation or insufflation of powders or aerosols, including by nebulizer; intratracheal, intranasal, epidermal and transdermal, oral or parenteral. The compounds and compositions as described herein can be administered directly to a tissue or organ.

In certain embodiments, the compounds and compositions as described herein are administered parenterally. "Parenteral administration" means administration through injection or infusion. Parenteral administration includes subcutaneous administration, intravenous administration, intramuscular administration, intraarterial administration, intraperitoneal administration, or intracranial administration, e.g. intracerebral administration, intrathecal administration, intraventricular administration, ventricular administration, intracerebroventricular administration, cerebral intraventricular administration or cerebral ventricular administration. Administration can be continuous, or chronic, or short or intermittent.

In certain embodiments, parenteral administration is by injection. The injection can be delivered with a syringe or a pump. In certain embodiments, the injection is a bolus injection. In certain embodiments, the injection is administered directly to a tissue or organ.

In certain embodiments, the compounds and compositions as described herein are administered parenterally.

In certain embodiments, parenteral administration is subcutaneous.

In further embodiments, the formulation for administration is the compounds described herein and saline.

In certain embodiments, an antisense oligonucleotide is delivered by injection or infusion once every month, every two months, every 90 days, every 3 months, every 6 months, twice a year or once a year.

Certain Combination Therapies

In certain embodiments, one or more pharmaceutical compositions of the present invention are co-administered with one or more other pharmaceutical agents. In certain embodiments, such one or more other pharmaceutical agents are designed to treat the same disease, disorder, or condition as the one or more pharmaceutical compositions described herein. In certain embodiments, such one or more other pharmaceutical agents are designed to treat a different disease, disorder, or condition as the one or more pharmaceutical compositions described herein. In certain embodiments, such one or more other pharmaceutical agents are designed to treat an undesired side effect of one or more pharmaceutical compositions as described herein. In certain embodiments, one or more pharmaceutical compositions are co-administered with another pharmaceutical agent to treat an undesired effect of that other pharmaceutical agent. In certain embodiments, one or more pharmaceutical compositions are co-administered with another pharmaceutical agent to produce a combinational effect. In certain embodiments, one or more pharmaceutical compositions are co-administered with another pharmaceutical agent to produce a synergistic effect.

In certain embodiments, a first agent and one or more second agents are administered at the same time. In certain embodiments, the first agent and one or more second agents are administered at different times. In certain embodiments, the first agent and one or more second agents are prepared together in a single pharmaceutical formulation. In certain embodiments, the first agent and one or more second agents are prepared separately.

In certain embodiments, the second compound is administered prior to administration of a pharmaceutical composition of the present invention. In certain embodiments, the second compound is administered following administration of a pharmaceutical composition of the present invention. In certain embodiments, the second compound is administered at the same time as a pharmaceutical composition of the present invention. In certain embodiments, the dose of a co-administered second compound is the same as the dose that would be administered if the second compound was administered alone. In certain embodiments, the dose of a co-administered second compound is lower than the dose that would be administered if the second compound was administered alone. In certain embodiments, the dose of a co-administered second compound is greater than the dose that would be administered if the second compound was administered alone.

In certain embodiments, the co-administration of a second compound enhances the effect of a first compound, such that co-administration of the compounds results in an effect that is greater than the effect of administering the first compound alone. In certain embodiments, the co-administration results in effects that are additive of the effects of the compounds when administered alone. In certain embodiments, the co-administration results in effects that are supra-additive of the effects of the compounds when administered alone. In certain embodiments, the first compound is an antisense compound. In certain embodiments, the second compound is an antisense compound.

In certain embodiments, second agents include, but are not limited to, a glucose-lowering agent. The glucose lowering agent can include, but is not limited to, a therapeutic lifestyle change, PPAR agonist, a dipeptidyl peptidase (IV) inhibitor, a GLP-1 analog, insulin or an insulin analog, an insulin secretagogue, a SGLT2 inhibitor, a human amylin analog, a biguanide, an alpha-glucosidase inhibitor, or a combination thereof. The glucose-lowering agent can include, but is not limited to metformin, sulfonylurea, rosiglitazone, meglitinide, thiazolidinedione, alpha-glucosidase inhibitor or a combination thereof. The sulfonylurea can be acetohexamide, chlorpropamide, tolbutamide, tolazamide, glimepiride, a glipizide, a glyburide, or a gliclazide. The meglitinide can be nateglinide or repaglinide. The thiazolidinedione can be pioglitazone or rosiglitazone. The alpha-glucosidase can be acarbose or miglitol.

In some embodiments, the glucose-lowering therapeutic is a GLP-1 analog. In some embodiments, the GLP-1 analog is exendin-4 or liraglutide.

In other embodiments, the glucose-lowering therapeutic is a sulfonylurea. In some embodiments, the sulfonylurea is acetohexamide, chlorpropamide, tolbutamide, tolazamide, glimepiride, a glipizide, a glyburide, or a gliclazide.

In some embodiments, the glucose-lowering drug is a biguanide. In some embodiments, the biguanide is metformin, and in some embodiments, blood glucose levels are decreased without increased lactic acidosis as compared to the lactic acidosis observed after treatment with metformin alone.

In some embodiments, the glucose-lowering drug is a meglitinide. In some embodiments, the meglitinide is nateglinide or repaglinide.

In some embodiments, the glucose-lowering drug is a thiazolidinedione. In some embodiments, the thiazolidinedione is pioglitazone, rosiglitazone, or troglitazone. In some embodiments, blood glucose levels are decreased without greater weight gain than observed with rosiglitazone treatment alone.

In some embodiments, the glucose-lowering drug is an alpha-glucosidase inhibitor. In some embodiments, the alpha-glucosidase inhibitor is acarbose or miglitol.

In a certain embodiment, a co-administered glucose-lowering agent is ISIS 113715.

In a certain embodiment, glucose-lowering therapy is therapeutic lifestyle change.

In certain embodiments, second agents include, but are not limited to, lipid-lowering agents. The lipid-lowering agent can include, but is not limited to atorvastatin, simvastatin, rosuvastatin, and ezetimibe. In certain such embodiments, the lipid-lowering agent is administered prior to administration of a pharmaceutical composition of the present invention. In certain such embodiments, the lipid-lowering agent is administered following administration of a pharmaceutical composition of the present invention. In certain such embodiments the lipid-lowering agent is administered at the same time as a pharmaceutical composition of the present invention. In certain such embodiments the dose of a co-administered lipid-lowering agent is the same as the dose that would be administered if the lipid-lowering agent was administered alone. In certain such embodiments the dose of a co-administered lipid-lowering agent is lower than the dose that would be administered if the lipid-lowering agent was administered alone. In certain such embodiments the dose of a co-administered lipid-lowering agent is greater than the dose that would be administered if the lipid-lowering agent was administered alone.

In certain embodiments, a co-administered lipid-lowering agent is a HMG-CoA reductase inhibitor. In certain such embodiments the HMG-CoA reductase inhibitor is a statin. In certain such embodiments the statin is selected from atorvastatin, simvastatin, pravastatin, fluvastatin, and rosuvastatin.

In certain embodiments, a co-administered lipid-lowering agent is a cholesterol absorption inhibitor. In certain such embodiments, cholesterol absorption inhibitor is ezetimibe.

In certain embodiments, a co-administered lipid-lowering agent is a co-formulated HMG-CoA reductase inhibitor and cholesterol absorption inhibitor. In certain such embodiments the co-formulated lipid-lowering agent is ezetimibe/simvastatin.

In certain embodiments, a co-administered lipid-lowering agent is a microsomal triglyceride transfer protein inhibitor (MTP inhibitor).

In certain embodiments, a co-administered lipid-lowering agent is an oligonucleotide targeted to ApoB.

In certain embodiments, second agents include, but are not limited to an anti-obesity drug or agent. Such anti-obesity agents include but are not limited to Orlistat, Sibutramine, or Rimonabant, and may be administered as described above as adipose or body weight lowering agents. In certain embodiments, the antisense compound may be co-administered with appetite suppressants. Such appetite suppressants include but are not limited to diethylpropion tenuate, mazindol, orlistat, phendimetrazine, phentermine, and sibutramine and may be administered as described herein. In certain embodiment, the anti-obesity agents are CNS based such as, but not limited to, sibutramine or GLP-1 based such as, but not limited to, liraglutide.

Formulations

The compounds provided herein may also be admixed, conjugated or otherwise associated with other molecules, molecule structures or mixtures of compounds, as for example, liposomes, receptor-targeted molecules, or other formulations, for assisting in uptake, distribution and/or absorption. Representative United States patents that teach the preparation of such uptake, distribution and/or absorption-assisting formulations include, but are not limited to, U.S. Pat. Nos. 5,108,921; 5,354,844; 5,416,016; 5,459,127; 5,521,291; 5,543,158; 5,547,932; 5,583,020; 5,591,721; 4,426,330; 4,534,899; 5,013,556; 5,108,921; 5,213,804; 5,227,170; 5,264,221; 5,356,633; 5,395,619; 5,416,016; 5,417,978; 5,462,854; 5,469,854; 5,512,295; 5,527,528; 5,534,259; 5,543,152; 5,556,948; 5,580,575; and 5,595,756, each of which is herein incorporated by reference.

The antisense compounds provided herein encompass any pharmaceutically acceptable salts, esters, or salts of such esters, or any other compound which, upon administration to an animal, including a human, is capable of providing (directly or indirectly) the biologically active metabolite or residue thereof.

The term "pharmaceutically acceptable salts" refers to physiologically and pharmaceutically acceptable salts of the compounds provided herein: i.e., salts that retain the desired biological activity of the parent compound and do not impart undesired toxicological effects thereto. The term "pharmaceutically acceptable salt" includes a salt prepared from pharmaceutically acceptable non-toxic acids or bases, including inorganic or organic acids and bases. For oligonucleotides, preferred examples of pharmaceutically acceptable salts and their uses are further described in U.S. Pat. No. 6,287,860, which is incorporated herein in its entirety. Sodium salts have been shown to be suitable forms of oligonucleotide drugs.

The term "pharmaceutically acceptable derivative" encompasses, but is not limited to, pharmaceutically acceptable salts, solvates, hydrates, esters, prodrugs, polymorphs, isomers, isotopically labeled variants of the compounds described herein.

The present invention also includes pharmaceutical compositions and formulations which include the antisense compounds provided herein. The pharmaceutical compositions of the present invention may be administered in a number of ways depending upon whether local or systemic treatment is desired and upon the area to be treated. Administration may be parenteral. Parenteral administration includes intravenous, intraarterial, subcutaneous, intraperitoneal or intramuscular injection or infusion; or intracranial, e.g., intracerebral administration, intrathecal administration, intraventricular administration, ventricular administration, intracerebroventricular administration, cerebral intraventricular administration or cerebral ventricular administration.

Parenteral administration, is preferred to target PTP1B expression in the liver and plasma. Oligonucleotides with at least one 2'-O-methoxyethyl modification are believed to be particularly useful for oral administration. Pharmaceutical compositions and formulations for topical administration may include transdermal patches, ointments, lotions, creams, gels, drops, suppositories, sprays, liquids and powders. Conventional pharmaceutical carriers, aqueous, powder or oily bases, thickeners and the like may be necessary or desirable. Coated condoms, gloves and the like may also be useful.

The pharmaceutical formulations of the present invention, which may conveniently be presented in unit dosage form, may be prepared according to conventional techniques well known in the pharmaceutical industry. Such techniques include the step of bringing into association the active ingredients with the pharmaceutical carrier(s) or excipient (s). In general, the formulations are prepared by uniformly and intimately bringing into association the active ingredients with liquid carriers or finely divided solid carriers or both, and then, if necessary, shaping the product.

The compositions of the present invention may be formulated into any of many possible dosage forms such as, but not limited to, tablets, capsules, gel capsules, liquid syrups, soft gels, suppositories, and enemas. The compositions of the present invention may also be formulated as suspensions in aqueous, non-aqueous or mixed media. Aqueous suspensions may further contain substances which increase the viscosity of the suspension including, for example, sodium carboxymethylcellulose, sorbitol and/or dextran. The suspension may also contain stabilizers.

Pharmaceutical compositions of the present invention include, but are not limited to, solutions, emulsions, foams and liposome-containing formulations. The pharmaceutical compositions and formulations of the present invention may comprise one or more penetration enhancers, carriers, excipients or other active or inactive ingredients.

Emulsions are typically heterogenous systems of one liquid dispersed in another in the form of droplets usually exceeding 0.1 μm in diameter. Emulsions may contain additional components in addition to the dispersed phases, and the active drug which may be present as a solution in the aqueous phase, oily phase or itself as a separate phase. Microemulsions are included as an embodiment of the present invention. Emulsions and their uses are well known in the art and are further described in U.S. Pat. No. 6,287,860, which is incorporated herein in its entirety.

Formulations of the present invention include liposomal formulations. As used in the present invention, the term "liposome" means a vesicle composed of amphiphilic lipids arranged in a spherical bilayer or bilayers. Liposomes are unilamellar or multilamellar vesicles which have a membrane formed from a lipophilic material and an aqueous interior that contains the composition to be delivered. Cationic liposomes are positively charged liposomes which are believed to interact with negatively charged DNA molecules to form a stable complex. Liposomes that are pH-sensitive or negatively-charged are believed to entrap DNA rather than complex with it. Both cationic and noncationic liposomes have been used to deliver DNA to cells.

Liposomes also include "sterically stabilized" liposomes, a term which, as used herein, refers to liposomes comprising one or more specialized lipids that, when incorporated into liposomes, result in enhanced circulation lifetimes relative to liposomes lacking such specialized lipids. Liposomes and their uses are further described in U.S. Pat. No. 6,287,860, which is incorporated herein in its entirety.

In another embodiment, formulations of the present invention include saline formulations. In certain embodiments, a formulation consists of the compounds described herein and saline. In certain embodiments, a formulation consists essentially of the compounds described herein and saline. In certain embodiments, the saline is pharmaceutically acceptable grade saline. In certain embodiments, the saline is buffered saline. In certain embodiments, the saline is phosphate buffered saline (PBS).

In certain embodiments, a formulation excludes liposomes. In certain embodiments, the formulation excludes sterically stabilized liposomes. In certain embodiments, a formulation excludes phospholipids. In certain embodiments, the formulation consists essentially of the compounds described herein and saline and excludes liposomes.

The pharmaceutical formulations and compositions of the present invention may also include surfactants. Surfactants and their uses are further described in U.S. Pat. No. 6,287,860, which is incorporated herein in its entirety.

In one embodiment, the present invention employs various penetration enhancers to affect the efficient delivery of nucleic acids, particularly oligonucleotides. Penetration enhancers and their uses are further described in U.S. Pat. No. 6,287,860, which is incorporated herein in its entirety.

One of skill in the art will recognize that formulations are routinely designed according to their intended use, i.e. route of administration.

Formulations for topical administration include those in which the oligonucleotides provided herein are in admixture with a topical delivery agent such as lipids, liposomes, fatty acids, fatty acid esters, steroids, chelating agents and surfactants. Preferred lipids and liposomes include neutral (e.g. dioleoylphosphatidyl DOPE ethanolamine, dimyristoylphosphatidyl choline DMPC, distearolyphosphatidyl choline) negative (e.g. dimyristoylphosphatidyl glycerol DMPG) and cationic (e.g. dioleoyltetramethylaminopropyl DOTAP and dioleoylphosphatidyl ethanolamine DOTMA).

Compositions and formulations for parenteral administration, including intravenous, intraarterial, subcutaneous, intraperitoneal, intramuscular injection or infusion, or intracranial may include sterile aqueous solutions which may also contain buffers, diluents and other suitable additives such as, but not limited to, penetration enhancers, carrier compounds and other pharmaceutically acceptable carriers or excipients.

Certain embodiments provided herein provide pharmaceutical compositions containing one or more oligomeric compounds and one or more other chemotherapeutic agents which function by a non-antisense mechanism. Examples of such chemotherapeutic agents include but are not limited to cancer chemotherapeutic drugs such as daunorubicin, daunomycin, dactinomycin, doxorubicin, epirubicin, idarubicin, esorubicin, bleomycin, mafosfamide, ifosfamide, cytosine arabinoside, bis-chloroethylnitrosurea, busulfan, mitomycin C, actinomycin D, mithramycin, prednisone, hydroxyprogesterone, testosterone, tamoxifen, dacarbazine, procarbazine, hexamethylmelamine, pentamethylmelamine, mitoxantrone, amsacrine, chlorambucil, methylcyclohexylnitrosurea, nitrogen mustards, melphalan, cyclophosphamide, 6-mercaptopurine, 6-thioguanine, cytarabine, 5-azacytidine, hydroxyurea, deoxycoformycin, 4-hydroxyperoxycyclophosphoramide, 5-fluorouracil (5-FU), 5-fluorodeoxyuridine (5-FUdR), methotrexate (MTX), colchicine, taxol, vincristine, vinblastine, etoposide (VP-16), trimetrexate, irinotecan, topotecan, gemcitabine, teniposide, cisplatin and diethylstilbestrol (DES). When used with the compounds provided herein, such chemotherapeutic agents may be used individually (e.g., 5-FU and oligonucleotide), sequentially (e.g., 5-FU and oligonucleotide for a period of time followed by MTX and oligonucleotide), or in combination with one or more other such chemotherapeutic agents (e.g., 5-FU, MTX and oligonucleotide, or 5-FU, radiotherapy and oligonucleotide). Anti-inflammatory drugs, including but not limited to nonsteroidal anti-inflammatory drugs and corticosteroids, and antiviral drugs, including but not limited to ribivirin, vidarabine, acyclovir and ganciclovir, may also be combined in compositions provided herein. Combinations of antisense compounds and other non-antisense drugs are also within the scope of this invention. Two or more combined compounds may be used together or sequentially.

In another related embodiment, compositions provided herein may contain one or more antisense compounds, particularly oligonucleotides, targeted to a first nucleic acid and one or more additional antisense compounds targeted to a second nucleic acid target. Alternatively, compositions provided herein may contain two or more antisense compounds targeted to different regions of the same nucleic acid target. Numerous examples of antisense compounds are known in the art. Two or more combined compounds may be used together or sequentially.

Dosing

The formulation of therapeutic compositions and their subsequent administration (dosing) is believed to be within the skill of those in the art. Dosing is dependent on severity and responsiveness of the disease state to be treated, with the course of treatment lasting from several days to several months, or until a cure is effected or a diminution of the disease state is achieved. Optimal dosing schedules can be calculated from measurements of drug accumulation in the body of the patient. Optimum dosages may vary depending on the relative potency of individual oligonucleotides, and can generally be estimated based on $EC_{50}$s found to be effective in in vitro and in vivo animal models. In general, dosage is from 0.01 μg to 100 g per kg of body weight, and may be given once or more daily, weekly, monthly or yearly, or at desired intervals. Following successful treatment, it may be desirable to have the patient undergo maintenance therapy to prevent the recurrence of the disease state, wherein the oligonucleotide is administered in maintenance doses, ranging from 0.01 μg to 100 g per kg of body weight, once or more daily.

While the present invention has been described with specificity in accordance with certain of its preferred embodiments, the following examples serve only to illustrate the invention and are not intended to limit the same. Each of the references, GenBank accession numbers, and the like recited in the present application is incorporated herein by reference in its entirety.

Certain Compounds

About two hundred and seventy six newly designed antisense compounds of various lengths, motifs and backbone composition were tested for their effect on human PTP1B mRNA in vitro in several cell types. The new compounds were compared with about five hundred previously designed compounds including ISIS 107772, ISIS 107831, ISIS 142025, ISIS 142026, ISIS 142027, ISIS 142028, ISIS 142082, ISIS 146908, and ISIS 146909 which have previously been determined to be some of the most potent antisense compounds in vitro (see e.g., U.S. Patent Publication No. US 2003/0220282 published Nov. 27, 2003 and PCT Patent Publication No. WO2007/131237 published Nov. 15, 2007). Of the about two hundred and eight five newly designed and previously designed antisense compounds, about eleven compounds were selected for further study based on in vitro potency. The selected compounds were tested for dose dependent inhibition in HuVEC, HepG2, HuVEC, LLC-MK2, and cynomolgus primary hepatocytes. Additional oligonucleotides were designed based on microwalk of ISIS 409826, one of the selected compounds which demonstrated significant reduction of PTP1B mRNA in all the cell lines tested. The oligonucleotides were tested in HuVEC cells (Example 5) along with gapmers from the earlier screen (Example 1). Several antisense oligonucleotides from the screen in Example 5 were selected and tested for dose-dependent inhibition in HuVEC cells (Example 6) and HepG2 cells (Example 7). Additionally, two oligonucleotides were designed as shortmers to ISIS 1428082, one of the selected compounds. These two shortmers (ISIS 446431 and ISIS 446432), as well as five ISIS oligonucleotides selected from the study described in Examples 6 and 7 were tested in HepG2 cells, LLC-MK2 cells, HuVEC cells, and cynomolgus primary hepatocytes (Examples 8-11). ISIS oligonucleotides that demonstrated dose-dependent reduction of PTP1B mRNA in all cell lines were tested for in vivo tolerability. Two more oligonucleotides ISIS 446433 and ISIS 446434, designed as shortmers to ISIS 409826, were included in the in vivo tolerability studies as well.

The twelve gapmers chosen were tested in a mouse model (see Example 12) and a rat model (Example 13). By virtue of their complementary sequence, the compounds are complementary to the regions 3291-3310, 989-1008, 3290-3309, 3287-3306, 3291-3310, 3288-3307, 3292-3309, 3293-3308, 3288-3305, and 3289-3304 of SEQ ID NO: 1. In the in vivo models, body weights and organ weights, the liver metabolic markers, such as alanine transaminase, aspartate transaminase and bilirubin, kidney metabolic markers, such as BUN and creatinine, plasma glucose levels, cholesterol and triglyceride levels, and inflammatory cytokine levels were measured. Of the twelve compounds tested, five compounds, ISIS 142082, ISIS 404173, ISIS 410003, ISIS 446431, and ISIS 446432 were selected and their viscosity was measured (Example 14). All the five oligonucleotides were considered optimal in their viscosity according to the criteria stated for the study.

Final evaluation of these studies (Examples 12-14), led to the selection of four compounds having a nucleobase sequence of a sequence recited in SEQ ID NO: 27 (ISIS 142082), 46 (ISIS 446431), 26 (ISIS 404173), and 23 (ISIS 409826). By virtue of their complementary sequence, the compounds are complementary to the regions 3291-3310, 3292-3309, 3290-3309, 3287-3306 of SEQ ID NO: 1. In certain embodiments, the compounds targeting the listed regions, as further described herein, comprise a modified oligonucleotide having some nucleobase portion of the sequence recited in the SEQ ID NOs, as further described herein, In certain embodiments, the compounds targeting the listed regions or having a nucleobase portion of a sequence recited in the listed SEQ ID NOs can be of various length, as further described herein, and can have one of various motifs, as further described herein. In certain embodiments, a compound targeting a region or having a nucleobase portion of a sequence recited in the listed SEQ ID NOs has the specific length and motif, as indicated by the ISIS NOs: ISIS 142082, ISIS 446431, ISIS 404173, and ISIS 409826.

Three compounds having a nucleobase sequence of a sequence recited in SEQ ID NO: 27 (ISIS 142082), 23 (ISIS 404173), and 46 (ISIS 446431), were further tested in a long-term, six month tolerability study in a mouse model (See Example 15). The half life in the liver of CD1 mice of all four of the compounds having a nucleobase sequence of a sequence recited in SEQ ID NOs: 53 (ISIS 409826), 27 (ISIS 142082), 26 (ISIS 404173), and 46 (ISIS 446431) was also evaluated (Example 16).

These four compounds were tested for efficacy, pharmacokinetic profile and tolerability in cynomolgus monkeys (Example 17). The inhibition studies in these monkeys indicated that treatment with some of these compounds caused reduction of PTP1B mRNA in the liver and fat tissues. Specifically, treatment with ISIS 409826, ISIS 142082, ISIS 446431 and ISIS 404173 caused 45%, 48%, 18 and 22% reduction of PTP1B mRNA in liver tissue, respectively compared to the PBS control. Treatment with ISIS 409826, ISIS 142082, ISIS 446431 and ISIS 404173 caused 21%, 28%, 12% and 31% reduction of PTP1B mRNA in fat tissue, respectively compared to the PBS control. It was noted that ISIS 404173 caused similar reduction of PTP1B mRNA compared to ISIS 142082, even though the two oligonucleotides differ from each other by a single base-pair shift of their target region on SEQ ID NO: 1. Protein analysis of liver tissue was also conducted by western blot analysis. PTP1B mRNA reduction using ISIS 409826, ISIS 142082, ISIS 446431 and ISIS 404173 was measured at a maximum dose of 40 mgk/week for efficacy and at a lower dose of 8 mgk/week for potency (See table 45). Protein analysis at a lower dose of 8 mgk/week demonstrated that ISIS 404173 caused greater reduction (33%) of PTP1B protein than ISIS 142082 (20%) demonstrating that ISIS 404173 was more potent than ISIS 142082 (See Table 47 and FIG. 1). Protein analysis at the higher dose of 40 mg/week demonstrated that ISIS 404173 (60% protein reduction) was as efficacious as ISIS 142082 (65% protein reduction). Finally, treatment with ISIS 409826 and ISIS 142082 resulted in 22% decrease in triglyceride levels while treatment with ISIS 404173 resulted in 37% decrease in triglyceride levels compared to the PBS control.

Tolerability studies in cynomolgus monkeys (Example 17) indicated that treatment with ISIS 142082 was not as tolerable to the primates as treatment with ISIS 404173. The levels of C-reactive protein, which is synthesized in the liver and which serves as a marker of inflammation, were measured on day 93. At the higher dose of 40 mg/week, treatment with ISIS 142082 caused a significant increase of CRP levels of 12 mg/L compared to the control level of 1.2 mg/L. Treatment with ISIS 404173 at 40 mg/L caused an increase of CRP levels to 1.6 mg/L. The other compounds tested, ISIS 409826 and ISIS 446431 caused increase of CRP levels to 4.8 mg/L and 6.7 mg/L. Therefore, ISIS 404173 caused the least increase in CRP levels indicating that ISIS 404173 is extremely tolerable and non-proinflammatory. Organ weights were also measured to evaluate the tolerability of ISIS oligonucleotides by the monkeys. Treatment with ISIS 142082 at a dose of 40 mg/L caused increases in kidney and liver weights of 21 g and 18 g respectively, which is two-fold increase over the control (kidney 10 g and liver 10.5 g). Treatment with ISIS 409826 caused a two-fold increase in liver weight (18.5 g vs. 10.5 g of control) and a three-fold increase in spleen weight (6.0 g vs. 2.3 g of control). Treatment with ISIS 446431 caused a four-fold increase in spleen weight (9.6 g vs. 2.3 g control). Treatment with ISIS 404173 caused less than one-fold increase in all organs (kidney 14.8 g; liver 15.5 g; spleen 3.7 g) See (FIG. 2). Hence, treatment with ISIS 142082, ISIS 409826, and ISIS 446431 were not considered tolerable in the monkeys, whereas treatment with ISIS 404173 was tolerable.

Treatment with ISIS 142082 caused increase in organ weights and elevated levels of CRP, indicating an inflammatory state. Treatment with ISIS 409826 also caused elevated levels of CRP and low complement C3 levels, indicating a diseased state. Treatment with ISIS 404173 and ISIS 446431 were considered optimal in terms of their tolerability profiles in cynomolgus monkeys. However, ISIS 446431 demonstrated less potency compared to ISIS 404173.

In case of the pharmacokinetic profile studies of the oligonucleotides in liver and kidney, none of the ISIS oligonucleotides demonstrated any abnormal ratios in concentration in the liver versus the kidney. ISIS 404173 was a better renal accumulator compared to ISIS 142082, as indicated in the results.

Hence, the in vivo studies, particularly in the cynomolgus monkeys, indicate that ISIS 404173 was just as potent and considerably more tolerable compared to the other compounds. The studies demonstrate that ISIS 142082, although shifted from ISIS 407173 by only one nucleobase, was as efficacious but less potent and tolerable than ISIS 404173, as demonstrated by assays for metabolic and inflammatory markers. Overall, ISIS 404173 was more potent and tolerable compared to any other compound.

Accordingly, provided herein are antisense compounds with any one or more of the improved characteristics. In a certain embodiments, provided herein are compounds comprising a modified oligonucleotide as further described herein targeted to or specifically hybridizable with the region of nucleotides of SEQ ID NO: 1.

Accordingly, provided herein are antisense compounds with any one or more of the improved characteristics. In a certain embodiments, provided herein are compounds comprising a modified oligonucleotide as further described herein targeted to or specifically hybridizable with the region of nucleotides of SEQ ID NO: 2.

In certain embodiments, the compounds as described herein are efficacious by virtue of having at least one of an in vitro $IC_{50}$ of less than 0.4 μM, less than 0.35 μM, less than 0.3 μM, less than 2.5 μM, less than 2.0 μM, less than 1.5 μM, less than 1.0 μM, when delivered to a cynomolgus monkey hepatocyte cell line using electroporation as described in Example 11. In certain embodiments, the compounds as described herein are highly tolerable, as demonstrated by having at least one of an increase an ALT or AST value of no more than 4 fold, 3 fold, or 2 fold over saline treated animals; or an increase in liver, spleen or kidney weight of no more than 30%, 20%, 15%, 12%, 10%, 5% or 2%.

EXAMPLES

Non-Limiting Disclosure and Incorporation by Reference

While certain compounds, compositions and methods described herein have been described with specificity in accordance with certain embodiments, the following examples serve only to illustrate the compounds described herein and are not intended to limit the same. Each of the references, GenBank accession numbers, and the like recited in the present application is incorporated herein by reference in its entirety.

Example 1

Antisense Inhibition of Human PTP1B mRNA in HuVEC Cells

Antisense oligonucleotides targeted to a human PTP1B nucleic acid were designed and tested for their effect on PTP1B RNA transcript in vitro. ISIS 107772, ISIS 107831, ISIS 142025, ISIS 142026, ISIS 142027, ISIS 142028, ISIS 142082, ISIS 146908, and ISIS 146909, claimed in a previous patent (BIOL001USP2) were included in this assay for comparison. Cultured HuVEC cells at a density of 5,000 cells per well were transfected using LipofectAMINE 2000® with 2 nM antisense oligonucleotide. After approximately 24 hours, RNA was isolated from the cells and PTP1B mRNA levels were measured by quantitative real-time PCR. PTP1B mRNA levels were adjusted according to total RNA content, as measured by RIBOGREEN®. Results are presented as percent inhibition of PTP1B mRNA levels, relative to untreated control cells.

The antisense oligonucleotides in Table 1 are 5-10-5 MOE gapmers or 2-13-5 MOE gapmers. The 5-10-5 MOE gapmers have a gap segment comprising ten 2'-deoxynucleosides and two wing segment comprising five 2'-MOE nucleosides. The 2-13-5 MOE gapmers have a gap segment comprising thirteen 2'-deoxynucleosides, a 5' wing segment comprising two 2'-MOE nucleosides, and a 3' wing segment comprising three 2'-MOE nucleosides. The internucleoside linkages throughout each gapmer are phosphorothioate (P═S) linkages. All cytosine residues throughout each gapmer are 5-methylcytosines. 'Target start site' indicates the 5'-most nucleotide to which the antisense oligonucleotide is targeted in the human gene sequence. 'Target stop site' indicates the 3'-most nucleotide to which the antisense oligonucleotide is targeted in the human gene sequence. All the antisense oligonucleotides listed in Table 1 target either the mRNA sequence, designated herein as SEQ ID NO: 1 (GENBANK Accession No. NM_002827.2) or the genomic sequence, designated herein as SEQ ID NO: 2 (GENBANK Accession NT_011362.9 truncated from nucleotides 14178000 to 14256000), or both.

Some of the human oligonucleotides of Table 1 are also fully cross-reactive with rhesus monkey gene sequences. 'n/a' indicates that there were more than 3 base mismatches between the human oligonucleotide and the rhesus monkey gene sequence. The greater the complementarity between the human oligonucleotide and the rhesus monkey sequence, the more likely the human oligonucleotide can cross-react with the rhesus monkey sequence. The human oligonucleotides in Table 1 were compared to SEQ ID NO: 3 (exons 1-9, intron 9 and exon 10 from the rhesus monkey PTP1B scaffold). "Rhesus monkey Target start site" indicates the 5'-most nucleotide to which the gapmer is targeted in the rhesus monkey gene sequence. "Rhesus monkey Target stop site" indicates the 3'-most nucleotide to which the gapmer is targeted rhesus monkey gene sequence.

TABLE 1

Inhibition of human PTP1B RNA transcript in HuVEC cells by antisense oligonucleotides targeting SEQ ID NO: 1, SEQ ID NO: 2, and SEQ ID NO: 3

| ISIS No | Sequence | Motif | % inhibition | Start Site at SEQ ID NO: 1 | Start Site at SEQ ID NO: 2 | Start Site at SEQ ID NO: 3 | SEQ ID NO |
|---|---|---|---|---|---|---|---|
| 142025 | TTGTCGATCTGCTCGAACTC | 5-10-5 | 43 | 190 | 1989 | 197 | 4 |
| 142026 | GACTTGTCGATCTGCTCGAA | 5-10-5 | 59 | 193 | 1992 | 989 | 5 |

TABLE 1-continued

Inhibition of human PTP1B RNA transcript in HuVEC cells by antisense oligonucleotides targeting SEQ ID NO: 1, SEQ ID NO: 2, and SEQ ID NO: 3

| ISIS No | Sequence | Motif | % inhibi-tion | Start Site at SEQ ID NO: 1 | Start Site at SEQ ID NO: 2 | Start Site at SEQ ID NO: 3 | SEQ ID NO |
|---|---|---|---|---|---|---|---|
| 107772 | CCCGGACTTGTCGATCTGCT | 5-10-5 | 66 | 197 | 1996 | 3754 | 6 |
| 142027 | GCTCCCGGACTTGTCGATCT | 5-10-5 | 55 | 200 | 1999 | 3759 | 7 |
| 142028 | CCAGCTCCCGGACTTGTCGA | 5-10-5 | 60 | 203 | 2002 | 4498 | 8 |
| 373125 | GGCACCTTCGATCACAGCCA | 5-10-5 | 55 | 989 | 70726 | 4487 | 9 |
| 113715 | GCTCCTTCCACTGATCCTGC | 5-10-5 | 50 | 1035 | n/a | 4500 | 10 |
| 107831 | GGTCATGCACAGGCAGGTTG | 5-10-5 | 70 | 2360 | 75039 | 3753 | 11 |
| 409988 | AGGTCATGCACAGGCAGGTT | 2-13-5 | 83 | 2361 | 75040 | 3759 | 12 |
| 409821 | GATCAGGTCATGCACAGGCA | 5-10-5 | 86 | 2365 | 75044 | 3575 | 13 |
| 404176 | TGATCAGGTCATGCACAGGC | 5-10-5 | 87 | 2366 | 75045 | 4493 | 14 |
| 146908 | ACCCTTGGAATGTCTGAGTT | 5-10-5 | 56 | 2544 | 75223 | 3746 | 15 |
| 404169 | CCCATACCCTTGGAATGTCT | 5-10-5 | 77 | 2549 | 75228 | 3756 | 16 |
| 409815 | TCCCATACCCTTGGAATGTC | 5-10-5 | 72 | 2550 | 75229 | 3566 | 17 |
| 146909 | TTCCCATACCCTTGGAATGT | 5-10-5 | 43 | 2551 | 75230 | 3569 | 18 |
| 409845 | TATTCCATGGCCATTGTAAA | 5-10-5 | 23 | 3283 | 75962 | 4485 | 19 |
| 410030 | TTATTCCATGGCCATTGTAA | 2-13-5 | 24 | 3284 | 75963 | 4486 | 20 |
| 409825 | TTTATTCCATGGCCATTGTA | 5-10-5 | 34 | 3285 | 75964 | 192 | 21 |
| 409883 | GTTTATTCCATGGCCATTGT | 3-14-3 | 36 | 3286 | 75965 | 198 | 22 |
| 409999 | GGTTTATTCCATGGCCATTG | 2-13-5 | 54 | 3287 | 75966 | 190 | 23 |
| 409826 | GGTTTATTCCATGGCCATTG | 5-10-5 | 73 | 3287 | 75966 | 201 | 23 |
| 410000 | TGGTTTATTCCATGGCCATT | 2-13-5 | 55 | 3288 | 75967 | 194 | 24 |
| 404172 | TGGTTTATTCCATGGCCATT | 5-10-5 | 61 | 3288 | 75967 | 192 | 24 |
| 410001 | ATGGTTTATTCCATGGCCAT | 2-13-5 | 51 | 3289 | 75968 | 198 | 25 |
| 409827 | ATGGTTTATTCCATGGCCAT | 5-10-5 | 44 | 3289 | 75968 | 195 | 25 |
| 410002 | AATGGTTTATTCCATGGCCA | 2-13-5 | 0 | 3290 | 75969 | 204 | 26 |
| 404173 | AATGGTTTATTCCATGGCCA | 5-10-5 | 48 | 3290 | 75969 | 201 | 26 |
| 410003 | AAATGGTTTATTCCATGGCC | 2-13-5 | 64 | 3291 | 75970 | 193 | 27 |
| 142082 | AAATGGTTTATTCCATGGCC | 5-10-5 | 52 | 3291 | 75970 | 190 | 27 |
| 410004 | AAAATGGTTTATTCCATGGC | 2-13-5 | 46 | 3292 | 75971 | 196 | 28 |
| 409828 | AAAATGGTTTATTCCATGGC | 5-10-5 | 44 | 3292 | 75971 | 194 | 28 |
| 409829 | AAAAATGGTTTATTCCATGG | 5-10-5 | 36 | 3293 | 75972 | 198 | 29 |
| 404161 | GGTCATTTCCATGGCCAGAG | 2-13-5 | 78 | n/a | 73855 | 3746 | 31 |
| 409975 | GGAGGTCATTTCCATGGCCA | 2-13-5 | 85 | n/a | 73858 | n/a | 32 |
| 409976 | AGGAGGTCATTTCCATGGCC | 2-13-5 | 85 | n/a | 73859 | 2379 | 30 |

Example 2

Dose-Dependent Antisense Inhibition of Human PTP1B mRNA in HuVEC Cells

Several antisense oligonucleotides, which displayed significant antisense inhibition of PTP1B mRNA in the study described in Example 1 were further tested in HuVEC cells at various doses. Cells were plated at a density of 5,000 cells per well and transfected using LipofectAMINE 2000® with 0.9375 nM, 1.875 nM, 3.75 nM, 7.5 nM, 15 nM, and 30 nM concentrations of each antisense oligonucleotide. After approximately 16 hours, RNA was isolated from the cells and PTP1B mRNA transcript levels were measured by quantitative real-time PCR using primer probe set RTS3000 (forward sequence CTGGTTTAACCTCCTATCCTTGGA, designated herein as SEQ ID NO: 33; reverse sequence CAGAGCAGCTCGCTACCTCTCT, designated herein as SEQ ID NO: 34, probe sequence CAGCTGGCTCTCCACCTTGTTACACATTATGT, designated herein as SEQ ID NO: 35). PTP1B mRNA levels were normalized to total RNA content, as measured by RIBOGREEN®. Results are presented in Table 2 as percent inhibition of PTP1B mRNA, relative to untreated control cells.

TABLE 2

Dose-dependent antisense inhibition of human PTP1B in HuVEC cells

| ISIS No | 0.9375 nM | 1.875 nM | 3.75 nM | 7.5 nM | 15.0 nM | 30.0 nM | $IC_{50}$ (nM) |
|---|---|---|---|---|---|---|---|
| 113715 | 0 | 0 | 2 | 11 | 23 | 33 | >30 |
| 404161 | 1 | 0 | 7 | 29 | 42 | 57 | 17 |
| 404169 | 0 | 6 | 17 | 37 | 57 | 72 | 7 |
| 404176 | 0 | 0 | 20 | 38 | 68 | 79 | 6 |
| 409815 | 0 | 0 | 7 | 30 | 48 | 65 | 12 |
| 409821 | 0 | 1 | 17 | 41 | 68 | 82 | 5 |
| 409826 | 0 | 0 | 10 | 30 | 47 | 64 | 12 |
| 409975 | 0 | 0 | 23 | 50 | 74 | 86 | 4 |
| 409976 | 0 | 0 | 21 | 46 | 65 | 82 | 5 |
| 409988 | 0 | 0 | 23 | 49 | 70 | 83 | 5 |
| 410003 | 0 | 0 | 4 | 16 | 28 | 46 | >30 |

Example 3

Dose-Dependent Antisense Inhibition of PTP1B mRNA in LLC-MK2 Cells

The antisense oligonucleotides from the study described in Example 2 are also cross-reactive with rhesus monkey the gene sequence (SEQ ID NO: 3) and were further tested in rhesus monkey LLC-MK2 cells at various doses. Cells were plated at a density of 3,000 cells per well and transfected using Lipofectin with 3.125 nM, 6.25 nM, 12.5 nM, 25 nM, 50 nM, and 100 nM concentrations of each antisense oligonucleotide. After approximately 16 hours, RNA was isolated from the cells and PTP1B mRNA levels were measured by quantitative real-time PCR using primer probe set RTS198 (forward sequence GGAGTTCGAGCAGATCGACAA, designated herein as SEQ ID NO: 36; reverse sequence GGCCACTCTACATGGGAAGTC, designated herein as SEQ ID NO: 37, probe sequence AGCTGGGCGGCCATTTACCAGGAT, designated herein as SEQ ID NO: 38). PTP1B mRNA levels were normalized to total RNA content, as measured by RIBOGREEN®. Results are presented in Table 3 as percent inhibition of PTP1B mRNA, relative to untreated control cells. The start and stop sites of each oligonucleotide on rhesus monkey SEQ ID NO: 3 (the concatenation of exons 1-9, intron 9 and exon 10 from the rhesus PTP1B scaffold (gene scaffold 240) are presented in Table 4.

TABLE 3

Dose-dependent antisense inhibition of PTP1B mRNA in LLC-MK2 cells

| ISIS No | 3.125 nM | 6.25 nM | 12.5 nM | 25.0 nM | 50.0 nM | 100.0 nM | $IC_{50}$ (nM) |
|---|---|---|---|---|---|---|---|
| 113715 | 9 | 18 | 18 | 42 | 71 | 88 | 12 |
| 404161 | 18 | 26 | 37 | 49 | 67 | 79 | 9 |
| 404169 | 9 | 33 | 36 | 52 | 70 | 85 | 8 |
| 404176 | 4 | 21 | 28 | 52 | 73 | 85 | 10 |
| 409815 | 19 | 27 | 32 | 51 | 67 | 83 | 9 |
| 409821 | 4 | 20 | 37 | 53 | 74 | 85 | 9 |
| 409826 | 7 | 31 | 63 | 46 | 62 | 78 | 8 |
| 409975 | 13 | 20 | 28 | 43 | 62 | 74 | 15 |
| 409976 | 12 | 20 | 37 | 42 | 65 | 77 | 12 |
| 409988 | 3 | 20 | 39 | 56 | 73 | 86 | 8 |
| 410003 | 16 | 24 | 36 | 43 | 65 | 80 | 11 |

TABLE 4

Target sites of antisense oligonucleotides targeting PTP1B on rhesus monkey gene sequence (SEQ ID NO: 3)

| ISIS No | Start Site | Stop Site |
|---|---|---|
| 113715 | 1035 | 1054 |
| 404161 | 2385 | 2404 |
| 409975 | 2388 | 2407 |
| 409976 | 2389 | 2408 |
| 409988 | 3566 | 3585 |
| 409821 | 3570 | 3589 |
| 404176 | 3571 | 3590 |
| 404169 | 3754 | 3773 |
| 409815 | 3755 | 3774 |
| 409826 | 4491 | 4510 |
| 410003 | 4495 | 4514 |

Example 4

Dose-Dependent Antisense Inhibition of PTP1B mRNA in Cynomolgus Primary Hepatocytes Some of the antisense oligonucleotides from the study described in Examples 1, 2 and 3 were further tested in cynomolgus primary hepatocytes at various doses. Cells were plated at a density of 35,000 cells per well and transfected using Lipofectin with 6.25 nM, 12.5 nM, 25 nM, 50 nM, 100 nM, and 200 nM concentrations of each antisense oligonucleotide. After approximately 16 hours, RNA was isolated from the cells and PTP1B mRNA levels were measured by quantitative real-time PCR using primer probe set RTS198. PTP1B mRNA levels were normalized to total RNA content, as measured by RIBOGREEN®. Results are presented in Table 5 as percent inhibition of PTP1B mRNA, relative to untreated control cells.

TABLE 5

Dose-dependent antisense inhibition of PTP1B mRNA in cynomolgus primary hepatocytes

| ISIS No | 6.25 nM | 12.5 nM | 25.0 nM | 50.0 nM | 100.0 nM | 200.0 nM | $IC_{50}$ (nM) |
|---|---|---|---|---|---|---|---|
| 373125 | 16 | 4 | 13 | 32 | 48 | 67 | 104 |
| 404161 | 7 | 3 | 24 | 40 | 56 | 77 | 72 |
| 404169 | 0 | 13 | 27 | 44 | 57 | 77 | 67 |
| 404176 | 16 | 17 | 27 | 42 | 64 | 76 | 59 |
| 409815 | 0 | 24 | 26 | 40 | 57 | 75 | 69 |
| 409821 | 0 | 9 | 25 | 37 | 60 | 73 | 73 |
| 409826 | 8 | 28 | 10 | 37 | 56 | 71 | 82 |
| 409975 | 13 | 19 | 29 | 38 | 57 | 75 | 67 |
| 409976 | 2 | 18 | 13 | 35 | 60 | 80 | 70 |
| 409988 | 16 | 22 | 28 | 41 | 59 | 77 | 61 |
| 410003 | 17 | 10 | 37 | 46 | 60 | 78 | 56 |

Example 5

Antisense Inhibition of Human PTP1B mRNA in HuVEC Cells by Oligonucleotides Designed by Microwalk Additional gapmers were designed based on ISIS 409826 that demonstrated significant inhibition of PTP1B in all cell lines tested. These gapmers were designed by creating gapmers shifted slightly upstream and downstream (i.e. "microwalk") of ISIS 409826. Oligonucleotides were also created with various motifs, e.g. 5-10-5 MOE, 5-8-5 MOE, 2-13-5 MOE, 6-8-6 MOE motifs, or were uniform oligonucleotides with deoxy and MOE units. These gapmers were tested in vitro. ISIS oligonucleotides ISIS 142082, ISIS 113715, ISIS 373125, ISIS 404161, ISIS 404172, ISIS 404173, ISIS 404176, ISIS 409825, ISIS 409827, ISIS 409828, ISIS 409829, ISIS 409845, ISIS 409998, ISIS 409999, ISIS 410000, ISIS 410001, ISIS 410002, ISIS 410003, ISIS 410004, and ISIS 410030 (from Example 1), as well as ISIS 399038, ISIS 404159, and ISIS 404174, from a previous application (CORE0061WO15), were also included in the assay for comparison. Cultured HuVEC cells at a density of 20,000 cells per well were transfected using electroporation with 2,000 nM antisense oligonucleotide. After a treatment period of approximately 24 hours, RNA was isolated from the cells and PTP1B mRNA levels were measured by quantitative real-time PCR. The human primer probe set RTS3000 was used to measure PTP1B mRNA levels. PTP1B mRNA levels were adjusted according to total RNA content, as measured by RIBOGREEN®. Results are presented as percent inhibition of PTP1B mRNA, relative to untreated control cells. The results are presented in Tables 6 and 7.

The 5-10-5 MOE gapmers are 20 nucleotides in length, wherein the central gap segment is comprised of ten 2'-deoxynucleotides and is flanked on both sides (in the 5' and 3' directions) by wings comprising five nucleotides each. The 5-8-5 MOE gapmers are 18 nucleotides in length, wherein the central gap segment is comprised of eight 2'-deoxynucleotides and is flanked on both sides (in the 5' and 3' directions) by wings comprising five nucleotides each. The 2-13-5 MOE gapmers are 20 nucleotides in length, wherein the central gap segment is comprised of thirteen 2'-deoxynucleotides and is flanked on the 5' and the 3' directions with wings comprising two and five nucleotides respectively. The 6-8-6 MOE gapmers are 18 nucleotides in length, wherein the central gap segment is comprised of eight 2'-deoxynucleotides and is flanked on both sides (in the 5' and 3' directions) by wings comprising six nucleotides each. For each of the motifs (5-10-5, 5-8-5, 2-13-5, and 6-8-6), each nucleotide in the 5' wing segment and each nucleotide in the 3' wing segment has a 2'-MOE modification. The uniform oligonucleotides have deoxy and MOE units distributed throughout the length of the oligonucleotide. The symbols for the various unit chemistries in the uniform oligonucleotide sequences are as follows: 'd'=2'-deoxyribose; 'e'=2'-O-methoxyethyl ribose. The internucleoside linkages throughout each gapmer are phosphorothioate (P═S) linkages. All cytidine residues throughout each gapmer are 5-methylcytidines. "Target start site" indicates the 5'-most nucleotide to which the gapmer is targeted. "Target stop site" indicates the 3'-most nucleotide to which the gapmer is targeted. Each gapmer listed in Table 6 is targeted SEQ ID NO: 1 (GENBANK Accession No. NM_002827.2). All the antisense oligonucleotides listed in Table 7 target SEQ ID NO: 2 (GENBANK Accession NT_011362.9 truncated from nucleotides 14178000 to 14256000).

As shown in Tables 6 and 7, several of the gapmers exhibited at least 50% inhibition, including ISIS numbers: 113715, 142082, 373125, 399038, 404159, 404161, 404172, 404173, 404176, 409826, 409827, 409999, 410000, 410001, 410002, 410003, 410004, 438371, 438372, 438373, 438374, 438375, 438377, 438379, 438380, 438381, 438382, 438383, 438384, 438439, 438442, 438443, 438444, 438445, 438450, 438451, 438452, 438453, 438454, 438455, 438456, 438458, 438459, 438460, 438461, 438462, 438464, 438465, 438468, 438469, 438472, 438473, and 438474.

Several of the gapmers exhibited at least 60% inhibition, including ISIS numbers: 113715, 142082, 373125, 399038, 404161, 404172, 404173, 404176, 409826, 409827, 409999, 410000, 410001, 410002, 410003, 438373, 438374, 438380, 438381, 438382, 438442, 438444, 438445, 438450, 438451, 438452, 438453, 438459, 438460, 438461, 438462, 438468, 438469, 438472, and 438474.

Several of the gapmers exhibited at least 70% inhibition, including ISIS numbers: 142082, 373125, 399038, 404161, 404172, 404173, 404176, 409826, 409827, 409999, 410000, 410001, 410002, 410003, 438373, 438374, 438444, 438451, 438452, 438453, 438460, 438461, 438462, 438468, 438469, 438472, and 438474.

Several of the gapmers exhibited at least 80% inhibition, including ISIS numbers: 142082, 404161, 404173, 404176, 409826, 410000, 410001, 410002, 410003, 438451, 438452, 438460, 438461, and 438474.

Several of the gapmers exhibited at least 85% inhibition, including ISIS numbers: 142082, 404161, 404173, 404176, 409826, 410001, 410002, and 410003.

Several of the gapmers exhibited at least 90% inhibition, including ISIS numbers: 142082, 404161, and 409826.

TABLE 6

Inhibition of human PTP1B mRNA levels by chimeric antisense oligonucleotides targeted to SEQ ID NO: 1

| Start Site | Stop Site | ISIS No | Sequence | Motif | % inhibition | SEQ ID NO |
|---|---|---|---|---|---|---|
| 989 | 1008 | 373125 | GGCACCTTCGATCACAGCCA | 5-10-5 MOE | 72 | 9 |
| 1035 | 1054 | 113715 | GCTCCTTCCACTGATCCTGC | 5-10-5 MOE | 68 | 10 |
| 2366 | 2385 | 404176 | TGATCAGGTCATGCACAGGC | 5-10-5 MOE | 89 | 14 |
| 3283 | 3302 | 409845 | TATTCCATGGCCATTGTAAA | 5-10-5 MOE | 32 | 19 |
| 3284 | 3303 | 404174 | TTATTCCATGGCCATTGTAA | 5-10-5 MOE | 47 | 20 |
| 3284 | 3303 | 410030 | TTATTCCATGGCCATTGTAA | 2-13-5 MOE | 47 | 20 |
| 3284 | 3303 | 438377 | $T_eT_eA_dT_dT_dC_eC_eA_dT_dG_dG_dC_dC_dA_dT_dT_dG_dT_dA_eA_e$ | Deoxy and MOE units | 52 | 20 |
| 3284 | 3303 | 438439 | $T_eT_eA_dT_dT_dC_dC_dA_dT_dG_eG_eC_dC_dA_dT_dT_dG_dT_dA_eA_e$ | Deoxy and MOE units | 53 | 20 |
| 3284 | 3303 | 438448 | $T_eT_eA_eT_dT_dC_eC_eA_dT_dG_dG_dC_dC_dA_dT_dT_dG_dT_eA_eA_e$ | Deoxy and MOE units | 34 | 20 |
| 3284 | 3303 | 438457 | $T_eT_eA_eT_dT_dC_dC_dA_eT_eG_dG_dC_dC_dA_dT_dT_dG_dT_eA_eA_e$ | Deoxy and MOE units | 35 | 20 |
| 3284 | 3303 | 438466 | TTATTCCATGGCCATTGTAA | 6-8-6 MOE | 25 | 20 |
| 3285 | 3304 | 409825 | TTTATTCCATGGCCATTGTA | 5-10-5 MOE | 47 | 21 |
| 3285 | 3304 | 409998 | TTTATTCCATGGCCATTGTA | 2-13-5 MOE | 49 | 21 |
| 3285 | 3302 | 438368 | TATTCCATGGCCATTGTA | 5-8-5 MOE | 32 | 39 |
| 3285 | 3304 | 438378 | $T_eT_eT_dA_dT_dT_eC_eC_dA_dT_dG_dG_dC_dC_dA_dT_dT_dG_dT_eA_e$ | Deoxy and MOE units | 46 | 21 |
| 3285 | 3304 | 438440 | $T_eT_eT_dA_dT_dT_dC_dC_dA_dT_eG_eG_dC_dC_dA_dT_dT_dG_dT_eA_e$ | Deoxy and MOE units | 30 | 21 |
| 3285 | 3304 | 438449 | $T_eT_eT_eA_dT_dT_eC_eC_dA_dT_dG_dG_dC_dC_dA_dT_dT_dG_eT_eA_e$ | Deoxy and MOE units | 43 | 21 |
| 3285 | 3304 | 438458 | $T_eT_eT_eA_dT_dT_dC_dC_eA_eT_dG_dG_dC_dC_dA_dT_dT_dG_eT_eA_e$ | Deoxy and MOE units | 53 | 21 |
| 3285 | 3304 | 438467 | TTTATTCCATGGCCATTGTA | 6-8-6 MOE | 33 | 21 |
| 3286 | 3305 | 399038 | GTTTATTCCATGGCCATTGT | 5-10-5 MOE | 74 | 22 |
| 3286 | 3305 | 404159 | GTTTATTCCATGGCCATTGT | 2-13-5 MOE | 54 | 22 |
| 3286 | 3303 | 438369 | TTATTCCATGGCCATTGT | 5-8-5 MOE | 33 | 40 |
| 3286 | 3305 | 438379 | $G_eT_eT_dT_dA_dT_eT_eC_dC_dA_dT_dG_dG_dC_dC_dA_dT_dT_dG_eT_e$ | Deoxy and MOE units | 51 | 22 |
| 3286 | 3305 | 438441 | $G_eT_eT_dT_dA_dT_dT_dC_dC_dA_eT_eG_dG_dC_dC_dA_dT_dT_dG_eT_e$ | Deoxy and MOE units | 40 | 22 |
| 3286 | 3305 | 438450 | $G_eT_eT_eT_dA_dT_eT_eC_dC_dA_dT_dG_dG_dC_dC_dA_dT_dT_eG_eT_e$ | Deoxy and MOE units | 64 | 22 |
| 3286 | 3305 | 438459 | $G_eT_eT_eT_dA_dT_dT_dC_eC_eA_dT_dG_dG_dC_dC_dA_dT_dT_eG_eT_e$ | Deoxy and MOE units | 68 | 22 |
| 3286 | 3305 | 438468 | GTTTATTCCATGGCCATTGT | 6-8-6 MOE | 76 | 22 |
| 3287 | 3306 | 409826 | GGTTTATTCCATGGCCATTG | 5-10-5 MOE | 93 | 23 |
| 3287 | 3306 | 409999 | GGTTTATTCCATGGCCATTG | 2-13-5 MOE | 75 | 23 |
| 3287 | 3304 | 438370 | TTTATTCCATGGCCATTG | 5-8-5 MOE | 33 | 41 |

TABLE 6-continued

Inhibition of human PTP1B mRNA levels by chimeric antisense oligonucleotides targeted to SEQ ID NO: 1

| Start Site | Stop Site | ISIS No | Sequence | Motif | % inhibition | SEQ ID NO |
|---|---|---|---|---|---|---|
| 3287 | 3306 | 438380 | $G_eG_eT_dT_dT_dA_eT_eT_dC_dC_dA_dT_dG_dG_dC_dC_dA_dT_dT_eG_e$ | Deoxy and MOE units | 63 | 23 |
| 3287 | 3306 | 438442 | $G_eG_eT_dT_dT_dA_dT_dT_dC_dC_eA_eT_dG_dG_dC_dC_dA_dT_dT_eG_e$ | Deoxy and MOE units | 67 | 23 |
| 3287 | 3306 | 438451 | $G_eG_eT_eT_dT_dA_eT_eT_dC_dC_dA_dT_dG_dG_dC_dC_dA_dT_eT_eG_e$ | Deoxy and MOE units | 83 | 23 |
| 3287 | 3306 | 438460 | $G_eG_eT_eT_dT_dA_dT_dT_eC_eC_dA_dT_dG_dG_dC_dC_dA_dT_eT_eG_e$ | Deoxy and MOE units | 82 | 23 |
| 3287 | 3306 | 438469 | GGTTTATTCCATGGCCATTG | 6-8-6 MOE | 71 | 23 |
| 3288 | 3307 | 404172 | TGGTTTATTCCATGGCCATT | 5-10-5 MOE | 76 | 24 |
| 3288 | 3307 | 410000 | TGGTTTATTCCATGGCCATT | 2-13-5 MOE | 83 | 24 |
| 3288 | 3305 | 438371 | GTTTATTCCATGGCCATT | 5-8-5 MOE | 54 | 42 |
| 3288 | 3307 | 438381 | $T_eG_eG_dT_dT_dT_eA_eT_dT_dC_dC_dA_dT_dG_dG_dC_dC_dAT_eT_e$ | Deoxy and MOE units | 69 | 24 |
| 3288 | 3307 | 438443 | $T_eG_eG_dT_dT_dT_dA_dT_dT_dC_eC_eA_dT_dG_dG_dC_dC_dA_dT_eT_e$ | Deoxy and MOE units | 50 | 24 |
| 3288 | 3307 | 438452 | $T_eG_eG_eT_dT_dT_eA_eT_dT_dC_dC_dA_dT_dG_dG_dC_dC_dA_eT_eT_e$ | Deoxy and MOE units | 82 | 24 |
| 3288 | 3307 | 438461 | $T_eG_eG_eT_dT_dT_dA_dT_eT_eC_dC_dA_dT_dG_dG_dC_dC_dA_eT_eT_e$ | Deoxy and MOE units | 81 | 24 |
| 3288 | 3307 | 438470 | TGGTTTATTCCATGGCCATT | 6-8-6 MOE | 46 | 24 |
| 3289 | 3308 | 409827 | ATGGTTTATTCCATGGCCAT | 5-10-5 MOE | 74 | 25 |
| 3289 | 3308 | 410001 | ATGGTTTATTCCATGGCCAT | 2-13-5 MOE | 85 | 25 |
| 3289 | 3306 | 438372 | GGTTTATTCCATGGCCAT | 5-8-5 MOE | 52 | 43 |
| 3289 | 3308 | 438382 | $A_eT_eG_dG_dT_dT_eT_eA_dT_dT_dC_dC_dA_dT_dG_dG_dC_dC_dA_eT_e$ | Deoxy and MOE units | 65 | 25 |
| 3289 | 3308 | 438444 | $A_eT_eG_dG_dT_dT_dT_dA_dT_dT_eC_eC_dA_dT_dG_dG_dC_dC_dA_eT_e$ | Deoxy and MOE units | 72 | 25 |
| 3289 | 3308 | 438453 | $A_eT_eG_eG_dT_dT_eT_eA_dT_dT_dC_dC_dA_dT_dG_dG_dC_dC_eA_eT_e$ | Deoxy and MOE units | 72 | 25 |
| 3289 | 3308 | 438462 | $A_eT_eG_eG_dT_dT_dT_dA_eT_eT_dC_dC_dA_dT_dG_dG_dC_dC_eA_eT_e$ | Deoxy and MOE units | 70 | 25 |
| 3289 | 3308 | 438471 | ATGGTTTATTCCATGGCCAT | 6-8-6 MOE | 45 | 25 |
| 3290 | 3309 | 404173 | AATGGTTTATTCCATGGCCA | 5-10-5 MOE | 85 | 26 |
| 3290 | 3309 | 410002 | AATGGTTTATTCCATGGCCA | 2-13-5 MOE | 85 | 26 |
| 3290 | 3307 | 438373 | TGGTTTATTCCATGGCCA | 5-8-5 MOE | 70 | 44 |
| 3290 | 3309 | 438383 | $A_eA_eT_dG_dG_dT_eT_eT_dA_dT_dT_dC_dC_dA_dT_dG_dG_dC_dC_eA_e$ | Deoxy and MOE units | 54 | 26 |
| 3290 | 3309 | 438445 | $A_eA_eT_dG_dG_dT_dT_dT_dA_dT_eT_eC_dC_dA_dT_dG_dG_dC_dC_eA_e$ | Deoxy and MOE units | 66 | 26 |
| 3290 | 3309 | 438454 | $A_eA_eT_eG_dG_dT_eT_eT_dA_dT_dT_dC_dC_dA_dT_dG_dG_dC_eC_eA_e$ | Deoxy and MOE units | 52 | 26 |
| 3290 | 3309 | 438463 | $A_eA_eT_eG_dG_dT_dT_dT_eA_eT_dT_dC_dC_dA_dT_dG_dG_dC_eC_eA_e$ | Deoxy and MOE units | 39 | 26 |

TABLE 6-continued

Inhibition of human PTP1B mRNA levels by chimeric antisense oligonucleotides targeted to SEQ ID NO: 1

| Start Site | Stop Site | ISIS No | Sequence | Motif | % inhibition | SEQ ID NO |
|---|---|---|---|---|---|---|
| 3290 | 3309 | 438472 | AATGGTTTATTCCATGGCCA | 6-8-6 MOE | 73 | 26 |
| 3291 | 3310 | 142082 | AAATGGTTTATTCCATGGCC | 5-10-5 MOE | 90 | 27 |
| 3291 | 3310 | 410003 | AAATGGTTTATTCCATGGCC | 2-13-5 MOE | 86 | 27 |
| 3291 | 3308 | 438374 | ATGGTTTATTCCATGGCC | 5-8-5 MOE | 79 | 45 |
| 3291 | 3310 | 438384 | $A_eA_eA_dT_dG_dG_eT_eT_dT_dA_dT_dT_dC_dC_dA_dT_dG_dG_dC_eC_e$ | Deoxy and MOE units | 53 | 27 |
| 3291 | 3310 | 438446 | $A_eA_eA_dT_dG_dG_dT_dT_dT_dA_eT_eT_dC_dC_dA_dT_dG_dG_dC_eC_e$ | Deoxy and MOE units | 38 | 27 |
| 3291 | 3310 | 438455 | $A_eA_eA_eT_dG_dG_eT_eT_dT_dA_dT_dT_dC_dC_dA_dT_dG_dG_eC_eC_e$ | Deoxy and MOE units | 58 | 27 |
| 3291 | 3310 | 438464 | $A_eA_eA_eT_dG_dG_dT_dT_eT_eA_dT_dT_dC_dC_dA_dT_dG_dG_eC_eC_e$ | Deoxy and MOE units | 58 | 27 |
| 3291 | 3310 | 438473 | AAATGGTTTATTCCATGGCC | 6-8-6 MOE | 57 | 27 |
| 3292 | 3311 | 409828 | AAAATGGTTTATTCCATGGC | 5-10-5 MOE | 43 | 28 |
| 3292 | 3311 | 410004 | AAAATGGTTTATTCCATGGC | 2-13-5 MOE | 58 | 28 |
| 3292 | 3309 | 438375 | AATGGTTTATTCCATGGC | 5-8-5 MOE | 55 | 46 |
| 3292 | 3311 | 438385 | $A_eA_eA_dA_dT_dG_eG_eT_dT_dT_dA_dT_dT_dC_dC_dA_dT_dG_dG_eC_e$ | Deoxy and MOE units | 36 | 28 |
| 3292 | 3311 | 438447 | $A_eA_eA_dA_dT_dG_dG_dT_dT_dT_eA_eT_dT_dC_dC_dA_dT_dG_dG_eC_e$ | Deoxy and MOE units | 35 | 28 |
| 3292 | 3311 | 438456 | $A_eA_eA_eA_dT_dG_eG_eT_dT_dT_dA_dT_dT_dC_dC_dA_dT_dG_eG_eC_e$ | Deoxy and MOE units | 58 | 28 |
| 3292 | 3311 | 438465 | $A_eA_eA_eA_dT_dG_dGT_eT_eT_dA_dT_dT_dC_dC_dA_dT_dG_eG_eC_e$ | Deoxy and MOE units | 51 | 28 |
| 3292 | 3311 | 438474 | AAAATGGTTTATTCCATGGC | 6-8-6 MOE | 82 | 28 |
| 3293 | 3312 | 409829 | AAAAATGGTTTATTCCATGG | 5-10-5 MOE | 42 | 29 |
| 3293 | 3310 | 438376 | AAATGGTTTATTCCATGG | 5-8-5 MOE | 36 | 47 |

TABLE 7

Inhibition of human PTP1B mRNA levels by chimeric antisense oligonucleotides targeted to SEQ ID NO: 2

| Start Site | Stop Site | ISIS No | Sequence | Motif | % inhibition | SEQ ID NO |
|---|---|---|---|---|---|---|
| 70726 | 70745 | 373125 | GGCACCTTCGATCACAGCCA | 5-10-5 MOE | 72 | 9 |
| 73855 | 73874 | 404161 | GGTCATTTCCATGGCCAGAG | 2-13-5 MOE | 93 | 31 |
| 75045 | 75064 | 404176 | TGATCAGGTCATGCACAGGC | 5-10-5 MOE | 89 | 14 |
| 75962 | 75981 | 409845 | TATTCCATGGCCATTGTAAA | 5-10-5 MOE | 32 | 19 |
| 75963 | 75982 | 404174 | TTATTCCATGGCCATTGTAA | 5-10-5 MOE | 47 | 20 |
| 75963 | 75982 | 410030 | TTATTCCATGGCCATTGTAA | 2-13-5 MOE | 47 | 20 |
| 75963 | 75982 | 438377 | $T_eT_eA_dT_dT_dC_eC_eA_dT_dG_dG_dC_dC_dA_dT_dT_dG_dT_dA_eA_e$ | Deoxy and MOE units | 52 | 20 |

TABLE 7-continued

Inhibition of human PTP1B mRNA levels by chimeric antisense oligonucleotides targeted to SEQ ID NO: 2

| Start Site | Stop Site | ISIS No | Sequence | Motif | % inhibition | SEQ ID NO |
|---|---|---|---|---|---|---|
| 75963 | 75982 | 438439 | $T_eT_eA_dT_dT_dC_dC_dA_dT_dG_eG_eC_dC_dA_dT_dT_dG_dT_dA_eA_e$ | Deoxy and MOE units | 53 | 20 |
| 75963 | 75982 | 438448 | $T_eT_eA_eT_dT_dC_eC_eA_dT_dG_dG_dC_dA_dT_dT_dG_dT_eA_eA_e$ | Deoxy and MOE units | 34 | 20 |
| 75963 | 75982 | 438457 | $T_eT_eA_eT_dT_dC_dC_dA_eT_eG_dG_dC_dC_dA_dT_dT_dG_dT_eA_eA_e$ | Deoxy and MOE units | 35 | 20 |
| 75963 | 75982 | 438466 | TTATTCCATGGCCATTGTAA | 6-8-6 MOE | 25 | 20 |
| 75964 | 75983 | 409825 | TTTATTCCATGGCCATTGTA | 5-10-5 MOE | 47 | 21 |
| 75964 | 75983 | 409998 | TTTATTCCATGGCCATTGTA | 2-13-5 MOE | 49 | 21 |
| 75964 | 75981 | 438368 | TATTCCATGGCCATTGTA | 5-8-5 MOE | 32 | 39 |
| 75964 | 75983 | 438378 | $T_eT_eT_dA_dT_dT_eC_eC_dA_dT_dG_dG_dC_dC_dA_dT_dT_dG_dT_eA_e$ | Deoxy and MOE units | 46 | 21 |
| 75964 | 75983 | 438440 | $T_eT_eT_dA_dT_dT_dC_dC_dA_dT_eG_eG_dC_dC_dA_dT_dT_dG_dT_eA_e$ | Deoxy and MOE units | 30 | 21 |
| 75964 | 75983 | 438449 | $T_eT_eT_eA_dT_dT_eC_eC_dA_dT_dG_dG_dC_dC_dA_dT_dT_dG_eT_eA_e$ | Deoxy and MOE units | 43 | 21 |
| 75964 | 75983 | 438458 | $T_eT_eT_eA_dT_dT_dC_dC_eA_eT_dG_dG_dC_dC_dA_dT_dT_dG_eT_eA_e$ | Deoxy and MOE units | 53 | 21 |
| 75964 | 75983 | 438467 | TTTATTCCATGGCCATTGTA | 6-8-6 MOE | 33 | 21 |
| 75965 | 75984 | 399038 | GTTTATTCCATGGCCATTGT | 5-10-5 MOE | 74 | 22 |
| 75965 | 75984 | 404159 | GTTTATTCCATGGCCATTGT | 2-13-5 MOE | 54 | 22 |
| 75965 | 75982 | 438369 | TTATTCCATGGCCATTGT | 5-8-5 MOE | 33 | 40 |
| 75965 | 75984 | 438379 | $G_eT_eT_dT_dA_dT_eT_eC_dC_dA_dT_dG_dG_dC_dC_dA_dT_dT_dG_eT_e$ | Deoxy and MOE units | 51 | 22 |
| 75965 | 75984 | 438441 | $G_eT_eT_dT_dA_dT_dT_dC_dC_dA_eT_eG_dG_dC_dC_dA_dT_dT_dG_eT_e$ | Deoxy and MOE units | 40 | 22 |
| 75965 | 75984 | 438450 | $G_eT_eT_eT_dA_dT_eT_eC_dC_dA_dT_dG_dG_dC_dC_dA_dT_dT_eG_eT_e$ | Deoxy and MOE units | 64 | 22 |
| 75965 | 75984 | 438459 | $G_eT_eT_eT_dA_dT_dT_dC_eC_eA_dT_dG_dG_dC_dC_dA_dT_dT_eG_eT_e$ | Deoxy and MOE units | 68 | 22 |
| 75965 | 75984 | 438468 | GTTTATTCCATGGCCATTGT | 6-8-6 MOE | 76 | 22 |
| 75966 | 75985 | 409826 | GGTTTATTCCATGGCCATTG | 5-10-5 MOE | 93 | 23 |
| 75966 | 75985 | 409999 | GGTTTATTCCATGGCCATTG | 2-13-5 MOE | 75 | 23 |
| 75966 | 75983 | 438370 | TTTATTCCATGGCCATTG | 5-8-5 MOE | 33 | 41 |
| 75966 | 75985 | 438380 | $G_eG_eT_dT_dT_dA_eT_eT_dC_dC_dA_dT_dG_dG_dC_dC_dA_dT_dT_eG_e$ | Deoxy and MOE units | 63 | 23 |
| 75966 | 75985 | 438442 | $G_eG_eT_dT_dT_dA_dT_dT_dC_dC_eA_eT_dG_dG_dC_dC_dA_dT_dT_eG_e$ | Deoxy and MOE units | 67 | 23 |
| 75966 | 75985 | 438451 | $G_eG_eT_eT_dT_dA_eT_eT_dC_dC_dA_dT_dG_dG_dC_dC_dA_dT_eT_eG_e$ | Deoxy and MOE units | 83 | 23 |
| 75966 | 75985 | 438460 | $G_eG_eT_eT_dT_dA_dT_dT_eC_eC_dA_dT_dG_dG_dC_dC_dA_dT_eT_eG_e$ | Deoxy and MOE units | 82 | 23 |
| 75966 | 75985 | 438469 | GGTTTATTCCATGGCCATTG | 6-8-6 MOE | 71 | 23 |
| 75967 | 75986 | 404172 | TGGTTTATTCCATGGCCATT | 5-10-5 MOE | 76 | 24 |

TABLE 7-continued

Inhibition of human PTP1B mRNA levels by chimeric antisense oligonucleotides targeted to SEQ ID NO: 2

| Start Site | Stop Site | ISIS No | Sequence | Motif | % inhibition | SEQ ID NO |
|---|---|---|---|---|---|---|
| 75967 | 75986 | 410000 | TGGTTTATTCCATGGCCATT | 2-13-5 MOE | 83 | 24 |
| 75967 | 75984 | 438371 | GTTTATTCCATGGCCATT | 5-8-5 MOE | 54 | 42 |
| 75967 | 75986 | 438381 | $T_eG_eG_dT_dT_dT_eA_eT_dT_dC_dC_dA_dT_dG_dG_dC_dC_dAT_eT_e$ | Deoxy and MOE units | 69 | 24 |
| 75967 | 75986 | 438443 | $T_eG_eG_dT_dT_dT_dA_dT_dT_dC_eC_eA_dT_dG_dG_dC_dC_dA_dT_eT_e$ | Deoxy and MOE units | 50 | 24 |
| 75967 | 75986 | 438452 | $T_eG_eG_eT_dT_dT_eA_eT_dT_dC_dC_dA_dT_dG_dG_dC_dC_dA_eT_eT_e$ | Deoxy and MOE units | 82 | 24 |
| 75967 | 75986 | 438461 | $T_eG_eG_eT_dT_dT_dA_dT_eT_eC_dC_dA_dT_dG_dG_dC_dC_dA_eT_eT_e$ | Deoxy and MOE units | 81 | 24 |
| 75967 | 75986 | 438470 | TGGTTTATTCCATGGCCATT | 6-8-6 MOE | 46 | 24 |
| 75968 | 75987 | 409827 | ATGGTTTATTCCATGGCCAT | 5-10-5 MOE | 74 | 25 |
| 75968 | 75987 | 410001 | ATGGTTTATTCCATGGCCAT | 2-13-5 MOE | 85 | 25 |
| 75968 | 75985 | 438372 | GGTTTATTCCATGGCCAT | 5-8-5 MOE | 52 | 43 |
| 75968 | 75987 | 438382 | $A_eT_eG_dG_dT_dT_eT_eA_dT_dT_dC_dC_dA_dT_dG_dG_dC_dC_dA_eT_e$ | Deoxy and MOE units | 65 | 25 |
| 75968 | 75987 | 438444 | $A_eT_eG_dG_dT_dT_dT_dA_dT_dT_eC_eC_dA_dT_dG_dG_dC_dC_dA_eT_e$ | Deoxy and MOE units | 72 | 25 |
| 75968 | 75987 | 438453 | $A_eT_eG_eG_dT_dT_eT_eA_dT_dT_dC_dC_dA_dT_dG_dG_dC_dC_eA_eT_e$ | Deoxy and MOE units | 72 | 25 |
| 75968 | 75987 | 438462 | $A_eT_eG_eG_dT_dT_dT_dA_eT_eT_dC_dC_dA_dT_dG_dG_dC_dC_eA_eT_e$ | Deoxy and MOE units | 70 | 25 |
| 75968 | 75987 | 438471 | ATGGTTTATTCCATGGCCAT | 6-8-6 MOE | 45 | 25 |
| 75969 | 75988 | 404173 | AATGGTTTATTCCATGGCCA | 5-10-5 MOE | 85 | 26 |
| 75969 | 75988 | 410002 | AATGGTTTATTCCATGGCCA | 2-13-5 MOE | 85 | 26 |
| 75969 | 75986 | 438373 | TGGTTTATTCCATGGCCA | 5-8-5 MOE | 70 | 44 |
| 75969 | 75988 | 438383 | $A_eA_eT_dG_dG_dT_eT_eT_dA_dT_dT_dC_dC_dA_dT_dG_dG_dC_dC_eA_e$ | Deoxy and MOE units | 54 | 26 |
| 75969 | 75988 | 438445 | $A_eA_eT_dG_dG_dT_dT_dT_dA_dT_eT_eC_dC_dA_dT_dG_dG_dC_dC_eA_e$ | Deoxy and MOE units | 66 | 26 |
| 75969 | 75988 | 438454 | $A_eA_eT_eG_dG_dT_eT_eT_dA_dT_dT_dC_dC_dA_dT_dG_dG_dC_eC_eA_e$ | Deoxy and MOE units | 52 | 26 |
| 75969 | 75988 | 438463 | $A_eA_eT_eG_dG_dT_dT_dT_eA_eT_dT_dC_dC_dA_dT_dG_dG_dC_eC_eA_e$ | Deoxy and MOE units | 39 | 26 |
| 75969 | 75988 | 438472 | AATGGTTTATTCCATGGCCA | 6-8-6 MOE | 73 | 26 |
| 75970 | 75989 | 142082 | AAATGGTTTATTCCATGGCC | 5-10-5 MOE | 90 | 27 |
| 75970 | 75989 | 410003 | AAATGGTTTATTCCATGGCC | 2-13-5 MOE | 86 | 27 |
| 75970 | 75987 | 438374 | ATGGTTTATTCCATGGCC | 5-8-5 MOE | 79 | 45 |
| 75970 | 75989 | 438384 | $A_eA_eA_dT_dG_dG_eT_eT_dT_dA_dT_dT_dC_dC_dA_dT_dG_dG_dC_eC_e$ | Deoxy and MOE units | 53 | 27 |
| 75970 | 75989 | 438446 | $A_eA_eA_dT_dG_dG_dT_dT_dT_dA_eT_eT_dC_dC_dA_dT_dG_dG_dC_eC_e$ | Deoxy and MOE units | 38 | 27 |
| 75970 | 75989 | 438455 | $A_eA_eA_eT_dG_dG_eT_eT_dT_dA_dT_dT_dC_dC_dA_dT_dG_dG_eC_eC_e$ | Deoxy and MOE units | 58 | 27 |

TABLE 7-continued

Inhibition of human PTP1B mRNA levels by chimeric antisense oligonucleotides targeted to SEQ ID NO: 2

| Start Site | Stop Site | ISIS No | Sequence | Motif | % inhibition | SEQ ID NO |
|---|---|---|---|---|---|---|
| 75970 | 75989 | 438464 | $A_eA_eA_eT_dG_dG_dT_dT_eT_eA_dT_dT_dC_dC_dA_dT_dG_dG_eC_eC_e$ | Deoxy and MOE units | 58 | 27 |
| 75970 | 75989 | 438473 | AAATGGTTTATTCCATGGCC | 6-8-6 MOE | 57 | 27 |
| 75971 | 75990 | 409828 | AAAATGGTTTATTCCATGGC | 5-10-5 MOE | 43 | 28 |
| 75971 | 75990 | 410004 | AAAATGGTTTATTCCATGGC | 2-13-5 MOE | 58 | 28 |
| 75971 | 75988 | 438375 | AATGGTTTATTCCATGGC | 5-8-5 MOE | 55 | 46 |
| 75971 | 75990 | 438385 | $A_eA_eA_dA_dT_dG_eG_eT_dT_dT_dA_dT_dT_dC_dC_dA_dT_dG_dG_eC_e$ | Deoxy and MOE units | 36 | 28 |
| 75971 | 75990 | 438447 | $A_eA_eA_dA_dT_dG_dG_dT_dT_dT_eA_eT_dT_dC_dC_dA_dT_dG_dG_eC_e$ | Deoxy and MOE units | 35 | 28 |
| 75971 | 75990 | 438456 | $A_eA_eA_eA_dT_dG_eG_eT_dT_dT_dA_dT_dT_dC_dC_dA_dT_dG_eG_eC_e$ | Deoxy and MOE units | 58 | 28 |
| 75971 | 75990 | 438465 | $A_eA_eA_eA_dT_dG_dGT_eT_eT_dA_dT_dT_dC_dC_dA_dT_dG_eG_eC_e$ | Deoxy and MOE units | 51 | 28 |
| 75971 | 75990 | 438474 | AAAATGGTTTATTCCATGGC | 6-8-6 MOE | 82 | 28 |
| 75972 | 75991 | 409829 | AAAAATGGTTTATTCCATGG | 5-10-5 MOE | 42 | 29 |
| 75972 | 75989 | 438376 | AAATGGTTTATTCCATGG | 5-8-5 MOE | 36 | 47 |

Example 6

Dose-Dependent Antisense Inhibition of Human PTP1B mRNA in HuVEC Cells

Several antisense oligonucleotides, which displayed significant antisense inhibition of PTP1B mRNA in the study described in Example 5 were further tested in HuVEC cells at various doses. Cells were plated at a density of 2,000 cells per well and transfected by electroporation with 31.25 nM, 62.5 nM, 125 nM, 250 nM, 500 nM, 1000 nM, 2000 nM and 4000 nM concentrations of each antisense oligonucleotide. After approximately 16 hours, RNA was isolated from the cells and PTP1B mRNA levels were measured by quantitative real-time PCR using primer probe set RTS3000. PTP1B mRNA levels were normalized to total RNA content, as measured by RIBOGREEN®. Results are presented in Table 8 as percent inhibition of PTP1B mRNA, relative to untreated control cells.

TABLE 8

Dose-dependent antisense inhibition of human PTP1B in HuVEC cells

| ISIS No | 31.25 nM | 62.5 nM | 125.0 nM | 250.0 nM | 500.0 nM | 1000.0 nM | 2000.0 nM | 4000.0 nM | $IC_{50}$ (μM) |
|---|---|---|---|---|---|---|---|---|---|
| 142082 | 15 | 30 | 40 | 42 | 71 | 84 | 90 | 94 | 0.2 |
| 404173 | 15 | 19 | 33 | 54 | 69 | 81 | 86 | 93 | 0.2 |
| 404176 | 9 | 26 | 34 | 34 | 67 | 80 | 88 | 94 | 0.3 |
| 409826 | 17 | 16 | 28 | 44 | 60 | 73 | 85 | 95 | 0.3 |
| 410002 | 0 | 0 | 24 | 52 | 54 | 77 | 90 | 96 | 0.4 |
| 410003 | 9 | 7 | 19 | 46 | 60 | 80 | 91 | 95 | 0.4 |
| 438374 | 20 | 22 | 40 | 44 | 59 | 70 | 79 | 85 | 0.3 |
| 438460 | 14 | 21 | 23 | 42 | 62 | 78 | 85 | 95 | 0.3 |
| 438474 | 27 | 0 | 13 | 34 | 42 | 68 | 74 | 86 | 0.6 |

Example 7

Dose-Dependent Antisense Inhibition of Human mRNA PTP1B in HepG2 Cells

The antisense oligonucleotides, tested in the study described in Example 6, were further tested in HepG2 cells at various doses. Cells were plated at a density of 20,000 cells per well and transfected by electroporation with 31.25 nM, 62.5 nM, 125 nM, 250 nM, 500 nM, 1000 nM, 2000 nM and 4000 nM concentrations of each antisense oligonucleotide. After approximately 16 hours, RNA was isolated from the cells and PTP1B mRNA levels were measured by quantitative real-time PCR using primer probe set RTS3000. PTP1B mRNA levels were normalized to total RNA content, as measured by RIBOGREEN®. Results are presented in Table 9 as percent inhibition of PTP1B mRNA, relative to untreated control cells. The mRNA levels were also analyzed using rhesus monkey primer probe set RTS198, and the results are presented in Table 10. The start and stop sites of each oligonucleotide on rhesus monkey SEQ ID NO: 3 are presented in Table 11.

TABLE 9

Analysis of dose-dependent antisense inhibition of human PTP1B in HepG2 cells using RTS3000

| ISIS No | 31.25 nM | 62.5 nM | 125.0 nM | 250.0 nM | 500.0 nM | 1000.0 nM | 2000.0 nM | 4000.0 nM | $IC_{50}$ (μM) |
|---|---|---|---|---|---|---|---|---|---|
| 142082 | 0 | 0 | 7 | 0 | 26 | 38 | 60 | 82 | 1.4 |
| 404173 | 2 | 0 | 1 | 19 | 0 | 29 | 47 | 80 | 1.9 |
| 404176 | 0 | 0 | 5 | 13 | 2 | 33 | 62 | 79 | 1.7 |
| 409826 | 0 | 0 | 0 | 2 | 15 | 29 | 46 | 76 | 1.9 |
| 410002 | 13 | 6 | 0 | 11 | 8 | 28 | 44 | 75 | 2.0 |
| 410003 | 0 | 0 | 9 | 11 | 22 | 33 | 30 | 83 | 1.9 |
| 438374 | 0 | 0 | 17 | 11 | 23 | 38 | 33 | 61 | 2.9 |
| 438460 | 4 | 0 | 10 | 11 | 9 | 26 | 52 | 79 | 1.8 |
| 438474 | 0 | 0 | 2 | 11 | 6 | 20 | 52 | 54 | 2.8 |

TABLE 10

Analysis of dose-dependent antisense inhibition of human PTP1B in HepG2 cells using RTS198

| ISIS No | 31.25 nM | 62.5 nM | 125.0 nM | 250.0 nM | 500.0 nM | 1000.0 nM | 2000.0 nM | 4000.0 nM | $IC_{50}$ (μM) |
|---|---|---|---|---|---|---|---|---|---|
| 142082 | 14 | 19 | 2 | 0 | 80 | 41 | 63 | 80 | 1.5 |
| 404173 | 0 | 0 | 2 | 0 | 16 | 26 | 60 | 83 | 1.6 |
| 404176 | 0 | 0 | 0 | 5 | 0 | 31 | 59 | 80 | 1.9 |
| 409826 | 0 | 0 | 0 | 16 | 23 | 10 | 49 | 72 | 2.3 |
| 410002 | 0 | 0 | 0 | 0 | 0 | 0 | 40 | 100 | >4.0 |
| 410003 | 0 | 1 | 12 | 0 | 10 | 41 | 51 | 82 | 1.6 |
| 438374 | 0 | 0 | 0 | 9 | 43 | 22 | 49 | 55 | 2.8 |
| 438460 | 0 | 0 | 0 | 9 | 30 | 42 | 47 | 81 | 1.4 |
| 438474 | 2 | 0 | 9 | 38 | 19 | 31 | 49 | 60 | 2.5 |

TABLE 11

Target sites of antisense oligonucleotides targeting PTP1B on rhesus monkey gene sequence (SEQ ID NO: 3)

| OligoID | Start Site | Stop Site | SEQ ID NO |
|---|---|---|---|
| 142082 | 4495 | 4514 | 27 |
| 404173 | 4494 | 4513 | 26 |
| 404176 | 3571 | 3590 | 14 |
| 409826 | 4491 | 4510 | 23 |
| 410002 | 4494 | 4513 | 26 |
| 410003 | 4495 | 4514 | 27 |
| 438374 | 4495 | 4512 | 45 |
| 438460 | 4491 | 4510 | 23 |
| 438474 | 4496 | 4515 | 28 |

Example 8

Dose-Dependent Antisense Inhibition of Human PTP1B mRNA in HepG2 Cells

Short antisense oligonucleotides to the target site of ISIS 142082 were designed. The target sites, motifs and sequence details of these shortmers are presented in Table 12. These antisense oligonucleotides were tested in HepG2 cells at various doses. Some of the antisense oligonucleotides from the study described in Example 7 were included in the assay for comparison. Cells were plated at a density of 20,000 cells per well and transfected by electroporation with 78.125 nM, 156.25 nM, 312.5 nM, 625 nM, 1,250 nM, 2,500 nM, 5,000 nM and 10,000 nM concentrations of each antisense oligonucleotide. After approximately 16 hours, RNA was isolated from the cells and PTP1B mRNA levels were measured by quantitative real-time PCR using primer probe set RTS3000. PTP1B mRNA levels were normalized to total RNA content, as measured by RIBOGREEN®. Results are presented in Table 13 as percent inhibition of PTP1B mRNA, relative to untreated control cells.

TABLE 12

Target sites of antisense oligonucleotides targeting SEQ ID NO: 1

| ISIS No | Start Site | Stop Site | Sequence | Motif | SEQ ID NO |
|---|---|---|---|---|---|
| 142082 | 3291 | 3310 | AAATGGTTTATTCCATGGCC | 5-10-5 | 27 |
| 446431 | 3292 | 3309 | AATGGTTTATTCCATGGC | 4-10-4 | 46 |
| 446432 | 3293 | 3308 | ATGGTTTATTCCATGG | 3-10-3 | 48 |

TABLE 13

Dose-dependent antisense inhibition of human PTP1B in HepG2 cells

| ISIS No | 78.125 nM | 156.25 nM | 312.5 nM | 625.0 nM | 1250.0 nM | 2500.0 nM | 5000.0 nM | 10000.0 nM | $IC_{50}$ (μM) |
|---|---|---|---|---|---|---|---|---|---|
| 113715 | 6 | 12 | 17 | 17 | 16 | 45 | 61 | 86 | 3.3 |
| 142082 | 14 | 34 | 23 | 47 | 60 | 81 | 86 | 90 | 0.8 |
| 404173 | 8 | 22 | 29 | 45 | 60 | 73 | 83 | 88 | 0.8 |
| 409826 | 19 | 18 | 41 | 56 | 75 | 84 | 89 | 91 | 0.5 |
| 410003 | 0 | 0 | 19 | 39 | 55 | 81 | 91 | 92 | 1.0 |
| 446431 | 10 | 24 | 26 | 38 | 57 | 74 | 85 | 92 | 1.0 |
| 446432 | 0 | 8 | 10 | 10 | 10 | 26 | 40 | 67 | 6.0 |

Example 9

Dose-Dependent Antisense Inhibition of PTP1B mRNA in LLC-MK2 Cells

The antisense oligonucleotides from the study described in Example 8 are also cross-reactive with rhesus monkey PTP1B gene sequence (SEQ ID NO: 3) and were further tested in rhesus monkey LLC-MK2 cells at various doses. Cells were plated at a density of 25,000 cells per well and transfected using electroporation with 78.125 nM, 156.25 nM, 312.5 nM, 625 nM, 1250 nM, 2500 nM, 5,000 nM, and 10,000 nM concentrations of each antisense oligonucleotide. After approximately 16 hours, RNA was isolated from the cells and PTP1B mRNA levels were measured by quantitative real-time PCR using primer probe set RTS198. PTP1B mRNA levels were normalized to total RNA content, as measured by RIBOGREEN®. Results are presented in Table 14 as percent inhibition of PTP1B mRNA, relative to untreated control cells. The start and stop sites of each oligonucleotide on rhesus monkey SEQ ID NO: 3 are presented in Table 15.

TABLE 14

Dose-dependent antisense inhibition of PTP1B mRNA in LLC-MK2 cells

| ISIS No | 78.125 nM | 156.25 nM | 312.5 nM | 625.0 nM | 1250.0 nM | 2500.0 nM | 5000.0 nM | 10000.0 nM | $IC_{50}$ (μM) |
|---|---|---|---|---|---|---|---|---|---|
| 113715 | 0 | 0 | 4 | 13 | 27 | 53 | 57 | 70 | 3.3 |
| 142082 | 2 | 12 | 31 | 41 | 69 | 74 | 80 | 92 | 0.9 |
| 404173 | 2 | 0 | 22 | 29 | 36 | 61 | 78 | 84 | 1.6 |
| 409826 | 12 | 0 | 19 | 38 | 66 | 66 | 82 | 92 | 1.2 |
| 410003 | 0 | 0 | 0 | 26 | 32 | 65 | 81 | 91 | 1.8 |
| 446431 | 0 | 0 | 9 | 32 | 45 | 70 | 79 | 58 | 1.4 |
| 446432 | 0 | 0 | 7 | 16 | 10 | 20 | 26 | 43 | 37.0 |

TABLE 15

Target sites of antisense oligonucleotides targeting SEQ ID NO: 3

| ISIS No | Start Site | Stop Site | Sequence | SEQ ID NO |
|---|---|---|---|---|
| 113715 | 1035 | 1054 | GCTCCTTCCACTGATCCTGC | 10 |
| 142082 | 4495 | 4514 | AAATGGTTTATTCCATGGCC | 27 |
| 404173 | 4494 | 4513 | AATGGTTTATTCCATGGCCA | 26 |
| 409826 | 4491 | 4510 | GGTTTATTCCATGGCCATTG | 23 |
| 410003 | 4495 | 4514 | AAATGGTTTATTCCATGGCC | 27 |
| 446431 | 4496 | 4513 | AATGGTTTATTCCATGGC | 46 |
| 446432 | 4497 | 4512 | ATGGTTTATTCCATGG | 48 |

Example 10

Dose-Dependent Antisense Inhibition of Human PTP1B mRNA in HuVEC Cells

The antisense oligonucleotides, tested in the study described in Examples 8 and 9, were further tested in HuVEC cells at various doses. Cells were plated at a density of 20,000 cells per well and transfected by electroporation with 31.25 nM, 62.5 nM, 125 nM, 250 nM, 500 nM, 1000 nM, 2000 nM and 4000 nM concentrations of each antisense oligonucleotide. After approximately 16 hours, RNA was isolated from the cells and PTP1B mRNA levels were measured by quantitative real-time PCR using primer probe set RTS3000. PTP1B mRNA levels were normalized to total RNA content, as measured by RIBOGREEN®. Results are presented in Table 16 as percent inhibition of PTP1B mRNA, relative to untreated control cells.

TABLE 16

Dose-dependent antisense inhibition of human PTP1B in HuVEC cells

| ISIS No | 31.25 nM | 62.5 nM | 125.0 nM | 250.0 nM | 500.0 nM | 1000.0 nM | 2000.0 nM | 4000.0 nM | $IC_{50}$ (μM) |
|---|---|---|---|---|---|---|---|---|---|
| 113715 | 10 | 0 | 22 | 24 | 65 | 86 | 92 | 98 | 0.2 |
| 142082 | 52 | 78 | 89 | 93 | 95 | 96 | 98 | 98 | <0.3 |
| 404173 | 35 | 66 | 80 | 89 | 95 | 98 | 97 | 97 | 0.05 |
| 409826 | 57 | 72 | 82 | 64 | 97 | 98 | 98 | 98 | <0.3 |
| 410003 | 43 | 47 | 75 | 84 | 48 | 95 | 96 | 91 | 0.05 |
| 446431 | 33 | 63 | 75 | 87 | 96 | 97 | 98 | 98 | 0.05 |
| 446432 | 0 | 11 | 30 | 45 | 66 | 79 | 85 | 76 | 0.3 |

Example 11

Dose-Dependent Antisense Inhibition of PTP1B mRNA in Cynomolgus Primary Hepatocytes The antisense oligonucleotides from the study described in Examples 8-10 were further tested in cynomolgus primary hepatocytes at various doses. Cells were plated at a density of 35,000 cells per well and transfected using electroporation with 31.25 nM, 62.5 nM, 125 nM, 250 nM, 500 nM, 1,000 nM, 2,000 nM, and 4,000 nM concentrations of each antisense oligonucleotide. After approximately 16 hours, RNA was isolated from the cells and PTP1B mRNA levels were measured by quantitative real-time PCR using primer probe set RTS198. PTP1B mRNA levels were normalized to total RNA content, as measured by RIBOGREEN®. Results are presented in Table 17 as percent inhibition of PTP1B mRNA, relative to untreated control cells.

TABLE 17

Dose-dependent antisense inhibition of PTP1B mRNA in cynomolgus primary hepatocytes

| ISIS No | 31.25 nM | 62.5 nM | 125.0 nM | 250.0 nM | 500.0 nM | 1000.0 nM | 2000.0 nM | 4000.0 nM | $IC_{50}$ (μM) |
|---|---|---|---|---|---|---|---|---|---|
| 113715 | 4 | 26 | 25 | 43 | 46 | 73 | 82 | 95 | 0.4 |
| 142082 | 25 | 37 | 50 | 67 | 74 | 87 | 86 | 88 | 0.1 |
| 404173 | 18 | 20 | 43 | 54 | 67 | 82 | 85 | 89 | 0.2 |
| 409826 | 34 | 47 | 51 | 65 | 76 | 87 | 88 | 90 | 0.1 |
| 410003 | 8 | 20 | 44 | 53 | 68 | 79 | 80 | 83 | 0.2 |
| 446431 | 9 | 14 | 35 | 54 | 57 | 79 | 79 | 88 | 0.3 |
| 446432 | 4 | 0 | 1 | 3 | 0 | 11 | 6 | 37 | >4.0 |

Example 12

Tolerability of Antisense Oligonucleotides Targeting Human PTP1B in a Mouse Model ISIS oligonucleotides that demonstrated dose-dependent inhibition in the studies described in Examples 8-11 were evaluated for tolerability in a mouse model by monitoring changes in the levels of various metabolic markers in CD1 mice. Two more ISIS oligonucleotides, ISIS 446433 (4-10-4 MOE; 5'-GTTTATTCCATGGCCATT-3' (SEQ ID NO: 42); target start site at SEQ ID NO: 1 is 3288) and ISIS 446434 (3-10-3; 5'-TTTATTCCATGGCCAT-3' (SEQ ID NO: 49); target start site at SEQ ID NO: 1 is 3289) were designed as shortmers to ISIS 409826 (target start site at SEQ ID NO: 1 is 3287) and were also evaluated in this study.

Treatment

CD1 mice (available from Jackson Labs, Bar Harbor, Me.) were maintained on a 12-hour light/dark cycle and fed ad libitum normal lab chow (Harlan Laboratories, Indianapolis, Ind.). Animals were acclimated for at least 7 days in the research facility before initiation of the experiment. Antisense oligonucleotides were prepared in PBS and sterilized by filtering through a 0.2 micron filter. Oligonucleotides were dissolved in 0.9% PBS for injection.

Groups of five CD1 mice each were injected subcutaneously twice a week with 100 mg/kg of ISIS 142082, ISIS 373125, ISIS 404173, ISIS 409826, ISIS 410002, ISIS 410003, ISIS 438452, ISIS 438460, ISIS 446431, ISIS 446432, ISIS 446433, or ISIS 446434 for 4 weeks. One group of five CD1 mice was injected subcutaneously twice a week with PBS for 4 weeks. This PBS group served as the control group. Blood samples were collected via tail snipping. Two days after the last dose, body weights were taken, mice were euthanized and organs and plasma were harvested for further analysis.

Body and Organ Weights

The body weights of the mice were measured weekly. The body weights are presented in Table 18. Liver, spleen and kidney weights were measured at the end of the study, and are presented in Table 19. The results demonstrate that none of the ISIS oligonucleotides had any adverse effect on the overall health of the mice.

TABLE 18

Weekly body weights of CD1 mice during antisense oligonucleotide treatment (g)

| | Week 1 | Week 2 | Week 3 | Week 4 |
|---|---|---|---|---|
| PBS | 29 | 31 | 32 | 34 |
| ISIS 142082 | 31 | 34 | 34 | 36 |
| ISIS 373125 | 29 | 31 | 32 | 35 |
| ISIS 404173 | 31 | 33 | 34 | 36 |
| ISIS 409826 | 31 | 34 | 34 | 37 |
| ISIS 410002 | 32 | 35 | 35 | 36 |
| ISIS 410003 | 31 | 34 | 34 | 37 |
| ISIS 438452 | 32 | 35 | 36 | 39 |

TABLE 18-continued

| Weekly body weights of CD1 mice during antisense oligonucleotide treatment (g) | | | | |
|---|---|---|---|---|
| | Week 1 | Week 2 | Week 3 | Week 4 |
| ISIS 438460 | 31 | 34 | 34 | 37 |
| ISIS 446431 | 30 | 33 | 33 | 36 |
| ISIS 446432 | 27 | 30 | 30 | 33 |
| ISIS 446433 | 30 | 33 | 33 | 37 |
| ISIS 446434 | 30 | 33 | 34 | 37 |

TABLE 19

| Organ weights of CD1 mice after antisense oligonucleotide treatment (g) | | | | |
|---|---|---|---|---|
| | Liver | Fat | Spleen | Kidney |
| PBS | 1.7 | 0.45 | 0.11 | 0.53 |
| ISIS 142082 | 2.3 | 0.33 | 0.18 | 0.52 |
| ISIS 373125 | 1.9 | 0.38 | 0.16 | 0.53 |
| ISIS 404173 | 2.3 | 0.41 | 0.23 | 0.59 |
| ISIS 409826 | 2.2 | 0.37 | 0.17 | 0.54 |
| ISIS 410002 | 1.9 | 0.22 | 0.30 | 0.76 |
| ISIS 410003 | 2.1 | 0.44 | 0.22 | 0.60 |
| ISIS 438452 | 2.2 | 0.42 | 0.18 | 0.55 |
| ISIS 438460 | 2.2 | 0.34 | 0.17 | 0.52 |
| ISIS 446431 | 2.1 | 0.34 | 0.19 | 0.53 |
| ISIS 446432 | 1.7 | 0.31 | 0.13 | 0.46 |
| ISIS 446433 | 2.2 | 0.35 | 0.17 | 0.53 |
| ISIS 446434 | 2.2 | 0.36 | 0.18 | 0.56 |

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured bi-weekly. The results are presented in Tables 20 and 21, and indicate that most of the ISIS oligonucleotides were considered tolerable in the mice, as demonstrated by their liver transaminase profile.

TABLE 20

| Effect of antisense oligonucleotide treatment on ALT (IU/L) of CD1 mice | | | |
|---|---|---|---|
| | Week 0 | Week 2 | Week 4 |
| PBS | 27 | 26 | 20 |
| ISIS 142082 | 38 | 35 | 105 |
| ISIS 373125 | 30 | 27 | 51 |
| ISIS 404173 | 30 | 31 | 124 |
| ISIS 409826 | 26 | 34 | 236 |
| ISIS 410002 | 27 | 203 | 219 |
| ISIS 410003 | 31 | 29 | 99 |
| ISIS 438452 | 32 | 40 | 217 |
| ISIS 438460 | 30 | 40 | 216 |
| ISIS 446431 | 29 | 38 | 114 |
| ISIS 446432 | 26 | 27 | 35 |
| ISIS 446433 | 25 | 76 | 115 |
| ISIS 446434 | 23 | 44 | 146 |

TABLE 21

| Effect of antisense oligonucleotide treatment on AST (IU/L) of CD1 mice | | | |
|---|---|---|---|
| | Week 0 | Week 2 | Week 4 |
| PBS | 54 | 62 | 50 |
| ISIS 142082 | 75 | 59 | 103 |
| ISIS 373125 | 55 | 57 | 97 |
| ISIS 404173 | 52 | 61 | 117 |

TABLE 21-continued

| Effect of antisense oligonucleotide treatment on AST (IU/L) of CD1 mice | | | |
|---|---|---|---|
| | Week 0 | Week 2 | Week 4 |
| ISIS 409826 | 49 | 59 | 192 |
| ISIS 410002 | 51 | 151 | 417 |
| ISIS 410003 | 64 | 47 | 122 |
| ISIS 438452 | 59 | 56 | 157 |
| ISIS 438460 | 65 | 56 | 217 |
| ISIS 446431 | 56 | 66 | 140 |
| ISIS 446432 | 50 | 51 | 74 |
| ISIS 446433 | 54 | 87 | 121 |
| ISIS 446434 | 42 | 64 | 132 |

Plasma Glucose Levels

To evaluate the effect of ISIS oligonucleotides on glucose metabolism, plasma levels of glucose were measured using an automated clinical chemistry analyzer (Hitachi Olympus AU400e, Melville, N.Y.). Results are presented in Table 22, expressed in mg/dL. None of the ISIS oligonucleotides had any adverse effects on the glucose metabolism of the mice.

TABLE 22

| Effect of antisense oligonucleotide treatment on plasma glucose levels in CD1 mice | | | |
|---|---|---|---|
| | Week 0 | Week 2 | Week 4 |
| PBS | 175 | 188 | 182 |
| ISIS 142082 | 195 | 178 | 161 |
| ISIS 373125 | 187 | 201 | 177 |
| ISIS 404173 | 185 | 213 | 168 |
| ISIS 409826 | 183 | 187 | 187 |
| ISIS 410002 | 183 | 164 | 137 |
| ISIS 410003 | 198 | 218 | 168 |
| ISIS 438452 | 168 | 197 | 175 |
| ISIS 438460 | 212 | 203 | 169 |
| ISIS 446431 | 192 | 188 | 148 |
| ISIS 446432 | 194 | 193 | 175 |
| ISIS 446433 | 216 | 198 | 151 |
| ISIS 446434 | 199 | 189 | 159 |

Plasma Lipid and Triglyceride Levels

To evaluate the effect of ISIS oligonucleotides on cholesterol and triglyceride metabolism, plasma levels of each were measured using an automated clinical chemistry analyzer (Hitachi Olympus AU400e, Melville, N.Y.). Results are presented in Tables 23 and 24, expressed in mg/dL. Most of the ISIS oligonucleotides did not have any adverse effects of the lipid metabolism of the mice.

TABLE 23

| Effect of antisense oligonucleotide treatment on plasma cholesterol levels in CD1 mice | | | |
|---|---|---|---|
| | Week 0 | Week 2 | Week 4 |
| PBS | 162 | 145 | 153 |
| ISIS 142082 | 156 | 136 | 126 |
| ISIS 373125 | 137 | 106 | 104 |
| ISIS 404173 | 162 | 124 | 154 |
| ISIS 409826 | 153 | 142 | 146 |
| ISIS 410002 | 136 | 63 | 47 |
| ISIS 410003 | 160 | 131 | 96 |
| ISIS 438452 | 143 | 128 | 121 |
| ISIS 438460 | 146 | 140 | 129 |
| ISIS 446431 | 139 | 124 | 116 |
| ISIS 446432 | 146 | 135 | 137 |
| ISIS 446433 | 152 | 144 | 145 |
| ISIS 446434 | 147 | 147 | 144 |

TABLE 24

Effect of antisense oligonucleotide treatment on plasma triglyceride levels in CD1 mice

| | Week 0 | Week 2 | Week 4 |
|---|---|---|---|
| PBS | 153 | 153 | 162 |
| ISIS 142082 | 170 | 153 | 114 |
| ISIS 373125 | 142 | 116 | 112 |
| ISIS 404173 | 195 | 140 | 107 |
| ISIS 409826 | 182 | 120 | 80 |
| ISIS 410002 | 137 | 99 | 51 |
| ISIS 410003 | 152 | 138 | 102 |
| ISIS 438452 | 123 | 134 | 93 |
| ISIS 438460 | 165 | 146 | 85 |
| ISIS 446431 | 131 | 160 | 123 |
| ISIS 446432 | 168 | 194 | 136 |
| ISIS 446433 | 186 | 117 | 133 |
| ISIS 446434 | 145 | 101 | 84 |

Cytokine Levels

To evaluate the effect of ISIS oligonucleotides on factors involved in inflammation, blood was collected after the end of the treatment period for measurement of cytokine levels. The samples were sent to Aushon Biosystems (Woburn, Mass.) for analysis. Levels of murine IL-6, JE, MIP-1α, and TNF-α were measured using murine antibodies. The results are presented in Table 25. Most of the ISIS oligonucleotides did not have any adverse effects on the cytokine levels of the mice.

TABLE 25

Effect of antisense oligonucleotide treatment on plasma cytokine levels in CD1 mice

| | mIL-6 | mJE | mMIP-1α | mTNF-α |
|---|---|---|---|---|
| PBS | 250 | 20 | 1 | 4 |
| ISIS 142082 | 225 | 145 | 4 | 23 |
| ISIS 373125 | 77 | 91 | 3 | 17 |
| ISIS 404173 | 88 | 155 | 1 | 24 |
| ISIS 409826 | 33 | 112 | 3 | 15 |
| ISIS 410002 | 113 | 225 | 28 | 84 |
| ISIS 410003 | 111 | 138 | 4 | 24 |
| ISIS 438452 | 62 | 148 | 1 | 15 |
| ISIS 438460 | 64 | 184 | 2 | 9 |
| ISIS 446431 | 52 | 170 | 1 | 15 |
| ISIS 446432 | 57 | 75 | 1 | 3 |
| ISIS 446433 | 64 | 138 | 3 | 61 |
| ISIS 446434 | 59 | 127 | 0 | 21 |

Example 13

Tolerability of Antisense Oligonucleotides Targeting Human PTP1B in a Rat Model The ISIS oligonucleotides from the study described in Example 12 were further evaluated for tolerability in a rat model by monitoring changes in the levels of various metabolic markers in Sprague Dawley rats.

Treatment

Sprague Dawley rats were maintained on a 12-hour light/dark cycle and fed ad libitum normal lab chow (Harlan Laboratories, Indianapolis, Ind.). Animals were acclimated for at least 7 days in the research facility before initiation of the experiment. Antisense oligonucleotides were prepared in PBS and sterilized by filtering through a 0.2 micron filter. Oligonucleotides were dissolved in 0.9% PBS for injection.

Groups of four rats each were injected subcutaneously twice a week with ISIS 142082, ISIS 373125, ISIS 404173, ISIS 409826, ISIS 410002, ISIS 410003, ISIS 438452, ISIS 438460, ISIS 446431, ISIS 446432, ISIS 446433, or ISIS 446434 at a dose of 50 mg/kg twice a week for 4 weeks, followed by a dose of 30 mg/kg twice a week for 8 weeks. One group of four rats was injected subcutaneously twice a week with PBS for 12 weeks. This PBS group served as the control group. Blood samples were collected via tail snipping. Two days after the last dose, body weights were taken, rats were euthanized and organs and plasma were harvested for further analysis.

Body and Organ Weights

The body weights of the rats were measured weekly. The body weights are presented in Table 26. Liver, spleen and kidney weights were measured at the end of the study, and are presented in Table 27. 'n/a' indicates no data being available for that particular group at that particular time point due to all the rats in the group being euthanized before the time point.

TABLE 26

Bi-weekly body weights of Sprague Dawley rats during antisense oligonucleotide treatment (g)

| | Week 0 | Week 2 | Week 4 | Week 6 | Week 8 | Week 10 | Week 12 |
|---|---|---|---|---|---|---|---|
| PBS | 288 | 369 | 405 | 442 | 463 | 500 | 495 |
| ISIS 142082 | 295 | 348 | 318 | 345 | 337 | 347 | 345 |
| ISIS 373125 | 304 | 385 | 399 | 419 | 427 | 421 | 448 |
| ISIS 404173 | 294 | 346 | 352 | 377 | 384 | 391 | 401 |
| ISIS 409826 | 292 | 346 | 350 | 355 | 356 | 373 | 356 |
| ISIS 410002 | 297 | 333 | 323 | 324 | 306 | 335 | n/a |
| ISIS 410003 | 299 | 341 | 328 | 320 | 307 | 305 | 301 |
| ISIS 438452 | 301 | 327 | 335 | 333 | 327 | 347 | 332 |
| ISIS 438460 | 304 | 345 | 346 | 347 | 356 | 377 | n/a |
| ISIS 446431 | 307 | 376 | 340 | 357 | 353 | 357 | 349 |
| ISIS 446432 | 287 | 340 | 344 | 363 | 372 | 399 | 404 |
| ISIS 446433 | 298 | 331 | 318 | 354 | n/a | n/a | n/a |
| ISIS 446434 | 303 | 366 | 356 | n/a | n/a | n/a | n/a |

TABLE 27

Organ weights of Sprague Dawley rats during antisense oligonucleotide treatment (g)

| | Liver | Fat | Spleen | Kidney |
|---|---|---|---|---|
| PBS | 15.9 | 2.1 | 0.8 | 3.6 |
| ISIS 142082 | 21.8 | 0.7 | 4.5 | 5.2 |
| ISIS 373125 | 17.9 | 1.1 | 1.9 | 3.4 |
| ISIS 404173 | 17.7 | 1.1 | 2.3 | 4.3 |
| ISIS 409826 | 19.8 | 0.5 | 3.6 | 4.4 |
| ISIS 410003 | 18.7 | 0.5 | 3.8 | 3.5 |
| ISIS 438452 | 17.3 | 0.6 | 3.1 | 3.8 |
| ISIS 446431 | 22.1 | 0.4 | 6.1 | 5.3 |
| ISIS 446432 | 18.1 | 1.2 | 3.3 | 3.8 |

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) were measured bi-weekly. Plasma levels of bilirubin (mg/dL) were also measured using the same clinical chemistry analyzer. The results are presented in Tables 28, 29 and 30. 'n/a' indicates no data being available for that particular group at that particular time point due to all the rats in the group being euthanized before the time point.

TABLE 28

Effect of antisense oligonucleotide treatment on ALT (IU/L) of Sprague Dawley rats

| | Week 0 | Week 2 | Week 4 | Week 6 | Week 8 | Week 10 | Week 12 |
|---|---|---|---|---|---|---|---|
| PBS | 58 | 68 | 54 | 48 | 48 | 46 | 46 |
| ISIS 142082 | 54 | 75 | 40 | 44 | 49 | 62 | 57 |
| ISIS 373125 | 57 | 61 | 60 | 48 | 48 | 45 | 38 |
| ISIS 404173 | 49 | 52 | 53 | 41 | 51 | 53 | 42 |
| ISIS 409826 | 51 | 59 | 56 | 50 | 42 | 37 | 40 |
| ISIS 410002 | 46 | 65 | 75 | 73 | 103 | 126 | n/a |
| ISIS 410003 | 49 | 78 | 62 | 49 | 61 | 59 | 66 |
| ISIS 438452 | 46 | 57 | 58 | 53 | 51 | 52 | 50 |
| ISIS 438460 | 49 | 88 | 162 | 96 | 114 | 91 | n/a |
| ISIS 446431 | 51 | 57 | 45 | 45 | 40 | 55 | 49 |
| ISIS 446432 | 52 | 59 | 48 | 43 | 44 | 49 | 46 |
| ISIS 446433 | 53 | 120 | 65 | 86 | n/a | n/a | n/a |
| ISIS 446434 | 53 | 76 | 161 | n/a | n/a | n/a | n/a |

TABLE 29

Effect of antisense oligonucleotide treatment on AST (IU/L) of Sprague Dawley rats

| | Week 0 | Week 2 | Week 4 | Week 6 | Week 8 | Week 10 | Week 12 |
|---|---|---|---|---|---|---|---|
| PBS | 84 | 92 | 86 | 79 | 91 | 74 | 81 |
| ISIS 142082 | 87 | 89 | 86 | 126 | 136 | 154 | 149 |
| ISIS 373125 | 79 | 72 | 93 | 124 | 111 | 95 | 81 |
| ISIS 404173 | 75 | 69 | 88 | 75 | 89 | 96 | 83 |
| ISIS 409826 | 75 | 74 | 96 | 112 | 108 | 90 | 106 |
| ISIS 410002 | 67 | 87 | 155 | 173 | 229 | 245 | n/a |
| ISIS 410003 | 71 | 95 | 106 | 136 | 161 | 160 | 186 |
| ISIS 438452 | 70 | 84 | 104 | 157 | 164 | 174 | 167 |
| ISIS 438460 | 79 | 122 | 214 | 287 | 216 | 172 | n/a |
| ISIS 446431 | 73 | 79 | 93 | 137 | 129 | 158 | 153 |
| ISIS 446432 | 80 | 76 | 86 | 99 | 96 | 105 | 102 |
| ISIS 446433 | 77 | 151 | 128 | 234 | n/a | n/a | n/a |
| ISIS 446434 | 81 | 137 | 359 | n/a | n/a | n/a | n/a |

TABLE 30

Effect of antisense oligonucleotide treatment on Bilirubin (mg/dL) of Sprague Dawley rats

| | Week 0 | Week 2 | Week 4 | Week 6 | Week 8 | Week 10 | Week 12 |
|---|---|---|---|---|---|---|---|
| PBS | 0.11 | 0.15 | 0.14 | 0.16 | 0.25 | 0.16 | 0.13 |
| ISIS 142082 | 0.12 | 0.11 | 0.18 | 0.12 | 0.12 | 0.15 | 0.15 |
| ISIS 373125 | 0.13 | 0.13 | 0.15 | 0.36 | 0.14 | 0.15 | 0.13 |
| ISIS 404173 | 0.11 | 0.13 | 0.14 | 0.13 | 0.13 | 0.14 | 0.10 |
| ISIS 409826 | 0.12 | 0.12 | 0.15 | 0.12 | 0.11 | 0.10 | 0.10 |
| ISIS 410002 | 0.11 | 0.13 | 0.18 | 0.13 | 0.19 | 0.54 | n/a |
| ISIS 410003 | 0.12 | 0.12 | 0.14 | 0.16 | 0.14 | 0.17 | 0.14 |
| ISIS 438452 | 0.12 | 0.13 | 0.15 | 0.13 | 0.14 | 0.13 | 0.13 |
| ISIS 438460 | 0.11 | 0.14 | 0.22 | 0.28 | 0.15 | 0.17 | n/a |
| ISIS 446431 | 0.14 | 0.17 | 0.19 | 0.13 | 0.10 | 0.16 | 0.16 |
| ISIS 446432 | 0.12 | 0.14 | 0.13 | 0.12 | 0.11 | 0.14 | 0.13 |
| ISIS 446433 | 0.12 | 0.12 | 0.18 | 0.20 | n/a | n/a | n/a |
| ISIS 446434 | 0.12 | 0.17 | 0.20 | n/a | n/a | n/a | n/a |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, N.Y.). Results are presented in Tables 31 and 32, expressed in mg/dL. The total urine protein to creatinine ratio was also calculated and the results are presented in Table 33.

TABLE 31

Effect of antisense oligonucleotide treatment on BUN (mg/dL) of Sprague Dawley rats

| | Week 0 | Week 2 | Week 4 | Week 6 | Week 8 | Week 10 | Week 12 |
|---|---|---|---|---|---|---|---|
| PBS | 17 | 20 | 20 | 18 | 26 | 18 | 16 |
| ISIS 142082 | 21 | 23 | 31 | 23 | 31 | 24 | 29 |
| ISIS 373125 | 21 | 21 | 24 | 19 | 31 | 21 | 21 |
| ISIS 404173 | 18 | 19 | 21 | 19 | 25 | 21 | 20 |
| ISIS 409826 | 20 | 21 | 24 | 23 | 28 | 22 | 26 |
| ISIS 410002 | 19 | 22 | 25 | 23 | 29 | 32 | n/a |
| ISIS 410003 | 18 | 20 | 23 | 23 | 30 | 29 | 26 |
| ISIS 438452 | 19 | 22 | 27 | 25 | 29 | 22 | 24 |
| ISIS 438460 | 20 | 23 | 25 | 26 | 31 | 24 | n/a |
| ISIS 446431 | 19 | 21 | 24 | 23 | 29 | 24 | 23 |
| ISIS 446432 | 20 | 21 | 24 | 20 | 29 | 23 | 19 |
| ISIS 446433 | 18 | 21 | 25 | 53 | n/a | n/a | n/a |
| ISIS 446434 | 18 | 23 | 120 | n/a | n/a | n/a | n/a |

TABLE 32

Effect of antisense oligonucleotide treatment on creatinine (mg/dL) of Sprague Dawley rats

| | Week 0 | Week 2 | Week 4 | Week 6 | Week 8 | Week 10 | Week 12 |
|---|---|---|---|---|---|---|---|
| PBS | 0.2 | 0.3 | 0.4 | 0.3 | 0.5 | 0.4 | 0.3 |
| ISIS 142082 | 0.3 | 0.3 | 0.5 | 0.4 | 0.5 | 0.5 | 0.4 |
| ISIS 373125 | 0.3 | 0.5 | 0.6 | 0.4 | 0.6 | 0.6 | 0.4 |
| ISIS 404173 | 0.3 | 0.3 | 0.5 | 0.4 | 0.5 | 0.6 | 0.4 |
| ISIS 409826 | 0.3 | 0.4 | 0.6 | 0.4 | 0.5 | 0.5 | 0.4 |
| ISIS 410002 | 0.3 | 0.3 | 0.6 | 0.4 | 0.5 | 0.5 | n/a |
| ISIS 410003 | 0.3 | 0.3 | 0.6 | 0.4 | 0.6 | 0.6 | 0.4 |
| ISIS 438452 | 0.3 | 0.3 | 0.6 | 0.4 | 0.5 | 0.5 | 0.4 |
| ISIS 438460 | 0.3 | 0.4 | 0.5 | 0.3 | 0.5 | 0.5 | n/a |
| ISIS 446431 | 0.3 | 0.3 | 0.5 | 0.4 | 0.5 | 0.5 | 0.4 |
| ISIS 446432 | 0.3 | 0.3 | 0.6 | 0.4 | 0.5 | 0.5 | 0.4 |
| ISIS 446433 | 0.3 | 0.3 | 0.5 | 0.4 | n/a | n/a | n/a |
| ISIS 446434 | 0.3 | 0.4 | 0.8 | n/a | n/a | n/a | n/a |

TABLE 33

Effect of antisense oligonucleotide treatment on total urine protein to urine creatinine ratio of Sprague Dawley rats

| | Week 0 | Week 2 | Week 4 | Week 6 | Week 8 | Week 10 | Week 12 |
|---|---|---|---|---|---|---|---|
| PBS | 1.5 | 1.4 | 1.2 | 1.6 | 1.3 | 1.2 | 1.2 |
| ISIS 142082 | 1.2 | 4.3 | 4.0 | 7.7 | 6.6 | 7.5 | 7.4 |
| ISIS 373125 | 1.3 | 3.9 | 3.8 | 6.7 | 6.2 | 8.8 | 9.7 |
| ISIS 404173 | 1.1 | 4.8 | 5.5 | 6.4 | 7.4 | 10.2 | 11.9 |
| ISIS 409826 | 1.2 | 3.7 | 3.8 | 5.9 | 9.8 | 28.8 | 37.6 |
| ISIS 410002 | 1.2 | 3.9 | 4.1 | 6.0 | 9.7 | 26.3 | n/a |
| ISIS 410003 | 1.3 | 4.5 | 5.3 | 5.9 | 7.6 | 10.8 | 18.0 |
| ISIS 438452 | 1.4 | 3.3 | 3.1 | 5.1 | 8.0 | 9.2 | 10.5 |
| ISIS 438460 | 1.3 | 4.0 | 4.5 | 7.3 | 16.0 | 53.9 | n/a |
| ISIS 446431 | 1.2 | 4.5 | 5.0 | 5.3 | 7.2 | 8.0 | 8.8 |
| ISIS 446432 | 1.3 | 4.2 | 4.4 | 6.2 | 9.1 | 7.6 | 9.2 |
| ISIS 446433 | 1.1 | 3.4 | 5.7 | 81.5 | n/a | n/a | n/a |
| ISIS 446434 | 1.1 | 3.7 | 25.8 | n/a | n/a | n/a | n/a |

Plasma Glucose Levels

To evaluate the effect of ISIS oligonucleotides on glucose metabolism, plasma levels of glucose were measured using an automated clinical chemistry analyzer (Hitachi Olympus AU400e, Melville, N.Y.). Results are presented in Table 34, expressed in mg/dL.

TABLE 34

Effect of antisense oligonucleotide treatment on plasma glucose levels in Sprague Dawley rats

| | Week 0 | Week 2 | Week 4 | Week 6 | Week 8 | Week 10 | Week 12 |
|---|---|---|---|---|---|---|---|
| PBS | 150 | 140 | 155 | 152 | 163 | 138 | 144 |
| ISIS 142082 | 153 | 137 | 155 | 145 | 142 | 130 | 135 |
| ISIS 373125 | 153 | 135 | 136 | 143 | 133 | 106 | 135 |
| ISIS 404173 | 162 | 138 | 149 | 152 | 145 | 144 | 154 |
| ISIS 409826 | 155 | 141 | 150 | 145 | 143 | 132 | 135 |
| ISIS 410002 | 152 | 139 | 148 | 151 | 130 | 124 | n/a |
| ISIS 410003 | 152 | 138 | 146 | 140 | 132 | 126 | 143 |
| ISIS 438452 | 166 | 134 | 162 | 153 | 135 | 143 | 147 |
| ISIS 438460 | 166 | 140 | 151 | 156 | 150 | 130 | n/a |
| ISIS 446431 | 154 | 143 | 155 | 147 | 153 | 139 | 145 |
| ISIS 446432 | 159 | 141 | 155 | 152 | 152 | 138 | 153 |
| ISIS 446433 | 158 | 138 | 141 | 118 | n/a | n/a | n/a |
| ISIS 446434 | 166 | 149 | 124 | n/a | n/a | n/a | n/a |

Plasma Lipid and Triglyceride Levels

To evaluate the effect of ISIS oligonucleotides on total cholesterol and triglyceride levels, plasma levels of each were measured using an automated clinical chemistry analyzer (Hitachi Olympus AU400e, Melville, N.Y.). Results are presented in Tables 35 and 36, expressed in mg/dL.

TABLE 35

Effect of antisense oligonucleotide treatment on plasma cholesterol levels (mg/dL) in Sprague Dawley rats

| | Week 0 | Week 2 | Week 4 | Week 6 | Week 8 | Week 10 | Week 12 |
|---|---|---|---|---|---|---|---|
| PBS | 55 | 57 | 64 | 51 | 73 | 64 | 53 |
| ISIS 142082 | 62 | 41 | 54 | 62 | 70 | 64 | 62 |
| ISIS 373125 | 73 | 59 | 66 | 51 | 66 | 61 | 39 |
| ISIS 404173 | 57 | 41 | 68 | 62 | 87 | 85 | 75 |
| ISIS 409826 | 57 | 42 | 79 | 65 | 86 | 122 | 110 |
| ISIS 410002 | 69 | 57 | 75 | 65 | 73 | 96 | n/a |
| ISIS 410003 | 72 | 44 | 70 | 67 | 89 | 76 | 73 |
| ISIS 438452 | 63 | 33 | 53 | 51 | 71 | 70 | 61 |
| ISIS 438460 | 64 | 40 | 98 | 81 | 94 | 146 | n/a |
| ISIS 446431 | 64 | 41 | 56 | 54 | 63 | 68 | 59 |
| ISIS 446432 | 62 | 44 | 70 | 50 | 80 | 80 | 65 |
| ISIS 446433 | 59 | 63 | 95 | 139 | n/a | n/a | n/a |
| ISIS 446434 | 63 | 48 | 91 | n/a | n/a | n/a | n/a |

TABLE 36

Effect of antisense oligonucleotide treatment on plasma triglyceride levels (mg/dL) in Sprague Dawley rats

| | Week 0 | Week 2 | Week 4 | Week 6 | Week 8 | Week 12 |
|---|---|---|---|---|---|---|
| PBS | 66 | 73 | 82 | 80 | 98 | 106 |
| ISIS 142082 | 92 | 30 | 71 | 44 | 25 | 28 |
| ISIS 373125 | 66 | 28 | 20 | 24 | 24 | 28 |
| ISIS 404173 | 48 | 28 | 28 | 35 | 31 | 49 |
| ISIS 409826 | 68 | 29 | 28 | 25 | 31 | 68 |
| ISIS 410002 | 71 | 23 | 23 | 27 | 71 | n/a |
| ISIS 410003 | 78 | 22 | 22 | 37 | 30 | 64 |
| ISIS 438452 | 89 | 33 | 39 | 34 | 50 | 35 |
| ISIS 438460 | 98 | 20 | 34 | 35 | 33 | n/a |
| ISIS 446431 | 72 | 29 | 38 | 36 | 35 | 48 |
| ISIS 446432 | n/a | 41 | 37 | 31 | 37 | 53 |
| ISIS 446433 | 68 | 21 | 29 | 129 | n/a | n/a |
| ISIS 446434 | 69 | 27 | 103 | n/a | n/a | n/a |

Cytokine Levels

To evaluate the effect of ISIS oligonucleotides on factors involved in inflammation, blood was collected after the end of the treatment period for measurement of cytokine levels. The samples were sent to Aushon Biosystems (Woburn, Mass.) for analysis. Levels of rat IL-6, MCP-1, MIP-1α, and TNF-α were measured with their respective antibodies. The results are presented in Table 37.

TABLE 37

Effect of antisense oligonucleotide treatment on plasma cytokine levels in Sprague Dawley rats

| | rIL-6 | rMCP-1 | rMIP-1α | rTNF-α |
|---|---|---|---|---|
| PBS | 315 | 403 | 6 | 77 |
| ISIS 142082 | 74 | 3082 | 38 | 697 |
| ISIS 373125 | <25 | 2215 | 7 | 15 |
| ISIS 404173 | 125 | 2244 | 60 | 499 |
| ISIS 409826 | <25 | 6041 | 52 | 100 |
| ISIS 410003 | 245 | 3315 | 40 | 444 |
| ISIS 438452 | 105 | 4513 | 26 | 519 |
| ISIS 446431 | 924 | 3104 | 54 | 402 |
| ISIS 446432 | 29 | 2007 | 46 | 610 |

Example 14

Measurement of Viscosity of ISIS Antisense Oligonucleotides Targeting Human PTP1B The viscosity of the antisense oligonucleotides selected from studies described in Examples 12 and 13 was measured with the aim of screening out antisense oligonucleotides which have a viscosity more than 40 cP at a concentration of 165-185 mg/mL. Oligonucleotides having a viscosity greater than 40 cP would be too viscous to be administered to any subject.

ISIS oligonucleotides (32-35 mg) were weighed into a glass vial, 120 μL of water was added and the antisense oligonucleotide was dissolved into solution by heating the vial at 50° C. Part of (75 μL) the pre-heated sample was pipetted to a micro-viscometer (Cambridge). The temperature of the micro-viscometter was set to 25° C. and the viscosity of the sample was measured. Another part (20 μL) of the pre-heated sample was pipetted into 10 mL of water for UV reading at 260 nM at 85° C. (Cary UV instrument). The results are presented in Table 38 and indicate that all the antisense oligonucleotides solutions are optimal in their viscosity under the criterion stated above.

TABLE 38

Viscosity and concentration of ISIS antisense oligonucleotides targeting human PTP1B

| ISIS No. | Viscosity (cP) | Concentration (mg/mL) |
|---|---|---|
| 142082 | 3.8 | 188 |
| 404173 | 3.8 | 163 |
| 410003 | 4.5 | 176 |
| 446431 | 3.2 | 180 |
| 446432 | 2.4 | 175 |

Example 15

Six Month Tolerability Study of Antisense Oligonucleotides Targeting Human PTP1B in a Mouse Model ISIS oligonucleotides selected from the studies described in Examples 12-14 were evaluated for long-term tolerability in a mouse model by monitoring changes in the levels of various metabolic markers in CD1 mice.

Treatment

Male CD1 mice were maintained on a 12-hour light/dark cycle and fed ad libitum normal lab chow (Harlan Laboratories, Indianapolis, Ind.). Animals were acclimated for at least 7 days in the research facility before initiation of the experiment. Antisense oligonucleotides were prepared in PBS and sterilized by filtering through a 0.2 micron filter. Oligonucleotides were dissolved in 0.9% PBS for injection.

Groups of ten CD1 mice each were injected subcutaneously twice a week with 25 mg/kg of ISIS 142082, ISIS 404173, or ISIS 446431 for 24 weeks. One group of ten CD1 mice was injected subcutaneously twice a week with PBS for 24 weeks. This PBS group served as the control group. Blood samples were collected on days 140 via mandibular bleeds. On day 168, blood was collected via terminal cardiac puncture under $CO_2$ anesthesia, the mice were euthanized and organs were harvested for further analysis.

Plasma Glucose Levels

To evaluate the effect of ISIS oligonucleotides on glucose metabolism, plasma levels of glucose were measured using an automated clinical chemistry analyzer (Hitachi Olympus AU400e, Melville, N.Y.). Results are presented in Table 39, expressed in mg/dL.

TABLE 39

Effect of antisense oligonucleotide treatment on plasma glucose levels on day 168

| | Glucose |
|---|---|
| PBS | 214 |
| ISIS 142082 | 177 |
| ISIS 404173 | 204 |
| ISIS 446431 | 191 |

Liver Function

To evaluate the effect of ISIS oligonucleotides on hepatic function, plasma levels of transaminases were measured using an automated clinical chemistry analyzer (Hitachi Olympus AU400e, Melville, N.Y.). Plasma levels of ALT (alanine transaminase) and AST (aspartate transaminase) on day 168 were measured. Plasma levels of bilirubin (mg/dL) were also measured using the same clinical chemistry analyzer. Alkaline phosphatase, which is synthesized in increased amounts by damaged liver cells, is also a marker of liver disease (Narayanan, S. Ann. Clin. Lab. Sci. 21: 12-8, 1991) and was similarly measured. Albumin, which is typically decreased in liver disease (Oettl, K. et al., Biochim Biophys. Acta. 1782: 469-73, 2008), was also similarly measured. The results are presented in Table 40.

TABLE 40

Effect of antisense oligonucleotide treatment on liver metabolic markers on day 168

| | ALT (IU/L) | AST (IU/L) | Bilirubin (mg/dL) | Alkaline phos-phatase (IU/L) | Albumin (g/dL) |
|---|---|---|---|---|---|
| PBS | 50 | 82 | 0.2 | 44 | 2.5 |
| ISIS 142082 | 148 | 197 | 0.1 | 56 | 2.3 |
| ISIS 404173 | 68 | 137 | 0.1 | 57 | 2.5 |
| ISIS 446431 | 115 | 173 | 0.1 | 42 | 2.4 |

Cardiac Function

To evaluate the effect of ISIS oligonucleotides on heart function, plasma levels of creatine phosphokinase (CPK) were measured using an automated clinical chemistry analyzer (Hitachi Olympus AU400e, Melville, N.Y.) on day 168. An increased level of this marker indicates heart muscle injury (Barohn, R. J. In: Goldman L, Ausiello D, eds. Cecil Medicine. 23rd ed. Philadelphia, Pa.: Saunders Elsevier; 2007: chapter 447). The results are presented in Table 41.

TABLE 41

Effect of antisense oligonucleotide treatment on cardiac marker CPK on day 168

| | CPK (IU/L) |
|---|---|
| PBS | 98 |
| ISIS 142082 | 120 |
| ISIS 404173 | 107 |
| ISIS 446431 | 159 |

Pancreatic Function

To evaluate the effect of ISIS oligonucleotides on pancreatic function, plasma levels of amylase were measured using an automated clinical chemistry analyzer (Hitachi Olympus AU400e, Melville, N.Y.) on day 168. An increased level of this marker indicates acute pancreatitis (Sternby, B. et al., Mayo Clin. Proc. 71: 1138-44, 1996). The results are presented in Table 42.

TABLE 42

Effect of antisense oligonucleotide treatment on pancreatic marker amylase on day 168

| | Amylase (IU/L) |
|---|---|
| PBS | 1101 |
| ISIS 142082 | 1374 |
| ISIS 404173 | 1280 |
| ISIS 446431 | 1232 |

Kidney Function

To evaluate the effect of ISIS oligonucleotides on kidney function, plasma levels of blood urea nitrogen (BUN) and creatinine were measured using an automated clinical chemistry analyzer (Hitachi Olympus AU400e, Melville, N.Y.). Results are presented in Table 43, expressed in mg/dL.

TABLE 43

Effect of antisense oligonucleotide treatment on kidney metabolic markers on day 168

| | BUN | Creatinine |
|---|---|---|
| PBS | 20 | 0.3 |
| ISIS 142082 | 24 | 0.2 |
| ISIS 404173 | 21 | 0.2 |
| ISIS 446431 | 19 | 0.3 |

Example 16

Measurement of Half-Life of Antisense Oligonucleotide in CD1 Mouse Liver

CD1 mice were treated with the ISIS antisense oligonucleotides selected from studies described in Example 14, and the oligonucleotide half-life as well as the elapsed time for oligonucleotide degradation and elimination from the liver was evaluated.

Treatment

Groups of ten CD1 mice each were injected subcutaneously twice per week for 2 weeks with 50 mg/kg of ISIS 142082, ISIS 446431, ISIS 404173, or ISIS 409826. Five mice from each group were sacrificed 3 days and 56 days following the final dose. Livers were harvested for analysis.

Measurement of Oligonucleotide Concentration

The concentration of the full-length oligonucleotide was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-O-methoxyethyl modified phosphorothioate oligonucleotide, GCGTTTGCTCTTCTTCTTGCGTTTTTT, designated herein as SEQ ID NO: 50) was added prior to extraction. Tissue sample concentrations were calculated using calibration curves, with a lower limit of quantitation (LLOQ) of approximately 1.14 μg/g. Half-lives were then calculated using WinNonlin software (PHARSIGHT).

The results are presented in Table 44. Antisense oligonucleotides with half-lives within 11-34 days were chosen for further studies.

TABLE 44

Full-length oligonucleotide concentration (μg/g) and half-life (days) of oligonucleotide in CD1 mouse liver

| | Days | Full length conc. (mg/g) | Half-life (days) |
|---|---|---|---|
| 142082 | | 265 | 19.8 |
| | 56 | 42 | |
| 446431 | 3 | 293 | 19.6 |
| | 56 | 45 | |
| 404173 | 3 | 281 | 14.8 |
| | 56 | 24 | |
| 409826 | 3 | 304 | 18.4 |
| | 56 | 41 | |

Example 17

Effect of ISIS Antisense Oligonucleotides Targeting Human PTP1B in Cynomolgus Monkeys Cynomolgus monkeys were treated with ISIS antisense oligonucleotides from studies described in Examples 15 and 16. Antisense oligonucleotide efficacy and tolerability, as well as their pharmacokinetic profile in the liver and kidney, were evaluated.

Treatment

Prior to the study, the monkeys were kept in quarantine for a 30-day time period, during which standard panels of serum chemistry and hematology, examination of fecal samples for ova and parasites, and a tuberculosis test, were conducted to screen out abnormal or ailing monkeys. Six groups of randomly assigned three male and two female cynomolgus monkeys each were injected subcutaneously thrice per week for the first week, and subsequently, once a week for the next 12 weeks with either 8 mg/kg or 40 mg/kg of ISIS 142082, ISIS 446431, or ISIS 404173. One group of three male and two female cynomolgus monkeys was injected subcutaneously thrice per week for the first week, and subsequently, once a week for the next 12 weeks with 40 mg/kg of ISIS 409826. A control group of three male and two female cynomolgus monkeys was injected subcutaneously thrice per week for the first week, and subsequently, once a week for the next 12 weeks with PBS. Terminal sacrifices of all groups were conducted 48 hours after the last dose, on day 93.

During the study period, the monkeys were observed daily for signs of illness or distress. Any animal showing adverse effects to the treatment was removed and referred to the veterinarian and Study Director.

Inhibition Studies

RNA Analysis

RNA was extracted from liver and the abdominal adipose tissues for real-time PCR analysis of PTP1B using primer probe set 1 (forward sequence GACCAGCTGCGCTTCTCCTA, designated herein as SEQ ID NO: 51; reverse sequence CAGAGGAGTCCCCCATGATG, designated herein as SEQ ID NO: 52; probe sequence TTGGCTGTGATCGAAGGTGCCAAA, designated herein as SEQ ID NO: 53) or primer probe set 2 (forward sequence GGGCCCTTTGCCTAACACA, designated herein as SEQ ID NO: 54; reverse sequence CGACACCCCTGCTTTTCTG, designated herein as SEQ ID NO: 55; probe sequence CGGTCACTTTTGGGAGATGGTGTGG, designated herein as SEQ ID NO: 56), each targeting different regions of the PTP1B mRNA. Results are presented as percent reduction of PTP1B mRNA, relative to PBS control, normalized with RIBOGREEN®. As shown in Table 45, treatment with ISIS antisense oligonucleotides resulted in significant reduction of PTP1B mRNA in comparison to the PBS control. Treatment with ISIS 404173 caused reduction of PTP1B mRNA levels similar to that with treatment with ISIS 142082.

TABLE 45

Inhibition of PTP1B mRNA in the cynomolgus monkey liver and fat tissue relative to the PBS control

| ISIS No. | Dose (mg/kg) | % inhibition in liver (probe set 1) | % inhibition in liver (probe set 2) | % inhibition in fat (probe set 1) | % inhibition in fat (probe set 2) |
|---|---|---|---|---|---|
| 409826 | 40 | 38 | 45 | 17 | 21 |
| 142082 | 8 | 12 | 14 | 13 | 16 |
| | 40 | 46 | 48 | 34 | 28 |
| 446831 | 8 | 0 | 8 | 6 | 1 |
| | 40 | 8 | 18 | 14 | 12 |
| 404173 | 8 | 4 | 13 | 8 | 4 |
| | 40 | 26 | 22 | 38 | 31 |

Protein Analysis

Tissue was extracted from liver For measuring PTP1B protein levels by western blot analysis. Specifically, PTP1B protein samples from monkeys treated with ISIS 404173 were compared with those treated with ISIS 142082. The results are presented in Tables 46, 47 and 48 expressed as percentage reduction compared to control levels. The levels of PTP1B levels were normalized against total protein levels, as well as against a constitutively expressed protein, IR-β. Treatment with ISIS 404173 caused greater reduction of PTP1B liver protein to that with treatment with ISIS 142082 at the lower dose of 8 mg/kg (Table 47).

TABLE 46

PTP1B protein level reduction after treatment with ISIS 404173 in the cynomolgus monkey liver

| Dose (mg/kg) | % inhibition (normalized to total protein) | % inhibition (normalized to IR-β) |
|---|---|---|
| 8 | 49 | 42 |
| 40 | 67 | 66 |

TABLE 47

PTP1B protein level reduction after treatment with ISIS 404173 or ISIS 142082 at 8 mg/kg in the cynomolgus monkey liver

| ISIS No | % inhibition (normalized to total protein) | % inhibition (normalized to IR-β) |
|---|---|---|
| 142082 | 20 | 4 |
| 404173 | 33 | 27 |

TABLE 48

PTP1B protein level reduction after treatment with ISIS 404173 or ISIS 142082 at 40 mg/kg in the cynomolgus monkey liver

| ISIS No | % inhibition (normalized to total protein) | % inhibition (normalized to IR-β) |
|---|---|---|
| 142082 | 65 | 63 |
| 404173 | 60 | 56 |

Tolerability Studies

Body and Organ Weight Measurements

To evaluate the effect of ISIS oligonucleotides on the overall health of the animals, body and organ weights were measured after terminal sacrifice. Body weights were measured and compared to that of the PBS control animals. Organ weights were measured and treatment group weights were compared to the corresponding PBS control weights. The data is presented in Table 49. Treatment with ISIS 142082 did cause increases in liver and kidney weights at the higher dose.

TABLE 49

Final body and organ weight weights in the cynomolgus monkey relative to the control

| | Dose (mg/kg) | Body weight (kg) | Kidney (g) | Liver (g) | Spleen (g) | Gastocnemius muscle (g) |
|---|---|---|---|---|---|---|
| PBS | — | 2.2 | 9.6 | 10.5 | 2.3 | 10.6 |
| 409826 | 40 | 2.3 | 14.0 | 18.5 | 6.0 | 8.8 |
| 142082 | 8 | 2.3 | 10.6 | 13.0 | 3.7 | 9.5 |
| | 40 | 2.2 | 20.9 | 17.7 | 7.0 | 9.0 |
| 446431 | 8 | 2.3 | 11.6 | 12.7 | 4.8 | 10.2 |
| | 40 | 2.3 | 15.9 | 16.1 | 9.6 | 7.7 |
| 404173 | 8 | 2.3 | 11.6 | 12.8 | 4.8 | 11.1 |
| | 40 | 2.2 | 14.8 | 15.5 | 3.7 | 8.7 |

Liver Function

To evaluate the effect of ISIS oligonucleotides on hepatic function, blood samples were collected from all the study groups 7 days before the start of treatment, as well as on days 30, 58, and 93 of the treatment period. The blood samples were collected in tubes without any anticoagulant for serum separation. The tubes were kept at room temperature for 90 min and then centrifuged (3000 rpm for 10 min at room temperature) to obtain serum.

Levels of transaminases were measured using a Toshiba 200FR NEO chemistry analyzer (Toshiba Co., Japan). Plasma levels of ALT (alanine transaminase) and AST (aspartate transaminase) were measured and the results are presented in Tables 50 and 51, expressed in IU/L. Alkaline phosphatase, which is synthesized in increased amounts by damaged liver cells and is also a marker of liver disease and was similarly measured, and the data is presented in Table 52. The levels of AST, ALT and alkaline phosphatase in all the treatment groups were similar to that of the PBS control group.

C-reactive protein (CRP), which is synthesized in the liver and which serves as a marker of inflammation, was also similarly measured, and the data is presented in Table 53. Treatment with ISIS 142082 and ISIS 409826 at the higher dose resulted in high levels of CRP, suggesting liver inflammation.

Bilirubin is also a liver metabolic marker and was similarly measured and is presented in Table 54, expressed in mg/dL. Bilurubin levels of all the treatment groups were found to be similar to that of the PBS control group. Gamma-glutamyltransferase (GGT) is an enzyme produced in the liver and is a useful laboratory marker for early liver damage or cholestatic disease (Betro, M. G. et al., Am. J. Clin. Pathol. 60: 672-8, 1973). GGT levels were measured and the results are presented in Table 55, and demonstrate no difference between the PBS control and the treatment groups.

TABLE 50

Effect of antisense oligonucleotide treatment on ALT (IU/L) in cynomolgus monkey serum

| | Dose (mg/kg) | Day −7 | Day 30 | Day 58 | Day 93 |
|---|---|---|---|---|---|
| PBS | — | 37 | 44 | 42 | 35 |
| 409826 | 40 | 39 | 51 | 86 | 74 |
| 142082 | 8 | 37 | 39 | 45 | 36 |
| | 40 | 49 | 62 | 59 | 69 |
| 446431 | 8 | 52 | 54 | 67 | 86 |
| | 40 | 38 | 58 | 87 | 99 |
| 404173 | 8 | 34 | 50 | 41 | 45 |
| | 40 | 44 | 50 | 63 | 73 |

TABLE 51

Effect of antisense oligonucleotide treatment on AST (IU/L) in cynomolgus monkey serum

| | Dose (mg/kg) | Day −7 | Day 30 | Day 58 | Day 93 |
|---|---|---|---|---|---|
| PBS | | 40 | 49 | 55 | 44 |
| 409826 | 40 | 48 | 53 | 73 | 59 |
| 142082 | 8 | 44 | 45 | 49 | 42 |
| | 40 | 54 | 70 | 72 | 69 |
| 446431 | 8 | 57 | 43 | 48 | 50 |
| | 40 | 41 | 60 | 63 | 81 |
| 404173 | 8 | 44 | 53 | 57 | 59 |
| | 40 | 46 | 65 | 71 | 74 |

TABLE 52

Effect of antisense oligonucleotide treatment on alkaline phosphatase (IU/L) in cynomolgus monkey serum

| | Dose (mg/kg) | Day −7 | Day 30 | Day 58 | Day 93 |
|---|---|---|---|---|---|
| PBS | — | 784 | 834 | 1021 | 838 |
| 409826 | 40 | 728 | 883 | 1178 | 981 |
| 142082 | 8 | 718 | 739 | 788 | 688 |
| | 40 | 666 | 656 | 711 | 774 |
| 446431 | 8 | 742 | 745 | 885 | 908 |
| | 40 | 778 | 759 | 768 | 735 |
| 404173 | 8 | 888 | 957 | 1135 | 1155 |
| | 40 | 931 | 958 | 1135 | 1263 |

TABLE 53

Effect of antisense oligonucleotide treatment on CRP (mg/L) in cynomolgus monkey plasma

| | Dose (mg/kg) | Day −7 | Day 30 | Day 58 | Day 93 |
|---|---|---|---|---|---|
| PBS | | 1.0 | 1.8 | 1.4 | 1.2 |
| 409826 | 40 | 1.0 | 4.3 | 4.8 | 4.8 |
| 142082 | 8 | 0.8 | 1.2 | 0.9 | 1.0 |
| | 40 | 0.8 | 2.6 | 3.4 | 12.1 |
| 446431 | 8 | 1.4 | 1.4 | 0.9 | 1.1 |
| | 40 | 0.8 | 2.4 | 2.2 | 6.7 |
| 404173 | 8 | 1.4 | 1.9 | 1.5 | 1.8 |
| | 40 | 3.1 | 1.6 | 1.2 | 1.6 |

TABLE 54

Effect of antisense oligonucleotide treatment on bilirubin (mg/dL) in cynomolgus monkey plasma

| | Dose (mg/kg) | Day −7 | Day 30 | Day 58 | Day 93 |
|---|---|---|---|---|---|
| PBS | — | 0.19 | 0.20 | 0.20 | 0.17 |
| 409826 | 40 | 0.17 | 0.13 | 0.13 | 0.10 |
| 142082 | 8 | 0.17 | 0.18 | 0.16 | 0.14 |
| | 40 | 0.16 | 0.13 | 0.13 | 0.08 |
| 446431 | 8 | 0.21 | 0.17 | 0.18 | 0.15 |
| | 40 | 0.19 | 0.18 | 0.15 | 0.12 |
| 404173 | 8 | 0.23 | 0.19 | 0.20 | 0.16 |
| | 40 | 0.22 | 0.15 | 0.14 | 0.13 |

TABLE 55

Effect of antisense oligonucleotide treatment on GGT (IU/L) in cynomolgus monkey plasma

| | Dose (mg/kg) | Day −7 | Day 30 | Day 58 | Day 93 |
|---|---|---|---|---|---|
| PBS | — | 65 | 74 | 79 | 71 |
| 409826 | 40 | 84 | 86 | 94 | 87 |
| 142082 | 8 | 63 | 67 | 68 | 62 |
| | 40 | 67 | 72 | 71 | 61 |
| 446431 | 8 | 60 | 62 | 62 | 63 |
| | 40 | 61 | 58 | 62 | 60 |
| 404173 | 8 | 57 | 66 | 66 | 68 |
| | 40 | 56 | 63 | 69 | 79 |

Kidney Function

To evaluate the effect of ISIS oligonucleotides on kidney function, blood samples were collected from all the study groups. The blood samples were collected in tubes without any anticoagulant for serum separation. The tubes were kept at room temperature for 90 min and then centrifuged (3000 rpm for 10 min at room temperature) to obtain serum. Levels of BUN and creatinine were measured 7 days before the start of treatment, as well as on days 30, 58, and 93 of the treatment period using a Toshiba 200FR NEO chemistry analyzer (Toshiba Co., Japan). Results are presented in Tables 56 and 57, expressed in mg/dL. Treatment with ISIS oligonucleotides had no adverse effect on either BUN or creatinine levels.

TABLE 56

Effect of antisense oligonucleotide treatment on serum BUN levels (mg/dL) in cynomolgus monkeys

| | Dose (mg/kg) | Day −7 | Day 30 | Day 58 | Day 93 |
|---|---|---|---|---|---|
| PBS | — | 28 | 28 | 25 | 28 |
| 409826 | 40 | 32 | 30 | 28 | 32 |
| 142082 | 8 | 26 | 25 | 24 | 26 |
| | 40 | 28 | 28 | 25 | 25 |
| 446431 | 8 | 28 | 27 | 25 | 26 |
| | 40 | 28 | 27 | 25 | 28 |
| 404173 | 8 | 28 | 30 | 24 | 27 |
| | 40 | 28 | 24 | 25 | 23 |

TABLE 57

Effect of antisense oligonucleotide treatment on serum creatinine levels (mg/dL) in cynomolgus monkeys

| | Dose (mg/kg) | Day −7 | Day 30 | Day 58 | Day 93 |
|---|---|---|---|---|---|
| PBS | | 0.83 | 0.88 | 0.94 | 0.78 |
| 409826 | 40 | 0.77 | 0.84 | 0.92 | 0.82 |
| 142082 | 8 | 0.74 | 0.78 | 0.79 | 0.71 |
| | 40 | 0.72 | 0.80 | 0.86 | 0.73 |
| 446431 | 8 | 0.79 | 0.75 | 0.83 | 0.71 |
| | 40 | 0.76 | 0.83 | 0.88 | 0.77 |
| 404173 | 8 | 0.81 | 0.91 | 0.87 | 0.82 |
| | 40 | 0.76 | 0.84 | 0.92 | 0.76 |

Cholesterol and Triglyceride Levels

To evaluate the effect of ISIS oligonucleotides on lipid metabolism, blood samples were collected from all the study groups. The blood samples were collected in tubes without any anticoagulant for serum separation. The tubes were kept at room temperature for 90 min and then centrifuged (3000 rpm for 10 min at room temperature) to obtain serum. Concentrations of cholesterol and triglycerides were measured 7 days before the start of treatment, as well as on days 30, 58, and 93 of the treatment period using a Toshiba 200FR NEO chemistry analyzer (Toshiba Co., Japan). Results are presented in Tables 58 and 59, expressed in mg/dL. Treatment with ISIS oligonucleotides had no adverse effect on either cholesterol or triglyceride levels.

TABLE 58

Effect of antisense oligonucleotide treatment on serum cholesterol levels (mg/dL) in cynomolgus monkeys

| | Dose (mg/kg) | Day −7 | Day 30 | Day 58 | Day 93 |
|---|---|---|---|---|---|
| PBS | — | 135 | 163 | 162 | 143 |
| 409826 | 40 | 153 | 150 | 140 | 116 |
| 142082 | 8 | 116 | 151 | 159 | 141 |
| | 40 | 110 | 140 | 138 | 128 |

TABLE 58-continued

Effect of antisense oligonucleotide treatment on serum cholesterol levels (mg/dL) in cynomolgus monkeys

| | Dose (mg/kg) | Day −7 | Day 30 | Day 58 | Day 93 |
|---|---|---|---|---|---|
| 446431 | 8 | 125 | 144 | 141 | 133 |
| | 40 | 93 | 99 | 95 | 81 |
| 404173 | 8 | 123 | 147 | 149 | 136 |
| | 40 | 135 | 135 | 125 | 124 |

TABLE 59

Effect of antisense oligonucleotide treatment on serum triglyceride levels (mg/dL) in cynomolgus monkeys

| | Dose (mg/kg) | Day −7 | Day 30 | Day 58 | Day 93 |
|---|---|---|---|---|---|
| PBS | — | 47 | 55 | 45 | 54 |
| 409826 | 40 | 30 | 29 | 33 | 42 |
| 142082 | 8 | 23 | 31 | 37 | 32 |
| | 40 | 28 | 28 | 35 | 42 |
| 446431 | 8 | 24 | 46 | 34 | 93 |
| | 40 | 31 | 44 | 47 | 56 |
| 404173 | 8 | 28 | 38 | 25 | 28 |
| | 40 | 30 | 38 | 45 | 34 |

Hematology

To evaluate any inflammatory effect of ISIS oligonucleotides in cynomolgus monkeys, blood samples were approximately 0.5 mL of blood was collected from each of the available study animals in tubes containing the potassium salt of EDTA. Samples were analyzed for red blood cell (RBC) count, white blood cells (WBC) count, platelet count and hemoglobin content, using an ADVIAl20 hematology analyzer (Bayer, USA). The data is presented in Tables 60-63. Treatment with ISIS oligonucleotides did not significantly alter the blood cell count or hemoglobin levels, compared to the control.

TABLE 60

Effect of antisense oligonucleotide treatment on WBC ($\times 10^3/\mu L$) in cynomolgus monkeys

| | Dose (mg/kg) | Day −7 | Day 30 | Day 58 | Day 93 |
|---|---|---|---|---|---|
| PBS | — | 11.6 | 12.6 | 11.1 | 8.9 |
| 409826 | 40 | 12.4 | 12.7 | 15.3 | 10.8 |
| 142082 | 8 | 11.3 | 15.2 | 12.8 | 9.7 |
| | 40 | 11.9 | 13.2 | 12.5 | 8.5 |
| 446431 | 8 | 9.7 | 13.4 | 12.7 | 9.3 |
| | 40 | 10.7 | 11.5 | 11.9 | 10.2 |
| 404173 | 8 | 14.9 | 18.9 | 14.9 | 11.8 |
| | 40 | 11.1 | 14.2 | 12.9 | 10.8 |

TABLE 61

Effect of antisense oligonucleotide treatment on ABC ($\times 10^6/\mu L$) in cynomolgus monkeys

| | Dose (mg/kg) | Day −7 | Day 30 | Day 58 | Day 93 |
|---|---|---|---|---|---|
| PBS | — | 5.5 | 5.6 | 5.8 | 5.1 |
| 409826 | 40 | 5.6 | 5.8 | 6.1 | 5.6 |
| 142082 | 8 | 5.4 | 5.4 | 5.6 | 5.2 |
| | 40 | 5.7 | 5.6 | 5.8 | 5.5 |

TABLE 61-continued

Effect of antisense oligonucleotide treatment on ABC ($\times 10^6/\mu L$) in cynomolgus monkeys

| | Dose (mg/kg) | Day −7 | Day 30 | Day 58 | Day 93 |
|---|---|---|---|---|---|
| 446431 | 8 | 5.5 | 5.3 | 5.5 | 5.4 |
| | 40 | 5.5 | 5.4 | 5.8 | 5.3 |
| 404173 | 8 | 5.9 | 5.9 | 6.1 | 5.7 |
| | 40 | 5.1 | 5.4 | 5.5 | 5.5 |

TABLE 62

Effect of antisense oligonucleotide treatment on platelets ($\times 10^3/\mu L$) in cynomolgus monkeys

| | Dose (mg/kg) | Day −7 | Day 30 | Day 58 | Day 93 |
|---|---|---|---|---|---|
| PBS | — | 592 | 555 | 571 | 516 |
| 409826 | 40 | 536 | 493 | 400 | 338 |
| 142082 | 8 | 439 | 477 | 349 | 284 |
| | 40 | 461 | 454 | 401 | 263 |
| 446431 | 8 | 438 | 397 | 359 | 282 |
| | 40 | 516 | 337 | 369 | 323 |
| 404173 | 8 | 489 | 491 | 420 | 355 |
| | 40 | 520 | 470 | 389 | 316 |

TABLE 63

Effect of antisense oligonucleotide treatment on hemoglobin levels (g/dL) in cynomolgus monkeys

| | Dose (mg/kg) | Day −7 | Day 30 | Day 58 | Day 93 |
|---|---|---|---|---|---|
| PBS | — | 12.5 | 12.8 | 13.1 | 11.9 |
| 409826 | 40 | 12.6 | 12.8 | 13.3 | 12.5 |
| 142082 | 8 | 12.3 | 12.5 | 13.0 | 12.2 |
| | 40 | 12.1 | 12.0 | 12.1 | 11.5 |
| 446431 | 8 | 12.3 | 12.1 | 12.4 | 12.6 |
| | 40 | 12.7 | 12.6 | 13.3 | 12.4 |
| 404173 | 8 | 12.7 | 13.0 | 13.3 | 12.7 |
| | 40 | 11.6 | 12.3 | 12.4 | 12.6 |

Analysis of Factors of Inflammation

To evaluate the effect of ISIS oligonucleotides for complement C3 analysis as an inflammation factor, blood was collected from all available animals in tubes without anticoagulant for serum separation. The tubes were kept at room temperature for 90 min and then centrifuged (3000 rpm for 10 min at room temperature) to obtain serum. Complement C3 was measured using an automatic analyzer (Toshiba 200 FR NEO chemistry analyzer, Toshiba co., Japan). The data is presented in Table 64, expressed in mg/dL. Treatment with ISIS 409826 resulted in low complement C3 levels, indicating a diseased state.

TABLE 64

Effect of antisense oligonucleotide treatment on serum C3 levels (mg/dL) in cynomolgus monkeys

| | Dose (mg/kg) | Day −7 | Day −1 | Day 30 | Day 58 | Day 93 |
|---|---|---|---|---|---|---|
| PBS | — | 136 | 138 | 148 | 149 | 129 |
| 409826 | 40 | 129 | 131 | 101 | 101 | 90 |
| 142082 | 8 | 126 | 135 | 126 | 127 | 111 |
| | 40 | 133 | 134 | 106 | 121 | 111 |
| 446431 | 8 | 130 | 144 | 128 | 132 | 125 |
| | 40 | 129 | 130 | 111 | 117 | 114 |

TABLE 64-continued

Effect of antisense oligonucleotide treatment on serum C3 levels (mg/dL) in cynomolgus monkeys

| | Dose (mg/kg) | Day −7 | Day −1 | Day 30 | Day 58 | Day 93 |
|---|---|---|---|---|---|---|
| 404173 | 8 | 127 | 136 | 137 | 136 | 127 |
| | 40 | 125 | 134 | 101 | 103 | 102 |

Analysis of Insulin Levels

To evaluate the effect of ISIS oligonucleotides on the thyroid gland, blood was collected on days 42, 84 and 91 from animals fasted overnight in tubes treated with EDTA. The tubes were kept on ice and plasma was obtained after centrifugation (3000 rpm for 10 min at 4° C.) within 30 min of blood collection. Insulin levels were measured using an automatic analyzer (Toshiba 200 FR NEO chemistry analyzer, Toshiba co., Japan). The data is presented in Table 65, expressed in ng/mL.

TABLE 65

Effect of antisense oligonucleotide treatment on plasma insulin levels (ng/mL) in cynomolgus monkeys

| | Dose (mg/kg) | Day 42 | Day 84 | Day 91 |
|---|---|---|---|---|
| PBS | — | 29 | 26 | 26 |
| 409826 | 40 | 14 | 22 | 15 |
| 142082 | 8 | 8 | 4 | 8 |
| | 40 | 8 | 10 | 10 |
| 404173 | 8 | 9 | 10 | 7 |
| | 40 | 6 | 3 | 2 |

Pharmacokinetic Studies

Measurement of Oligonucleotide Concentration

The concentration of the full-length oligonucleotide as well as the total oligonucleotide concentration (including the degraded form) was measured. The method used is a modification of previously published methods (Leeds et al., 1996; Geary et al., 1999) which consist of a phenol-chloroform (liquid-liquid) extraction followed by a solid phase extraction. An internal standard (ISIS 355868, a 27-mer 2'-β-methoxyethyl modified phosphorothioate oligonucleotide, GCGTTTGCTCTTCTTCTTGCGTTTTTT, designated herein as SEQ ID NO: 50) was added prior to extraction. Tissue sample concentrations were calculated using calibration curves, with a lower limit of quantitation (LLOQ) of approximately 1.14 μg/g. The results are presented in Tables 66 and 67, expressed as ug/g tissue. The ratio of the concentrations in the kidney versus the liver was calculated. Treatment with ISIS oligonucleotides did not result in any abnormality in the ratio. The results indicate that ISIS 404173 is a better renal accumulator than ISIS 142082 at the higher dose.

TABLE 66

Total oligonucleotide concentration (μg/g) in the liver of cynomolgus monkey

| ISIS No. | Dose (mg/kg) | Kidney | Liver | Kidney/ Liver ratio |
|---|---|---|---|---|
| 409826 | 40 | 4424 | 954 | 4.64 |
| 142082 | 8 | 1688 | 1044 | 1.62 |
| | 40 | 6385 | 1774 | 3.60 |
| 446431 | 8 | 1323 | 641 | 2.06 |
| | 40 | 6662 | 1159 | 5.75 |
| 404173 | 8 | 971 | 712 | 1.36 |
| | 40 | 7180 | 1464 | 4.90 |

TABLE 67

Full-length oligonucleotide concentration (μg/g) in the liver of cynomolgus monkey

| ISIS No. | Dose (mg/kg) | Kidney | Liver | Kidney/ Liver ratio |
|---|---|---|---|---|
| 409826 | 40 | 3472 | 728 | 4.77 |
| 142082 | 8 | 1232 | 653 | 1.89 |
| | 40 | 4103 | 1244 | 3.30 |
| 446431 | 8 | 1204 | 416 | 2.89 |
| | 40 | 5645 | 846 | 6.67 |
| 404173 | 8 | 650 | 424 | 1.53 |
| | 40 | 5039 | 1094 | 4.61 |

SEQUENCE LISTING

```
<160> NUMBER OF SEQ ID NOS: 56

<210> SEQ ID NO 1
<211> LENGTH: 3318
<212> TYPE: DNA
<213> ORGANISM: Homo sapiens

<400> SEQUENCE: 1

gtgatgcgta gttccggctg ccggttgaca tgaagaagca gcagcggcta gggcggcggt      60

agctgcaggg gtcggggatt gcagcgggcc tcggggctaa gagcgcgacg cggcctagag     120

cggcagacgg cgcagtgggc cgagaaggag gcgcagcagc cgccctggcc cgtcatggag     180

atggaaaagg agttcgagca gatcgacaag tccgggagct gggcggccat ttaccaggat     240

atccgacatg aagccagtga cttcccatgt agagtggcca agcttcctaa gaacaaaaac     300
```

-continued

```
cgaaataggt acagagacgt cagtcccttt gaccatagtc ggattaaact acatcaagaa    360
gataatgact atatcaacgc tagtttgata aaaatggaag aagcccaaag gagttacatt    420
cttacccagg gccctttgcc taacacatgc ggtcactttt gggagatggt gtgggagcag    480
aaaagcaggg gtgtcgtcat gctcaacaga gtgatggaga aaggttcgtt aaaatgcgca    540
caatactggc cacaaaaaga agaaaaagag atgatctttg aagacacaaa tttgaaatta    600
acattgatct ctgaagatat caagtcatat tatacagtgc gacagctaga attggaaaac    660
cttacaaccc aagaaactcg agagatctta catttccact ataccacatg gcctgacttt    720
ggagtccctg aatcaccagc ctcattcttg aactttcttt tcaaagtccg agagtcaggg    780
tcactcagcc cggagcacgg gcccgttgtg gtgcactgca gtgcaggcat cggcaggtct    840
ggaaccttct gtctggctga tacctgcctc ttgctgatgg acaagaggaa agacccttct    900
tccgttgata tcaagaaagt gctgttagaa atgaggaagt ttcggatggg gctgatccag    960
acagccgacc agctgcgctt ctcctacctg gctgtgatcg aaggtgccaa attcatcatg   1020
ggggactctt ccgtgcagga tcagtggaag gagctttccc acgaggacct ggagccccca   1080
cccgagcata tccccccacc tccccggcca cccaaacgaa tcctggagcc acacaatggg   1140
aaatgcaggg agttcttccc aaatcaccag tgggtgaagg aagagaccca ggaggataaa   1200
gactgcccca tcaaggaaga aaaaggaagc cccttaaatg ccgcacccta cggcatcgaa   1260
agcatgagtc aagacactga agttagaagt cgggtcgtgg ggggaagtct tcgaggtgcc   1320
caggctgcct ccccagccaa aggggagccg tcactgcccg agaaggacga ggaccatgca   1380
ctgagttact ggaagccctt cctggtcaac atgtgcgtgg ctacggtcct cacggccggc   1440
gcttacctct gctacaggtt cctgttcaac agcaacacat agcctgaccc tcctccactc   1500
cacctccacc cactgtccgc ctctgcccgc agagcccacg cccgactagc aggcatgccg   1560
cggtaggtaa gggccgccgg accgcgtaga gagccgggcc ccggacggac gttggttctg   1620
cactaaaacc catcttcccc ggatgtgtgt ctcacccctc atccttttac tttttgcccc   1680
ttccactttg agtaccaaat ccacaagcca ttttttgagg agagtgaaag agagtaccat   1740
gctggcggcg cagagggaag gggcctacac ccgtcttggg gctcgcccca cccagggctc   1800
cctcctggag catcccaggc gggcggcacg ccaacagccc ccccccttgaa tctgcaggga   1860
gcaactctcc actccatatt tatttaaaca attttttccc caaaggcatc catagtgcac   1920
tagcattttc ttgaaccaat aatgtattaa aatttttttga tgtcagcctt gcatcaaggg   1980
ctttatcaaa aagtacaata ataaatcctc aggtagtact gggaatggaa ggctttgcca   2040
tgggcctgct gcgtcagacc agtactggga aggaggacgg ttgtaagcag ttgttattta   2100
gtgatattgt gggtaacgtg agaagataga acaatgctat aatatataat gaacacgtgg   2160
gtatttaata agaaacatga tgtgagatta ctttgtcccg cttattctcc tccctgttat   2220
ctgctagatc tagttctcaa tcactgctcc cccgtgtgta ttagaatgca tgtaaggtct   2280
tcttgtgtcc tgatgaaaaa tatgtgcttg aaatgagaaa ctttgatctc tgcttactaa   2340
tgtgccccat gtccaagtcc aacctgcctg tgcatgacct gatcattaca tggctgtggt   2400
tcctaagcct gttgctgaag tcattgtcgc tcagcaatag ggtgcagttt tccaggaata   2460
ggcatttgcc taattcctgg catgacactc tagtgacttc ctggtgaggc ccagcctgtc   2520
ctggtacagc agggtcttgc tgtaactcag acattccaag ggtatgggaa gccatattca   2580
cacctcacgc tctggacatg atttagggaa gcagggacac cccccgcccc ccacctttgg   2640
gatcagcctc cgccattcca agtcaacact cttcttgagc agaccgtgat ttggaagaga   2700
```

```
ggcacctgct ggaaaccaca cttcttgaaa cagcctgggt gacggtcctt taggcagcct   2760

gccgccgtct ctgtcccggt tcaccttgcc gagagaggcg cgtctgcccc accctcaaac   2820

cctgtggggc ctgatggtgc tcacgactct tcctgcaaag ggaactgaag acctccacat   2880

taagtggctt tttaacatga aaaacacggc agctgtagct cccgagctac tctcttgcca   2940

gcattttcac attttgcctt tctcgtggta gaagccagta cagagaaatt ctgtggtggg   3000

aacattcgag gtgtcaccct gcagagctat ggtgaggtgt ggataaggct taggtgccag   3060

gctgtaagca ttctgagctg ggcttgttgt ttttaagtcc tgtatatgta tgtagtagtt   3120

tgggtgtgta tatatagtag catttcaaaa tggacgtact ggtttaacct cctatccttg   3180

gagagcagct ggctctccac cttgttacac attatgttag agaggtagcg agctgctctg   3240

ctatatgcct taagccaata tttactcatc aggtcattat tttttacaat ggccatggaa   3300

taaaccattt ttacaaaa                                                 3318
```

<210> SEQ ID NO 2
<211> LENGTH: 78001
<212> TYPE: DNA
<213> ORGANISM: Homo sapiens

<400> SEQUENCE: 2

```
cagattccgg gtctcatccc tagaccaaag atatctgaat catttggcga tgggtccagg     60

aacctgcatt attcaacaca cttcccaggt gaccgtaaat gtcaaaagac aaaattacaa    120

caaacttaaa catcttaatt ggcttcattc atgattctag aatcgggcaa gacttcattc    180

ctcaaaatag cacaagtgtc ccaatgagct gagcagagga ggttggtttt atagacagaa    240

aagggctgaa aaaagcagaa acaaagaaca aaaagcagat tggtcatttc aaagttactt    300

tccttgtaag gcaggaacag ggaaacagaa caagagagaa ataactgatt ggtcgcatcg    360

ggttacttca ggttactttt tgttgtaagg attaaagcaa agggaacttc attatgttga    420

ttaaaacggt ctgcttggga aatcagggtg tgtatctctc ttctgatttt gtgaaaggtt    480

atcagtctga tgatgtagaa ctttagcatg agtgactcca ttttgatttt tagtctagtc    540

tgttgagacc ctaatgccag aactttttt gtttgtttgt ttcgctcttg ttgcccaggc    600

tggagtgcag tggagctatc ttggctcact gcaacctctg cctccagggt tcaagcgatt    660

ctcctgcctc agcctcccaa gtagctggga ttacaggcat gcgccaccac gcccggctaa    720

tttttttttt tttttttttt tttagcagaa accgagtttc accatgttgg tcaggctggt    780

ctcggactct tgacctcagg tgatccacct gcgtcggtct cccaaagtgc tgggattaca    840

ggtgtgagcc accacaccca gccctttttt ttcaagacag ggtctctctc tgccacccaa    900

ggtggagtgc agtggcgcca aaacagctca ctgcagcttc cacctcctgg gctcaggtga    960

tcttcctgcc tcagcctccc cagcagctgg gccccaccac accggctaat tttttaactt   1020

ttagtagtga cgaggtctga ttctgttacc caggctggtc tggaactcct ggcctcaaga   1080

catccgcctg cctctgcctc ccaaagtgct gggattacag atgtaagcca ccgcgcctgg   1140

gctcctatga tttttattta acataatgca ccatggaatt tgtgctctgc ttagttcagt   1200

ctgagcagga gttccttgat acttcgggaa acactgaaaa tcattccatc cccatccatt   1260

cattcctgca gcacccaagt ggaaattctg cgtttcagac agggacacta cccttagaga   1320

gcagtgggct tccccagcag cgtagtgaaa catgatactc ctgagtttca tgaaaaaagg   1380

gcagacatct ggccagagct gggaggcagg aaatagagca cggtgccctc ctcccatact   1440
```

-continued

```
ccagcttgga ttactgaggc tggggcccag gccctgcagg aaaggaggtg catgactact   1500
ttaaggccac tcactctgtg actcaacggg ccgggtcggg gctggaactc aatgccctcc   1560
cgggcctgga gagcccacgc gccgtgggcg gggctcccgg ggtcgcctag gcaacaggcg   1620
cgcgccgcgc ccgagcccag agccccaaag cggaggaggg aacgcgcgct attagatatc   1680
tcgcggtgct ggggccactt cccctagcac cgcccccggc tcctccccgc ggaagtgctt   1740
gtcgaaattc tcgatcgctg attggtcctt ctgcttcagg ggcggagccc ctggcaggcg   1800
tgatgcgtag ttccggctgc cggttgacat gaagaagcag cagcggctag ggcggcggta   1860
gctgcagggg tcggggattg cagcgggcct cggggctaag agcgcgacgc ggcctagagc   1920
ggcagacggc gcagtgggcc gagaaggagg cgcagcagcc gccctggccc gtcatggaga   1980
tggaaaagga gttcgagcag atcgacaagt ccgggagctg ggcggccatt taccaggtgc   2040
gggagcgccc cggagcgtgg cgggcccttc gcttaggccg cttgaacatc ccctcagacc   2100
tccaggcccc agactccctc tgggtcttgc cctctgcctc gctcctactg cttgaggatt   2160
cgatgggaca gcgacgcact gcgtcccccc acccttttgtc cccggggcgg gcgtgtttct   2220
cgccgcagcg tcggagcccc cttcgatccc ccacctccct tctgttctcc agctcgggtg   2280
atctctcaag ccgggggacc gccggtctgt gctctcaacg cgaatccctc gcaccccgac   2340
cccgccccct gcctgtccac tctttgtccc ctggggtgat ttagcacccc cactatttcc   2400
ttttctggag tggaccacct cagactctct tcctttgtct ccctgggggga aaaggttact   2460
ccccccgtcc ctccttcaca tttcctttcc cctagtctca gtgtgcgtcg agtcccagag   2520
atgacagtcc cctttcccct ttctgttcat tcatttattg gataggagtt ggcaagctta   2580
ttctgtgcta ggcaccgctt aggcattgga ggtggtgttt gctaatcagg acaggcaaga   2640
tcctagcctt agtggggcct agagtcgaat agggcaatca aacacaaaag caaataattt   2700
cagatagtga caggtgctgt gaagagaacg acttcctaac ggggtacagg gtgactgcat   2760
agaaggccgg ctgtcttaga gaaggggatc agggaaggcc tgtcaaagga ggagacattt   2820
gctttgtgag ctgaaccaag aggagcagaa agccgtgaga atatggggct aaagaacctt   2880
ctagccagga ggcctgcggt acccactcca ttggggccat gatattattc tttcaggcag   2940
ggactcagga aggttaacgt tttaaccctc tctaaaatag catctttcct caatgagcag   3000
cttagtcttt ggtcgtggca gagatgacct tgtcttagga gtcatctcct tgtgtgttaa   3060
aaagttagga aaggagggtt tctcatatat ctataaaaca agtagttaaa aacacaaaga   3120
gctcttcctt tcacaagcag ctgaataaga tacatactcc caattaaatg tcattgcggg   3180
ggttgttaag attaactaaa accacacttg cacagtatct taaataagcg atatacagaa   3240
tagagagatt ttgttacttg tgtaaaggga gacagcagat gattctgttt tcagcttata   3300
ggctcaaaag gcaaattgtg agatccatca gctgtagtat taaaatctat tttgagctcc   3360
gcttagaaag gaaaaaaggt ttaagcagtt ctttggtatg cttgactaac aaaagccttt   3420
ttttttggca gccttgattt tcatgtggat ttacatcaag cttatttgac aggattcttt   3480
ttatttggac tgtagtgtgt atattagttt ctgctagact aatatttcta accactgtaa   3540
tctatatact aataagtatg attgatcagt atataaaatt tgtatgccat atctggtctc   3600
tgaattagct gaatgaattc cataagggac tttgagactg tgtagacaaa ttttctgcat   3660
cagtttaatg cagtagagtc taaaatgtct ttaaatgaaa attgttggtc tgaagtgttg   3720
gagttgatta tgatacaccc catcacagtg gaagcattgt ggagagaagt cttttccact   3780
gaaattgact gagttgacaa caagaaatac gtattgtaac ttagttctta gttgaatttt   3840
```

```
atttcttaca attttaagcc agagtgggtt gacctgtcac ccaagcatgg ttaaaattgt   3900
attcagcatg caactagcat ggagtgtgtc agtcttcaat tcatttcctt cattgttctt   3960
aagtttttct gccacaatta aaccccacaa gttagtcaag gtgttgagat tttcactgct   4020
tcttaatgga ttgccacatt ccctgaggta gtttcttttg gtcttagaga attgtcaggg   4080
ccagcttttc tcacctccac tgtatggata tttttctttt ctaagatctt gaaatcagaa   4140
gcttttctcc taagtgtaaa agtagctctt tgtcatacaa ctgtagcgtt ttctgaaaca   4200
gagttcagat gaccttgagt ctaaagtggc taactttcca aggtgtgtat cgctttacca   4260
aaaccattat ttttcaagga ttcaaagaat gtgtttacaa ttgatagaaa atggaagttt   4320
aaaaaaatta atactttata gcatgttgaa atgagggcag ccttatacaa agtcatactt   4380
tgagcttgcc tagcctattg tgatcagaga ataatgtaat ttttgcttac aacttggtaa   4440
gcaggtcagt tattctaact tattttctga ttagaacaaa aagatgtaaa aacttgaaaa   4500
ctattgggaa aagaacaaag agtgaagagg acttttgagt gctgaggaat gtggcagctt   4560
ggaaaacaaa ctttttaggc agagattctt tgctaggtca gtttgataaa gtgagcataa   4620
ccgtattttt aatctttaat gctaatgaat agcatagatg ctaataagca tctaggtcta   4680
taaaaagtca gctttgatag tgtatataga tggctttaaa cattgttttc tagcatttaa   4740
acactttcaa atcatccggt tgcttgattg ggcctagctg tctaagagga gagaatgagc   4800
ccagatgagg aaaagagatt gattttactg agctagaatg agaggagaga gggttgagtg   4860
aatgaaaaga atagctcatg tgctcccctc catctgtagt ttaagagggg ttgggtccgg   4920
tgttttgctt gttttctcgt ctgtaaattc tttgattctc tgacaccact cactatattt   4980
cattgtgaat gatttgattg tttcagataa aggggactgc aataatacct tgtgacatga   5040
aggcaagatt tattcatgtt agaggcaggc tttgtaaaat gggccactct tccaattgac   5100
atttgttttt atagctgttt tcattatgaa atacaatcta atgcctgact aggttaaaac   5160
catgttgtaa caatagttca ctaaaattcc ttactgatat acagcttatg ttgttatatt   5220
ccaaaaagat gaatattaaa atttgccaat aatgtttatt taaatactat tttcttcaga   5280
ggaaaaaaaa ctattttatg caaaggagaa agatctatac actatgactc acttcactta   5340
aaaaaaaaaa gactaacgga aatgacatgg agagactggg aagttctagt catcttgagt   5400
gacccattag atctaaatgt tcttgtttag ccctggtttg agtgaactaa atttaggtgt   5460
ctgatcagta ctttggaaat ggtgtaaatg cctttgtaat tgtctggact gatattagat   5520
taactgggag cacaagtaga aatagtgaag gaaagaactt tttgctattg ttatttgaca   5580
tcactggcat atttatagga atactttggt gtttttggaa gtaagtaaac caaccagtgg   5640
ttctaaaaag tcagctgggg gataatggta atgccgctgt ttcttagctg caagttatct   5700
gccgttactt ctcctccatt ttgcatttta tcttgaatag ctcctcaaaa cctattaaaa   5760
tacctggtat tgaataatgt aattgaatgt gtactgaatt tcacagtgga aatgaataag   5820
aaatttcctg tggaggtttt ttgacttagc tactgaaata acggcctttt gttgtgtgat   5880
tctttccctt ttctctttgt taaagaaaac tgtcttgtga tcttgtagat tacagaatcc   5940
ttttggcaat ttctgttcct agcactgctt tttctttctt tctttctttt aaatagaaat   6000
ggggttttgc tgtgttgccc aggttggtct tgaactcctg gcttcaagcg atcctcccac   6060
cttggcctcc tgaagttggg attgcaggcg tgagcaggta ctttttctga ggcctgcctg   6120
agcctatata tattttgcac aatttggcat tcctccctac agtgtttatg ctgatttgtt   6180
```

```
tctggtaaca actaatactg gcaaatcggc tgggcatgtt actttatgct gcccatattc   6240
aggaaaattg gaattctagc tgggtcattg ttcccagatg atgtagtttg gcaccagcca   6300
ttccatgttc acattttgag tatccaggag ggctggggac tttggagtag ttggtgattc   6360
cctctgccac atttcactgg ttggtcacta tggcatcctt tccaccacac tagtagtcta   6420
ggttctcaga tgttgcttat gagcctgcaa tggtttctag tttcacactg cagaaatgag   6480
tgaagccggt tacccgttaa tatggtccca tcatcactag agtaattcat tgttctaaaa   6540
ccagatctga gtctctcact cctctgcaac tacttctgat tctttcataa cacttgtaaa   6600
gtccaaactc ctctttagca tggcagccag cttccagtcc ttccctccta tgtggcttcc   6660
attctagcca gacaagaaag ggcagcgttc tccaaactca tcctcgccct tcattcctct   6720
ataccattgc tgagcacttt gttgaggatg cctctcccgt tcaatctagc ttgcatcttc   6780
cagctcgaat gtgtgcttcc ttgcaccaga gttttgttcc gtcacctgtg tgttttcata   6840
caagctggca catatctctt ctaaagccct gctgtcattg tagctgcgtc tttacaaaca   6900
tttttttttt aaatttttat aaagtcaagg tctcactata ttgcccaggc tggtctcaaa   6960
ctcctgggct caagtgatcc tcctgccttg gcctcccaga gtgctgggat tataggtatg   7020
agacactgtg cccagctgta gctgctactt tatatcccag gtctatctcc aatggagccc   7080
aagcttcctg aggccacctg ttgtatcttt ctcattcatc ttgaagtcct ctgctcctgg   7140
cacagagtag gtacctaaca agagttggga ttgaattgat ggtcagtact ttgctagcct   7200
gatggtataa agatgtacaa aacatgttcc tggctcccac tctagggggg caatgatgga   7260
aacaaataga ttagcccaca ttagtaccaa tagtagaggt cactctggga gaaggccccc   7320
accacatttt gagtcatggc ctaatgaggt aatttagtat tgcctgctgc agtggctttg   7380
gaagaaaggc tggcattctt agccagtaga agctgatacc actgatttgt ttcacagaag   7440
ctttaaatat aacaataaat ttgtgcttgg cctacggtga actttacagg caacttggag   7500
gtaatatgtt tgtctctcta agaattgttg aattcctctt ccctcatccc tcctgactgg   7560
ttctcacaag cctagcgggc ctttgcatgt ggttggttca taaaatactt tttgattttg   7620
ggatataaaa tatagttctc cataaaataa cgactgttac caagtctttg atttttttt    7680
tcaaactata aatggtaatg acattctttg gcctttgatc agaccaccct taggggcaag   7740
agagtagttt catgttttgc tttttctagt gtcccctgtg tctgggtata gttgcagtct   7800
cagctgtcat actaacagtg ctgagtgagt cccttacttt ctttgggttt tggtttctcc   7860
cttgtaaaaa tgatcctgga ctaactgatc attaagttca ggtcaagtaa taaaaatcct   7920
taatgtactc acaaatacaa tttaatgttc ctgaataatc cttgtaaaaa ctgcagcagt   7980
tactcagttt tgtaaggtgt ggttgggtac tattaggctc aaaagtttat aggagctttg   8040
tgagtatagt taacaactca aaagaatggg gtgtttttc ccgaggggca tgaaatgttt    8100
ttgataaata gagttcattt gacttggtaa tgtggaaaat gagtagccct gacacgtacg   8160
ctatgctttt gcagtttttc tctcaagtag caattgggtg gcttttcctg taaaagatag   8220
aggaactgat tcttgagaat ttacgaaagc ttcaacccta actaggtatg caaagaatag   8280
ttgcccttta tgttgtaatt ttaggaagaa acctacatct ggtctaagtt tcatttgaat   8340
aatatgatag tttacacatc tgccatattt gagaagaaag tacctaagtc tccagcattt   8400
tagaaataat gctttacttt gtgtagaaat ggtctttaga gtttaatagc tgctgccctc   8460
tccttttca aagcagcttg acataatcat gagtatcttg ctgacagctt gtaaattttg    8520
attgtatgaa aactgaaaat aagaccattt cacatggaag attccctcct gccctgaaac   8580
```

```
agccaaagaa aactgtagcc atcaaatcta ttgatctctg ggctttggta caagtcacac   8640
tactacaaat aaaataatac caagtactta taaatgattt tcagtccttt taaagtttat   8700
ttttttaata tttttttga gatggggtct tgctgtgtcg tccaggctgg agtgcagtgg   8760
cacaatcttg gctcactgca acctccacct cctgggctca agtgatcctc ccacctcagg   8820
ctcccaagta gctgagacta caggcatgtg ccatcacgcc cagctaattt ttgtattttt   8880
ttggagtaga gatgggattt tgctgtgttg cccaggctgg tcttgaactc ctgggcttaa   8940
gccatctgtc tgcctcaggc tcccaaagtg ttgggattac aggtgtgagc cactgtgccc   9000
ggcccagccc tttttttaag agaaaaacgt atgacatcgt tcgatttact gagtgcttat   9060
ggttttacta aggcagtaag gttttatgga taccctatgg taattagata gaattagtgc   9120
tctgaagtca gctctgtaat atggactcag agtaaacatg gcaaagggac acttaaggtc   9180
tgcattttct ctgggaaata aacgtattct ttactactct gaatctagtg ctgggaaatt   9240
ctaaatcctt cttgaggatt aaccacttga agtaaagttt tgggtcccaa gtaggcttgt   9300
gtccctgtct ccttctcttt acttttcaga tgtttcttcc tagagactga ggtatatttt   9360
acttttacag atgaagaagg aagcctcggc tgtgtttgtg gcttttgtgg gtgagcaaca   9420
tcacttgcaa agataagatg agcatagcaa aactaggctt tcaaaataat ttttaaaaat   9480
ttcttagtga ttagaaaagg aaaactcttc ccttgtctct gttaagaaac gtttttcgac   9540
ttttttcctt tcttaatgga tcttttattg gcacttctct tccttttgca gaatcttact   9600
taaaagtcac tacgttacat tacagcaaac agcttagcta atttttatcc agatgggccc   9660
cggttacagg attgtacact attgcgaatt tcttacagga aagtgaacat caagtaatta   9720
ttccaaatag agttctctta agaacgtgag ttacttaaaa atgtctaagg atgaagtcac   9780
ttctgaatat aacttcactc aagagaacaa ataagcaaac tgcatttagc ataacatggt   9840
aaattagctt taactctcct tgatgtttga acatttgtcg ctgttaacta ctgtttcact   9900
tttcaaatag tcagggctta gtttgcttct gtaaggataa agggaaaata cgccttcact   9960
gagtcataaa tatttttgtg gctaactttt gcacagagaa aagaggcctc taagaaggta  10020
cccagtgaat tttttttcg gggcagggag agaatatgtc atttttggt ttgttgttgt  10080
tgttgtcatt gttttgcttt gttgttttta ctctgaactg aactgtatct tgacagcact  10140
tttgaattaa gagcattact cttattgttc tctactacct ggacgccacc tccctgttgc  10200
catagtgtta aggatcatgc tccgaggtgg ggtgaggcag aatggggcca agatcagaaa  10260
gttacattaa gctacatcag gtttatacaa gcataaaacc aaatttttgg agcagtcccc  10320
agaatacaac ctggtttagc cacacctaaa ggttgctctt gaatattcct tgagaatcca  10380
catccctaga atgctgggtt tcaatgggcc ctttatgtac ctatcatggt gtcatttctg  10440
agcatttcta aatattcctt catgtcttac tgacagtttt tcttgaataa atcttaggaa  10500
tattagtgcc attatcagta ttttgtttgg tctgttcaca ccacaaataa ctacccaggt  10560
ctgctacttg cccctatttc tctacctgct aatgaaaatg cttttgaaag tttgagtaac  10620
agtattggag tgtgcacagt ggtattggta ggttctgtac tcatccttaa ccacttgttt  10680
tcatcctttg tgagcttgaa gtttctccaa aaaatttatc acaaaactta tcagacatag  10740
ttaatacact cagagagaga atcactgaaa aagtagatgt agtttaacaa acccagtgcc  10800
tttttttac ccatgaatac atatttgtca actaaacctc attttgcaac ttgttccact  10860
actcgaatgg taacaaactt ttggtttccc aatagatttg gaagatgttg cttttgaaag  10920
```

```
taggaaatag atggctttag aagatggaag aatattttgt ttgaagtggg agcgtggtat  10980
gtccttagct gtctgtgaaa tgcagctgaa gatgggtgtg ggccttcatc tgcatttccc  11040
atcttcagtt tgaggaggta gttacccttc taaccactta agaactgcat ggtacatgct  11100
gttttattta cagggcaaaa ctgtgctccc gtagtttccc tggtgcttgc cttcacgtta  11160
acacagtgtc atcgtttggc agtgtttatg tgccagggtc catgttagaa ggaggaaagg  11220
tatagcgaag ttaaagggtg cagttggcct cccaccttta gttttgtaag tgcctttaaa  11280
gtttgatttt tgtaggttga tcataaggaa gtgataagta tgttaggtta tttgtggttt  11340
gagctaattt tagtctcttt ttacagcttg ctttgtatcc tttgccatta aaacatgctt  11400
tctagaaaga caacttttga atgtaggaca cagtctatat tctatacttg gctacatttc  11460
aaaaaatatt ttctcagtac tttggaagtt ggacagttgg aagcatagtg acagtattta  11520
aaaatctttg attccggccg ggcatggtgg ctcacgcctg taatcccagc actttgggag  11580
gccgaggtgg gtggatcact tgaggtccgg agttcaggac cagcctgacc aacatggtga  11640
aaccctgtct ctactaaaaa tacaaaatta gccgagcgtg gtggtacatg cctgtaatcc  11700
cagctactca ggaggctgag gcaggagaat cgcttgaatc tgggaggcgg aggttgcatt  11760
gagccgagat cataccattg cactacagcc tgggggacaa gagtgaaact ctgtctcaaa  11820
aaaaaaaaaa aaattaagtg atttctttgc tttgtgacac ttctactttt ccagcaagta  11880
aattatattc tttcatacag gtatgaaatt cttgttccaa gctagtggtt aaaaaggcac  11940
agttgatatt agaggatttg taaaagatta tgaccacgcc tgcaatgtac tgaagcaagg  12000
ctttgctggg ctgtgtatag gaaaccttcc ccagcctgtg cccttgcttg atagaacatt  12060
ttgctcctaa gggtaggtgc ctgtatctgt ctccagtact ggttagtttc acacagaaca  12120
gttgtgtttc agagctttag tctcaagctg ccctgctccc ctgaagcagc caccctgagc  12180
atgtgcactc acaggagggg acatgtgagg tcatggaaga agacgactca ggaagaagaa  12240
gacttgggtt tgggttctga ctctgccttt gactgttgtg ggattttgag gagttgcata  12300
caggatctgt aaaatgtagt cattagacta gactagacag ccatatagca ttacctagat  12360
gtaactttct acaaagacat ggtcacagga gaagaccaga gggtggggtg atctttctgg  12420
aaaaattggg gcttcatgcc ttactcatgc tagatatggt agcattatat ggctgtgcct  12480
gatcccccta atctaaaagt gggacagaac tttaaaattt catattaact caaattaaaa  12540
cttgaaaaaa acccattatt tccttaaaaa taataaaatg ccctgtgggg gcataagtca  12600
cattatattt taaaattcct gaatgccaca tggatgaatg tagttccttt tgaaattctt  12660
cttttgtcta aagaggaatg ttggattttg taattggact aaaaaatctt ccatttgaga  12720
gagaaacagt ctgctgcatg ttctaccctt gttcaggata aaacccacta atagctaaca  12780
tttattgaat tctgtgttgt gcctcaggca ctgtgcaaag tcctttacat gcaatgctgt  12840
ttattatata ctgtcaattg gtctataaca gcaggaaatg tttcaggagg acaatgaggt  12900
cccagaccct cagtcttctc ctgtgtcctg gattcagctt cacaatagca ctatggcagt  12960
gtggccactg cttcagcttc cacatacatg gctgtgaaga gagacagggg attgtgctaa  13020
gcctccccga tttattagga cataggagga gagagtttgt agtttttgac ctttgcctag  13080
ttttctaacc tctttcctag atgtcacaaa ttggccaccc acagtcatat tttgcttgct  13140
tcacgcaatg ctttttaaaa aagagaagag tttaatttgt gccattgttt ataaatgaat  13200
caggagaaat gacatgcaac tctggattct ggcctctctt gaaaaatctg aaaatcacac  13260
cgtctgagct tacactggca gtggtctgct ggactgaggg acacaactcc ttttggatgt  13320
```

acatgtgtgc gttgcagagt ttaccacagt cccacagtgg gtcacactgt ccttgtcggt 13380
gtacactacc tagcacttga gtttgcaacc cctaccccaa gctgagtttt ctcgtcaagc 13440
ttgatgttaa tgttatgtga tgcttggcct tgtaggtatt tggtatatta tcgttagata 13500
aaattgaagc aaagggctaa agggttggtg gcctgaggga gtgcccttga cagtaaagtc 13560
taggataaaa tcattggcca ggtactcctt cccttcccgc ccttcctctt ttctctttat 13620
cctcagcctc cttctgctat tttgaggaag ttagaagcca ccaccatttt ttcccacctc 13680
aggcaactga gtgtggctgt atttctgtcc catgttcagt tatttccagg aactattttt 13740
gatgaccaac ttgaagttac attgggtggg cctaatgggg gctgataaaa gaatgaggtg 13800
accaaatatg cttgcactga gacggctacg aagtaaggtt tttaatgact tgctttgtga 13860
cttggtcagg agtgatacca tttgtcatgt gtccaacttc atgactaaat ggttgctcta 13920
ccttatcctc atagctataa taaaataaaa taaatacata cattgcaggg aggaatgtat 13980
cttgttaaag gtctctccct tttagcaaca aaagtacata ttatgttgta gaacatgctt 14040
tttctttgat ccttcttgaa cacctattac tctatagagg tatgttgtgt atggcaaatt 14100
agaacaagca atagataagg atgattcttt accattataa cccagtcaag gtctttgtcc 14160
taagttttgt acctttctcc agagggaaag gtatttgtat ttatttattt atttttgagg 14220
cagagttttg ctcttgttgc ccaggctggg gtgcaatggc acgatctcag ctcactgtaa 14280
catccgcctc ccgagttcaa gtgattctcc tgcctcagcc tcccgagtag ctgggattac 14340
aggtgcctgc cacgatgccc ggctaatttt tttttttttt tttgtatttt tagtagagat 14400
ggggtttcat catgttggcc aggctggtct tgaactcctg acctcaggtg atccatccac 14460
ctcggcctcc caaagtgttg ggattacagg catcagccac tgcctccggc caggtatttg 14520
tatttttagt ctctatgcct taccgtctca gatcaggagg atttggtgat ttatcgaatg 14580
tgggggaagg ggaagaagag gaaacgggag gaatgttcca gattagggaa atagctagat 14640
ggaagatgca gcccctcatc aaggtgggga cacaggaaaa ggaacgtgtg caaagaagat 14700
ggtgatctgg ttgtgaccat gttgttagag gacgtccagg gaagcatctg gtaggtggtg 14760
gggtgtttaa atatagaaca ttcggagaat gctccgaagc ttcagagaac ccttcccaaa 14820
aggacaaaac cagctcagtg ttttagcact ccgggatcat atggcatgac agcatggctg 14880
ctttatactt ttttgtgtat gtgaaattaa aaccaaccac tcaggaccaa tttctctgaa 14940
gctttttgtc aatctttcat ttgcttttct cgtctagatt gtaagctcct tgcagccagt 15000
gtctgttgat tcagtcattc aaaaaataat acatgaacag ctactaggta ccaggctctg 15060
tgctgggcag ttgggatatg tggtgaggaa gacaaacttg gtccctgccc ttaggaagtt 15120
cagtagtcca gcagacaaag tggctgaata aagataatct cagttcacag tgataagagc 15180
tcttacaggc ctaggctcca ggtgctgtgg ggatgctcag gaaaaggtat ctaattggga 15240
ttgggagcag gcaaaacaaa taaaggatag tgtataaagg taatatctag ttgaagttct 15300
gaagggcaag gaggagtgag cctgtatatt ctctgagtct ctccctaatc tgggattgac 15360
ttcttgtccg tctctgttca tattaagtgt cacctaggct tgaaagggtg agatcatatt 15420
tcacttcctt cctctttggt cttaaccttt ctctgctacc ccctcacaca atgcatatgc 15480
attattctct tattgtatat atttttcctc tcttcctttt catgtttcct ctgccattac 15540
ttttaacctc gactgccata tggcctctaa acgcttccag aagggtagcc tagtggaggt 15600
tattccatca tggccttgag ctcatgcgac cagatagtga aggcatctgt gtaggtgtct 15660

```
tctccaggag ggtgatattt gtttcattgt aaattttgta gccctagaac accaacaaca  15720
gtgcacagta attagtaggc aggcagtaca ggattcattg aagtgaagtg ataactttta  15780
tccaagtatg tatgcagata atctttgatt tgtacaaaaa aaattatatt ttaatatgta  15840
aagatttttt aaaagaatct tcaagtttta gccttcccac taggaatata ttgaaaacat  15900
gtgcctagtt cactgacttg cagctgccac tatgagaata aaggtctcat ttagttgttg  15960
tgaattttaa gggatatttt caatgatgtt ggctggttta tcccattatg tggtcttttt  16020
tttttttttt tttttttttt gaggtggagt ctcgctctgt cacccaggct ggagtgcagt  16080
ggcgcaatct cgactcactg caacctccgc ctcccgggtt caagcgattc tgctgtctca  16140
gcctcctaag tagctgggat tacaggcgcc tgccactacg cccagctaat ttttggtatt  16200
tttggtagag aagggtttca ccatgttggt caggctggtc tcgaactcct gacctcatga  16260
tccactcact tcagcctccc aaagtgctgg gattacaggc gtgagccacc atgcccagcc  16320
tatgtgctct tattagcaat tctcagtaca cagatagctt tgagtgattc tttcaagtca  16380
agtaccttat taaaaaactc aagtgtactg ataattatct tacttttaaa tggctaagtg  16440
ataagactga atttttaggt actgtaacac ttcagattac agattctgat atttttatgg  16500
ttatttatat ttatttattt ttgagatgga gttttgctct tgctgcctag gctggagtgc  16560
aatggcacga tctcggctca ctgcaacctc cgcctcccag gttcaagcga ttctcctgcc  16620
tcagcctcct gagtagctgg gattacagtc acccgccact acagccggct aatttttgtt  16680
atttttaata gagacaatgt ttcaccatgt tggccagggt ggtctcgcac ttctgacctc  16740
tggcgatccg cccgcctcgg cctcccaaag tgctgggatt acaggcgtga gccaccgcac  16800
ctggcctggt tacttaaatt taaatacaaa aattatgttg attaattctg aatgatttcc  16860
tgattgctcc ccgtttacca ttcacacatt tattaaattc ttcgcttgcc atatagaagc  16920
agtctctctg ccatatatgc catatagata acagaactag ctgtctgcaa accactgaaa  16980
ttgtgaaaac atctcccctt ttttcctgtt tctaattcta gctatgagga ttatatacag  17040
aagtagtcct ggatttgatt tttttttttt tttgatgatt gtttttttgat agttgttgac  17100
tacaaatcat ttaaacgtct gaaaggggaa aggttttcct taaaaatgga tgacaaagga  17160
gaataaaaag gtattttgac tattttttttg aatgatgagt tttttttttc tctttcttgt  17220
tttcttttgg agtcatttat gtgtcactga gtggatacca tggaacatgt ggcagaagta  17280
gatatatggg gtaaaagaac catagttcat aagctccttg acagaatcac tgaagtgtag  17340
ccgttatatg gccactgtcg caggggggagg cagcagtttt gaagaagggg atgagtaata  17400
atgagtgata aaaaggcatc ctggatagaa gaccaaactc tgcagaagac cccagtttga  17460
ttatgctttt gttttctgat ttgcggagga gagtgaaaat gcctgagggg tgcgggggag  17520
cacatagggt gtatgtgtgt gtgtgtgcgc gtgcagattc tctctttcac tgtatgtatt  17580
tgtatgcatg tatgtatctt aggacttaag ctttctagtc aataaattgc catagtgggg  17640
aattgcttaa ttgcttgcct tctgttgttg tatttaattt aattttattt ttaatgattt  17700
ttttggtggg gtacagggtc ttaactatgt tgtccaggct ggtcttgaac tcctaaactc  17760
aagtgatcct cccgcctcgg gctcccaaaa tgctgggatt acaggtgtga gccaccatgc  17820
ccagcttagt tgtattttaa atgggcctgt ttgcagcatt ccctactccc cttagtttac  17880
ctggctcaca acctgtcttt ccatatcaag gcttctgtca cccctggccc atgtcagtgc  17940
atttgggcag cccacccagc atcatcacct catgtcccag ggaacttcct gttcctctct  18000
tccagctatt tccttccctg gcagttgaga tagtctctac ctttgaccta ctgttaagct  18060
```

cagaccttct gctctctagt tacagcctct gtgctgccag attccctcgc tcagttgctt 18120
tctctagttt gggttttctc ctttattcag atttccagct gtttctctcc tccccccacc 18180
gcagcctcct cacttccctc cttatgcatc tgagactgtg gtcagtcact ttagatgctg 18240
cctctccact gtacttgtgt ccatcttctt acctaccacc tctagccctg gagcaggctc 18300
ttcccctgtc tttgtcttcc tgggcccagg ctcctaagcg ctgctggaaa aaaaatcccc 18360
cagtattgag cccctagaaa tccagtcttt aatcccaaat ctgtctcccc cagcatctgg 18420
ccatcagatc taaagcttac ctgccatcct ttccacctca tttctctcac aggggaaaag 18480
gagcctttgc tcctagagtc tgcgctcctg acccccttccc atctcacctg ttcaaggcat 18540
cttgcaataa ggggttggtg actctcgagg aatggatccc aggccctccc tattatcatc 18600
ttatgtatgc cagttcaacg ttctcagctt cctccagccg agacggcccc tccagccact 18660
gctttatact ctccttctct ggttgaaatt tttgaagtaa ataggtcact ctgcccatcg 18720
ttcatcttcc agtcactctg tgtgtttatc ttccagggaa gtgaggctct atgctaccaa 18780
gccactgaaa taattttttt ttttttccag actgagtctt gctctgtcac ccaggctgga 18840
gtgcagtgcc gcagtcttgg ctcactgcaa cctctgcctc ccggcttcag gcgattctcc 18900
tgccccagcc tcctgagtag ctgggattac aggtgcctgt catcacgcct ggctaatttt 18960
ttgtattttt ggtagagatg gggcttcacc atgttggcca ggcttgttgg catgttgacc 19020
atgttggcca ggctagcctc aagtgatcca cccgtcagcc tcccaaagtg ctgagattac 19080
aggtgtgagc caccgcacct ggcctgaaat aattcttgac aagatctgct tccttgttac 19140
taatacagtg gatattttgc atcctaattt taatgcagtt cagtgtggta gacctgtatt 19200
tgcatattga atattccctt ccctgtttta ataactctat tttttccttt tcttttatat 19260
ctcctgcttc tctagctagt cctagacctt actcatcggt gtcttctctg tttgttcctc 19320
aacttgagga gttcctacag ggtttaccca atctgctgct ttcatttagc ccttttgttc 19380
tttttgagcc atctcattca ctcacccagg atgtagcatc ggcccttgaa ttcagtgtgc 19440
acacatacac tgtgcactat gggacagcct tcagaggcac tttgttcctg aaattgtggt 19500
ggtctttgcc tctcatggag ccttgcatat gctgtttcct ctgcctggaa tatcctacct 19560
tttacttaac tgattctcgt tcttctttcc agtcacattt tgtacatttc ttctgggaag 19620
ctttctctga tttccccttt ccacaggtcc aagttaactg ccttgtctag gtcctcccat 19680
ggccctctga aggcctcctt tcatagcacc atgtctgagt atactgtaat aacacgcatt 19740
gctctgtaat agcctgttta cttacctatt gccaagtaat ctatcaagtc ttataaaggg 19800
cggggctgct tttgttctag tcatttgtat ctcttagtac ccaatatagt gtttggcata 19860
tagaaaatac ccaacaaggc cagtcgcagt ggctcatacc tgtaatccga gcactttggt 19920
aggctgaggt gggcggatca cttgaggtca ggagtttgag accagcctgg ccaacatggt 19980
gaaaccctgt ctctactaaa aatacaaaaa ttagccaggc gtggtggcgg gtgcctgtag 20040
tcccagctac ttgggaggct gaggcaggag aatcacttga actggggagg tggaggttgc 20100
agtgagctga gatcactcca ctgcactcca gcctgggtga cagagtgaga ctccatctta 20160
aaaaaaaaaa agactccatc ttaaaaaaaa aaaaaaagaa aaaagaaaga aaatacccaa 20220
taagtagttc ctgaatgaat agatgagaat gctgtttaga aggttcatga attggaaacc 20280
gtgattgcta gggaggcttt gagttgatgg tattgtgttg aaccatgtgt tacccaggat 20340
caatttagat tttacacttt gttttctctg ttccttttta tagtaatttt ctgtatgtgg 20400 tgttttcccc ccatgagatt gtataccatt tctcagcgag aactgtgtgt aatgcttggt 20460
ggctccctca tggtgccttg catggaattg gacttcgttt cagtggatct gatcccagtt 20520
atgttaatgc tcgatggagc taagtcttat ctcgaagcag tccatgtctt catcagctgg 20580
ccctgcctcc atgccctgca cagaccatgc cactctggag aggtagtttc cctgtggctt 20640
attagtctta tgttccagtg tgctggccaa gtatgagaga catcagtggt atgagagagt 20700
ctctctcatt caaacttcgt aggttttgta gctgggactg accagtgctg acaggaaata 20760
gaggcattta ttaaaagcca gagatttttc aagttgcagg aagcaaagct cttgttagct 20820
atgattttgt ggtgggtttg gtagtccaat ataaaagtaa aaactggatg acaatgggag 20880
gagcatgctt gggtctccaa agttagatca tttttcctaa gtaatttgtc tttaaacttt 20940
tactggtttg gaatttcctg agattttgat cttgccagaa agtttatagc aaaagttctg 21000
agcagatgac acttttgcgt ctgaaaccaa atcattgttt ttgtttttaa ctttttttctt 21060
aatatattat ccttagttca gccctgaaga ttattctgtt atttgtggat ctcaactttc 21120
cccccatctc ctggatcttt gtgaaatgaa tggtattaat tgaatagaga aggaagatat 21180
aaacataaac ttagtcaaaa acttgttctt gactaggcaa gttgggcttt atagctttga 21240
gctgatgaca tgtctattct tgtgaaaaag ggatttttag tgttggtttg gcttcttgtt 21300
atatttgatt tattattatt atcattatca ttatttttga gacagagtct tgctctgtcg 21360
cccaggctgg agtgcagtgg ctcaatctcg gctcagtgca acctccgcct cccaggttca 21420
agcgattctc gtgcctcagc ctctggagta gctgggatta caggcgggtg ccactacacc 21480
tggctaatat ttgtattttt agtagagaca ggtttcacca tgttggctag gctggtcttg 21540
aactcctgac ctcaggtgat ccacctgcct tggcctccca aagtgctggg attacaggcc 21600
ttagccactg tgcctggctg attttttttt tttttttttt tttaggtttg ttttaactgg 21660
aactttacgt gaatgtaatt gaatttagaa taaaagcact taatttcaca gtgtgcagtg 21720
aactttctgt tacttatttt aacagtaaaa ccccttgcag taaatgactt ggagcaaaga 21780
ttgctttttt aaaaaatgtt ttaatttgtt tttcttttct tgagatggag tcttgctctg 21840
tcaccaggct ggagtatggt ggcgcgatct tggctcactg cagcctcccc gcctcctagg 21900
ttcaagcgaa tctcctgcct cagcctcctg agtagctggg actacaggca catgccacca 21960
tgcccagcta atttttgtat ttttagtaga gacagggttt caccatgttg gtcaggatgg 22020
tcttgatctc ttgaccccgt gatccaccct cctcggcctc ccaaagtgct gggattacaa 22080
ctgctgggat tacaagtgct gggattacaa gcgtgagcca ccacgcctgg ccaatttttt 22140
tttttttttt ctttttgaga cagagtttca ctctgtcacc caggctggag tgcagtgtca 22200
cagtcaaaac tcactggcag ccttaacctc ctgggctcga atgatcctcc tgcctcagcc 22260
tcccaagtaa ctgagactac aggcatgtac cactgtgccc agctaattgt ttttttattt 22320
tttatttttt gtagggacag ggtctcgcta ttttgcccag gctagtctac aactcttggg 22380
ctcaagcagt cctcctgcct tgacctccca aaatgttggg attacaggga caagccactg 22440
cacctggcca aggattgttt tttaagtgaa ctgagaccca gccttattag tggtcccaga 22500
gcagacctgg gacctgaagg gaacccttttt cttctggtcc agcgtctttc ctctgatggg 22560
ctactttcct ggagcctttg attgcctgtc atcagagtaa ctgagtttga acagagtagg 22620
tagttcctct ccagaccacc acactcacca gctttcattc tgcttctctc gtttagactg 22680
tggttctgaa tcctcagttc tatttactga gtgtttttaa acataaaaat gccttttaat 22740
gagattgaag gccagaggtg ggacagttga ggacaaagta gaaataaaac cttcaaggcg 22800

```
gggttgttgg tgggagtctt tttttgtttg tttgtttttt gagactgagt ctcgctctgt  22860
cacccaggct ggagtgcagt ggcacaatct cagctcactg caacctccgc ctcccgagtt  22920
caagctattc tcctgcctca gcctccttag tagctgggat ttcaggctcc cgccaccatg  22980
cccagctaat ttttgtattt ttggtagaaa cggggtttca ccatgttggc caggctggtc  23040
tcaaactcct gacctcaggt gatctgtctg cctcagcctc ccaaagtgct gggattacag  23100
gcgtgagcca ctgtgcctgg cagggagtct tatagaagct gtcgtggaca atgtgggaag  23160
tagtgagcct ttgtattcca gtatgctggg ctccactgtg cttgctctgg cccccggtcg  23220
ctctctgtgt gttattgagt ccccatccac ggccatactc ttcgtcctgc ttctctcctt  23280
accatcctct ccccgctagt ggtaccacgg ctaccactag caattactga catgtgggat  23340
cttagggcta cttccctata aggctgcagg gcatgtggtg ttggctacgc gcatggtaac  23400
catggtagcc ctgtggttct ccacatgtgc gccttgtgac ctgggattgg ctgcagacta  23460
gtaataaact gcgtcttctg gtatggaatc tgtctgtagt tgtactttct acctctgtat  23520
ttaaggggag atctgtaacc taccaatgcc agttgaagag gatggatgat agagatgtta  23580
acaaacagct gaaaaactaa ctacaatggc ctgcaaaata gaacagcagg tttttgtggc  23640
aaaactttgt gtccatgagt ttgtttttta aatatcctca tataatctgt tttaaatcga  23700
gaggctttgg gtaaaagcca tggctagtct tacatgtcat ggagtaccta gcttgtgagg  23760
ttcacagttt attatttaca gagtgtcccc ttaaatcttc tttgggtcgg ttcagcgaat  23820
gttgctcaga tggacttttt tggctgacat agagtcaaaa tggtaatcaa gcatgaaagt  23880
acagacagtc cttaacgcac aaatgtgtca tgcttgaaaa gttggaaagt tggttctctg  23940
gagctctgat tgtattgtcc tgtagaatcc gtgttgtgaa tggtggttaa atcccaaatg  24000
agtccgtaga acctatataa tctgcaatat acctgcagta ttccaattaa tatgtaattc  24060
ccccatagaa ctatgttaat gatttgtatg tatggtattt aatattatac ataataatga  24120
ttgtatgaat aaaaaacatt ctgggctcca tgtggatgat ggggtgtgtg tgtgtgtctg  24180
tctatgtgtg ggtgggtgtg tgttcataga tccctttttcc tgcaatcctg gcactggaat  24240
tggttttatc atttccaatt aagtttcatt cccatgaatt ttggagtaca gactgggtcc  24300
aggtatgcag ggcatagatt agagccctga gaaataggat taggctggaa ttgctgggtt  24360
ggagatcagt agcttccagg aacacttttt gggcctggct gtcttcatta tccccttttg  24420
ttttctcctg gggtctgcag gtattgccct gttttgttcc tctaatatca ctttttttt  24480
ttttctgctt ttgaccaggg tttttgcctc tggtctacaa ctgaatatcc tatcagactc  24540
tcctgatttt gaaataaata tatagttttt ttgaggtgtt ctagcgaatt tctaaatcta  24600
aatgttgtgg cagagttatt acatactaat tttgctatga gaggttgtag aatcccagat  24660
gactaatctt gtaaaccata cacgcatttc catctaattc tccattgtat atcatgttgc  24720
agaaaataac agcctctaga gtttacattg cctcctttga ctatatttct tatttaagat  24780
tagttttcag ataagacctt ttcatggcag tacataactg tacagagggc ttccaacttg  24840
tcttgggagc tctcatctct gggagacatc acattaccca ctgccccctg ccccccgccc  24900
ccagcctgga tgcactcagc ctgtacccca tttctgtcct cagccaaaca ctgctgaaat  24960
gcaagagctt tcaattgcta gccagtgaag atgcagacta agggatttcc atgtagaagc  25020
ccgctctttt cagctggctc gtcgagagct ggaggcccct tgcttgttca catgaggctt  25080
tttgtccctg acttggtggc tgctgtttca cttctcagca gaaagggaca cccttgcccc  25140
```

```
cccccagaaa ggaagatttg atgtaccact tccgaaaggt tcagtcgggc atcactgtaa  25200
ccaagaagat aggtcaggtg aggctggagg tggaacaggg ctgctcgcta gaactccaga  25260
ttgttccaca agtgccttct ggcagagaat gatggaagct tccgtgattt ttttttctcc  25320
ttaatagtta tgagcacaga agaggagcag attgtctggc tatagaagct gtcttatttt  25380
ttatttttgt ttttgagatg gagtctttct ctcttgccca ggctaaagtg caatggcgcg  25440
atctcggctc actgcaacct ccgcctcccg agttcaagcg attctcctgc ctcagcctcc  25500
tgagtagctg ggaattacag gcatgcgcca ccatgccaga ctgatttttg tattagagac  25560
agggtttcac catgttggtc agtctggttt cgaactcctg acctcaagat ctgcccacct  25620
cagcctccca aagtgttggg attacaggtg ttagccactg cacccggccg aagctgtcat  25680
attaaatagc actttctgct tttagcaaat ttaatccaaa tgagacttta gattttcttg  25740
ctctgactta ccagcagttc cttgaaacac atttaattat ttttgccaga aaatcactca  25800
agcacttacg ccatttttt accgtgaaaa tatgctgcat tattttaaaa tatattagaa  25860
gtcagtaacc ataagatttt atatgttttc taatgtattc tgtaagcttt ctgctgcttt  25920
tgtttggaag gtgtattttg taacgtagag gactgcttta tctgcttgta agcttgattt  25980
ttgtttttac tgtaattttt ttttcttttg ctgtattgag aaatacattg agtaattata  26040
aagtcagtgg catgtttata agttaatatt tgtatctatt ccttagttac tctaactcaa  26100
aacctaaagt aatcttcaac tctaatttac tctgacatcc agttgactgc caagtcctcc  26160
aacttaatcc ttatcctttt ttttttaaag agatgcagtc ttgctttgtc acccaggctg  26220
gagtgcagtg gtgcaatcat agcttactgt aacctcaaat tcctgggctc aaatgatcct  26280
cccacgtcag cctctggagt agctggggct acaggctctt gctaccatgc ccagctaact  26340
ttttattttt atttttata gagacagagt ctcactgttg ctcaggctgg ccttgaactc  26400
ctgccttcag gcggaactcc tgccttcagg cggtcctcct gcattggcct cccaaagtgc  26460
tggaattaca ggcccaattt tattcttggg atgtatgtct gaaactcttt ccttcacttc  26520
cttcccaagc cttagttcag gcccttctca tctgtggtct tcaaagtcgc cttcagctgg  26580
ttcaggtcct tcctttctgc tgtatctttc atgggaggac atgttatgta tcactgtcct  26640
acttgaaaac ttccattccc cattgatgag ggtgttacct ccagattcct aacacaggtg  26700
ctgaaggcat gcctggataa aggcactccc ttgatctcct ggccaggtcc ccgtacacct  26760
gcagcgcatg ctccacattc tgtctttact gatgctgtgt cttctgcctg cggagccacc  26820
caccattcta ttcacagccc ctgcctcagc ggagcacgtg cctccctctt cctacactga  26880
gctgtccttt ctattgaatc ccctcttttt tgtagtatgg gaaatatttt attatgaata  26940
ctcttttctc tgttgcctcc gtgaccacgt taactttgcc ctaattcgcc ttaggactcc  27000
atctgcttag gggaaagtta ggatttggtt acagaaagca agctgctaga aagaacagtg  27060
tttagcttct gacaggcaaa ataggatttt gcaacatgct tttccttttt aatgcttaga  27120
cattttatat gaattaatat ttttatttgg ttgcttatac attactttct ttttagctag  27180
aatgtgaacc ctataggaac atggggattg cctttcacat ctttgtatcc tcagtaccta  27240
atgttcagtc accctgtggt cttgtgtcgt atatacattt agccttcctt aattaaacca  27300
tatgtactgg tccccgtccc ccacccccaa atagagagaa agaaattcct tgaatactac  27360
attgccagta tcaaaccaca ccttgatatc ctctggggaa agggaggtat cagttgaaaa  27420
gagaaaagag gttaaaatct aggcattaaa atgtgtaagg cttagatgct ggcaatttaa  27480
ggtatgtttt cctgaggtta attttgattg tgtgcaaatt ttacctcata tctaactgta  27540
```

```
ggatttagtc accacataag atgggatacc tccataaatc cttcagaaat gtttgtgaaa  27600
ttaaataaag ccttattgaa gactcagctc ttgagagtca tctacctacc taacagttat  27660
tcttgaacag aagagtctta cttttcccta taaggcagtg tgatagccat ctgtatattc  27720
atataattta tgttggcgct tacttcattt aaaaatgtat tccgtgaatg cagttgccag  27780
gcggtgtgct gatcagaaac gtgtaccaat ggcctctttt ataattataa gaggaagacc  27840
aacctgaaac agtcacacaa atgattaatt ttaattgtgg aggagtgctg ggaaagaaaa  27900
ataaaagatg caatgcaagt gtttacaaag gagctttgag cttgtttgaa gtggtccttg  27960
ggcacttaag caaggcttaa agaatgatgt gattagaagt ggcttagcaa ttctaaagaa  28020
cacagggaag gcgtgtggcc agaacattgg tccctagagc acatcgcctc ctgacatacc  28080
atttccttaa gttaatgttt taccactata cataggccct ccccttttgtt tacccagatt  28140
tttttaattt taaggatgtt tttaataact tagaatcctg taatttgttg aacagtcctg  28200
tattcccttt acttatattc cttgagattt tataaaatat tttttacatg tcccaagtct  28260
tgattatatc tttttacctc ttgttaagaa atacttactt ttctattttt atgctatatt  28320
tcatgtttac tgtagaaaac aaaaaaagta aaatttttct ttattcctat cactgcagct  28380
tataagcact ctaaacattt tgatctatat tttgccaatc atatatttta gttaaaattg  28440
ttgttgacat aattgtagat tcctgtgcag ttgaaagaaa taatacagag ctgagcgcgg  28500
tggctcacgc ctgtaatccc agcactttgg gaggccgagg caggcagatc atgaggtcag  28560
gagtttgaga ccagactggc caacatggcg aaaccctgtc tctactaaaa atacaaaaat  28620
tagctgggtg tggtggcggg cacctgtaat cccagctagt tgggaggctg aggcaggaga  28680
atcgtttgaa ctccggaggc agaggttgca gtgagccgag atggtaccat tccactccag  28740
cctgggcaac aagagcaaga ctgcatctca aaaataataa taataataat aaataaactt  28800
taaaaataaa acagagagat cccatgtgcg ctttgcctag ttcccccatc cactgcccat  28860
aacattttgc agaactgcag tacagtatca caaccacaat actgacattg atacagtctg  28920
ctcatcttat tcatatttcc ccagtgttac tcgtatccac gtgtgtatgc attgtgtttt  28980
caatactctt ttattataaa gctgttttta atgtgattca attctaggtt gttttgttct  29040
gccctcaaaa agcattccct ctcctaatca tatctccgtc ataccccttgt atgttttctt  29100
taaacctgtt ttaagaaagc agctacctgt aagagaaatg agattgaaaa cagaattgcc  29160
aatctgcttg tactttataa gcctgttgat tgtttagata cggtttagcc agtttatagt  29220
taccctgggt gctgaaaggt atgctggatg atacctaacc aacagagaac cattgaatgc  29280
cgttcaaaat ggactgaagc atcagcaatg tctgaaaaag gcctgacagt aatgtacatg  29340
tcaaatggcc cgtaatttaa gcagagtaga gtaagtagaa gaataaacat ggggaaagtt  29400
ccagcaacag aggaggcttt gagcttttgc tcttcatctt gagtggatgt tgttctcagg  29460
tggtaatagg ccatcgagct ttctccactg gctgcctctc tggggaacaa ataaccgaaa  29520
agatactcag caccctggtt ggtacatagg tggtcagttg atttatactt cctggttttc  29580
agtgttgctt gaattttcta aatggaaaca cagtaccttt ataatcagaa aacaatcccg  29640
agttttgatt tgagggtgtt gtaaaaagtt aaaaaaaaaa aaacagaaat gtgaaaagga  29700
agttgtgtta gagtatttgg agttgagaaa gcatgaaaag gacagaagag aagctggttg  29760
tcaggttgca tggggtagct acaagcacac tgaccagaaa gtcagctgga aaaaaaatgt  29820
agaaacagga gataaaacgg ccaaggggct atacaagcaa acagcaagga cctgagaaga  29880
```

```
aaaactagtt aggtgtgact gtcagagtga tgtgtacagt gtgatccttt ctgtgtaaaa  29940
acaagcagta agaattcgct gtttacgttt gcgtgtgttt ggagaagagt ggggaagagt  30000
aggcactgcc agactgtgaa cactggttag gttattgtta tatctttgta ttatatacac  30060
tggacatgtt atttgtataa tatgagaaga aattttataa atcattaaat cttttggcat  30120
ttaggaacat ttgtgttttc taatagttgc ttctatacta ttatctttat tatatgccct  30180
tcatcttctc agtgtttggc tgttgttgtg attccctttt gtgagcagtg ttgaagttag  30240
ctaatattca tttcttctcc cttctttcac cctcctccag agtctgattt gaagtattcc  30300
tagctgctac ctataaaagc aataagcaag attgttttac ttttcacaaa ctcgtcctgt  30360
tctgtgcctc tgcctcggac atagctgtag tatagagtgt tgtctccctt acatccttct  30420
atcttagacc tactagtaaa tattaatgct cactctaagt tcttctcaat tctttttttt  30480
tttttttttt tttttttga gaaagagttt cgctcttgtt gcccaggctg gagtgcaacg  30540
gcacgatttc ggctcaccgc aacctccacc ttctgggttt aagcgactct cctgcctcag  30600
cctcctgagt agctgggatt acagtcacgt gccaccaccc ctggcaaatt ttgtattttt  30660
agtagagaca aggtttcttc catgttggcc aggctggtct caaactcccg acctcaggtg  30720
atccacctgc ctcagccttc caaagtgctg ggattccagg cgtgagccac cgcgcccagc  30780
ctcttctctc aattcttcct gaagctcttt ctgcactaga ttcctcagga agggcttgtg  30840
ggaacaatct tctgtgaatc aacagtacat attcataata gtttgtcagc agcctattat  30900
tttaaggcca tttggtctgt atataaaaat gtttggatca cattttcttt ctttaaggta  30960
aatatgttat tctgttgtct tctggtataa agcattgctg taaatgtttg acagtctaat  31020
tatcttttgc ttataagtga cttagggttt tttgtctatg tgcccaaagg atttttttccc  31080
tctttctctc tttttttttt tttttttttt tttttaaaca gacaggatct caccctgttg  31140
cccaggcttt agtgcagtga ggcagtcaga gcttactgaa gttttgaact cctgggcttg  31200
aggaacaaag gatttttta acctttttaat tcaaagtctc atcatttatg caaccatgtc  31260
ttggtgttgg ctgttttggg ttgttctccc tcaaaaatcc atgtgctctt tcaatatgta  31320
gttttaaatc tttttttttt aatttcagga aaatcttgaa ttagagtttt ccgtttttcg  31380
tctggtacat tgcttgggtt tccttcttca ggaactcagc ctgttatgtg tatgtttgat  31440
cttctttgcc tgtcgtctgt ttctttcact tcctctcact tttttaaact tcatttatta  31500
aaaaaaaatt tttttttcga gacagagttt cgctcttgtt gcccaggctg gagtgcaatg  31560
gcgtgatctc ggctcactgc aacctccgcc tcccaggttc aagtgattct cctgcctcag  31620
tctcccaagt agctgggatt acaggcatgc gccaccacgc ccagctaatt ttttgtattt  31680
ttagtagaga cagggtttct ccatgttggt caggctggtc ttgaactcct gacctcgtga  31740
tctgcccgcc tcagcctccc aaagtgctgg gattacaggc gtgagccact gtgcccagcc  31800
ttattaaaaa ttttaaaaac atacatttaa acttaacaga aaaattatga gagagaaggg  31860
ggtggtgcca ggctttttta aacaaccagc tcttacatga actcatagag tgataactca  31920
ttaccatgag gacggcatca agccgttcat gaaggatctg gccccgtgac ccagacacct  31980
cctactaggt ccatttttaa cattggggat cacatttcaa cgtgagattt ggagggggca  32040
aaactacaaa ccatgtcact cagggattgg aggagcaagt accacctata ctttggactc  32100
aggtagaaag gcaaaatatc caggaaataa gctgctaccg tccagggttc agcagaggtg  32160
cccatcagcc tgccaagtac tcaagagtcc agcctctagg gagctaatca tcatggtgag  32220
ctcttcgagg cacagggagc tgggaagaca gtgcttgcca cccctgcctg aatagtgttt  32280
```

```
gcacagagag ttctgttgtg tcttgattgg gtcctcctgc cactgggaat gctgtggatt  32340
atactaggtc tctatctggc ttgtttcagg gctccatgtg aaaaccttct tgatatccta  32400
gccatccacc tgctcagtcc ctagtttgca aggaggctgt ggggagccta gattctgtgt  32460
cagatagaat gtactacatt ccgtctcagg aatgtaccac atcagaaaac agtgcgacct  32520
gcaggagaag tagaggtgaa gaggcacatt cttccgagaa atgtttctct caacacccag  32580
cattccctgg atatcagcag gaaattactc actgctagaa aatgccccat gagccttctg  32640
ttaaggaggt caagggagag aacagagaaa gttctcaaag ttgacttggt cactggtact  32700
ttcttatgcg gttcttattt tgtttgccat cgtcatcatc atgctatgtc tattttctca  32760
atccaaatcc actgctttca ccttggttct ttctgaccgg tttggcacac tcattcagta  32820
aatccttatg gagagcccaa tgtctgcata attgtgctgt gctgatgacc aagctagacc  32880
tacgagtgtc ggctcctttg agatgtacgg gacagctctt ctgtcatctc ttctgggaag  32940
cctctccagg cttggtgaac agtggcaaga tgtttaacag ttgtacatgt gtcccatgtt  33000
cctttctaag agcctgggca aaccagaccc ggtcgcaggt catcgtagta tggcgtgagc  33060
ttcctctctc ctttctgacc ttttgtgtga tggcaagaac ctgcagagtg acacaagcag  33120
caggcttctg aggttgctct agcctcagaa tggccgtccc ttctccaccc tggccctcat  33180
tgctgaggtt tcctttgaag caacagtgcc ggaacagact aggggaagca gcttggacat  33240
agctgtatga tttattacca cccattgagg ccaaccaaag tcggcaagga gaggtagcag  33300
gtcagtggtg cctggaagct tcctctttcc tttgcaccag atgtgactgc tctgcaatta  33360
ctcctaaatt tgctactctc gtttttacta gccaaccttg atgtttttcc cttcttcctg  33420
tagaatagac ttcccctctg atcagtactt tctactcaac actatttgtg gccacagtgg  33480
gaactcattg aggacaggga ccatgacatt actacctgac ccatcaacac ttggcataac  33540
ttgaaatgca aggacaaaaa ttggctgcaa gtacaatgtg gtcttcactc tgaaggtgat  33600
ccttaaaact tggctttggc atcatattgc cttaatatac ctaggggatt gggtaaaacc  33660
agttacttta aaagagtttt acaattctgg ccttctagct atcttgtctt cttaaacaag  33720
agcacaagat gaatgtatct tagtgaaatt ttatatggtt tgctttgagt aatcttgcga  33780
agattgattt ttagcacagt aggaaagaca cattctaata gtgatttttt tccccgagtt  33840
tatgtactgc tgttgcatga aaatctgact agatttaatg ttcctaaagt tctttgttca  33900
tcctgatttt tgcaggtcct agggaaagct ttgttttcct cttaacctaa cttagatgtt  33960
gtcatttcat gagctttgga ggaagagtgt atagccaatt gtgtaatgtc tttaaaggat  34020
attatctctg caatagttgt ttataaggcc taagttattc atgtaataat agtggccccg  34080
gatctgtttc tagcaatagg tatatggatt ttggttccta tatagttgta gttgtggctt  34140
tgagatattg agcaagccct tttaagaaag gatttggcat ccctcagcct tcaaaagctt  34200
ctcaaaattg atcatatgtt attagcaaag gtttactgcc tgcttccatt gtatagacaa  34260
tttatttttt atgtattccg ttctaagaag gcagatgacc aaaagatctt gcatctgttg  34320
cccaaggctt gtgactagag aggaaagaga taagaatact tttttaaaat cccattttac  34380
taaatatgtt gaggaagtgg taagatatat taatttgttg agatttttct gttatgccta  34440
ttatatgaaa taggtactct gaacatggct tcttaattaa atatatttga taaaatacaa  34500
cttgcttccc ctggagttta gaagtcagat aactgccatg gagagctatg ctttctttgt  34560
tttaaagatc tgcttatgaa catgataaac aggaacaatt taatgttttc aatattttct  34620
```

```
tgtattttac tgcaagttta tacacaacat aaatatgggg gaagggggaa atgtttatac  34680
cagagccatc ctgcccattc tttccttaca gaaggacaaa ggagcagtat ttattttaac  34740
tacaaaaata ctattgtagg ttttaaaaat tccgtatatt ttgatatctt gtgttcctct  34800
tgacctttaa tttgctaaat agttgcaaag aatgaaggta acctgcatca tcttcttaaa  34860
aaccaactct atctaattat aatagtttgt ctatctctga aaaatagtga tgtgttcatt  34920
ctgaaatcag aactaccgga tgcagctgca ttttgttact atttgaattt cgggagaggg  34980
aggaggatgc agcctttcga gctgctgaaa tacacaaaca caaagaagac accaagcata  35040
gtagaactgt gttaagctga ccaagccaga agaagcacct attctcagca tagtatgaga  35100
cgtaaaggca atataatggg catagttgaa gatggtagaa ggaaaataga ctctgatggt  35160
ttaatgttaa atgctttttt taaaaaagtg gtattccaat atcgaagaag aagactttct  35220
acttttagaa gcaataaagg aaattgcaga ggaaagggtc aataggttgg aatacataaa  35280
aattaaaaac ttttaaactt tttttttttg agacagagtc tcactctgtc acccaggctg  35340
gagtgcaatg gtgcaatctc ggctcgctac aacctccgct tcctgagttc aagcaattct  35400
cctgcctcag cctcccgagt agctgggatt acaggcatgg gccaccactc ctggctaata  35460
tttgtatttt tagtagagac agggtttcac catgttgtcc aggctgatct caaactcctg  35520
acctcgtgat ccgcctgcct cggcctccca aagtgctggg attacaggca tgagccaccg  35580
cgcctggact aaattgtttc agtattaatt ttttttaaaa caagatctta ctgttgccca  35640
ggctgaagta cagtggccca atcatggcta actgcagcct tgacttctgg gcctcaaggg  35700
atcctcccac ctcagcgtcc cgagtagctg ggaccacaga catgtaccac cacacccagc  35760
tacttgtttt atttttattt ttgtagagat gaggtttcac catgttgccc aggctggtct  35820
cgaactcctg ggcccaagca atcctcctcc cttggcctcc caaagtgctg gtattacagg  35880
tgtaagccat tgcgccctgc ctgatttttt aaatgtgcaa acagataagt tggaaaagtg  35940
atttccaata aagataaaga gttgatggtt ttaaaatacg taaagagctt atatgaatga  36000
gaaaaacact aacattccaa aagattagaa ggcaaaggac agaaagaaac aaatcactat  36060
gtctgggaag ggacatgaag gagcaggttc ccactgggcc agcggggctc aaacccactg  36120
gggacgtccg agagactgca agggccatgc cttcacattg ccgtacctga gaagcaagga  36180
gctggggtat ttatctcttt cacactttgg gaggctgagg tgggcggatc acctgaggtc  36240
aggagttcga gactagcctg gccaacacag tgaaaccccg tctctactaa aactagaaat  36300
aattagctgg gtgtggtggc acacacctgt aatcccagct acttggaagg ctgaggcatg  36360
agaattgctt gagcccagga ggtagaggct gcagtgagca taaattgcac cactgcactc  36420
cagcctgggt gaaactctgt ctcaaaaagt aataataatc atgataaata aaataacatt  36480
agattgttag cagaagtagc cacaggtttc tcccacctct ctgcaagttg ctgagtgtga  36540
ttcccatcaa gaggtacaat gtctttttat ttttatttta tttattttat ttatattgcc  36600
tatgttgtct aggctggttc caaactcctg agctcaagtg atccttctac gtcagccccc  36660
caaagtgttg ggattacagg catcagccac tgcacctggc ccagatactt tttcttgagt  36720
aggaatttcg agtcaccctg aacattgcat gccttcgtag tggggaagac aataggaaac  36780
cacaggctgt aggctaaaat gggttgtgtt tcttgtaacg tcatgacaag gcataaccca  36840
tcttggcata gtaaatagta agcactcact gaactgatga ttttaaatct ttgctgttta  36900
ttcagcaata tcctaaatta gcgctatgtt agtggagttg catctccctc atggattagt  36960
ctgaaaaaga tgagaaatct gtatgtagac caagttatcc ttaaactgct cataatgtat  37020
```

gatgcacgtg gttttacgtg tacagcctgg taccattgtt cttaggcaca tttcagtgcc 37080
agaactctta atacccagga agaagcaaaa agaaagatgg aggtgcagct agaggttgtg 37140
gcctttgaac gattcattct gccttaataa gagtggtctg gctgagctcg gtggctcaca 37200
cctgtaatcc cagcactttg ggaggccaag gcaggcagat cgcttgagcc caggagttca 37260
agaccagccc aggcagcata gcgagacccc ccctcccccc gtctctacaa aaaaatagaa 37320
acaatgagcc aggcatggtg gaacgtagtg cgtggtgcct gtagtctcag ctacccagtt 37380
ggctgaggtg ggaggatcac ctgagcccta gaagtcgagg cttcagtgag cccttattgt 37440
gccactgcac tccactctag gtgacagagc gagacaggtc ctgtctcgaa aagaaagaag 37500
aagaattaaa aaaagtgatt agatcccttg tgtttgggac acttgttggc agcagggatg 37560
gtagcgttta tgagggttgc atgtaacatc gcctagctca gacatctgtt tgactgtctt 37620
ccccccctgaa gcgcaggctc tgtgagggca ggtcttttgt ctttcttgtt aatcttcata 37680
tgcttagtgc ttgccacata gttgatgctc agtcgatatt tggatgaatt gaagggatta 37740
atgcattgaa tctgaacctt gctttcttaa tgcatatggg gagttctttg gaaagccaca 37800
cagaggagct tggttgcctg cttcctctct tccccagatt gtctttttat tgttgtggct 37860
tcactgaagc actctcactt caaataattt tgggcattgg tcgtatttta ttctttgttc 37920
cttcttcatc cttacccctc agatggtatg tagaaaagta cactacatct agaaagtact 37980
ttataaactc atttggttga taataataca tatgcctttt ccttggtcct ggtagcagaa 38040
tcttgtgcca ctcttggaat acaaacgaaa ttcttaacca aagccagttt cattttgatg 38100
ttctattttc ctcccattca cactccaaat tgtgcaccaa agtatcatcc tagttttgtg 38160
aggatggttc tccatacttc agggtaggag tatcatgtgg attcctatga tacctttctc 38220
cctgggacca tggagggcag cagctggtga ttgatagtct gattcccggt gaggaaagct 38280
gtgagccttc cacttgcaga tgtctgccaa ctacatgtgt ccttagtcaa ctgtaccact 38340
gtcctccggc aaacagcaga agcccagggc ctgaagttct taagctgtca ttatggaaag 38400
cagaaggtaa acaaaacaga agtgaaagta gatttaattt tttagactgt tctcttacag 38460
gaatggtttt gtggttctca gcattttaaa aaaaatagtg gttccaatat gttttattga 38520
catcaattac tgtaagtctg attcattttc tgcctattga tttctaccca aggtgaaatt 38580
catgacattt aacagaaagc ataagtgatt ttttaaaagc agacactatt agggacggta 38640
aaaataagat ttaaagtcgg gacacttgaa aaagcaattt ttataccttt ggtaacgatt 38700
ctattctgat tctttgtata aataatataa acaaaggctc tagaagctta ctataatgaa 38760
gttggtgtgc tgtttctaaa ttctggttta aggcccaaat tcattttatc tgcattaact 38820
tttttttttt tgagagtctc gctctgtcac ccaggctaga gtgcaatggt atgatctcgg 38880
ctcactgcaa cctctgcctc ccgggttcaa gcgattctcc tgcctcagcc tcccgagtag 38940
ctgggattat aggtgtgcgc caccacgccc ggctaatttt tgtattttta gtagagacgg 39000
ggtttcacta tgctggtcag gctggtctca aactcctgac cttgtgatcc gcctgcctcg 39060
gcctcccaaa gtgctgggat tacaggcgtg agccactgca cccggccgtg ttaaaatttt 39120
tcagtggtag accactatgt caatatgttg ctttcactga caacagtatt ttcttaaaga 39180
taggataccc catttctaga tgaatctcat tctagctgga aaataatttt tcagttctga 39240
aactacatca ggcctcaggg aatcaaaact agctattagc cacacacata taaagtggct 39300
ttgctttata aacgatttag ggtcaccatc aatgacaatg gtccctttt attgtatttt 39360

```
taagagtttc ttatcttaaa tggctgcata actgtagagt tttaaaaaaa ttaagtaaat  39420
gaccatgtta atgctctatt aagcttccaa acaatattgt aatttacttt gaagattttt  39480
ttttattctc aacatcctgc agcttgaccg tttgcctccg tgtctcagtg ctgcttattt  39540
tgaggtgtgg actggagtcc atctgtcccc cttgcctctg aactgctccg ttttgtgttt  39600
cgtaattctt catgctgcat cctgggcgca tttctctgta gtagctttca atttgctcat  39660
gctttgactg ggcttagtct agcgtttatc ctatctctta aggtttttta aaaaattttc  39720
atgattattc atttatttcc aggatttctc atttcttcag tcacatctcc ttgttctggt  39780
tttacttctt cctgttttta ttcataacat ctttttttata cacgattcct tcatgtattt  39840
ctaatcttaa gtatatttaa ttgcttattt gattcttttt tttttttatt gagacagggt  39900
cttactctgc caccaggccg gagtgcagtg acatagtcat agctcactgc agcctcaact  39960
acttggactc aagcgacctt cccacctcag cctcccaggt agctaggaat acaggtgtga  40020
gagccgccac acccagctga tttgtcttac tatgttgccc aggctggtct tgaattcctg  40080
ggctcatgtg atctgccctt cttggcctcc tgaagtgctg agattatagg tgtgaaccac  40140
tgcacctggc caagtatgtt tatttattta ttctaatttg agagggagtc tcgctctgtc  40200
gtgcccaggc tgtagtgcag tggcacaatc ccagctcact gcaacctctg cctcctgggt  40260
tcatgcgatt ctcttgcctc agcctcctga gtacctgggg ttacagttgc gtgccaccac  40320
acctagctaa tttttgtgtt tttagtacag gcggggtttt accctgttgg ccaggctggt  40380
cttgaacttg tgacctgaag tgatccgccc gccttggcct cccaaagtgc tgggattaca  40440
ggcatgagcc accacgcttg gcccaagtat gtttattttt aaagtcccca acaagctata  40500
caataaattg catatggaat ggatttttgt tctagttgat ttgttggtta tcatttgtag  40560
aactaactag ttgtcttctg tgtttgatac cttgcttcta ggtcattttg agttgggagc  40620
cttttgtttt gtttttattc tcatgctgtt tttgagccta gctgtgcctt tatggttttc  40680
tctaaattta attgaccatt gttttatatt tggagcagtg ggtgtacatc agagtgtgaa  40740
agcagcccca ccctctccac cagaaggtct ccatgccagt ttcacgaagc atttttcatg  40800
ccctcattcc tgcccttatc ccttgatttg tggggagttt gtaaagcagt tgattgtttt  40860
ttttccacgt agttttccaa gtgcacataa ttgttctgtt agtgacttgt agctccatta  40920
tctattaacc ttgccccaga ccactgtaca agcggaccca acgcttcctc cagctgtggc  40980
agggacagtt acttggtatc ctgctgcctt ttcaatgctg accagttttg ccccttcctc  41040
ccctcaaccc ctgtctttca ttcaactatc accaaaccaa aagattctgg tttgcttttt  41100
agtatgtgtt cttattcagt acatagtcat tttaaaattt aaaccaaaac agacttggta  41160
ctgattagct taattttaag ctttttcttt attattaaac agtgtagttt atcttagcat  41220
ttcatattaa gtatatgatt tatttcatat tgcttatatg aatgtacaca taaatataat  41280
aaaaatattt tcctaaggtt tttgtagtaa attatatcgt ttcattaact ttcatatata  41340
gcattgcttt tgacctggaa gacattgaac ctctgatgat ttgtatattc ctcggagtat  41400
actttgttac atagaaattt tctcatttat aatgagattt gtgattaaca aaatttgttc  41460
aacatgcatt actttgaaga tctggtttct aaaattttat gctagttacc ccaccccccc  41520
ttctatatat atctccctat tcagcgacta ctgcaagagt tccaggaaat gtacactgtg  41580
tgttcactta ctgcatttta aatcattgcc tttactatat ttctgcattt cccttcaatc  41640
tagctctgtc tgtacatttc tgaaagccag tagcttccct gaagaaccag gtaacaaccc  41700
gaacaatcaa attagataac catttgtaga atggaggttc cgggagatct tagaagatgt  41760
```

gatgggtgct aagggacttt gtagttccct gaagttccag tgagtaaaag gtacccttgg 41820
aatttttat tccttcagac ttttaaaaca gagatcactt tcaaaaatta ctctttctgc 41880
tttgaatcca tgttttagta actattttga cactgtttgg tcagaaggct gtgtgggtca 41940
actgcaaata aataaaataa atgtgatttc agtaatttcc attttgtaac aagtaattga 42000
gaaaatagga ttggatcaga tatttgctta tacacattcc ctttcaggag cacttctgtt 42060
ctataaagaa tgttggtata ttgttaagga cacttcaagc tttgggaacc tttgaagtat 42120
ccattgattc agttaacaaa attatgttga gtgcctaccc tgggcctggg cctgtgttag 42180
gaggggacac taagatgaga gtccaaagca cttcttctca gactcctggc tgctaatggg 42240
ttgctgcctc tacttcttca cttagcagat agctttaaaa tgagtaatgc attttaccat 42300
ggagcccgta agagacattc acccagttgt ggaccgagga gaagggtgtt aaacccagat 42360
tgtgatgttt cacttgatga agtgcttaat ataaacatgg aaatatttcc gcaaggataa 42420
actggctttt atgcctgtgt gttttcagga gaaatagaaa tctctaatca aatattgcca 42480
gcttttcacc caagtttgac tttttgccta attgagtttg ggaggtgtct gaataatgga 42540
taatgagctt tcctgaataa atataaaaat taattaactc caggctctaa ttcattctgt 42600
taccagagtt ttgtaagcat gttacccctt tgtgttcatt gggagatcat ctgttacctt 42660
cttaaatgag tggggaagga tgggaaatga ggaagagcta taaaaactat tcaggtgaag 42720
aaggtttctg cccctccttg cccctttttaa aatctccagc tcagcagatg ctttgtttaa 42780
acttgatcaa gtgcttgtga atcttcctag cctagctaaa tcataacttt ggaaggactt 42840
gctttttct ctcatgacaa tggtttacca cagaaatgat tcagatcact ttgtgtgcct 42900
gatgcctatg taaaatgata cagtgaaatg gaaaccattt acctgtaagc tttgggcaca 42960
cccaagcctg cttcaggagc acatgatcag gcgtgcactc tgggagagcc gtacacattt 43020
gacatctatg atgtgtggcg ttttattcta tcacatttct gaaatctaca ctaagagaaa 43080
ggaggctctt aaaaaaccac tgaggtgtgg actgggggaa ggagagatcc gtaaagaacc 43140
tgtttgttac ctgttgatac tatttcccat tggtaaaatt tctaatttag tgtgatccag 43200
ccctgaaatg ctgaggcaca cactgaatga ctcctgacat ctttagtgtt tttgttcagg 43260
ggactcttct gggaatctgt ttcatggcaa gtttattatt ccctttttggt ttggctcatc 43320
agtttaccca gcagtcatct taatcggttt taaaggcttt tattttattt tgttttctct 43380
gtggaaattt tacacattca gtagattaga agtagttatt taatctttgg ttagcataat 43440
aaaagatctt ctagggacat tttttgcttg cagtggaagg ctagttaaat gtgttcatta 43500
gtcatgaatc tgctttttct atagctgttg gaaacgtagc tcccctgtga tacagttgta 43560
gaatacagaa atctcgtttt gctgttacgg tacggtagtc tacttacttt cttccaaacc 43620
attaatgtta tagttacctt taattgcgta ggtcctatca cccctcaatt ttaagactct 43680
aagcctggca ttttatctta caaaatgaaa tataaagact tgtactcaga gtatgtgtgt 43740
gttttccata taccattcta aagtagagaa agatgaggga ttcgccagaa actgatttct 43800
aataaattat ccagaaactg acccccttctc acctcttctg ttactgtcac tgtggtttca 43860
gccacagcat cctttgctgc attgttacct tagtttcctg actgtatcct tccttacacc 43920
attgatccct gcaatcccat ctgcgcgtag cagccagaag ggatccactt actgctgtga 43980
tcagaaatcc tcagccaggt gcagtggctc atgcctgtaa tctcagcact atgggaggct 44040
gagactggag aattatttga gcccaggagt ttgagaccag cctcaaactg ggtaatataa 44100

```
tgagacctca tctctacaaa caggaaaaaa aaaatttttt tttttttttt aactagccag  44160
gtatagtgct aatatacctg ttctgggatc cagcatgctc tccctgacct gcagcttcat  44220
ctccaccact ttgcccctca ctcccaccac aatggctttc ttctcttcct cagacatgcc  44280
gtgcgtcctc ctacctggaa tattcccctc caaacattcc catggctcac tccctcacct  44340
tcatcagatc tctgttccag tgtcactttt actggaaggt cttttgtgac catcctactt  44400
attataaaaa aataatctgc ccaaccttct ccttttattt cctctacttg atttttcaat  44460
ttagtactta tcagctgaca tatattttgt ctctctgtct ctctctgtct ctcatagaag  44520
gtaaattcta taaaggaagg aatttttatg tttggttctt tgctgtagct ccaatattca  44580
aaacagtgcc tgacacacag taggcccttt atatttgttg aataaatgtt gacactctga  44640
tatctaattt ttgtctggtg actaatacga aaactataga gtgataataa aagcattacc  44700
ttagtagact ggaaagggat gagcgctagg atgaactttc tgcctggcga tcttgctgaa  44760
tttaggaggc agattggggt tcaaaggagg ctgaaatggc taggatttgc agagcagggt  44820
actaaggatg agcaggctat gacagaaaga actccagaaa tctgcaaagg gatcaccttg  44880
agtctggctg gatacagtgt acactttgta gggtgtctct tcatgagctt ggataaagaa  44940
caactgttgg ggagtggata attcccagca ctcattcaag cttgcatcgg ccagaacgga  45000
gagagacaga cctctgtaat acgtaggata tttggtagaa acattcaacc gaaaaccatc  45060
agatatgcaa aaagtaataa taataagtaa acaatgtgat gcatagctag aagaaaaatc  45120
agacattaga agcaagccca gaaatgacag atgataaatt agcagataag gacattaaaa  45180
cagctattat aaataactta gcagatttaa agaaaaacaa cataatgagg ataatggaag  45240
aaaaacaacc gaataccatt tctaaagaag aaaaatacaa tatctgaaat gagaatttag  45300
ctggatagga ttaatagttt aggcactgca gaagaaaaaa acagcatcta tatgagaata  45360
tacccaaggg aagtacagag aggaaaaaaa tgtggattgg ggggtgcctc agtgacatat  45420
ggaacaatat taaacaagtc tgcccccaaa atacttgaag gaataaggtt caagtttttt  45480
ccaggtttaa tgaaaactat aagcctacag attcaagcat ttcaacaaac cttcagcaaa  45540
ataaacaaaa ccacagtagg cctggcacac tgtctcatgc ctgcaatccc agcactttgg  45600
gagcctgagt caggaggatt gcttgagatc tgcttgggca acatagccag accctgtctc  45660
tacaaaaaat aaaatgaaat aaattagctg gatgtggagg tccacacctg taactctagc  45720
tagcctggag gctaagaagg gaggattgcc tgagcccagt agttcaaggc tggagtgagc  45780
taggactgca tcactgcact ccagcctagg caacagcaag accacatctc tctctctctc  45840
tctctctctc tctcaaaagg cagtgaaata acgacttatt tggggaaaaa ataaaggcag  45900
agaatttgtt gccagcagac tagcataaaa aaaaggaagt ccttgaaaca gaagagaaat  45960
gataaaagat ggaaatttgg atatatacta aagaatgagg attgctaaaa gtgacataca  46020
tagataaata tgaaatatat ttttatttta aaatttattt aaagcaaaaa taaaaataca  46080
tcatatttat aacatagaaa taaaaaatgt atgataatag cataaaggat aagtggacaa  46140
atgctgttgt cgtatttttg gtaaaatgca ctattatttg aaagtagacc atcgtgaatt  46200
cgatgcatat tgtaaaccaa atagaacact aaaaaatgaa aataaagaga tatggctaat  46260
gtgccaatgg tggagataag atagatgcaa aaaaagaaaa acattcaaaa gaaggcagag  46320
acagaggaaa aaaggaccaa agatcaaatg agtcaaatag aaagcagcta aactagcaat  46380
atggcagatt taaatctagc catgtcaata gttatattaa atgtaaatgt tctaaatacc  46440
tgaattaaag gatgaagatt gtcagattag attgaaaaag catgacccaa ctacatgctg  46500
```

```
tctgtaagaa attagaaaaa gaacaaatta aatccaaagt aagaagaaag gaaatagagt  46560
agaagttagt gaagtataaa acaaagagca aagaaaatca attaaatgaa aagctggttc  46620
tttgtaaaga tcagtaaaat tgataaattt ctagctaaac tggccaagaa aaaagaaaag  46680
acatacaaat taacagtatc aggaagaaaa acagagaatt caaaggagtg taatgcaaac  46740
tttatgctag taaatgcaat aagttagatg gtatggaaaa aaatgtgaac aatacaaagc  46800
agactgtggt tgcctttggt ggcagtagcg gggtgggagt ggaaggttga attgactgga  46860
accagaagca caagtgaact ttttggggtg atggaaatgt tttgtatctt ggttgcattg  46920
atagttaaat ggttgtagac attgcttaaa actcactgaa cacttaagtg ggtatgtttt  46980
attatttgta aaatatacct caaaagcagt tttaaaaatg tattcaagta catacttaag  47040
atctttgcat tttactctga gtatacctta attttaaaat ctgtttttta aaaagtatta  47100
tgtagatacc ttttattttc ccaatgtctt tattaaatga catctccacg ttttgcttct  47160
tacctctatt tttttttttt tatttctctg tctctcaggc atgcacacac acacaccaaa  47220
aaaagtacat atgcataatc cttttggctg aataaaatca gttgcaactg ttatttcggc  47280
ccttatttgc tccgggtaaa tattcgttag ctgagtggtt tatctgtatc agatatttct  47340
tacatcttca tccagtcaca ccagctggac tgaccagatt gtttttcact tcaagggcag  47400
aatttgtact cactgctgaa tgcttccaaa tgatacgtag aataacaaat ttaagactta  47460
gatttttact ttttcaggtc tttttttttt tttctgtgct gtatagcatt tccctgaaag  47520
cttaatctca tctgtaagtg atgcagtgga tgtgttacta ttggattaat ttatttactc  47580
ttaggtaggt ttgtaatctg tcatcatgct gttgtttttt tgtgtgggtt tgtttttggt  47640
tttgagacag ggtctcactc tgctgcccag gctggagagg ctagagtgca gtgatgtgtt  47700
tatgggtcac tgcagattca atctcctggg ctcaagtgat cttcctgcct caaccccttg  47760
tgtagatgga agcacaggtg cacgccacca cacccggcta tttttttaaa tgtattgtag  47820
agacgaggca tcatttttt gcccaaggct gatcttgaac tcctgggctc aaacaatcct  47880
cccacctcgg ctcccaaagt gctgggatta cagatgtgaa ccaccactcg agctccatca  47940
ttctgttatt agttgttctc tagtatgagt caaaaactct tacctgccct tttacagttt  48000
tataaataag taagcagaat agcagaatgt ggacattttt taaatccaaa ttgaatatgc  48060
acatgactca aggagtcaaa tagtaccgta atcggtttat gataaaatcc agtggtttgg  48120
ctgggtgtcg tggctcacac ttgtaatccc agcaccttgg gaggctgagg caggtggatc  48180
acctgaagtc aggagtttga gaccagtctg acctacatgg tgaaactact aaaatacaaa  48240
attagctggg catggtggtg catgcctgta atcccagcta cttgggaggc tgaggcagga  48300
gaattgcttc aacccgggag gcagaggttg tggtgagccg atatcgcatt atttcagaac  48360
aattttccac aagatcagtg agtgctgtcc aatagacata taatacaacc cacatacatg  48420
actttacatt ttcttgtagc catagtagaa aaggtcaaaa gaagcagatg aaattaatag  48480
cctgggcaac aagagcaaaa ccccatcttt taaaaaataa aataaaatat ggtggtttgc  48540
tgtccccacc tcagaccatt tctctggtct ttctcattga ccaccactcc caatctttgt  48600
tctgctgatt gattacagct tgtatatatc tccatatttc taagcaaaat gtttatcttt  48660
tttaaattta taaattcttt ttattatttt tcagagacag ggtcttaact ctgtcgccca  48720
ggctggagta cagtggcacc atcgtagctc actgtagcct cgaactcctg ggctcaagca  48780
gtcttcctgc ctccgcctct caggtagctg agactacgct acaggcacat accaccatgc  48840
```

```
ccagctcaaa atgtttatct tttgatacat tattcgagac cattattaag gtggatgatt  48900
tagttttctt aaacagccat ccccttttctt ttcctcccct ctgcttcacc gcccccattt  48960
tcccaatgtt ttaccttttg gttaaatcag tactcattgt ttacattatt tgcctctgca  49020
catagtcaca gatagtattg tactgtactg tactgtgttt ctttttttaaa cattatttct  49080
gttgttaata attgactttt taattttttt cctattttgt tttttaaaga gatggggtct  49140
tactatattg cccaggctag agttcagtgg ctcttcgcgg gcatgatccc actgctgatc  49200
agtacaggaa tttccacctg ctccatttcc aacctggacc agttcacccc ttcttaggca  49260
acctggtggt cccccattcc cgggaggtca gcatattgat gccaaactta gtgcggacac  49320
ccgatcggca taacgcatgc agcccaggac tcctgggctc aagcagtcct cccgggctca  49380
agcagtcctc ccacctaagc ctcccgcgta gctgagacta cagacacttg ccaccacacc  49440
aggttaattt ttgtgttttt tgtagaggtg gggttttgcc atgttgtcca gactcatctc  49500
aaacttctca gctcaagtga gcctcctgcc tcagcttccc aagtagctgg gattatagac  49560
gcatgccacc acaccccatg ataattgcct tttttttaa tttgcataat tttctttgta  49620
gcttttgcta atgttcccat atcttcttat agccttacag aatgattttc cacaagatca  49680
gtgagtgctg tccagtagac atataataca acccacatac atgattttac ctttttttgt  49740
agccatagta aaaaaggtca aaagaagcag atgaaattaa tagtatcttt tacttaaccc  49800
agttcattca aaatgttatt tcaataaatg gtcaatattt aaaatacttg agatattttg  49860
cttttattta tttcttttgt tactaagtct tcaaaatcca atgtgtattt tacacttaca  49920
gaacatctct ttttagactg gccacatgta gctcagggtt actgtattgg acagagtggt  49980
ttcagtttca agtttttcct tggagacatc ctacttgaaa tttccattct ccatgtatct  50040
gggtggttgg tctatagact tgccactcac agctgtcatc ttgagacttt ctttgctttt  50100
cttctctatt ggatattcag tttcctggat ttcaggtctt ctcattttcc tctagtagtt  50160
ttgttaggtc atggttggta tggcatggtt gggatagcgt gttcacacag ctatctcgtg  50220
agtcatactc ctccaatcca gcctgctcgc ttcccgtgtc tgtcatgtag ttgtcaccct  50280
gctatctctc cctccagttt ttgcagaaat ttcctttgtc ttcactcttg gtcttcctct  50340
cccatccccc atgtatccta tatctttctc tttcttggtt tatttcatca ctcaggtgga  50400
aaagatgctc cagtggatta ctgggaaaag ggggagcatg gatgataaag gtattgagac  50460
cttacacgtc agggaatttt tttttttttt ttttttgag acggagtttt gctcttgtcc  50520
aggttggagt gcagtggcgc caactcggct cactgcaacc tccacctcct gggttcaagt  50580
gattctcctg cctcagcctc ctgagtagct gggattacag gtgcccgcca ccacgcccag  50640
ctaatttttt gtatttttaa tagagacgag gtttcactgt gttggccagg ctggtcttga  50700
actcctactt caggcaatcc acccacctcg gaatgttttt attgtccctt ctcatttcat  50760
gactgctggg ctaggtatag aattccagaa tcattgttct tagaatctcg aaggcattgc  50820
ttcattgctg gccagctttc agtgttcttg caaagtctga agctgtgcta atcacctcat  50880
cctttgaaag tgaactgttt tttcttccca gaaacttaca gaacattctc tttgtccgca  50940
gaattctggg attgcaatta ctgtgcctta gaatgggtct gtttttatca ttatgaagag  51000
tactggatgg gtcgggaggt tttcttgaat tacttcttga tgttttcttt ccttgtattt  51060
ttttgtttgc taattttcta tttttttttc ttggtttact ttcttgggca gggggatttc  51120
ttctacttat atttgattct tcagttgagc ttgtcatttt tgctatcttg tttttaagtt  51180
tcgagagaca tctttgtttt atataacatt ctgttcttaa tacatagatg caagatcttt  51240
```

```
tctttctgag tatattaata tgtatttgaa atctttctat tctctgcagt ttgtttcccc  51300
caagggtttt tttttttttc tggtttttgt tttttgtttt tatgttagag actttcctgt  51360
tatatctggt catcagtggt acctgcatgt ggtggagagt aggggcttat tggagtatga  51420
gaaccttgag caggtgtaag gagcctgtca acactgcgct ggcctcaggg cctctaggga  51480
ggctgccagt tgtgcattct gaggatacct tttggttgtg ccttttgtct ggtcagatta  51540
tctagagatg ctctgcctcc tacctggagg agaagggtct agctgccagc ggtgtgagtg  51600
tctcttgggg aaaaggactc gagttcctgg tgtttggctt gtgtatggcc gcttacccca  51660
tttttggtgg agcgctcaca tcttccactg tgccaacagt cttgctgcag ttcatagacc  51720
ttctggttta catttttcca gaaagtatgt ctttagattt ctgcagaagt ctgaggagca  51780
tggaaggagc ttggggaatg agatggcaat ccaggtcttc ccagatggct ctacctttat  51840
cccctgcagg gaatcccact cctccttcct gactgggagc acagccagag ccttgggagg  51900
aatctggagt ggaaatctcg ggcggtctgg ctttcttact gttcacttgt aattttgctt  51960
tctcacaact gccaaccact aatcagcctg atttccagct tccagaattc tattgctgtt  52020
gtctgctctc ctattcccac cgtaggggat ggggctgtct tttttttttt ttttaatttt  52080
ggtaaaacat acaaaacata aagtgttcca ttttagccat ttttaggtac acagttcagt  52140
ggcagtaagt acattcacgt tgtgtgtatt tgtttttta gtaataaaca atataaaatt  52200
ttttaagtaa taaaacacaa ataaaagatt gtttaatgtg attatcgtgg aattttaggt  52260
gtgatcagga gccatggtgt agtcttctgt tgaaacaggg tgataggatt tgtttaccac  52320
ctcctaggaa agcagttgga tagtttgttg gcataaaagt acattttatc tatttttaat  52380
aatcgtagct ttatagaaat tgcagttgga actcccaggc ctggcattca aggctctctg  52440
agatctgggc tacccaccca tgtcctccag ccgtctgtcg cacctcctac tgcccactca  52500
ctgttcctgg catgagatgt gatctccagc ccccatgcct ttgctgtgca gggtgttcca  52560
gagtgaattg tccctcctgt ctgtctctct gccctcttcc tcgtctttcc atcttcctgc  52620
cccacatcac tgcctcctac ccaaggcctg tgctcattcc tcctcggttt tcccccatgg  52680
cctggtacat acctctgaat tatcaccttg catttcccat attgcccggc tctctttgat  52740
gtctgtttct ttgctgggtc ttcctcagtg tctgacggtc agttaaatgt ctttattctt  52800
ttttgtagga tatccgacat gaagccagtg acttcccatg tagagtggcc aagcttccta  52860
agaacaaaaa ccgaaatagg tacagagacg tcagtccctg taagtatcca cgtggccggt  52920
accagtcttg ctcttccttt gctgcaggcc tttttagtca agactccttt cgcctcaggg  52980
tttagtataa taataaatca atgtagcaga ggtttatgac gcgattgttt cctatagtaa  53040
aggcattaga gacttatagt aatagctcat ttttccacca ttatagaagg gctcaggttt  53100
cagtttctgg aaaattcagt gaagttcaaa gcacttttct taagctttga ctgtttttgt  53160
gatgaatcat tttcctacca gctgaagcag agtatagcag gcataataaa acctttttctg  53220
gatgactcag cagcagcgtc attagggcat gagcactgtg ttccgctgta atgaagcccc  53280
gcacaggcat tcggggtggg cactgtcgtc ccctgcgctg aatatgcaag gcagctctgt  53340
ctggagtccc caccgcctcc acccccgcca acctcatcat ttttctccct ctttcctgct  53400
gttagttctt cctaggattg tcagtgtgcc tgctggcctg tggcagccct gtccgccttc  53460
tgagtgattg gctgtcagtc tgccggtagc tgaaaagtaa ataacttaac atgttagaat  53520
ttgcataaag taaggaaaac tggagctgag tacaggactt gaactgcgcc atctcctcta  53580
```

```
ggccacagag gccttttttga ccccccttcca ggtctttaga cattgtcagg cagtgagggg  53640
tcgtagctgc cagtgtctcc atggtagcgt gctctgccag ggatgcagaa gattctccag  53700
tcattcctcc agtgggcact tcctgcaggt cctgtgccca tggctgggag tggtggctgt  53760
cattgttctc tgccagaagg gttagcagtg catcctgacc tgacttatgt ggcgcccaga  53820
ttcctggaag gggtctaaaa atggacctag acttggtgta gaacgtgtgc ctcttggcct  53880
gccaccatgg ttccctgcct ggttttgtgt gtcagctctg ccgcttaaga actgagtggc  53940
ttcgggcaag ttgttctctc tcataggagt gtgtgaagat gaagcaacat aagctgctta  54000
gcccagcgcc cagtacctca cgcagacata agtgctcagt aaatgttgtc tgtggtgggg  54060
atggttgtca ccaacatctg aagtgcactt ctaggtcatc aggtgacatg attggcgcca  54120
acacatggta ctcttgattt agcacatctc agctgaggca cctcattgat atttgtttaa  54180
aaacaaaaac aaaaaacctt ggtgattctg ctgtgaagtc ctggccagaa acctccagac  54240
cgctgatcaa cacgcaacag aaccatcacc gttcacctct ttgacatggt gccaggatac  54300
cctggatctc tagcttttgc tatagttgct ctaattaggg aataatcttg tctttaatat  54360
tcctttgcta catttttaa catttcttat ctaaatggtt ttatgaatca gttttacaga  54420
gaaaaaaaac cagtatttaa aatattcttc caggggctgg tccaagtaca gtagtgttta  54480
caactatgtg atcacaacca gttacagatt tctttgttcc ttctccatcc ccactgcttt  54540
acttgactag ccaaaaaaaa aaaaaaaaaa agttattcca gggaaacaat tctccaactt  54600
tttcactccc aatctcactc ctcttatctt cctcccgtac tcctatcctc ctcccgtact  54660
cctatcctcc tcccctactc ctatcctcca gtagaaacag tcatttgctg tgaaggttat  54720
gggggagaat gagtcaaggt agaaggtcac ctgctgccca gctcacagtg ctgctggtga  54780
tgacagcagt ccacagttac aggcacttgc tgaacgaggg gctctgtata cacctcagct  54840
cattgactct tcccacaacc ctcttgtcac ctaccattta gcaaatgaaa aaaccaaggc  54900
tctgaggtga gttgtttgcc cagagtcacc cagtgctgtt tgaacccact cacataacca  54960
accaatacca ttatgtaatt tttgaggtct tttatctctg tgatccactt aaaaattatc  55020
caagtatctt tatttgtact aagcctccat aatgagaaac agtgttccag atggtggcta  55080
gttttcaaag acatctctct ttggaattct tctttagaac aaaaagcccc agaccactta  55140
tccccattca tatccccttt ggacctaggg agaaggtact atttataggt gatcacctga  55200
gtttattgtc ccttgtgctg tgccagaaat aaaggtcccc acctgctctt attagctcta  55260
ctaacaggat aaggaaagtg gccctcagag agctactgct tttgtgacaa acaaatgata  55320
caagaaaaaa aaagtggctt tttaatttta gtgacctggg gcaggacttc caaatgaaag  55380
tttatttcta aaaactaaaa ggtaaattta atatactttc agtgtttggg cttaaattct  55440
ctttcaagtg tctttgtgat atgctctgaa ttttaaaaat ttagaatcat tgaagttcat  55500
tatacttgaa ctttaaaaaa aaaaaacaaa aacctcgtat aaaggtcaag gtatgacttc  55560
atgctgctgt gtacttaggt catttaatct tcaaaccact ggatagaggt taggttgaag  55620
ttcgatctta aatcctacct actgtagctc attgtaccag caacagctgt agggactagg  55680
tggaattcat ggtgggtttt gttccctttt aaagattgaa gccaccatat tttctgccct  55740
ctaaaagttt atgtcagcca ggcatgggtg gctcacactt gtaatcccag cactttgggg  55800
aggctgaggt gggtggatca cttgaggcca ggagttcgag accagcctgg ccaacatggt  55860
gaaaccccat ctctactaaa aatagaaaaa ttaggtgagc atggtggcct gcgcctgtaa  55920
tcccagctac tcgggaggct gaggcaggag aaacatttga atccgggaga tggaggctgc  55980
```

```
agtgagctga gaacatgcca ctgcactcca gcctgggtga cagagtgaga ctcttgactc  56040
aaaaaaaaaa gttatgcatc agagaacaga tcctttgatg ccctcctctg ccctgaaagg  56100
tttttggggg agagtaataa gtatcacaac aagatatgac ctgagaacag atttcccaga  56160
taggacatga tccatgtttt aatatggctt actgctgttg cttcatagtg tgaagcttca  56220
gacacttctg aaaacccttt cagaaaatcc cagtcgcccc atactgatga ctaatctcaa  56280
ctaaaacagg gcttcagcca gtgtgaatgc cactaatgcc accaactcac ctttgctttt  56340
ctgtagggtg tgcacctgta tgtacacatt cagcttttcc gggattaacc tctgagttct  56400
ggtttgtctt tcagttgacc atagtcggat taaactacat caagaagata atgactatat  56460
caacgctagt ttgataaaaa tggaagaagc ccaaaggagt tacattctta cccaggtaag  56520
cagattgtct gaattttcta tttaatgtca atttaagagt ttgagagtgc tgttatccac  56580
acctcaaata aaatctgcca catcctttag aaggtcagga tttcagcata ccaaaaagca  56640
gcaaggaagg gggaaaaatc atccttcaaa ggttcagttt ggttataagg aacgctaatc  56700
ttttctggga agcataagat gacattgctg gaaatgagag cttatagaaa acaacattaa  56760
aatgccagag ttgcctgtgt ggtctgttgg cagagacagc agagccatgg ctggaggagg  56820
gtctgtacct gtgttgcttc cagaagtatt tgtcgtagag cacttgtgat ggcaaatcta  56880
agaacgttag cagtagacca ggaatctctg tccagagcca ttcagagtag ctcagcatgg  56940
ttctcattct ttggccagaa gaaaggcatc attggatcat gtgaacaagc atgaaaaatg  57000
acttaaaatt tctgttggct tttggcatct ttatggaaac aaaatcctga aagtggttta  57060
ataattgagc ctcttgtaaa acactcagtg gcatgtgacc aaaagggtat ctgggaaaga  57120
ggataaaaag agtttctttt taattaatct tctcaagtct taacttgtta cctgtaagtt  57180
ggtctaaaaa gactgggttt cttattttgt ttttcatcat aatttttgtt tctcattcca  57240
tgtcagcttt cagtcttata tggctttagg ccacagggcg attttgaaca tttgtaattt  57300
tgcttaataa ttaggaaatt aaaattctgg ggaagacaga atgctctatg aagaaaggct  57360
gctttgagca aggagctagg tcagggcgcg ttcaactgag gcctttcttc actgcctttt  57420
tgtcttgtcc cagttcctcc ccatttatga ctaaaatcag cccagatgct tctcgtcatc  57480
tgggatgcag agcatcagcc cagctgtgtt cagtcctatg gggccattga gtaagttctt  57540
ggtgcatgga tacagggcag gcctttacca ggccctgagc ccctggtcct cccagcacct  57600
ctggggtatt taggggaggc tgatggggga gggggttgat aaggcgggag atgtctgggg  57660
atgaggttga ggcaaaagtg acttcttgag gactttgctt tttggagaag tcaaatttcc  57720
tacttcttga tttcagccct tcaactctgg tatggagtca ggaagccctt taaatacctg  57780
ttgtcgggtg tatcatgtca agtgttgcat tagcaaatga ccatgtatcc ttgtgctact  57840
gtcctgccta ccccgcatcc tagcgcttcc ttgggacatg agaagctctg tctggtttgt  57900
gaggtggcac tggggatgtt gagaaactgt ttacacagtt tccctttgcc ctggggattt  57960
actaaaggag tcgaggcagc ctgaccccaa agcatcaccc ctggacacta tgaccgaaac  58020
atttccccag tgcccaaacc aagaacaccc ttcccatttt tttttcagtg gtgttcatta  58080
tgtaataata caagtctctc ttctcatttt ttaaaagtca gaagtacaga agagcagaga  58140
ataatgtcca aggggccctc cttcacctcc cccgtgcagt gtcagctaag tgtggtgcgt  58200
gtccttgcag atcttagggg attgtgatcc ttcagaccat tctaaactgg ggtggtgctg  58260
ggagttaggg aaggcatgaa gggagtagtg gagagctgca gtgactgggg tcttcatgcc  58320
```

-continued

```
agggtggaga atgcaaggcc caggtggcca gccatgtgcc acgggatttc tggctgccaa  58380
gagctgttta tctgttcact ggggagggaa gagttaaatg tggtctgctt ttctccgagt  58440
cccttcagca cagggagtgc tgacttgtct tgttcaggta gtaagttcaa gatgagctca  58500
ggaaagaaag tgagaggaca ctgagggcta gtggttgagc caagtgtgat gggacttaaa  58560
gggagaagat ttaaagaata aggagcttat gggccgggga cggtggctta cgcctgtaat  58620
cccagcactt tgggaggctg aagcaggtgg atcacttggg tcaggagttc gaggccagcc  58680
tggccaacat ggtgaaaccc cgtctctact aaaaatacag aaattagctg ggtgtggtag  58740
tgtgcacctg taatcccagc tacttgggag gctgagacag gagaatcgct tgagcccagg  58800
aggcagaggt tgcagtgagc caggattgcg cccctgtact ccagcctggg tgatggagcg  58860
agactctgcc tcaaaaaaaa ttaaaaaaaa ataaagaggt taggtgaaaa tagatgagaa  58920
tggaaaccat gagaagaagt gatgctggcc aaggacatga caggttctga tgtggaggtg  58980
ataggcaatg tctcttccag ccactgctaa taattgagac aaactcaagg cattcatacc  59040
ctgtgtccag taaacatctg tgcccattgc caggtgagct ggattgaaat gggccagctg  59100
ctcagcagac accctcatgc cccagtgact ctgttcccct tgggccacct cattgaccat  59160
ttatgtttct acatctccta agtttgttgg gccaaggatg gaggctgtct gccgtcaggg  59220
tcctcattgc tgatggtagg aatagttgct gatgtttcat tggatgttgc tgtattctag  59280
ggactgtgct aagtacttta tagaaatgaa catacttcat tttcacagtt ttatgaatag  59340
ggactattat tagtcaagta agcgatgggg aaactggggc agggagcgat gaagtgactt  59400
gcgcaaggtc acaagatgat gtgattggaa ccaagagaag tgttgtggtt ggccacgccc  59460
ccacactgcc tctcatctgc accaaggagt tttgtcccat agcccaaggg ccttggggac  59520
gaatctcagt ggaggccctt agcgggcctg cctgagccag aaagcagaat cggcattttt  59580
ctgtccttgg ttggcccagc cctgaactga gatgcggaaa tcgcctttcg ctgcctggta  59640
gaaaatggag ctgcagttac tgaccaccag gcagagagag gtgggtccct gtcccagcct  59700
cagccaccac tctgcctaag ctgtggggac tgagggcgct gtcgttagct gactgcagaa  59760
ggtgagcaca cgctgtagca tgttatgttt cagatgtcac atgttgtgtt attgtgtctt  59820
tgcagggccc tttgcctaac acatgcggtc acttttggga gatggtgtgg gagcagaaaa  59880
gcaggggtgt cgtcatgctc aacagagtga tggagaaagg ttcggtaagt ctcggcttca  59940
tttgctgtgt atgtgatcat gcataccact ccatatagtt accattttcg tccagatttt  60000
taaattattt ttcttgcctt tgtatttcct ttacgtagta tttttattta aaaaaattaa  60060
aacagcagca tataaatgca tgttggttgt caaccagtta atgaagtgaa taaaagggag  60120
gaggcggaag aactgcacgg acctcttcgc ccccgccttc tcctgtgtgg tgcgtgtggc  60180
gctccgccca cctgtgctgc ctgtgcggct ctcatcacag tgtggagttg tgtgtggagt  60240
tatggagacc tgcttttatc ttgaaaagca agttcttagt gcatcttcat ggtgtctgat  60300
tttttggctg gtgagagtgt ggctacctct gcggagctgt gggagcggct gactagatga  60360
gatttgcctc cattcagtac ctagactctt gccctgccac acctcttcgg agtgagcatt  60420
gacttcagga tgtgtgtcat tctaagttcc tgcaactttt caaacacccc tcgggctagc  60480
gtgtggctgc acggtgtcca tttgtgcagg ccaccactcc tcttgcatct gggtctagcc  60540
acctctcctt cttgacttac catagttcat tttgtaccat gctttcagaa tgagctttct  60600
caaatccaag tctcaccacg gttcttccca gctgaaaacc cttgtgcggt tccctttgcc  60660
tcacaggata atacatggtg tggcttacgg aaccctgcag gtctggccct aggcccctgg  60720
```

acacagacct ctcaccactc ttggaacttt agccaggaca aagttttctg tttttagttt 60780
cttaccatgt tctctgggcc gaggagtccc agtgcccacg ttcatcccac ttgcaggcac 60840
ccctggacgg ctgcccccag ctccccaact gcctgcattc tcccctgccc tcctcactct 60900
gttggaatag ctgagaatag ccgatttctg ggcagccggc ctcctgtgta gactgtcctg 60960
tgtagactgt cctgtgtaga ttgtctgtgt agactgtcct gtgtagattg tctgtgtaga 61020
ctgtcctgtg tagactgtcc atgtaaactg tcctgtgtag attgtctgtg tagactgtcc 61080
tgtgtagact gtcctgtgta gattgtctgt gtagactgtc tctgtagacc gtcgtgtata 61140
gactgtcctg tgtagactgt ctctgtagac cgtcgtgtat agactgtcct gtgtagactg 61200
tctctgtaga ccgtcctgtg tagattgtct gtgtagacca tcctgtgtag accatcccat 61260
ttagaccatc tgcctgtgca ggcgcaggcc agtgttcagc agggccacag gctcctcggc 61320
ctccctgccc tcgctgctcc ccaacactgc caaccctgct gcggggtcca ggaggagatg 61380
ggctgaggat cgtggagacc agcaggagcg tgtggcccag gagcagggaa ctgggtgtcc 61440
ttgggccttg ccaggtccag gctcagctag gacacggctc tcacagctgt cctggttgcc 61500
tccggccaca gaagaaggtg agggctccag agaggccacc tttccaaaaa aagcacagtc 61560
atggccctag aatgtaaaaa atccaagtgt taagaaggaa cacatcaaag gaaacttcag 61620
cagtgaaaac ttgaagcatt aaccacgaag cctctgcctc caccacacac aaagaaacgg 61680
ctttagttac tcgcagaaag tcttcctctt aggacagcgc gtgtttaaaa tcataggggt 61740
ttggtttgtt ttgttttggg gttggggttt tttgggggtt ttttaccctt gcctactttt 61800
taaaaaatga aagtgtttat ttgcccaaca ataacagaca gggagcttgc ctaagtgttc 61860
tgttgatgat ataatgtatc ttgtcttaga aaaaaacttt ttcagtgaaa ggtggttttt 61920
aaatttttc ttccctcctt agtagcttga ttagtaaaat gtgaagttac aaatgtgaag 61980
caaacccccca cccttcacca ctagtcagca attttgagta aagaaacaaa gcatcaggtg 62040
ctcacagcac acactgtctt agagggaagg ggaagcctgg tggcctgtgg aagccttcag 62100
catagctcca tctgcaggct tctgaccctc agcactactg acacttgggc tggatcattg 62160
tctgctaggg atccgggcag ggagtggctg tgctgggcgc tgtaggaagt ttagcagcat 62220
ctctggcctc tatccaccag atgccagtag cacccccctcc ccagatgtgg cagtcagatg 62280
tgtttctgtc tagactccag actttgtcca acgtcccctg gtaggccaaa ttgcccccgg 62340
ttgagaacca ccgctctaga tggtattgag ggttgggaat tttaaatcaa gacatttatt 62400
cagaaattac cagatatagt agcatttgct tcttatttat ttctttgttg ctaagtgttt 62460
ggcaaaacct ctttgctgtg agcacaaggt ttgctttagc aattgttgtc acattacagc 62520
aaggagtggt gtccagcgct gtagttatgt atttgagcag tgtccagtgc tgtagttatg 62580
tgttccagcc tcaccaggcc ctgtgcttca ttgtctccca ctcaagactg accacaaatg 62640
gcccacagat ccactgtgac aacctttccc tttgggttac tgtggtggca tcgagaacat 62700
ggctggttgg ctttgctgta gtttactgtg ataactgtgc cagcagtccc tgctttcctt 62760
tgttaagtat cccattccac tggaggatta cttgggcgtg cagattggca tgaaaagcaa 62820
tgtatggttt gagattgtta aagtttcttt gggatcaaca ttttcaattc tgtatcagca 62880
ttatccctcc cagagggctg gctgggagaa atcatgagaa gttacagtat cttatttgct 62940
cagctaatct aattataaat gatccacaca gcttgtggta aaaccagctt ttggggagtt 63000
ttcatttaat gcatacttgt cttctgattt ccttccttca ccaaatagtg taggatgctc 63060

```
cctcttattt ttggcaaaca tgcctgttat cttttgggac cctgggcttc ctggaaacca  63120
gttatgcaga agatgattgt gtgtgttaga ctggggtcat ccagatggct agagttctca  63180
ctggttctgt ttaaggattg actttagaca cctcagtgta ggctgcacca tggcgtaagg  63240
gttgggattg ttgtttagaa gggggaagta agcaaggtga gtttaattgg ccattgcaga  63300
atctcacccg tatctccctc ctgaaatcct cactaaagct gccgtttgct ttcaggtgct  63360
ttcatgcaca agacactgca ttttgtatca cagggtccat ataattcatt tttctctcgt  63420
acttagttct ctgtgttaag aattacttac ttagttctct gtgttaataa tttttggcga  63480
aaccaaatta cccgtcacag ggttactgta gatgtctttc ataggttttc caaacaccac  63540
ttgcccactt gtttgggaag gccccaagga ctgtttaaca tctgccttca tggtggaaac  63600
agcaactatg agagatgcta gcatgttggc actgccatgt tcctctggta ccagcccaag  63660
ataggactca atttgaggcc tggtgaagta ctgtgttcta ataaaaatcc atctactttt  63720
catggccgta tatatcaatg taatagggta actggaaatg tgatcttgtg ccttttaaaa  63780
attttgtgtg tttaaaacaa aaatttctat tggaaatgac agagcatagc ttgttgctgt  63840
agacacctga gagtccttaa aaataaatat tgggttattg acacttagtt gcatgacaga  63900
attcctcact tgtacagttc caaagtctta gtctttaccc agattacaga gggttattaa  63960
gcattaggtt tggttttgaa agtgagtgct tgctgtctgg aggtgagctt taagactcgt  64020
ctgccctgct tatgagatga ggaagggtgg cctcttcctc ctgcatttct gttcttcgct  64080
tccttctctg tctgctcact ctgtggaatg cccaccccag cacgggtggg gtggaacctg  64140
tcagatcagt ctcttgtttc tggggtcttg aggcattata agatctagtt gttagaagtg  64200
tgggattaat tcatcttttc acattcttct aagttcctgc ttttagctgc cacacccact  64260
ttggctaagt gggggtcttg ccatgtaatt agcgcctcca tgccaagtgg cagaattgct  64320
tcaatggtga cagattgtcc ccattcaaga gttcactttt ggcaactcat cattgatcca  64380
ggaaggtgac atggatgaaa ctggctaaga cttcagacag gcttgtgtcc agactcttga  64440
gaaagctctg ttggcttctg gtctggcact gtgaagtttg ctgtgatgct ggcaccacaa  64500
cctggtgttt cctaatttgt ttctcccaca ttttgctttg gttttgtctt ttgggcagct  64560
tccagctcca gtagagcagg accaataggc atttgtggtt ctatattcac cctcctcacg  64620
tgcttcctgg ctcctcattg cccccagatg atgccacagg tccctgggcc tgctgccagt  64680
cgtctgtgat ctgggcctct gctggcccct tctccagctg ctcttttcag cctcttattt  64740
gcagtcactg cctaggaaat cctagtcatc cttcaaaacc tgcctcttgc acagagcttt  64800
ctctgatctc tcttttctgt aaccttggct gacctgaaac atttccctct tctgaattcc  64860
tgctgcatgt ccgtagcatt tccccctcag ccctccccca tagtccacct tgtcactgct  64920
gggcacagca gtgtcttctg acagacagct ggccctgaag tggttccctt cacccacacc  64980
atcctttgcc ccagaggagg tattgagtgg gtcagtgcac gtgaactgcc agtgtcattt  65040
gccaaagagc tgttgacaca cgctgacatt tcttttgctg aaaatcataa gggctttgag  65100
cttccctctg tccaggcaca tggtcaggct gacccggtag ctctgcccct gctgacctgc  65160
catttttgtc cacaacagtt atccatgagc agaaacattt gtgtaactga ggcagaaact  65220
tagttcaagt aaaatgtcac taaattcgag tcagtttttg tcttagaccc taaatgaaac  65280
caaattttca taaattttct tgttttaaag aaaaatttaa tgagctacat ttaaactgag  65340
aacatcagat agtgtctgag attatcaaaa tagaacatca aaagtatttt tctgaatgaa  65400
ctgaaccaaa ccagaatgaa agggcaagcc ctggggagcc tgtctccaag ccttctctga  65460
```

aagggagtct gtatttggtg ataactgctc agcctctcca aagggcctca cctgctgtct 65520
ctcccagttt tatttttaat tgcctgtgag ttttctgtgc agggtaaggc acctacattc 65580
tatgccagca gcctgatcag gtcctgggta atgtttgaaa tggctacaca gaggagtttc 65640
aaagcctttt gttcaatctg gcttcacctc gtagacggtg agaaagcgtc agagccctgc 65700
aggatcccgt tgccacgttt gaccggggag ccgatgggtt tggaagtctg agccctgtct 65760
gcacaacctg ccccggtcag cagcttcgtg cccccacccc catctcccca tgaggcaggc 65820
atctgtgctg accatggctt ccatgttcag aaacccccag gcctttgagt tatcatgaag 65880
cttgtgggat gtgctccaag cctcctgcca tagaaaaact gccatattgc tcacaataat 65940
tcactattat ttgtttcccc agttaaaatg cgcacaatac tggccacaaa aagaagaaaa 66000
agagatgatc tttgaagaca caaatttgaa attaacattg atctctgaag atatcaagtc 66060
atattataca gtgcgacagc tagaattgga aaaccttaca gtgagtatag cacacacttc 66120
agcacttcag gcggctactg gttcacatgc ctcttccttt atcccttggg tgatattacc 66180
taatgtcagt gttcctggct tttgtatacc ccgagcaaga tgtggtttgg gcactgtggt 66240
gagcggagct tacttgtgta cctaccaagt gcccagggag ggtggaggcc acagtgctct 66300
ctctgacctt taacaacagt taacaccagt tcttagggaa aggagagttt cttacccaaa 66360
agactggttc ctgcttgtgc agctgcagag ggactggagc ggcagcctgc aagtcccagt 66420
gaagcatgct gccttctttg tggtcctcag tcttcgagtc tgaagagagg gaagaagggg 66480
tatagggggct cactccagtt tcatagctag tgaaagtttt ctgggccagg tcttgggttt 66540
ttttgttgtg ggaagagttt ataacaccag ctacttgctt ggtaaaagtt ggtcttggaa 66600
catggcaagg cattgtggca agcagcactg ccgctgaacg cgctgctcct ggggctttgg 66660
aataattccc ctggatccgt aacttggggg tgttcatgtc attctgggga acagtggagg 66720
gagtgcgcgg cagcacctgg gggcaccagt gaagagtggc cagccaccaa cctctagaac 66780
ctaactgggg tcgaatcctg gccccacctt actagctcat cacagtgtct ccgtttcctc 66840
ttctgtcaaa ctcaggtttt gcgagggttc tgggaggtcc tatacgggaa gggttagcag 66900
ttaccatggg tgtgtagcac gggctttatc tgaagggaag gtggagccgt agggagacca 66960
tgtggagtgg ggctccaggg ctgtgtgggt ggggagggat ctgcttctgg gttaccccat 67020
gcctcccctt ctcaagtact actttttaat catcatggct cctgccattc atttcatagt 67080
tgatgtaagc caggtgcggt ggctcacgtc tttaatccca gcacttgggg aggctgaggc 67140
caggaggatc actcgaggcc aggagttcaa gaccagcttg ggcaacatag tgagaccccc 67200
gtctctacaa aaaaacaaaa acagttagtc agacatcgtg gtgctcccct atagtccagc 67260
tactcaggag gctgaggcag gaggattgct tgtgcccggg agttcaaggc tgcagtgagc 67320
tatgcttgca ccactgcact ctagcctggg tgacagagca agaccctgtc tcaaaaataa 67380
ataaataaaa aaaatagtag aagtaagatc tagaatgtag cacaggttac caggacgtag 67440
gcaaggggtt cgggctgcct ggctcttgag gatggtagca gtgcagctga tgtgagtgct 67500
ttctgccctc tggtggtgac cgcgccggag tcaccagccc tgccatagcc ctgatggggc 67560
agagggttct gagtacggtg gatggaggtg ctttctggaa gattctcagg agtaacatgg 67620
gcagtgtgtt ggaatgtgct agaggattta tgcagtagcc ttttaaaaga atgcttttta 67680
gcatttgcaa gcctgacatt aagagtgact tctgggaaac tatttgcttg ttgagggaaa 67740
ctgaatttca acagagcaga agagctgtgc gctttttgct tggcagagtg aatacagcca 67800

```
gctcagaggt tttgatgtta ggatctgttt gctccaacag actttgtttt taaaaggctt  67860
ttctcagcca tagctgtctg ttctagcaca aggctggaat gagttccttg tgaaagaggt  67920
gagcaggtgt gagggagggt gtcagtgggc ggtaacccac accttcaagg attaaaggaa  67980
aacttgcatt tggcatgctt gcttcttatt caattttaaa atacatttta acggccgggc  68040
acggtggcta acacctgtaa tcccagcact ttgaggggct gaggtgggtg gttcacgagg  68100
ccaggggttc aagaccagcc tggccaagat ggtgaaaccc catctctact aaaaatacaa  68160
aaaaaaaaaa aattagccgg gcgtggtggc gggcacctgt aatcccagct actcgggagg  68220
ctgaggcaga gaattgcttg aacccaggag gcggaggttg cattgagccg agatcatgcc  68280
actgcattcc agcctgggcg gcagagcaag actctgtctc aaaataataa taataatttt  68340
ttaaaaatac attttaagtc cttttcttcc ccacctgcct ccacccacca aatagaagag  68400
gtatttcttc ttctttaatg tcattaaggt tatatggata ccattttcta gagaggaaag  68460
aatgatggaa ttgcctagtg tgagtctagc aattatccta acatacacaa atttctcctt  68520
gttctgtgcc aagatactgt atttaatatt taatgaacat taaatattat ttactagtgt  68580
atttaatggc tgaggcaggg ttaaatatgt attattttca tcccagcaga gttgggggag  68640
gtcctagtaa ctatgccatg agctctgtga gggtgaggtg gtgtctttgc ccccgcctcc  68700
ctggcacagt gactggcaca tgattggcat agtgtggaca ttcgtcaagt gaaggaaggc  68760
atcatgagca gatctctggc ctgaatcctt ctgccatcag ctgctcgcca ggtggccctg  68820
gcactgggcc acagggaaac tctccaggct ggtatggttc ctgtctgtgg ctgtcttccc  68880
gggcccatgt taggagactt tcacttccag agccctttcc ctctcagggc cttgcttacc  68940
aagtgactgg ttcccattta ctaggagctc ttaggtcatt gaagatgttg cgtactcccc  69000
ccagtgaggg ctgccttttg atcacagccg ccagaagcct caaggaagga gcagagctgg  69060
aaacagacgc caggccattg cttctgttcc tctggggcag acccagccac ggaagagaca  69120
ttctgggaca agggctgggg tccacctttc aaacgtgtct gcagcaggct ctcagcatgg  69180
actctctgcc tccaaacatc cacctcctca tcggaaaatg gatgggagtg cctgcctgga  69240
gcagctggtg ggagagcgca gcgccagcac gtaggacaca ctcggttcat gggctgatgc  69300
cgttcgcatt gactgcctct tcagctgggt gttgagccac accttggagt caccagtctt  69360
tggagaccaa gtctgctact tttttctcta aagtgacaat cctctgaaac ctccagatca  69420
tcttgaagcc cccgtctgaa agttgcccag agccagtgcc tcacctgctg ttccttgttc  69480
actttttcac gggaggcctt gcagggcttt atgacaagat tttatgggtg gctgcccagc  69540
atcattgtga ctcgtgagac agagagaaac cagttgtaac catgtagaca gtggaagtga  69600
tagggagaaa agaggtgagg ggactcttca atccgaaggg aaatgaagtc taagcaggcg  69660
caccctgcag gttcagtgtc aagcccaggg cctggcccca gggtgtggta tttgttgact  69720
gggtgtgtgg accctgggag aaagtctgag aatgaatgtt cctcttagag gtagagagtg  69780
gaaggtgact ctgtgtgtac ttggaattag tgatttctgt acagatgatt cttttagaat  69840
catcatgagt atttttctct ttcagaccca agaaactcga gagatcttac atttccacta  69900
taccacatgg cctgactttg gagtccctga atcaccagcc tcattcttga actttctttt  69960
caaagtccga gagtcagggt cactcagccc ggagcacggg cccgttgtgg tgcactgcag  70020
tgcaggcatc ggcaggtctg gaaccttctg tctggctgat acctgcctct tgctggtaag  70080
gaggccctcg cgggtgccct ggggagctcc tctacctgct ctgctgtgat gtttttcct  70140
aagtagaaac tgaagcgctc ctcttccaaa atacagagac tcactgtgtt agtctgtttt  70200
```

tgcgttacta ataaaggcgt acctgagact cggtaatttg taaagaaaag aggtttaact 70260
ggctcccggt tctgcaggct gtacaagcat ggcaccagca tctgctcggc tcctggggag 70320
gcctcaggga gcttccagtc atggtggaag gtgaagggga gcaggagcaa gagatggggg 70380
aggtcccaga ctcttaacca gctctcttgt gaatgcattg cctcagggag ggcaccaagc 70440
ctttcatgag ggacctgtcc ccctgaccca gacacctccc acccagcccc acctccaaca 70500
ctagggatca catttcagca tgagattggg aggggacaga catctaacgg tgttattaac 70560
gttgcccttg agaattggac ctggctgact tatatctcct ctctggcttt cagatggaca 70620
agaggaaaga cccttcttcc gttgatatca agaaagtgct gttagaaatg aggaagtttc 70680
ggatggggct gatccagaca gccgaccagc tgcgcttctc ctacctggct gtgatcgaag 70740
gtgccaaatt catcatgggg gactcttccg tgcaggtcag cattgccttt gtttgaatcc 70800
aggtgtgacc attttaactt ttttgtcttt gaaggaggct gtcagttgta aaagttcaaa 70860
caccgtctgg tgtcagggga aatagctacc cttcatgttt aaaatagcta gaaagttgtc 70920
aaaatgttca ccatgttgca ctttgtgcct ttgaagtgct cacatagaga gcattgatag 70980
gaagacgaga ctttattttc aaaagatttc atcttccaag tacatggctg cagccctgag 71040
aggccgagag cccctcgcca agccgtcacc tctgctcatg caaagggatt tcctgacaaa 71100
ccagccgaag tgaacactaa taggacttcc tcttgctgct ctttcaagga tcagtggaag 71160
gagctttccc acgaggacct ggagccccca cccgagcata tccccccacc tccccggcca 71220
cccaaacgaa tcctggagcc acacaatggg aaatgcaggg agttcttccc aaatcaccag 71280
tgggtgaagg aagagaccca ggaggataaa gactgcccca tcaaggaaga aaaaggaagc 71340
cccttaaatg ccgcacccta cggcatcgaa aggtaatatg attgggtccc agcttgttgg 71400
ggtgagggga aatgactttc tgttctagaa acacacgctg gtactgaaac cctgtggatg 71460
cagcctcctg ttggcaagca gcgcttccgc atccttgggg aacagggcgc gtggaccaca 71520
gccactccac tcctggctgc tggaggtccg gtattgggca cagggtggcc gcaggacatg 71580
agccacttct gtgggcttct agtgccacct tgtggtgctt gttggaatga ggggctcgga 71640
gccaccgagt agggtttttc tgcccccccct gacgacagcg ccctccccca ggtttccgga 71700
cagtcctgaa atgtgatgtc caggcttgag tgccctcagt ccccacagtg gtcctttggg 71760
gaatgtaacc ttttttatgt ggtcttgatt aaatcccatt ttacttcctt gcaggttaac 71820
aaccattatt gagtacctat tgatatgtgt ggtgtactga gttaactaga acatgtcccc 71880
tggtctgtgt tctagaccat cttgctggga aaaaggcaga cccaaagcat attttggtgg 71940
gggcccatgg acagtgatgt gatagaggtg tccgctgagg tggtcaggga aggctgcttg 72000
cagtaggtgg ccgtgcacgg aaagtttgca gaatgagcag gtgttagttc cagctggaga 72060
tgactgccgg ctgtgccctt ggtacctgct ttctggaggg aagttttaag acgtgtgcat 72120
acttgaccca gcagttgtat acatggagaa atttactttg cagcaactct caaaacaagc 72180
gtgtaaagat gtgtataggt agttgtgttt gttgtggcat tgtttgtagt agtgaaaaat 72240
tagagacagg ccaatgatat aaccagggac ctgatcaatt atgttctctc ccggtgttgg 72300
gatattctgt agctcttaaa gaatgagatc tgggtgtact gatgtggcca gacattgcaa 72360
ttgcagtaca tgagaaggca aatcatacag tagtgtgtac accagtgagt cctccagcca 72420
gataaatcct cacagtgacc agtcgcccag gcaccttgtg aaccctaccc tgggtgtggg 72480
tgctatctga agtacctggg ggagggggtg acaagtggac ttcaggctga tgtgggccct 72540

```
ggcctggccc tccctccaag cagagggggc tggctcgctg gaaggttaac atcatccaac  72600
tctgtctaca cgtggcttgt tttttcctag aattcctgcc acaatagcag catccttgcc  72660
attcattttc tccaaagtga gtaacccatc tctgccctct gattcctcag catgagtcaa  72720
gacactgaag ttagaagtcg ggtcgtgggg ggaagtcttc gaggtgccca ggctgcctcc  72780
ccagccaaag gggagccgtc actgcccgag aaggacgagg accatgcact gagttactgg  72840
aagcccttcc tggtcaacat gtgcgtggct acggtcctca cggccggcgc ttacctctgc  72900
tacagggtat gtttccactg acagacgcgc tggcgagatg ctcgtgtgca gagagcactg  72960
gccgctagcc cgatggtagg attcagttct gtggtgcatc tgagccagtc tcagaagaaa  73020
cagatcaaag gtttttaaag tctggaactg tggaagggct aacaagagaa ttaaggatcg  73080
atgcactggg gttttaagga gccctctggt cccaagaata taagagtcta atctcagggc  73140
cttaacctat tcaggagtaa gtagagaaaa tgccaaatac gtctgtttct ctctctcttt  73200
tttttttat tcctttgttt ttggaaaaaa atagagttac aacacattgt tgtttttaac  73260
ctttataaaa agcagctttt tgttatttct ggaacaaaaa aaaacaaagt aggcacttat  73320
gaaactttct catacccta ggtgatgtaa tcagccatat aatttatatt tgatttccca  73380
gggaaggaat cccaaacttt tacgaatgta aactcccttg gagaagaggg ttaggacgct  73440
gttgcgctca agcccccctc agctgtgtgc acactgagcc aggacagggt ctttgagctt  73500
tcccactata agaagaacag caacaaaagg ccgtctagaa aaacagaacc tgcctctgct  73560
tctgctcagg gtgtccccgc tgggtttcca ttgtcctttc tccattgctc cctcctgtga  73620
cagccatctt gctcatgtac cagccctcat caccccatcc ccataaatgg gtgtcctcga  73680
ggcctctgcc tgggggtcag aggtcaccac agggtggcca ttggcatgtc aacccgctgt  73740
taattcagag aagtgggctc cacctcattg ggagaagtgc catttcagca gaaattcaca  73800
cgttagacgt gtgttgctgt taagtaaggg gaagagagag gactagcctc agagctctgg  73860
ccatggaaat gacctcctaa gactttttcg tggttttaaa tattttacct ctttccaggt  73920
ggcatctgag tacatcagat ggttttgcaa aatgcaaaca atttttttcct tggggatgat  73980
ttttggggag agggggctac tgtaaaaaat aaaaccaaaa cccccttttgc tccctcggag  74040
gttgaagttg ccgggggggtg tggccggggt catgcatgag gcgacagctc tgcaggtgcg  74100
ggtctgggct catctgaact gtttggtttc attccagttc ctgttcaaca gcaacacata  74160
gcctgaccct cctccactcc acctccaccc actgtccgcc tctgcccgca gagcccacgc  74220
ccgactagca ggcatgccgc ggtaggtaag ggccgccgga ccgcgtagag agccgggccc  74280
cggacggacg ttggttctgc actaaaaccc atcttccccg gatgtgtgtc tcacccctca  74340
tccttttact ttttgcccct tccactttga gtaccaaatc cacaagccat tttttgagga  74400
gagtgaaaga gagtaccatg ctggcggcgc agagggaagg ggcctacacc cgtcttgggg  74460
ctcgccccac ccagggctcc ctcctggagc atcccaggcg ggcggcacgc caacagcccc  74520
ccccttgaat ctgcagggag caactctcca ctccatattt atttaaacaa ttttttcccc  74580
aaaggcatcc atagtgcact agcattttct tgaaccaata atgtattaaa atttttttgat  74640
gtcagccttg catcaagggc tttatcaaaa agtacaataa taaatcctca ggtagtactg  74700
ggaatggaag gctttgccat gggcctgctg cgtcagacca gtactgggaa ggaggacggt  74760
tgtaagcagt tgttatttag tgatattgtg ggtaacgtga gaagatagaa caatgctata  74820
atatataatg aacacgtggg tatttaataa gaaacatgat gtgagattac tttgtcccgc  74880
ttattctcct ccctgttatc tgctagatct agttctcaat cactgctccc ccgtgtgtat  74940
```

tagaatgcat gtaaggtctt cttgtgtcct gatgaaaaat atgtgcttga aatgagaaac 75000
tttgatctct gcttactaat gtgccccatg tccaagtcca acctgcctgt gcatgacctg 75060
atcattacat ggctgtggtt cctaagcctg ttgctgaagt cattgtcgct cagcaatagg 75120
gtgcagtttt ccaggaatag gcatttgcct aattcctggc atgacactct agtgacttcc 75180
tggtgaggcc cagcctgtcc tggtacagca gggtcttgct gtaactcaga cattccaagg 75240
gtatgggaag ccatattcac acctcacgct ctggacatga tttagggaag cagggacacc 75300
ccccgccccc cacctttggg atcagcctcc gccattccaa gtcaacactc ttcttgagca 75360
gaccgtgatt tggaagagag gcacctgctg gaaaccacac ttcttgaaac agcctgggtg 75420
acggtccttt aggcagcctg ccgccgtctc tgtcccggtt caccttgccg agagaggcgc 75480
gtctgcccca ccctcaaacc ctgtggggcc tgatggtgct cacgactctt cctgcaaagg 75540
gaactgaaga cctccacatt aagtggcttt ttaacatgaa aaacacggca gctgtagctc 75600
ccgagctact ctcttgccag cattttcaca ttttgccttt ctcgtggtag aagccagtac 75660
agagaaattc tgtggtggga acattcgagg tgtcaccctg cagagctatg gtgaggtgtg 75720
gataaggctt aggtgccagg ctgtaagcat tctgagctgg gcttgttgtt tttaagtcct 75780
gtatatgtat gtagtagttt gggtgtgtat atatagtagc atttcaaaat ggacgtactg 75840
gtttaacctc ctatccttgg agagcagctg gctctccacc ttgttacaca ttatgttaga 75900
gaggtagcga gctgctctgc tatatgcctt aagccaatat ttactcatca ggtcattatt 75960
ttttacaatg gccatggaat aaaccatttt tacaaaaata aaaacaaaaa aagcaaggtg 76020
ttttggtata ataccttttc aggtgtgtgt ggatacgtgg ctgcatgacc gggtgggtgg 76080
gggggagtgt ctcagggtct tctgtgacct cacagaactg tcagactgta cagttttcca 76140
acttgccata ttcatgatgg gtttgcattt tagctgcaac aataaaattt ttttctaaag 76200
aacatgaatt tggggtgctt cccatttttt tctttgctta atagagctaa accaggatga 76260
gtaactcctg tttctttcta tccctgctga tgtgaaacag atgttgtcaa tcagctgggg 76320
ttagagtttt ccacttctaa gaattaacct cagcatccct gcattgccag caccctcagg 76380
ctggagcgct ttccttgact gtgagcttgt tgaacacctt aggcctcagc ccatttcctt 76440
cccaaattga cgctttgcct gtgtagggcc ctcagataac ttaacaaact taccagtgtt 76500
gtttgaagaa cagtgttttg agttgtaatc tcaaaaccat atcccttacc caattacctg 76560
taagacacaa tggttaccac atctcagtac gtaaagtcca cttgatatag aattgactta 76620
gaaataagac agattagtat agtttttcat ttgtgtacaa aattaaacaa tgtaaattcc 76680
ccccaaagtg atttttttga ctttttgaag taattttgga cttgcaaaat gttgccaaaa 76740
tagtacgaag agttccccag taccctcgaa gtttcctcga ctgtttcaaa gctggctgca 76800
ggcccaggct catgagactg ggaagaggac aggctgtggt catgtggacc cacaggggcc 76860
tggggctgca gaagtcagtg tggcttccac catttcaggt ataaaaaagg gcatctaagc 76920
tttcaagaag agggaggatg ctctagggca gcggtcccca accttttctg gcaccaggaa 76980
ccggttccat ggaagacaat tttttcacag gcctgggggt ggtgagggat ggttttggga 77040
tagaaacttc cacctcagat catcaggcat cagattctca taaggagctt gcaacctgat 77100
ctcttgcaca cattcagttc acaatagggt tcacgctcct aagagaacct gatgctgcag 77160
ctgatctaac aggagatgga gctcaggtgg tcatgctcag tcgctcgcca ctcacctcct 77220
gccatgcagt ccagttccta acaggcctca gaccagtacc ggtctgtggc ctgggggttg 77280

```
aggacccctg ctctaggctg gtactgctga tgcttaaaaa gagagggttt gccagaaatc  77340

agatgggaca aaagggcaaa ggccgtgcca cagagtgccc atatagggga gagcacgcct  77400

ggagccttcg agagcatgca gagaagcctg gagactgcat ttaccggagc tgctgcctga  77460

ggccaccctc caagtgtccc cacagcgcac cacaagacca caggagtgac ctcctcactg  77520

gcaggtattt ggggaaacaa ctgctgtcta ctcttttggg taaaaagtga aacaccaata  77580

gtttaattga aatttcagaa aattgaacat atgaacaagg caaataaata ctaagtaagt  77640

taaaaacaca aaatatgtcc aggaagtatc gatgagaatg ttcaagttaa agttctccaa  77700

tgccattgct acagcaacct caaaccctag gttctctctg cactattaac acagacatct  77760

caggacatgg tttgcttttt tttaagactt aaataggaaa ctaatttttc tttctttaaa  77820

gcaattgcgt tcttcagtga actctttctt taggccagtt gatggcttct tagcagttta  77880

ttgacgagat cctagggtag cttccgaagc tgggttgatt gattgcattt gggtgcggat  77940

ggccaaagtg agtggcccta ctgcctgtgc tgctcagggc tcctgggctg atgtggtggc  78000

t                                                                  78001
```

<210> SEQ ID NO 3
<211> LENGTH: 4522
<212> TYPE: DNA
<213> ORGANISM: Macaca mulatta

<400> SEQUENCE: 3

```
gcggtgcgta gttccggctg ccggttgaca tgaagaagcc gcggcggcta gggcggcggt     60

agcggcagga gtcggtgctt gctgcggacc tcagggctaa gagcgcgacg cggcctagag    120

cggcggactg cgcagtgggc cgagaaggag gcgcagcagc cgccctggcc cgtcatggag    180

atggaaaagg agttcgagca gatcgacaag tccgggagct gggcggccat ttaccaggat    240

atccgacacg aagccagtga cttcccatgt agagtggcca agcttcctaa gaacaaaaac    300

cgaaataggt acagagacgt cagtcccttt gaccatagtc ggattaaact acatcaagaa    360

gataacgact atatcaacgc tagtttgata aaaatggaag aagcccaaag gagttacatc    420

cttacccagg gccctttgcc taacacatgc ggtcactttt gggagatggt gtgggaacag    480

aaaagcaggg gtgtcgtcat gctcaacaga gtgatggaga aaggttcgtt aaaatgcgca    540

cagtactggc cacaaaaaga agaaaaagaa atgatctttg aagacacaaa cttgaaatta    600

acattgatct ctgaagatat caaatcatat tatacagtgc gacagctaga attggaaaac    660

cttacaaccc aagaaactcg agagatctta catttccact ataccacatg gcctgacttt    720

ggagtccccg aatcgccagc ctcattcttg aactttcttt tcaaagtccg agagtcaggg    780

tcactcagcc cggagcatgg gcccgtcgtg gtgcactgca gtgcgggtat cggcaggtct    840

gggaccttct gtctggctga tacctgcctc ttgctgatgg acaagaggaa agacccttct    900

tccgttgata tcaagaaagt gctattagaa atgaggaagt ttcggatggg gctgatccag    960

acagcagacc agctgcgctt ctcctacttg gctgtgatcg aaggtgccaa attcatcatg   1020

ggggactcct ctgtgcagga tcagtggaag gagctttccc acgaggacct ggagccccca   1080

cccgagcacg tccccccacc tccccggcca cccaaacgaa tcctggagcc acacaatggg   1140

aaatgcaggg agttcttccc aaatcaccag tgggtgaagg atgagaccca ggaggataaa   1200

gactgcccca tcaaggaaga aacaggaagc cccttaaatg ccgcacccta cagcatggaa   1260

agcatgagtc aagacactga agttagaagt cgggtcgtgg ggggaagtct tcgaggtgcc   1320

caggctgcct ccctagccaa aggggagccg tcaccgccta agaaggagga ggaccatgca   1380
```

```
ctgagtcact ggaagccctt cctggtcaac atgtgtgtgg ctacggtcct cacggccggc   1440
gcgtacctct gctacagggt atgtttccac tgacagacgc gctggcgaga tgctcgtgtg   1500
cagagagcac tggccgctag cccgatggta ggattcagtt ctgtggcgca tctgagccag   1560
tctcagaaga aacagatcaa aggtttttaa agtctggaac tgtggaaggg ctaacgagaa   1620
ttaaggatcg atgcactggg gttttaagga gccctctggt cccaagaata taagagtcta   1680
atctcagggc cttaacctat tcaggagtaa gtagagaaaa tgccaaatac gtctgtctct   1740
ctctctctct ctttttttta ttcctttgtt tttggaaaaa aatagaatta caacacattg   1800
ttgtttttaa cctttataaa aagcagcttt ttgttatttc tggaaaaaaa acaaactagg   1860
cacttaatga aactttctcg tacccttagg tgatgtaatt agctatataa tttatatttg   1920
atttcccagg gaaggaatcc caaactttta cgaatgtaaa ctcccttgga gaagagggtt   1980
aggacgctct tgcgctcaag ccccccctcag ctgtgtgcac actgagccag gacagggtct   2040
ttgagctttc ccactgtaag aacagcaaca caaggccgtc tagagaaaca gaacctgcct   2100
ctgcttctgc tcagggtgtc cgttgtcctt tctccattgc tccctcctgt gacagccatc   2160
ttgctcatgt accagccctc atcaccccat tcccataaaa gagtgtcctc gaggcctctc   2220
cctgggggtc agaggtcacc acagggtggc cctcagcatg tcagccctct gttaattcag   2280
aggagtgggc tccacctcat tgggagaagt gccatttcag cagaaatcca cacgttagac   2340
gtgtgttgct gttaagtaag gggaagagag gactagcctc agagctctgg ccatggaaat   2400
gacctcctga gactttttca tcgttttaaa tattttacct cttttcaggt ggccatctga   2460
gtacatcaga tggttttgca aaatgcaaac aatttttcc ttgggggtga tttttgggga   2520
gaaggggcta ctgtaaaaaa taaaaccaaa acccccttg ctccctcgga ggttgaagtt   2580
gccgggggt gtggccgggg tcgtgcatga ggcgacagct ctgcgggtgc gggtctgggc   2640
tcatctgaac tgtttggttt cattccagtt cctgttcaac agcaacacat agcctgaccc   2700
tcctccactc cacctccacc cactgtccgc ctctgcccgc agagcccacg cccgactagc   2760
aggcatgccg cggtaggtaa gggccgccgg accgcgtaga gagccgggcc ccggacggac   2820
gttggttctg cactaaaacc catcttcccc ggatgtgtgt ctcacccctc atccttttac   2880
tttttgcccc ttccactttg agtaccaaat ccacaagcca ttttttgagg agagtgaaag   2940
agtaccatgc tggcggcgca gagggagggg gcctgcacct gtctggaggc tcgccccacc   3000
cagggctccc tcctggagca tcccaggcag gtggtacacc aacagccccc ttgactcgca   3060
gggagcaact ctccactcca tatttattta aacaattttt ccccaaaggt gtccatagtg   3120
cactagcatt ttcttgaacc aataatgtat taaaaatttt tgatgtcagc cttgcatcaa   3180
gggctttatc aaaaagtaca ataataaatc ctcaggtagt actgggaatg gaagactttg   3240
ccatgggcct gctgcgtcag accagtactg ggaaggagga cggttgtaag gcagtcgtta   3300
tttagtgata ttgtgggtaa cgtgagaaga tagaacaatg ctataatata taatgaacac   3360
gtgggtattt aataagaaac atgatgtgag attactttgt cccgcttatt ctcctccctg   3420
ttatctgcta gatctagttc tcaaatcact gctcccccgt gtgtactaga atgcatgtaa   3480
ggtcttcttg tgtcctgatg aaaaatatgt gcttgaaatg agaaactttg atctctgctt   3540
actaatgtgc cccatgtcca agtccaacct gcctgtgcat gacctgatca ttacatggct   3600
gtggttccta agcctgttgc tgaagtcgtt gtcactcagc aatagggtgc agttttccag   3660
gaataggcat ttgcctcatt cctggcctga cactctagtg acttcctggt gagacccggc   3720
```

```
ctgtcctggt gcagcagggt ctcgctgtaa ctcagacatt ccaagggtat gggaagccat   3780

attcacacct cacgctctgg acattattta ggcaagcagg gacacccccc gcccccccacc   3840

tttgggatca gcctctgcca ttccaagtca gcactcttct tgagcagact gtgatttgga   3900

agagaggcaa ctgctggaaa ccacacttct tgaaacagcc tgggtgacgg tcctttaggc   3960

agcctgccgc cgtctccgtc tgggttcacc ttgccgagag aggcgcgtct gccccaccct   4020

cgaaccctgt ggggcctgat ggtgctcacg actcttcctg caaagggaac tgaagacctc   4080

cacattaagt ggctttttaa caagaaaaac acggcagctg tagctcccga gctactctct   4140

tgccagcatt ttcacatttt gcctttctcg tggtagaagc cagtacagag aaattctgtc   4200

gtgggaacat tcgaggcatc accccataga gctgtggtga ggtgtggata aggcttaggt   4260

gccaggctgt aagcattctg agctgggctt gttgttttta agtcctgtat atgtatgtag   4320

tagtttgggt gtgtatatat agtagcattt caaaatggac gtactggttt aacctcctat   4380

cctcggagag cagctggctc tccaccttgt tacacgtatg ttagagaggt agcgagctgc   4440

tctgctatat gccttaagcc aatatttact catcaggtca ttatttttta caatggccat   4500

ggaataaacc atttttacaa aa                                            4522
```

<210> SEQ ID NO 4
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 4

```
ttgtcgatct gctcgaactc                                                20
```

<210> SEQ ID NO 5
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 5

```
gacttgtcga tctgctcgaa                                                20
```

<210> SEQ ID NO 6
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 6

```
cccggacttg tcgatctgct                                                20
```

<210> SEQ ID NO 7
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 7

```
gctcccggac ttgtcgatct                                                20
```

<210> SEQ ID NO 8
<211> LENGTH: 20

<212> TYPE: DNA
<213> ORGANISM: Artificial Sequence
<220> FEATURE:
<223> OTHER INFORMATION: Synthetic oligonucleotide

<400> SEQUENCE: 8 ccagctcccg gacttgtcga 20

<210> SEQ ID NO 9
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 9 ggcaccttcg atcacagcca 20

<210> SEQ ID NO 10
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 10 gctccttcca ctgatcctgc 20

<210> SEQ ID NO 11
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 11 ggtcatgcac aggcaggttg 20

<210> SEQ ID NO 12
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 12 aggtcatgca caggcaggtt 20

<210> SEQ ID NO 13
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 13 gatcaggtca tgcacaggca 20

<210> SEQ ID NO 14
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 14 tgatcaggtc atgcacaggc 20

<210> SEQ ID NO 15
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 15 acccttggaa tgtctgagtt 20

<210> SEQ ID NO 16
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 16 cccataccct tggaatgtct 20

<210> SEQ ID NO 17
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 17 tcccataccc ttggaatgtc 20

<210> SEQ ID NO 18
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 18 ttcccatacc cttggaatgt 20

<210> SEQ ID NO 19
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 19 tattccatgg ccattgtaaa 20

<210> SEQ ID NO 20
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 20 ttattccatg gccattgtaa 20

<210> SEQ ID NO 21
<211> LENGTH: 20
<212> TYPE: DNA
<213> ORGANISM: Artificial Sequence <220> FEATURE:
<223> OTHER INFORMATION: Synthetic oligonucleotide

<400> SEQUENCE: 21 tttattccat ggccattgta 20

<210> SEQ ID NO 22
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 22 gtttattcca tggccattgt 20

<210> SEQ ID NO 23
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 23 ggtttattcc atggccattg 20

<210> SEQ ID NO 24
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 24 tggtttattc catggccatt 20

<210> SEQ ID NO 25
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 25 atggtttatt ccatggccat 20

<210> SEQ ID NO 26
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 26 aatggtttat tccatggcca 20

<210> SEQ ID NO 27
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 27 aaatggttta ttccatggcc 20

<210> SEQ ID NO 28
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 28 aaaatggttt attccatggc 20

<210> SEQ ID NO 29
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 29 aaaaatggtt tattccatgg 20

<210> SEQ ID NO 30
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 30 aggaggtcat ttccatggcc 20

<210> SEQ ID NO 31
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 31 ggtcatttcc atggccagag 20

<210> SEQ ID NO 32
<211> LENGTH: 20
<212> TYPE: DNA
<213> ORGANISM: Artificial Sequence
<220> FEATURE:
<223> OTHER INFORMATION: Synthetic oligonucleotide

<400> SEQUENCE: 32 ggaggtcatt tccatggcca 20

<210> SEQ ID NO 33
<211> LENGTH: 24
<212> TYPE: DNA
<213> ORGANISM: Artificial Sequence
<220> FEATURE:
<223> OTHER INFORMATION: Primer

<400> SEQUENCE: 33 ctggtttaac ctcctatcct tgga 24

<210> SEQ ID NO 34
<211> LENGTH: 22
<212> TYPE: DNA
<213> ORGANISM: Artificial Sequence
<220> FEATURE:
<223> OTHER INFORMATION: Primer

<400> SEQUENCE: 34 cagagcagct cgctacctct ct 22

<210> SEQ ID NO 35
<211> LENGTH: 32
<212> TYPE: DNA
<213> ORGANISM: Artificial Sequence
<220> FEATURE:
<223> OTHER INFORMATION: Probe

<400> SEQUENCE: 35 cagctggctc tccaccttgt tacacattat gt 32

<210> SEQ ID NO 36
<211> LENGTH: 21
<212> TYPE: DNA
<213> ORGANISM: Artificial Sequence
<220> FEATURE:
<223> OTHER INFORMATION: Primer

<400> SEQUENCE: 36 ggagttcgag cagatcgaca a 21

<210> SEQ ID NO 37
<211> LENGTH: 21
<212> TYPE: DNA
<213> ORGANISM: Artificial Sequence
<220> FEATURE:
<223> OTHER INFORMATION: Primer

<400> SEQUENCE: 37 ggccactcta catgggaagt c 21

<210> SEQ ID NO 38
<211> LENGTH: 24
<212> TYPE: DNA
<213> ORGANISM: Artificial Sequence
<220> FEATURE:
<223> OTHER INFORMATION: Probe

<400> SEQUENCE: 38 agctgggcgg ccatttacca ggat 24

<210> SEQ ID NO 39
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 39 tattccatgg ccattgta 18

<210> SEQ ID NO 40
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 40 ttattccatg gccattgt 18

<210> SEQ ID NO 41

<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 41 tttattccat ggccattg 18

<210> SEQ ID NO 42
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 42 gtttattcca tggccatt 18

<210> SEQ ID NO 43
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 43 ggtttattcc atggccat 18

<210> SEQ ID NO 44
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 44 tggtttattc catggcca 18

<210> SEQ ID NO 45
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 45 atggtttatt ccatggcc 18

<210> SEQ ID NO 46
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 46 aatggtttat tccatggc 18

<210> SEQ ID NO 47
<211> LENGTH: 18
<212> TYPE: DNA
<213> ORGANISM: Artificial Sequence
<220> FEATURE:
<223> OTHER INFORMATION: Synthetic oligonucleotide

<400> SEQUENCE: 47 aaatggttta ttccatgg 18

<210> SEQ ID NO 48
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 48 atggtttatt ccatgg 16

<210> SEQ ID NO 49
<211> LENGTH: 16
<212> TYPE: DNA
<213> ORGANISM: Artificial Sequence
<220> FEATURE:
<223> OTHER INFORMATION: Synthetic oligonucleotide

<400> SEQUENCE: 49 tttattccat ggccat 16

<210> SEQ ID NO 50
<211> LENGTH: 27
<212> TYPE: DNA
<213> ORGANISM: Artificial Sequence
<220> FEATURE:
<223> OTHER INFORMATION: Synthetic oligonucleotide

<400> SEQUENCE: 50 gcgtttgctc ttcttcttgc gtttttt 27

<210> SEQ ID NO 51
<211> LENGTH: 20
<212> TYPE: DNA
<213> ORGANISM: Artificial Sequence
<220> FEATURE:
<223> OTHER INFORMATION: Primer

<400> SEQUENCE: 51 gaccagctgc gcttctccta 20

<210> SEQ ID NO 52
<211> LENGTH: 20
<212> TYPE: DNA
<213> ORGANISM: Artificial Sequence
<220> FEATURE:
<223> OTHER INFORMATION: Synthetic Primer

<400> SEQUENCE: 52 cagaggagtc ccccatgatg 20

<210> SEQ ID NO 53
<211> LENGTH: 24
<212> TYPE: DNA
<213> ORGANISM: Artificial Sequence
<220> FEATURE:
<223> OTHER INFORMATION: Probe

<400> SEQUENCE: 53 ttggctgtga tcgaaggtgc caaa 24

<210> SEQ ID NO 54
<211> LENGTH: 19
<212> TYPE: DNA

-continued

```
<213> ORGANISM: Artificial Sequence
<220> FEATURE:
<223> OTHER INFORMATION: Primer

<400> SEQUENCE: 54

gggccctttg cctaacaca                                                19


<210> SEQ ID NO 55
<211> LENGTH: 19
<212> TYPE: DNA
<213> ORGANISM: Artificial Sequence
<220> FEATURE:
<223> OTHER INFORMATION: Primer

<400> SEQUENCE: 55

cgacacccct gcttttctg                                                19


<210> SEQ ID NO 56
<211> LENGTH: 25
<212> TYPE: DNA
<213> ORGANISM: Artificial Sequence
<220> FEATURE:
<223> OTHER INFORMATION: Probe

<400> SEQUENCE: 56

cggtcacttt tgggagatgg tgtgg                                         25
```

What is claimed is:

1. A method of treating diabetes in a subject comprising administering to the subject a pharmaceutical composition suitable for parenteral administration to an animal comprising an aqueous solution, said aqueous solution comprising:

a pharmaceutically acceptable carrier or diluent; and a single stranded modified oligonucleotide targeted to PTP1B consisting of 20 linked nucleosides [having] *consisting of* a nucleobase sequence consisting of SEQ ID NO: 26, or salt thereof, wherein the carrier or diluent is sterile and the aqueous solution is suitably viscous for parenteral administration and wherein the composition is administered parenterally, thereby treating diabetes in the subject.

2. The method of claim 1, wherein the aqueous solution suitably viscous for parenteral administration has a viscosity level less than 40 centipoise (cP).

3. The method of claim 2, wherein the parenteral administration is subcutaneous injection.

4. The method of claim 2, wherein the parenteral administration is intravenous infusion.

5. The method of claim 1, wherein the *20 linked nucleosides of the single stranded* modified oligonucleotide [comprises] *consist of*:

a gap segment consisting of ten linked deoxynucleosides;

a 5' wing segment consisting of five linked nucleosides; and a 3' wing segment consisting of five linked nucleosides;

wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage, and wherein each cytosine of the *single stranded* modified oligonucleotide is a 5-methylcytosine.

6. The method of claim 5, wherein the aqueous solution suitably viscous for parenteral administration has a viscosity level less than 40 centipoise (cP).

7. The method of claim 6, wherein the aqueous solution comprises the *single stranded* modified oligonucleotide targeted to PTP1B at a concentration of about 165-185 mg/mL.

8. The method of claim 7, wherein the aqueous solution has a temperature of about 25° C.

9. The method of claim 8, wherein the parenteral administration is subcutaneous injection.

10. The method of claim 8, wherein the parenteral administration is intravenous infusion.

11. The method of claim 1, wherein the pharmaceutically acceptable carrier or diluent is water.

12. The method of claim [5] *11*, wherein the *20 linked nucleosides of the single stranded* modified oligonucleotide [comprises] *consist of*:

a gap segment consisting of ten linked deoxynucleosides;

a 5' wing segment consisting of five linked nucleosides; and a 3' wing segment consisting of five linked nucleosides;

wherein the gap segment is positioned between the 5' wing segment and the 3' wing segment, wherein each nucleoside of each wing segment comprises a 2'-O-methoxyethyl sugar, wherein each internucleoside linkage is a phosphorothioate linkage, and wherein each cytosine of the *single stranded* modified oligonucleotide is a 5-methylcytosine.

13. The method of claim 12, wherein the aqueous solution suitably viscous for parenteral administration has a viscosity level less than 40 centipoise (cP).

14. The method of claim 13, wherein the aqueous solution comprises the *single stranded* modified oligonucleotide targeted to PTP1B at a concentration of about 165-185 mg/mL.

15. The method of claim 14, wherein the aqueous solution has a temperature of about 25° C.

16. The method of claim 15, wherein the parenteral administration is subcutaneous injection.

17. The method of claim 16, wherein the parenteral administration is intravenous infusion.

18. The method of claim 1, wherein the subject is human.

19. The method of claim 18, wherein the diabetes is Type II diabetes.

20. The method of claim 19, wherein administering the [compound] *composition* decreases blood glucose levels in the human.

21. The method of claim 12, wherein the subject is human.

22. The method of claim 21, wherein the diabetes is Type II diabetes.

23. The method of claim 22, wherein administering the [compound] *composition* decreases blood glucose levels in the human.

24. The method of claim 13, wherein the subject is human.

25. The method of claim 24, wherein the diabetes is Type II diabetes.

26. The method of claim 25, wherein administering the [compound] *composition* decreases blood glucose levels in the human.

27. A method of decreasing blood glucose levels in a subject comprising administering to the subject a compound consisting of a single stranded modified oligonucleotide targeted to PTP1B consisting of 20 linked nucleosides [having] *consisting of* a nucleobase sequence consisting of SEQ ID NO: 26, wherein the *20 linked nucleosides of the single stranded* modified oligonucleotide [comprises] *consist of*:

a gap segment consisting of ten linked deoxynucleosides;

a 5' wing segment consisting of five linked nucleosides; and a 3' wing segment consisting of five linked nucleosides;

wherein the gap segment is positioned between the 5' wing segment and the 3' wing segment; each nucleoside of each wing segment comprises a 2'-O-methoxyethyl sugar; each internucleoside linkage is a phosphorothioate linkage; and each cytosine of the *single stranded* modified oligonucleotide is a 5-methylcytosine; and wherein the compound is administered to the subject parenterally, thereby decreasing blood glucose levels in the subject.

28. The method of claim 27, wherein the subject is human.

29. The method of claim 28, wherein the human has diabetes.

30. The method of claim 29, wherein the diabetes is Type II diabetes.

31. The method of claim 29, wherein administering the compound treats diabetes.

32. The method of claim 30, wherein administering the compound treats diabetes.

33. A single stranded modified oligonucleotide consisting of 20 linked nucleosides [having] *consisting of* a nucleobase sequence consisting of SEQ ID NO: 26 [and comprising], *wherein the 20 linked nucleosides of the single stranded modified oligonucleotide consist of*:

a gap segment consisting of ten linked deoxynucleosides;

a 5' wing segment consisting of five linked nucleosides; and a 3' wing segment consisting of five linked nucleosides;

wherein the gap segment is positioned between the 5' wing segment and the 3' wing segment; each nucleoside of each wing segment comprises a 2'-O-methoxyethyl sugar; each internucleoside linkage is a phosphorothioate linkage; and each cytosine of the *single stranded* modified oligonucleotide is a 5-methylcytosine.

34. A compound [consisting of] *comprising* a pharmaceutically acceptable salt of [the single-stranded] *a single stranded* oligonucleotide [of claim 33] *consisting of 20 linked nucleosides consisting of a nucleobase sequence consisting of SEQ ID NO: 26, wherein the 20 linked nucleosides of the single stranded modified oligonucleotide consist of:*

*a gap segment consisting of ten linked deoxynucleosides;*

*a 5' wing segment consisting of five linked nucleosides; and*

*a 3' wing segment consisting of five linked nucleosides;*

*wherein the gap segment is positioned between the 5' wing segment and the 3' wing segment; each nucleoside of each wing segment comprises a 2'-O-methoxyethyl sugar; each internucleoside linkage is a phosphorothioate linkage; and each cytosine of the single stranded modified oligonucleotide is a 5-methylcytosine.*

35. The compound of claim 34, wherein the pharmaceutically acceptable salt is a sodium salt.

36. The compound of claim 34, wherein the pharmaceutically acceptable salt is a potassium salt.

37. A compound consisting of a sodium salt of a single stranded modified oligonucleotide consisting of 20 linked nucleosides [having] *consisting of* a nucleobase sequence consisting of SEQ ID NO: 26 [and comprising], *wherein the 20 linked nucleosides of the single stranded modified oligonucleotide consist of*:

a gap segment consisting of ten linked deoxynucleosides;

a 5' wing segment consisting of five linked nucleosides; and a 3' wing segment consisting of five linked nucleosides;

wherein the gap segment is positioned between the 5' wing segment and the 3' wing segment; each nucleoside of each wing segment comprises a 2'-O-methoxyethyl sugar; each internucleoside linkage is a phosphorothioate linkage; and each cytosine of the *single stranded* modified oligonucleotide is a 5-methylcytosine.

* * * * *